(12) United States Patent
Sun et al.

(10) Patent No.: US 9,630,929 B2
(45) Date of Patent: Apr. 25, 2017

(54) BENZENESULFONAMIDE COMPOUNDS AND THEIR USE AS THERAPEUTIC AGENTS

(71) Applicant: XENON PHARMACEUTICALS INC., Burnaby (CA)

(72) Inventors: Shaoyi Sun, Burnaby (CA); Alla Yurevna Zenova, Burnaby (CA); Mikhail Chafeev, Burnaby (CA); Qi Jia, Burnaby (CA); Zaihui Zhang, Burnaby (CA); Renata Marcella Oballa, Burnaby (CA)

(73) Assignee: XENON PHARMACEUTICALS INC., Burnaby, BC (CA)

( * ) Notice: Subject to any disclaimer, the term of this patent is extended or adjusted under 35 U.S.C. 154(b) by 0 days.

(21) Appl. No.: 14/355,552

(22) PCT Filed: Oct. 30, 2012

(86) PCT No.: PCT/IB2012/056031
§ 371 (c)(1),
(2) Date: Apr. 30, 2014

(87) PCT Pub. No.: WO2013/064983
PCT Pub. Date: May 10, 2013

(65) Prior Publication Data
US 2014/0296245 A1  Oct. 2, 2014

Related U.S. Application Data

(60) Provisional application No. 61/553,616, filed on Oct. 31, 2011.

(51) Int. Cl.
| | |
|---|---|
| C07D 417/12 | (2006.01) |
| C07D 239/42 | (2006.01) |
| C07D 285/08 | (2006.01) |
| C07D 401/12 | (2006.01) |
| C07D 413/12 | (2006.01) |
| C07D 211/22 | (2006.01) |
| C07D 257/06 | (2006.01) |
| C07D 261/14 | (2006.01) |
| C07D 277/52 | (2006.01) |
| C07D 285/135 | (2006.01) |

(52) U.S. Cl.
CPC .......... *C07D 239/42* (2013.01); *C07D 211/22* (2013.01); *C07D 257/06* (2013.01); *C07D 261/14* (2013.01); *C07D 277/52* (2013.01); *C07D 285/08* (2013.01); *C07D 285/135* (2013.01); *C07D 401/12* (2013.01); *C07D 413/12* (2013.01); *C07D 417/12* (2013.01)

(58) Field of Classification Search
CPC .. C07D 417/12; C07D 239/42; C07D 285/08; C07D 285/135; C07D 277/52; C07D 261/14; C07D 257/06

USPC .......... 514/254.03, 256, 275, 326, 361, 363, 514/370, 378, 381; 544/238, 297, 327; 546/194, 207, 208, 209, 210, 211; 548/128, 138, 197, 246, 251
See application file for complete search history.

(56) References Cited

U.S. PATENT DOCUMENTS

| | | |
|---|---|---|
| 3,705,185 A | 12/1972 | Moore et al. |
| 5,171,748 A | 12/1992 | Roberts et al. |
| 5,573,653 A | 11/1996 | Bandlish |
| 5,580,982 A | 12/1996 | O'Malley |
| 5,753,653 A | 5/1998 | Bender et al. |
| 6,096,771 A | 8/2000 | Kojima |
| 7,262,304 B2 | 8/2007 | Ueno et al. |
| 7,291,638 B2 | 11/2007 | Lee |
| 7,858,639 B2 | 12/2010 | Sun |
| 8,153,814 B2 * | 4/2012 | Beaudoin et al. ............ 548/190 |
| 8,193,194 B2 | 6/2012 | Martinborough et al. |
| 8,642,660 B2 | 2/2014 | Goldfarb |
| 8,889,741 B2 * | 11/2014 | Shinozuka et al. ........... 514/602 |
| 8,933,236 B2 | 1/2015 | Chowdhury |
| 8,952,169 B2 | 2/2015 | Andrez |
| 9,102,621 B2 | 8/2015 | Brown et al. |
| 2006/0069093 A1 | 3/2006 | Scarborough et al. |
| 2007/0088015 A1 | 4/2007 | Silva et al. |
| 2008/0161303 A1 | 7/2008 | Zhang et al. |
| 2008/0312286 A1 | 12/2008 | Pinkerton et al. |
| 2009/0012103 A1 | 1/2009 | Abelman et al. |
| 2010/0179137 A1 | 7/2010 | Kamikubo |
| 2010/0197655 A1* | 8/2010 | Beaudoin et al. ....... 514/210.18 |
| 2010/0286110 A1 | 11/2010 | Fyfe et al. |

(Continued)

FOREIGN PATENT DOCUMENTS

| | | |
|---|---|---|
| CN | 101466665 A | 6/2009 |
| CN | 101653458 | 2/2010 |

(Continued)

OTHER PUBLICATIONS

Braga et al. "Making crystals . . . " Chem Commun J. Roy. Soc. Chem. p. 3635-3645 (2005).*
"Improper Markush" Fed. Reg. v.76(27) p. 7162-7175, slide 1, 64-67 (2011).*
Prodrug "Dictionary" p. 1-2 (internet) (2002).*
Seddon "Psudopolymor . . . " Crystal Growth and Design v.4(6) 1087 (2004).*
Vippagunta et al. "Crystalline solids . . . " Adv. Drug Del. Rev. v.48. p. 3-26 (2001).*
Wolff "Burger's medicinal chemistry . . . " p. 975-977 (1995).*
Catron et al. "Preparation of 4-[4-[2-phenylcclohexen . . . " CA156:638098 (2012).*
Sakuma et al. "Preparation of piperazine . . . " CA150:260220(2009).*

(Continued)

*Primary Examiner* — Celia Chang
(74) *Attorney, Agent, or Firm* — Viksnins Harris & Padys PLLP

(57) ABSTRACT

This invention is directed to benzensulfonamide compounds, as stereoisomers, enantiomers, tautomers thereof or mixtures thereof; or pharmaceutically acceptable salts, solvates or prodrugs thereof, for the treatment of sodium channel-mediated diseases or conditions, such as pain.

29 Claims, No Drawings

(56) References Cited

U.S. PATENT DOCUMENTS

| | | | |
|---|---|---|---|
| 2011/0092703 A1* | 4/2011 | Sakuma et al. | 544/392 |
| 2012/0004714 A1 | 1/2012 | Kleve et al. | |
| 2012/0010182 A1 | 1/2012 | Brown et al. | |
| 2012/0010183 A1 | 1/2012 | Bell et al. | |
| 2012/0010207 A1 | 1/2012 | Bell et al. | |
| 2012/0196869 A1 | 8/2012 | Hadida-Ruah et al. | |
| 2013/0109667 A1 | 5/2013 | Markworth | |
| 2013/0109696 A1 | 5/2013 | Greener | |
| 2013/0109701 A1 | 5/2013 | Brown | |
| 2013/0109708 A1 | 5/2013 | Brown | |
| 2013/0150339 A1 | 6/2013 | Boezio et al. | |
| 2013/0324525 A1 | 12/2013 | Abelman et al. | |
| 2013/0338111 A1 | 12/2013 | Beaudoin | |
| 2014/0045862 A1 | 2/2014 | Shinozuka et al. | |
| 2014/0213616 A1 | 7/2014 | Hadida-Ruah et al. | |
| 2014/0296266 A1 | 10/2014 | Hu et al. | |
| 2015/0057271 A1 | 2/2015 | Boezio et al. | |
| 2015/0291514 A1 | 10/2015 | Brown et al. | |

FOREIGN PATENT DOCUMENTS

| | | |
|---|---|---|
| EP | 0179619 B1 | 9/1990 |
| EP | 0516392 A2 | 12/1992 |
| EP | 2184278 | 5/2010 |
| WO | 9008128 | 7/1990 |
| WO | 0039077 | 7/2000 |
| WO | 03059882 | 7/2003 |
| WO | 2004014913 A2 | 2/2004 |
| WO | 2004052869 | 6/2004 |
| WO | 2004092145 | 10/2004 |
| WO | 2005013914 | 2/2005 |
| WO | 2005032488 A2 | 4/2005 |
| WO | 2006015158 A1 | 2/2006 |
| WO | 2006020830 | 2/2006 |
| WO | 2006039212 A2 | 4/2006 |
| WO | 2006121097 | 11/2006 |
| WO | 2006122800 | 11/2006 |
| WO | 2007030582 | 3/2007 |
| WO | 2007045572 | 4/2007 |
| WO | 2007062078 | 5/2007 |
| WO | 2007067994 A1 | 6/2007 |
| WO | 2007120647 A2 | 10/2007 |
| WO | 2008094602 A2 | 8/2008 |
| WO | 2008097991 A1 | 8/2008 |
| WO | 2008118758 | 10/2008 |
| WO | 2009010784 | 1/2009 |
| WO | 2009012242 | 1/2009 |
| WO | 2009157399 | 12/2009 |
| WO | 2010022055 | 2/2010 |
| WO | WO2010079443 * | 7/2010 |
| WO | 2011014462 | 2/2011 |
| WO | 2011016234 A1 | 2/2011 |
| WO | 2011037192 | 3/2011 |
| WO | 2011059042 | 5/2011 |
| WO | 2011063001 | 5/2011 |
| WO | 2011088201 A1 | 7/2011 |
| WO | 2011100433 A1 | 8/2011 |
| WO | 2011153588 | 12/2011 |
| WO | 2012004664 | 1/2012 |
| WO | 2012007836 | 1/2012 |
| WO | 2012007861 | 1/2012 |
| WO | 2012007868 | 1/2012 |
| WO | 2012007869 | 1/2012 |
| WO | 2012007877 | 1/2012 |
| WO | 2012007883 | 1/2012 |
| WO | WO 2012/004706 A2 | 1/2012 |
| WO | WO 2012/004714 A2 | 1/2012 |
| WO | WO 2012/004743 A1 | 1/2012 |
| WO | 2012035023 | 3/2012 |
| WO | 2012039657 | 3/2012 |
| WO | 2012085650 | 6/2012 |
| WO | 2012095781 | 7/2012 |
| WO | 2013025883 | 2/2013 |
| WO | 2013056232 | 4/2013 |
| WO | 2013063459 | 5/2013 |
| WO | 2013064983 | 5/2013 |
| WO | 2013064984 | 5/2013 |
| WO | 2013072758 A1 | 5/2013 |
| WO | 2013086229 | 6/2013 |
| WO | 2013088315 | 6/2013 |
| WO | 2013102826 | 7/2013 |
| WO | 2013118805 A1 | 8/2013 |
| WO | 2013118854 | 8/2013 |
| WO | 2013122897 | 8/2013 |
| WO | 2013134518 | 9/2013 |
| WO | 2013146969 | 10/2013 |
| WO | 2013177224 | 11/2013 |
| WO | 2014008458 | 1/2014 |
| WO | 2014014050 | 1/2014 |
| WO | 2014066490 | 5/2014 |
| WO | 2014066491 | 5/2014 |
| WO | 2014096941 | 6/2014 |
| WO | 2014144545 | 9/2014 |
| WO | 2014151472 | 9/2014 |
| WO | 2014153037 | 9/2014 |
| WO | 2015051043 | 4/2015 |
| WO | 2015078374 | 6/2015 |

OTHER PUBLICATIONS

Zuliani et al. "Sodium channel blockers . . . " Expert Opin. Ther. Patents 25(3) 279-290 (2015).*

Amaya et al., "The voltage-gated sodium channel Na(v)1.9 is an effector of peripheral inflammatory pain hypersensitivity", *J. Neurosci* 26 (50), 12852-12860 (2006).

Black et al., "Changes in the expression of tetrodotoxin-sensitive sodium channels within dorsal root ganglia neurons in inflammatory pain", *Pain* 108 (3), 237-247 (2004).

Blair et al., "Roles of tetrodotoxin (TTX)-sensitive Na+ current, TTX-resistant Na+ current, and Ca2+ current in the action potentials of nociceptive sensory neurons", *J. Neurosci* 22, 10277-10290 (2002).

Caldwell et al., "Sodium channel Na(v)1.6 is localized at nodes of ranvier, dendrites, and synapses", *Proc. Natl. Acad. Sci.* 97(10), 5616-5620 (2000).

Catterall, "From ionic currents to molecular mechanisms: the structure and function of voltage-gated sodium channels", *Neuron* 26 (1), 13-25 (2000).

Catterall, "Structural biology: A 3D view of sodium channels", *Nature*, vol. 409, 988-990 (2001).

Cestele et al., "Molecular mechanisms of neurotoxin action on voltage-gated sodium channels", *Biochimie* vol. 82 (9-10), 883-892 (2000).

Cox et al., "An SCN9A channelopathy causes congenital inability to experience pain", *Nature* 444, 894-898 (2006).

Devor et al., "Na+ Channel Immunolocalization in Peripheral Mammalian Axons and Changes following Nerve Injury and Neuroma Formation", *J. Neurosci.* 13 (5), 1976-1992 (1993).

Dib-Hajj et al., "NaN, a novel voltage-gated Na channel, is expressed preferentially in peripheral sensory neurons and down-regulated after axotomy", *Proc. Natl. Acad. Sci.* 95 (15), 8963-8968 (1998).

Dong et al., "Small interfering RNA-mediated selective knockdown of Na(V)1.8 tetrodotoxin-resistant sodium channel reverses mechanical allodynia in neuropathic rats", *Neuroscience* 146, 812-821 (2007).

England et al., "Isoform-selective voltage-gated Na(+) channel modulators as next-generation analgesics", *Future Med Chem* 2 (5), 775-790 (2010).

Estacion et al., "A sodium channel gene SCN9A polymorphism that increases nociceptor excitability", *Ann Neurol* 66 (6), 862-866 (2009).

Goldberg et al., "Loss-of-function mutations in the Nav1.7 gene underlie congenital indifference to pain in multiple human populations", *Clin. Genet.* 71, 311-319 (2007).

Goldin et al., "Nomenclature of Voltage-Gated Sodium Channels", *Neuron* vol. 28, 365-368 (2000).

Gould et al., "Development of inflammatory hypersensitivity and augmentation of sodium channels in rat dorsal root ganglia", *Brain Res.* 824 (2), 296-299 (1999).

(56) References Cited

OTHER PUBLICATIONS

Hains et al., "Upregulation of sodium channel Nav1.3 and functional involvement in neuronal hyperexcitability associated with central neuropathic pain after spinal cord injury", *J. Neurosci.* 23 (26), 8881-8892 (2003).
Klugbauer et al., "Structure and functional expression of a new member of the tetrodotoxin-sensitive voltage-activated sodium channel family from human neuroendocrine cells", *EMBO J.* 14 (6), 1084-1090 (1995).
Lai et al., "Inhibition of neuropathic pain by decreased expression of the tetrodotoxin-resistant sodium channel, NaV1.8", *Pain* 95 (1-2), 143-152 (2002).
Liu et al., "Mutations in cardiac sodium channels: clinical implications", *Am. J. Pharmacogenomics* 3(3), 173-179 (2003).
Meisler et al., "Sodium channel gene family: epilepsy mutations, gene interactions and modifier effects", *The Journal of Physiology* 588.11, 1841-1848 (2010).
Patent Cooperation Treaty, International Searching Authority, Search Report and Written Opinion for PCT/IB2012/056031, 13 pages, dated Feb. 14, 2013.
Priest et al., "Contribution of the tetrodotoxin-resistant voltage-gated sodium channel NaV1.9 to sensory transmission and nociceptive behavior", *Proc Natl Acad Sci* 102 (26), 9382-9387 (2005).
Raymond et al., "Expression of alternatively spliced sodium channel alpha-subunit genes. Unique splicing patterns are observed in dorsal root ganglia", *J. Biol. Chem.* 279(44), 46234-46241 (2004).
Reimann et al., "Pain perception is altered by a nucleotide polymorphism in SCN9A", *Proc. Natl. Acad. Sci.* 107, 5148-5153 (2010).
Rugiero et al., "Selective Expression of a Persistent Tetrodotoxin-Resistant Na$^+$ Current and Na$_v$1.9 Subunit in Myenteric Sensory Neurons", *J. Neurosci* 23 (7), 2715-2725 (2003).
Sangameswaran et al., "A novel tetrodotoxin-sensitive, voltage-gated sodium channel expressed in rat and human dorsal root ganglia", *J. Biol. Chem.* 272(23),14805-14809 (1997).
Sato et al., "The voltage-sensitive sodium channel is a bell-shaped molecule with several cavities", *Nature* 409, 1047-1051 (2001).
Tamaoka, "Paramyotonia congenita and skeletal sodium channelopathy", *Intern. Med.* 42 (9), 769-770 (2003).
Termin et al., "Recent Advances in Voltage-Gated Sodium Channel Blockers: Therapeutic Potential as Drug Targets in the CNS", *Annual Reports in Medicinal Chemistry* 43, 43-60 (2008).
Toledo-Aral et al., "Identification of PN1, a predominant voltage-dependent sodium channel expressed principally in peripheral neurons", *Proc. Natl. Acad. Sci.* 94(4), 1527-1532 (1997).
Wallace et al., "Efficacy of oral mexiletine for neuropathic pain with allodynia: a double-blind, placebo-controlled, crossover study", *Reg. Anesth. Pain Med.* 25 (5), 459-467 (2000).
Wood et al., "Voltage-gated sodium channels and pain pathways", *J. Neurobiol.* 61(1), 55-71 (2004).
Yang et al., "Mutations in SCN9A, encoding a sodium channel alpha subunit, in patients with primary erythermalgia", *J. Med. Genet.* 41 (3), 171-174 (2004).
Yu et al., "Sodium Channel β4, a New Disulfide-Linked Auxiliary Subunit with Similarity to β2", *J. Neurosci.* 23(20), 7577-7585 (2003).
Yu et al., "The VGL-chanome: a protein superfamily specialized for electrical signaling and ionic homeostasis", *Sci. STKE* 253, re15, 17 pages (2004).
Yu et al., "Reduced sodium current in GABAergic interneurons in a mouse model of severe myoclonic epilepsy in infancy", *Nat. Neurosci* 9, 1142-1149 (2006).
Arcangeli et al., "Targeting Ion Channels in Cancer: A Novel Frontier in Antineoplastic Therapy", *Current Medicinal Chemistry* 16, 66-93 (2009).
Bach et al., "A novel series of piperazinyl-pyridine ureas as antagonists of the purinergic P2T12 receptor", *Bioorganic & Medicinal Chemistry Letters* 21, 2877-2881 (2011).

Banks et al., "The Reaction of N-Alkylhydroxamic Acids with Sulphinyl Chlorides", *J. Chem. Soc. Perkin Trans.* II, 1211-1216 (1986).
Bean et al., "Lidocaine Block of Cardiac Sodium Channels", *J. Gen. Physiol.* 81, 613-642 (1983).
Binder et al., "Disease Mechanisms in Neuropathic Itch", *Nature Clinical Practice Neurology* 4(6), 329-337 (2008).
Brackenbury and Djamgoz, "Activity-dependent regulation of voltage-gated Na+ channel expression in Mat-LyLu rat prostate cancer cell line", *J. Physiol* 573.2, 343-356 (2006).
CAS Registry Nos. 1027529-26-5, 1027209-51-3 and 1026292-79-4, 1 page (2015).
Catterall, "Molecular mechanisms of gating and drug block of sodium channels", *Novartis Foundation Symposium* 241, 206-225 (2002).
Chan et al., "Rh(II)-Catalyzed Intermolecular Oxidative Sulfamidation of Aldehydes: A Mild Efficient Synthesis of N-Sulfonylcarboxamides", *J. Am. Chem. Soc.*, 129, 14106-14107 (2007).
Chioni et al., "A novel adhesion molecule in human breast cancer cell lines: Voltage-gated Na+ channel β1 subunit", Int'l *J. Biochem. Cell Biol.* 41, 1216-1227 (2009).
Chung and Chung, "Sodium channels and neuropathic pain", *Novartis Foundation Symposium* 261, 19-31 (2004).
Clare et al., "Voltage-gated sodium channels as therapeutic targets" *Drug Discovery Today* 5(11), 506-520 (2000).
Daeniker et al., "234. Uber bicyclische Sulfonamide", *Helvetica Chimica ACTA*, vol. 45 (6), 1972-1981 (1962).
Database Reaxys, XP002692384, Accession No. XRN: 6729065, 6731122, 1 page, (D. Bertoia et al., "Base promoted ring-opening reactions of 2-p-tolyl-5,6-dihydro-1, 4,3-oxathizaine 4,4-dioxides", *Gazetta Chimica Italiana*, vol. 118 (6), 435-440 (1988).
Dib-Hajj et al., "Genetics and Molecular Pathophysiology of NaV1.7-related Pain Syndromes", *Advances in Genetics* 63, 85-110 (2008).
Dickore, "Synthese and reaktionen von 1.3.4-oxathiazolin-3-dioxyden", *Justus Liebigs Annalen Der Chemie*, vol. 671, 135-146, XP055053742, Compounds IVa, IVb, IVd, V, VI (1964).
Diss et al. "Expression profiles of voltage-gated sodium channel α-subunit genes in rat and human prostate cancer cell lines", *The Prostate* 48, 165-178 (2001).
Diss et al. "A potential novel marker for human prostate cancer: voltage-gated sodium channel expression in vivo", *Prostate Cancer and Prostatic Diseases* 8, 266-273 (2005).
Diss et al. "Identification and characterization of the promoter region of the NaV1.7 voltage-gated sodium channel gene (SCN9A)", *Mol. Cell. Neurosci.* 37, 537-547 (2008).
Fishman et al. "Intravenous lidocaine for treatment-resistant pruritus", *American J. of Medicine* 102, 584-585 (1997).
Fraser et al., "Voltage-gated sodium channel expression and potentiation of human breast cancer metastasis", *Clin. Cancer Res.* 11(15), 5381-5389 (2005).
Hayes et al., "Na(V)1.7 Paint Control: A Novel Target", *Neurosurgery* 73, N16 (2013).
Ikoma et al., "Neuronal sensitization for histamine-induced itch in lesional skin of patients with atopic dermatitis", *Arch. Dermatol.* 139, 1445-1458 (2003).
Ikoma et al., "The neurobiology of itch", *Nature Reviews Neuroscience* 7, 535-547 (2006).
Kis-Toth et al., "Voltage-gated sodium channel NaV1.7 maintains the membrane potential and regulates the activation and chemokine-induced migration of a monocyte-derived dendritic cell subset", *J. Immunology* 187, 1273-1280 (2011).
Kutt et al., "A Comprehensive Self-Consistent Spectrophotometric Acidity Scale of Neutral Bronsted Acids in Acetonitrile", *J. Org. Chem.* 71, 2829-2838 (2006).
Lai et al., "The role of voltage-gated sodium channels in neuropathic pain", *Current Opinion in Neurobiology* 13, 291-297 (2003).
Mao et al., "Systemic lidocaine for neuropathic pain relief", *Pain* 87, 7-17 (2000).

(56) References Cited

OTHER PUBLICATIONS

Massah et al., "Synthesis, in vitro antibacterial and carbonic anyydrase II inhibitory activities of N-acylsulfonamides using silica sulfuric acid as an efficient catalyst under both solvent-free and heterogeneous conditions", Bioorganic & Medicinal Chemistry 16, 5465-5472 (2008).
Oaklander et al., "Intractable post-herpetic itch and cutaneous deafferentation after facial singles", Pain 96, 9-12 (2002).
Priest, "Future potential and status of selective sodium channel blockers for the treatment of pain", Current Opinion in Drug Discovery and Development, 12(5), 682-692 (2009).
PubChem, Compound Summary for CID 14280666, N-(1,2-benzoxazol-3-yl) methanesulfonamide, https://pubchem.ncbi.nim.nih.gov/summary/summary.cgi?cid=14280666, 3 pages (2007).
Patent Cooperation Treaty, International Searching Authority, Search Report and Written Opinion for PCT/IB2012/001324, 24 pages, May 21, 2013.
Roberts et al., "Novel Aryl and Heteroaryl Acyl Sulfamide Synthesis via Microwave-Assisted Palladium-Catalyzed Carbonylation", Organic Letters, vol. 12 (6), 1264-1267 (2010).
Roberts et al., "Molybdenum-Mediated Carbonylaiton of Aryl Halides with Nucleophiles Using Microwave Irradiation", Organic Letters, vol. 12 (19), 4280-4283 (2010).
Ruan et al., "Sodium channel mutations and arrhythmias", Nature Reviews Cardiology, 6, 337-348 (2009).
Schmelz, "Itch and pain", Neuroscience and Biobehaviorial Reviews, 34, 171-176 (2010).
Silos-Santiago, "Drugs in Clinical Development for Neuropathic Pain", presented at First World Conference Abdominal and Pelvic Pain, Amsterdam, pp. 1-23 (Jun. 6, 2013).
Smith et al., "Sodium channel protein expression enhances the invasiveness of rat and human prostate cancer cells", FEBS Letters, 423, 19-24 (1998).
Tanelian and Brose, "Neuropathic pain can be relieved by drugs that are use-dependent sodium channel blockers: lidocaine, carbamazepine and mexiletine", Anesthesiology, 74(5), 949-951 (1991).
Villamil et al., "Efficacy of lidocaine in the treatment of pruritus in patients with chronic chlolestatic liver disease", Am. J. Med, 118, 1160-1163 (2005).
Xiao and Bennett, "C-fiber spontaneous discharge evoked by chronic inflammation is suppressed by a long-term infusion of lidocaine yielding nanogram per milliliter plasma levels", Pain, 137, 218-228 (2008).
Zhao et al., "Voltage-gated sodium channel expression in rat and human epidermal keratinocytes: evidence for a role in pain", Pain, 139, 90-105 (2008).
Chemical Abstracts_1, XP002744143, Database accession No. 1321299-48-2 Abstract (Aug. 22, 2011).
Chemical Abstracts_2, XP002744144, Database accession No. 1320435-32-2 Abstract (Aug. 22, 2011).
Chemical Abstracts_3, XP002744145, Database accession No. 1319619-74-3 Abstract (Aug. 18, 2011).
Chemical Abstracts_4, XP002744146, Database accession No. 1294599-14-6 Abstract (May 15, 2011).
Chemical Abstracts_5, XP002744147, Database accession No. 1051238-85-7 Abstract (Sep. 21, 2008).
Chemical Abstracts_6, XP002744148, Database accession No. 1051172-94-1 Abstract (Sep. 21, 2008).
Chemical Abstracts_7, XP002744149, Database accession No. 1301192-24-4 (May 26, 2011).
Chemical Abstracts_8, XP002744150, Database accession No. 1299653-84-3 Abstract (May 24, 2011).
Chemical Abstracts_9, XP002744151, Database accession No. 299214-10-0 (May 24, 2011).
Chemical Abstracts_10, XP002744152, Database accession No. 1288553-28-5 Abstract (May 1, 2011).
Chemical Abstracts_11, XP002744153, Database accession No. 1278399-39-5 Abstract (Apr. 11, 2011).
Chemical Abstracts_12, XP002744154, Database accession No. 1297052-59-5 Abstract (May 19, 2011).
Chemical Abstracts_13, XP002744155, Database accession No. 1277490-84-2 Abstract (Apr. 10, 2011).
Daeniker et al., "234. Uber bicyclische Sulfonamide", Helvetica Chimica ACTA, vol. 45 (6), 1972-1981 (1962). [English Translation.].
Dickore, "Synthese and reaktionen von 1.3.4-oxathiazolin-3-dioxyden", Justus Liebigs Annalen Der Chemie, vol. 671, 135-146, XP055053742, Compounds IVa, IVb, IVd, V, VI (1964). [English Translation.].
Ikuma et al., "Preparation of 3-substituted proline derivatives as FXIa inhibitors", CA159:371450 (2013).
Leeman et al., "Preparation of 4-benzimidazolylmethoxy-3-halophenylmethoxybenzoates and analogs as tRNA synthetase inhibitors", CA133:35021 (2000).
Li et al., "Recent advances in the structure-activity relationship study of small-molecule sodium channel blockers with analgesic effects", Acta Pharmaceutica Sinica, vol. 44, (2), 101-108 (2009). [English Translation.].
Morinville et al., "Distribution of the voltage-gated sodium channel NaV1.7 in the rat: expression in the autonomic and endocrine systems" J. Comparative Neurology 504, 680-689 (2007).
Patani et al., "Bioisosterism: A Rational Approach in Drug Design", Chem Rev 96, 3147-3176 (1996).
Zuliani et al., "Sodium channel blockers for neuropathic pain", Expert Opinion on Therapeutic Patents, vol. 20, No. 6, 755-779 (2010).
Chemical Abstract Service, STN Registry Database No. 891026-77-0 [entered STN: Jul. 9, 2006].
Chemical Abstract Service, STN Registry Database No. 892698-09-8 [entered STN: Jul. 14, 2006].
Deng, et al., "Dynamic 1-15 Receptor-Based Pharmacophore Model Development and Its Application in Designing Novel HIV-1 Integrase Inhibitors", Journal of Medicinal Chemistry. vol. 48. No. 5, 1496-1505 (2005), Supporting Information, S1-S14. XP055285519. DOI: 10.1021jjm049410e (2005).
Kuo, et al., "Application of CoMFA and CoMSIA 3D-QSAR and Docking Studies in Optimization of Mercaptobenzenesulfonamides as HIV-1 Integrase Inhibitors", Journal of Medicinal Chemistry. American Chemical Society. US. vol. 47. No. 2, 385-399 (2003).
File Caplus, Registry No. 1333872-40-4, entered STN: Sep. 29, 2011.
Lamoureux, et al., "Use of the adamantane structure in medicinal chemistry", Curr Med Chem 17(26), 2967-2978 (2010).

\* cited by examiner

BENZENESULFONAMIDE COMPOUNDS AND THEIR USE AS THERAPEUTIC AGENTS

RELATED APPLICATIONS

This application is a 371 National Stage Application of International Application Number PCT/IB2012/056031, filed 30 Oct. 2012, which claims priority to U.S. Provisional Application No. 61/553,616 filed on 31 Oct. 2011. The entire content of International Application No. PCT/IB2012/056031 is incorporated by reference herein.

FIELD OF THE INVENTION

The present invention is directed to benzenesulfonamide compounds and pharmaceutical compositions comprising the compounds and methods of using the compounds and the pharmaceutical compositions in treating sodium channel-mediated diseases or conditions, such as pain, as well as other diseases and conditions associated with the mediation of sodium channels.

BACKGROUND OF THE INVENTION

Voltage-gated sodium channels, transmembrane proteins that initiate action potentials in nerve, muscle and other electrically excitable cells, are a necessary component of normal sensation, emotions, thoughts and movements (Catterall, W. A., Nature (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., Neuron (2000), Vol. 28, pp. 365-368). Electrophysiological recording, biochemical purification, and molecular cloning have identified ten different sodium channel alpha subunits and four beta subunits (Yu, F. H., et al., Sci. STKE (2004), 253; and Yu, F. H., et al., Neurosci. (2003), 20:7577-85).

The hallmarks of sodium channels include rapid activation and inactivation when the voltage across the plasma membrane of an excitable cell is depolarized (voltage-dependent gating), and efficient and selective conduction of sodium ions through conducting pores intrinsic to the structure of the protein (Sato, C., et al., Nature (2001), 409:1047-1051). At negative or hyperpolarized membrane potentials, sodium channels are closed. Following membrane depolarization, sodium channels open rapidly and then inactivate. Channels only conduct currents in the open state and, once inactivated, have to return to the resting state, favoured by membrane hyperpolarization, before they can reopen. Different sodium channel subtypes vary in the voltage range over which they activate and inactivate as well as their activation and inactivation kinetics.

The sodium channel family of proteins has been extensively studied and shown to be involved in a number of vital body functions. Research in this area has identified variants of the alpha subunits that result in major changes in channel function and activities, which can ultimately lead to major pathophysiological conditions. The members of this family of proteins are denoted $Na_v1.x$, where x=1 to 9. $Na_v1.1$ and $Na_v1.2$ are highly expressed in the brain (Raymond, C. K., et al., J. Biol. Chem. (2004), 279(44):46234-41) and are vital to normal brain function. Some loss of function mutations in $Na_v1.1$ in humans result in epilepsy, apparently because many of these channels are expressed in inhibitory neurons (Yu, F. H., et al., Nat Neurosci (2006), 9 (9), 1142-9). Thus, block of $Na_v1.1$ in the CNS may be counter-productive because it can produce hyperexcitability. However, $Na_v1.1$ is also expressed in the peripheral nervous system and block may afford analgesic activity.

$Na_v1.3$ is expressed primarily in the fetal central nervous system. It is expressed at very low levels or not at all in the peripheral nervous system, but expression is upregulated in the dorsal horn sensory neurons of rats after nervous system injury (Hains, B. D., et al., J. Neurosci. (2003), 23(26):8881-92). Thus, it is an inducible target for treatment of pain following nerve injury.

$Na_v1.4$ is expressed primarily in skeletal muscle (Raymond, C. K., et al., op. cit.). Mutations in this gene have been shown to have profound effects on muscle function including paralysis, (Tamaoka A., Intern. Med. (2003), (9): 769-70).

$Na_v1.5$, is expressed mainly in cardiac myocytes (Raymond, C. K., et al., op. cit.), including atria, ventricles, the sin θ-atrial node, atrio-ventricular node and cardiac Purkinje fibers. The rapid upstroke of the cardiac action potential and the rapid impulse conduction through cardiac tissue is due to the opening of $Na_v1.5$. Abnormalities in the function of $Na_v1.5$ can result in the genesis of a variety of cardiac arrhythmias. Mutations in human $Na_v1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H., et al., Am. J. Pharmacogenomics (2003), 3(3):173-9). Sodium channel blocker therapy has been used extensively in treating cardiac arrhythmias.

$Na_v1.6$ is a widely distributed voltage-gated sodium channel found throughout the central and peripheral nervous systems. It is expressed at high density in the nodes of Ranvier of myelinated neurons (Caldwell, J. H., et al., Proc. Natl. Acad. Sci. USA (2000), 97(10): 5616-20).

$Na_v1.7$ is a tetrodotoxin-sensitive voltage-gated sodium channel encoded by the gene SCN9A. Human $Na_v1.7$ was first cloned from neuroendocrine cells (Klugbauer, N., et al., 1995 EMBO J., 14 (6): 1084-90.) and rat $Na_v1.7$ was cloned from a pheochromocytoma PC12 cell line (Toledo-Aral, J. J., et al., Proc. Natl.Acad. Sci. USA (1997), 94:1527-1532) and from rat dorsal root ganglia (Sangameswaran, L., et al., (1997), J. Biol. Chem., 272 (23): 14805-9). $Na_v1.7$ is expressed primarily in the peripheral nervous system, especially nociceptors and olfactory neurons and sympathetic neurons. The inhibition, or blocking, of $Na_v1.7$ has been shown to result in analgesic activity. Knockout of $Na_v1.7$ expression in a subset of sensory neurons that are predominantly nociceptive results in resistance to inflammatory pain (Nassar, et al., op. cit.). Likewise, loss of function mutations in humans results in congenital indifference to pain (CIP), in which the individuals are resistant to both inflammatory and neuropathic pain (Cox, J. J., et al., Nature (2006); 444:894-898; Goldberg, Y. P., et al., Clin. Genet. (2007); 71:311-319). Conversely, gain of function mutations in $Na_v1.7$ have been established in two human heritable pain conditions, primary erythromelalgia and familial rectal pain, (Yang, Y., et al., J. Med. Genet. (2004), 41(3):171-4). In addition, a single nucleotide polymorphism (R1150W) that has very subtle effects on the time- and voltage-dependence of channel gating has large effects on pain perception (Estacion, M., et al., 2009. Ann Neurol 66: 862-6; Reimann, F., et al., Proc Natl Acad Sci USA (2010), 107: 5148-53). About 10% of the patients with a variety of pain conditions have the allele conferring greater sensitivity to pain and thus might be more likely to respond to block of $Na_v1.7$. Because $Na_v1.7$ is expressed in both sensory and sympathetic neurons, one might expect that enhanced pain perception would be accompanied by cardiovascular abnormalities such as hypertension, but no correlation has been reported. Thus, both the CIP mutations and SNP analysis suggest that human pain responses are more sensitive to changes in $Na_v1.7$ currents than are perturbations of autonomic function.

$Na_v1.8$ is expressed primarily in sensory ganglia of the peripheral nervous system, such as the dorsal root ganglia (Raymond, C. K., et al., op. cit.). There are no identified human mutations for $Na_v1.8$ that produce altered pain responses. $Na_v1.8$ differs from most neuronal $Na_v$'s in that it is insensitive to block by tetrodotoxin. Thus, one can isolate the current carried by this channel with tetrodotoxin. These studies have shown that a substantial portion of total sodium current is $Na_v1.8$ in some dorsal root ganglion neurons (Blair, N. T., et al., *J Neurosci* (2002), 22: 10277-90). Knock-down of $Na_v1.8$ in rats has been achieved by using antisense DNA or small interfering RNAs and virtually complete reversal of neuropathic pain was achieved in the spinal nerve ligation and chronic constriction injury models (Dong, X. W., et al., *Neuroscience* (2007), 146: 812-21; Lai J., et al. *Pain* (2002), 95: 143-52). Thus, $Na_v1.8$ is considered a promising target for analgesic agents based upon the limited tissue distribution of this $Na_v$ isoform and the analgesic activity produced by knock-down of channel expression.

$Na_v1.9$ is also a tetrodotoxin insensitive, sodium channel expressed primarily in dorsal root ganglia neurons (Dib-Hajj, S. D., et al. (see Dib-Hajj, S. D., et al., *Proc. Natl. Acad. Sci. USA* (1998), 95(15):8963-8). It is also expressed in enteric neurons, especially the myenteric plexus (Rugiero, F., et al., *J Neurosci* (2003), 23: 2715-25). The limited tissue distribution of this $Na_v$ isoform suggests that it may be a useful target for analgesic agents (Lai, J., et al., op. cit.; Wood, J. N., et al., op. cit.; Chung, J. M., et al., op. cit.). Knock-out of $Na_v1.9$ results in resistance to some forms of inflammatory pain (Amaya, F., et al., *J Neurosci* (2006), 26: 12852-60; Priest, B. T., et al., *Proc Natl Acad Sci USA* (2005), 102: 9382-7).

This closely related family of proteins has long been recognized as targets for therapeutic intervention. Sodium channels are targeted by a diverse array of pharmacological agents. These include neurotoxins, antiarrhythmics, anticonvulsants and local anesthetics (England, S., et al., *Future Med Chem* (2010), 2: 775-90; Termin, A., et al., *Annual Reports in Medicinal Chemistry* (2008), 43: 43-60). All of the current pharmacological agents that act on sodium channels have receptor sites on the alpha subunits. At least six distinct receptor sites for neurotoxins and one receptor site for local anesthetics and related drugs have been identified (Cestele, S., et al., Biochimie (2000), Vol. 82, pp. 883-892).

The small molecule sodium channel blockers or the local anesthetics and related antiepileptic and antiarrhythmic drugs interact with overlapping receptor sites located in the inner cavity of the pore of the sodium channel (Catterall, W. A., Neuron (2000), 26:13-25). Amino acid residues in the S6 segments from at least three of the four domains contribute to this complex drug receptor site, with the IVS6 segment playing the dominant role. These regions are highly conserved and as such most sodium channel blockers known to date interact with similar potency with all channel subtypes. Nevertheless, it has been possible to produce sodium channel blockers with therapeutic selectivity and a sufficient therapeutic window for the treatment of epilepsy (e.g., lamotrignine, phenyloin and carbamazepine) and certain cardiac arrhythmias (e.g., lignocaine, tocamide and mexiletine). However, the potency and therapeutic index of these blockers is not optimal and have limited the usefulness of these compounds in a variety of therapeutic areas where a sodium channel blocker would be ideally suited.

Sodium channel blockers have been shown to be useful in the treatment of pain, including acute, chronic, inflammatory and/or neuropathic pain (see, e.g., Wood, J. N., et al., *J. Neurobiol*. (2004), 61(1), 55-71. Preclinical evidence demonstrates that sodium channel blockers can suppress neuronal firing in peripheral and central sensory neurons, and it is via this mechanism that they are considered to be useful for relieving pain. In some instances, abnormal or ectopic firing can original from injured or otherwise sensitized neurons. For example, it has been shown that sodium channels can accumulate in peripheral nerves at sites of axonal injury and may function as generators of ectopic firing (Devor et al., *J. Neurosci*. (1993), 132: 1976). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., *Brain Res*., (1999), 824(2): 296-99; Black et al., *Pain* (2004), 108(3): 237-47). Alterations in either the level of expression or distribution of sodium channels, therefore, may have a major influence on neuronal excitability and pain-related behaviors.

Controlled infusions of lidocaine, a known sodium channel blocker, indicate that the drug is efficacious against neuropathic pain, but has a narrow therapeutic index. Likewise, the orally available local anesthetic, mexiletine, has dose-limiting side effects (Wallace, M. S., et al., *Reg. Anesth. Pain Med*. (2000), 25: 459-67). A major focus of drug discovery targeting voltage-gated sodium channels has been on strategies for improving the therapeutic index. One of the leading strategies is to identify selective sodium channel blockers designed to preferentially block $Na_v1.7$, $Na_v1.8$, $Na_v1.9$ and/or $Na_v1.3$. These are the sodium channel isoforms preferentially expressed in sensory neurons and unlikely to be involved in generating any dose-limiting side effects. For example, there is concern that blocking of $Na_v1.5$ would be arrhythmogenic, so that selectivity of a sodium channel blocker against $Na_v1.5$ is viewed as highly desirable. Furthermore, nearly 700 mutations of the SCN1A gene that codes for $Na_v1.1$ have been identified in patients with Severe Myoclonic Epilepsy of Infancy (SMEI), making this the most commonly mutated gene in human epilepsy. Half of these mutations result in protein truncation (Meisler, M. H., et al., *The Journal of Physiology* (2010), 588: 1841-8). Thus, selectivity of a sodium channel blocker against $Na_v1.1$ is also desirable.

In addition to the strategies of identifying selective sodium channel blockers, there is the continuing strategy of identifying therapeutic agents for the treatment of neuropathic pain. There has been some degree of success in treating neuropathic pain symptoms by using medications originally approved as anticonvulsants, such as gabapentin, and more recently pregabalin. However, pharmacotherapy for neuropathic pain has generally had limited success for a variety of reasons: sedation, especially by drugs first developed as anticonvulsants or anti-depressants, addiction or tachyphylaxis, especially by opiates, or lack of efficacy, especially by NSAIDs and anti-inflammatory agents. Consequently, there is still a considerable need to explore novel treatment modalities for neuropathic pain, which includes, but is not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

There are a limited number of effective sodium channel blockers for the treatment of pain with a minimum of adverse side effects which are currently in the clinic. There is also an unmet medical need to treat neuropathic pain and other sodium channel associated pathological states effectively and without adverse side effects due to the blocking of sodium channels not involved in nociception. The present invention provides methods to meet these critical needs.

SUMMARY OF THE INVENTION

The present invention is directed to benzensulfonamide compounds and pharmaceutical compositions comprising the compounds and methods of using the compounds and the pharmaceutical compositions of the invention for the treatment of sodium channel-mediated diseases or conditions, such as pain. The present invention is also directed to methods of using the compounds of the invention and pharmaceutical compositions comprising the compounds of the invention for the treatment of other sodium channel-mediated diseases or conditions, including, but not limited to, pruritus and cancer.

Accordingly, in one aspect, this invention is directed to benzenesulfonamide compounds of formula (I):

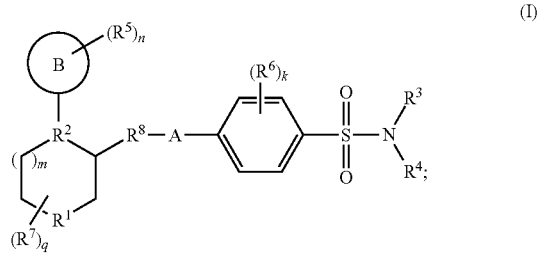

wherein:
k is 0, 1, 2, 3 or 4;
m is 0, 1 or 2;
n is 0, 1, 2, 3, 4 or 5;
q is 0, 1, 2, 3, 4, 5 or 6;
A is —O— or —S—;

is aryl or N-heteroaryl;
$R^1$ is —O—, —C($R^9$)$_2$—, —N($R^{10}$)—, —N($R^{11}$)— or —S(O)$_t$ (where t is 0, 1 or 2);
$R^2$ is C($R^9$) or N;
$R^3$ is hydrogen, alkyl, haloalkyl, optionally substituted aryl or optionally substituted aralkyl;
or $R^3$ is a direct bond to $R^4$;
$R^4$ is H, optionally substituted alkyl, optionally substituted heterocyclyl, optionally substituted heteroaryl, optionally substituted cycloalkyl, haloalkyl, —C(O)$R^{10}$, —C(O)N($R^{10}$)$_2$ or —C(=NCN)N($R^{10}$)$_2$;

or $R^3$ and $R^4$, together with the nitrogen to which they are both attached, form an optionally substituted N-heterocyclyl or optionally substituted N-heteroaryl;
each $R^5$ and each $R^6$ are independently hydrogen, alkyl, halo, haloalkyl, nitro, cyano, —OR$^{10}$, —S(O)$_t$R$^{10}$ (where t is 0, 1 or 2), —C(O)OR$^{10}$, —C(O)R$^{10}$ or —C(O)N(R$^{10}$)$_2$;
each $R^7$ is independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$;
or any two $R^7$'s on the same carbon may form an oxo and the other $R^7$'s are independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$;
or any two $R^7$'s on different carbons may form an optionally substituted straight or branched alkylene chain optionally containing one or more heteroatoms, and the other $R^7$'s, if present, are independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$,
$R^8$ is a direct bond or an optionally substituted straight or branched alkylene chain;
each $R^9$ is independently hydrogen, alkyl, halo, haloalkyl, —OR$^{10}$, —N(R$^{10}$)$_2$, —N(R$^{11}$)$_2$, —S(O)$_t$R$^{10}$ (where t is 0, 1 or 2), —C(O)OR$^{10}$, —C(O)R$^{10}$ or —C(O)N(R$^{10}$)$_2$;
each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and
each $R^{11}$ is independently —C(O)R$^{10}$; —C(O)OR$^{10}$, —C(O)N(R$^{10}$)$_2$, —S(O)$_p$N(R$^{10}$)$_2$ (where p is 1 or 2) or —S(O)$_p$N(R$^{10}$)$_2$ (where p is 1 or 2);
as individual stereoisomers, enantiomers or tautomers thereof or mixtures thereof;
or as pharmaceutically acceptable salts, solvates or prodrugs thereof.

The compounds of the invention, which are compounds of formula (I), as described above, as individual stereoisomers, enantiomers or tautomers thereof or mixtures thereof; or as pharmaceutically acceptable salts, solvates or prodrugs thereof, are voltage-gated sodium channel modulators, preferably voltage-gated sodium channel modulators. Preferably, the compounds of the invention are Na$_v$1.7 inhibitors. More preferably, the compounds of the invention show selectivity of inhibiting Na$_v$1.7 as compared with Na$_v$1.5. Without wishing to be bound by theory, such selectivity is thought to advantageously reduce any cardiovascular side effects which may be associated with the inhibition of Na$_v$1.5.

In another aspect, the invention provides pharmaceutical compositions comprising a pharmaceutically acceptable excipient and a compound of formula (I), as described above, as a stereoisomer, enantiomer or tautomer thereof or mixtures thereof; or a pharmaceutically acceptable salt, solvate or prodrug thereof.

In another aspect, the invention provides methods for the treatment of pain in a mammal, preferably a human, wherein the methods comprise administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the present invention provides a method for treating or lessening the severity of a disease, condition, or disorder in a mammal where activation or hyperactivity of one or more of $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ is implicated in the disease, condition or disorder, wherein the method comprises administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating a range of sodium channel-mediated diseases or conditions in a mammal, for example, pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke, glaucoma or neural trauma, tachy-arrhythmias, atrial fibrillation and ventricular fibrillation, wherein the methods comprise administering to the mammal in need thereof, preferably a human, a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating a range of sodium channel-mediated diseases or conditions in a mammal, preferably a human, by the inhibition of ion flux through a voltage-dependent sodium channel in the mammal, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or ameliorating, but not preventing, pain in a mammal, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating pruritus in a mammal, preferably a human, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating cancer in a mammal, preferably a human, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed in the invention.

In another aspect, this invention is directed to methods of selectively modulating a first voltage-gated sodium channel in a mammal over a second voltage-gated sodium channel, wherein the method comprises administering to the mammal a modulating amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a modulating amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, this invention is directed to the use of the compounds of the invention, as set forth above, as a stereoisomer, enantiomer or tautomer thereof or mixtures thereof, or a pharmaceutically acceptable salt, solvate or prodrug thereof, or the use of a pharmaceutical composition comprising a pharmaceutically acceptable excipient and a compound of the invention, as set forth above, as a stereoisomer, enantiomer or tautomer thereof or mixtures thereof, or a pharmaceutically acceptable salt, solvate or prodrug thereof, in the preparation of a medicament for the treatment of sodium channel-mediated diseases or conditions in a mammal.

In another aspect, this invention is directed to a compound of the invention, as set forth above, as a stereoisomer, enantiomer or tautomer thereof or mixtures thereof; or a pharmaceutically acceptable salt, solvate or prodrug thereof for use in medical therapy.

In another aspect, this invention is directed to a compound of the invention, as set forth above, as a stereoisomer, enantiomer or tautomer thereof or mixtures thereof; or a pharmaceutically acceptable salt, solvate or prodrug thereof for the prophylactic or therapeutic treatment of a disease or a condition in a mammal selected from the group consisting of pain, depression, cardiovascular diseases, respiratory diseases, and psychiatric diseases.

In another aspect, this invention is directed to a compound of the invention, as set forth above, as a stereoisomer, enantiomer or tautomer thereof or mixtures thereof; or a pharmaceutically acceptable salt, solvate or prodrug thereof for the prophylactic or therapeutic treatment of pain by the inhibition of ion flux through a voltage-dependent sodium channel.

In another aspect, this invention is directed to a compound of the invention, as set forth above, as a stereoisomer, enantiomer or tautomer thereof or mixtures thereof; or a pharmaceutically acceptable salt, solvate or prodrug thereof for decreasing ion flux through a voltage-dependent sodium channel in a cell.

In another aspect, this invention is directed to a compound of the invention, as set forth above, as a stereoisomer, enantiomer or tautomer thereof or mixtures thereof; or a pharmaceutically acceptable salt, solvate or prodrug thereof for the prophylactic or therapeutic treatment of pruritus.

In another aspect, this invention is directed to a compound of the invention, as set forth above, as a stereoisomer, enantiomer or tautomer thereof or mixtures thereof; or a pharmaceutically acceptable salt, solvate or prodrug thereof for the prophylactic or therapeutic treatment of cancer.

In another aspect, this invention is directed to a compound of the invention, as set forth above, as a stereoisomer, enantiomer or tautomer thereof or mixtures thereof; or a pharmaceutically acceptable salt, solvate or prodrug thereof for treating or ameliorating, but not preventing, pain.

In another aspect, this invention is directed to a compound of the invention, as set forth above, as a stereoisomer, enantiomer or tautomer thereof or mixtures thereof; or a pharmaceutically acceptable salt, solvate or prodrug thereof for selectively modulating a first voltage-gated sodium channel over a second voltage-gated sodium channel.

DETAILED DESCRIPTION OF THE INVENTION

Definitions

Certain chemical groups named herein may be preceded by a shorthand notation indicating the total number of carbon atoms that are to be found in the indicated chemical group. For example; $C_7$-$C_{12}$ alkyl describes an alkyl group, as defined below, having a total of 7 to 12 carbon atoms, and $C_4$-$C_{12}$ cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, $-OR^{20}$, $-OC(O)-R^{20}$, $-N(R^{20})_2$, $-C(O)R^{20}$, $-C(O)OR^{20}$, $-C(O)N(R^{20})_2$, $-N(R^{20})C(O)OR^{22}$, $-N(R^{20})C(O)R^{22}$, $-N(R^{20})S(O)_pR^{22}$ (where p is 1 to 2), $-S(O)_pOR^{22}$ (where p is 1 to 2), $-S(O)_tR^{22}$ (where t is 0 to 2), and $-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. When specifically stated in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, $-OR^{20}$, $-OC(O)-R^{20}$, $-N(R^{20})_2$, $-C(O)R^{20}$, $-C(O)OR^{20}$, $-C(O)N(R^{20})_2$, $-N(R^{20})C(O)OR^{22}$, $-N(R^{20})C(O)R^{22}$, $-N(R^{20})S(O)_pR^{22}$ (where p is 1 to 2), $-S(O)_pOR^{22}$ (where p is 1 to 2), $-S(O)_tR^{22}$ (where t is 0 to 2), and $-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O) N($R^{20}$)$_2$, —$R^{21}$—N($R^{20}$)C(O)$OR^{22}$, —$R^{21}$—N($R^{20}$)C(O) $R^{22}$, —$R^{21}$—N($R^{20}$)S(O)$_p R^{22}$ (where p is 1 to 2), —$R^{21}$— N=C($OR^{20}$)$R^{20}$, S(O)$_p OR^{22}$ (where p is 1 to 2), —$R^{21}$— S(O)$_t R^{22}$ (where t is 0 to 2), and —$R^{21}$—S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. When specifically stated in the specification, the alkylene chain part of the aralkyl radical may be optionally substituted as described above for an optionally substituted alkylene chain. When specifically stated in the specification, the aryl part of the aralkyl radical may be optionally substituted as described above for an optionally substituted aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O) N($R^{20}$)$_2$, —$R^{21}$—N$R^{20}$)C(O)$OR^{22}$, —$R^{21}$—N($R^{20}$)C(O) $R^{22}$, —$R^{21}$—N($R^{20}$)S(O)$_p R^{22}$ (where p is 1 to 2), —$R^{21}$— N=C($OR^{20}$)$R^{20}$, —$R^{21}$—S(O)$_p OR^{22}$ (where p is 1 to 2), —$R^{21}$—S(O)$_t R^{22}$ (where t is 0 to 2), and —$R^{21}$—S(O)$_p$N ($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_b R_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quatern/zed; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —C(O)$OR^{20}$, —$R^{21}$— C(O)N($R^{20}$)$_2$, —$R^{21}$—N($R^{20}$)C(O)$OR^{22}$, —$R^{21}$—N($R^{20}$)C (O)$R^{22}$, —$R^{21}$—N($R^{20}$)S(O)$_p R^{22}$ (where p is 1 to 2), —$R^{21}$—N=C($OR^{20}$)$R^{20}$, $R^{21}$—S(O)$_p OR^{22}$ (where p is 1 to 2), —$R^{21}$—S(O)$_t R^{22}$ (where t is 0 to 2), and —$R^{21}$ —S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen. The point of attachment of the N-heterocyclyl to the rest of the molecule can be through a nitrogen atom or a carbon atom in the N-heterocyclyl. When specifically stated in the specification, an N-heterocyclyl radical may be optionally substituted as described above for an optionally substituted heterocyclyl radical.

"Heterocyclylalkyl" refers to a radical of the formula —$R_b R_h$ where $R_b$ is an alkylene chain as defined above and Rh is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkyene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quatem/zed. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-c]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —R$^{21}$—OR$^{20}$, —R$^{21}$—OC(O)—R$^{20}$, —R$^{21}$—N(R$^{20}$)$_2$, —R$^{21}$—C(O)R$^{20}$, C(O)OR$^{20}$, —R$^{21}$—C(O)N(R$^{20}$)$_2$, —R$^{21}$—N(R$^{20}$)C(O)OR$^{22}$, —R$^{21}$—N(R$^{20}$)C(O)R$^{22}$, —R$^{21}$—N(R$^{20}$)S(O)$_p$R$^{22}$ (where p is 1 to 2), —R$^{21}$—N═C(OR$^{20}$)R$^{20}$, —R$^{21}$, —S(O)$_p$OR$^{22}$ (where p is 1 to 2), —R$^{21}$—S(O)$_t$R$^{22}$ (where t is 0 to 2), and —R$^{21}$—S(O)$_p$N(R$^{20}$)$_2$ (where p is 1 to 2) where each R$^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{21}$ is independently a direct bond or a straight or branched alkylene chain; and each R$^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —R$_b$R$_i$ where R$_b$ is an alkylene chain as defined above and R$_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildelife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, triethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a sodium channel-mediated disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, i.e., relieving pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure*, 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

The chemical naming protocol and structure diagrams used herein are a modified form of the I.U.P.A.C. nomenclature system, using ChemBioDraw Ultra Version 12.0 software program, wherein the compounds of the invention are named herein as derivatives of a central core structure, e.g., the benzenesulfonamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

The compounds of formula (I) contain the

ring and the $R^8$ group disposed in a 1,2 arrangement on the ring containing the $R^1$ and $R^2$ group. Accordingly, the

ring and the $R^8$ group are disposed in either a trans relationship relative to one another or a cis relationship relative to one another and the plane of the ring containing the $R^1$ and $R^2$ group.

Following the standard chemical literature description practice and as used in this specification, a solid full bond, as illustrated below in Structure (A) and a dashed full bond, as illustrated below in Structure (A), means that the substituents, in this case the

ring and the $R^8$ group, are in a relative trans-configuration with respect to the plane of the ring containing the $R^1$ and $R^2$ group.

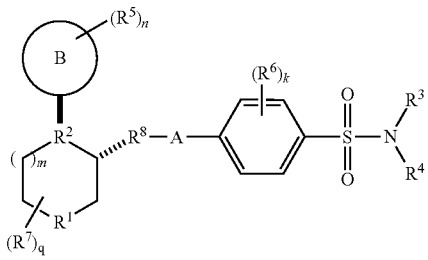

Structure (A)

It is understood that Structure (A) is meant to include a racemic or non-racemic mixture of the following two enantiomers:

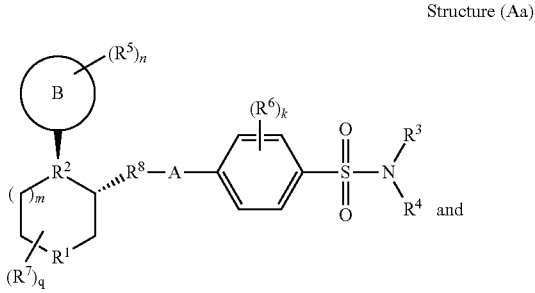

Structure (Aa)

and

Structure (Ab)

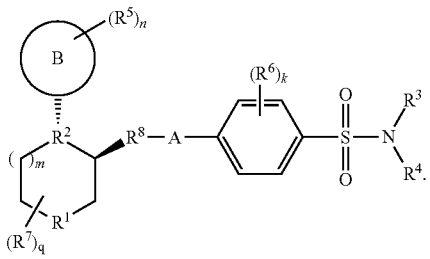

Following the standard chemical literature description practice and as used in this specification, a full wedge bond, as illustrated below in Structure (Aa), means that the substituent bonded to the ring containing the $R^1$ and $R^2$ group by this bond, in this case the

ring, is above the plane of the ring containing the $R^1$ and $R^2$ group if illustrated on the page in a two dimensional representation, and a dashed wedge bond, as illustrated below in Structure (Aa), means that the substituent bonded to the ring containing the $R^1$ and $R^2$ group by this bond, in this case the $R^8$ group, is below the plane of the ring containing the $R^1$ and $R^2$ group if shown on the page in a two dimensional representation:

Structure (Aa)

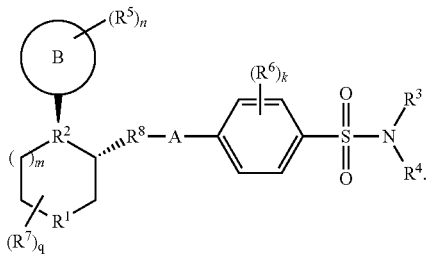

Following the standard chemical literature description practice and as used in this specification, two solid full bonds, as illustrated below in Structure (B), or two solid dashed bonds means that the substituents, in this case the

ring and the R⁸ group, are in a relative cis-configuration with respect to the plane of the ring containing the R¹ and R² group.

Structure (B)

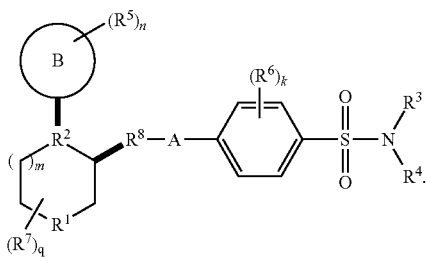

It is understood that Structure (B) is meant to include a racemic or non-racemic mixture of the following two enantiomers:

Structure (Ba)

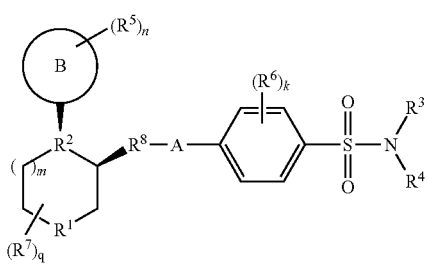

and

Structure (Bb)

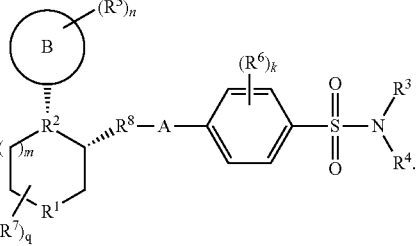

Following the standard chemical literature description practice and as used in this specification, a full wedge bond, as illustrated below in Structure (Ba), means that the substituents bonded to the ring containing the R¹ and R² group by this bond, in this case the

B ring and R⁸ group, are both above the plane of the ring containing the R¹ and R² group if illustrated on the page in a two dimensional representation:

Structure (Ba)

The compounds of the present invention contain at least one asymmetric carbon atom and thus can exist as racemates, enantiomers and/or diastereoisomers. For the present invention, the words diastereomer and diastereoisomer and related terms are equivalent and interchangeable. Unless otherwise indicated, the present invention includes all enantiomeric and diastereoisomeric forms of the compounds of formula (I). Pure stereoisomers, mixtures of enantiomers and/or diastereoisomers, and mixtures of different compounds of the invention are included within the present invention. Thus, compounds of formula (I) may occur as racemates, racemic or diastereoisomeric mixtures and as individual diastereoisomers, or enantiomers, unless a specific stereoisomer enantiomer or diastereoisomer is identified, with all isomeric forms being included in the present invention. For the present invention, a racemate or racemic mixture implies a 50:50 mixture of stereoisomers only. Other enantiomerically or diastereomerically enriched mixtures of varying ratios of stereoisomers are also contemplated.

"Enantiomers" refer to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions). The designations, "R" and "S", for the absolute configuration of an enantiomer of the invention may appear as a prefix or as a suffix in the name of the compound; they may or may not be separated from the enantiomer name by a hyphen; they may or may not be hyphenated; and they may or may not be surrounded by parentheses.

"Resolution" or "resolving" when used in reference to a racemic compound or a racemic mixture of a compound of the invention refers to the separation of the racemic compound or a racemic mixture into its two enantiomeric forms (i.e., (+) and (−); (R) and (S) forms).

"Enantiomeric excess" or "ee" as used herein refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this invention, the (S)-enantiomer of a compound prepared by the methods disclosed herein is considered to be "substantially free" of the corresponding (R)-enantiomer when the (S)-enantiomer is present in enantiomeric excess of greater than 80%, preferably greater than 90%, more preferably greater than 95% and most preferably greater than 99%.

Thus, for example, a compound of formula (Ia) wherein k is 2, m is 1, n is 1, q is 0, A is —O—,

is phenyl, $R^1$ is —N(H)—, $R^2$ is C(H), $R^3$ is hydrogen, $R^4$ is 1,2,4-thiadiazol-5-yl, $R^5$ is fluoro, each $R^6$ is fluoro and $R^8$ is methylene, i.e., a compound of the following formula:

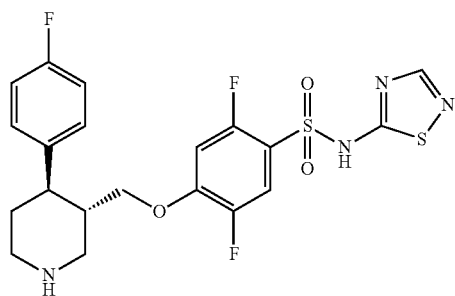 [SMILES: O=S(=O)(Nc1ncns1)c1cc(F)c(OC[C@@H]2CNCC[C@H]2c2ccc(F)cc2)cc1F]

is named herein as 2,5-difluoro-4-(((3S,4R)-4-(4-fluorophenyl)piperidin-3-yl)methoxy)-N-(1,2,4-thiadiazol-5-yl)benzenesulfonamide.

Embodiments of the Invention

One aspect of the invention is a compound of formula (I), as set forth above in the Summary of the Invention, as a stereoisomer, enantiomer or tautomer thereof or mixtures thereof; or a pharmaceutically acceptable salt, solvate or prodrug thereof.

Of this aspect, one embodiment is a compound of formula (I), as set forth in the Summary of the Invention, as a stereoisomer, enantiomer or tautomer thereof or mixtures thereof; or a pharmaceutically acceptable salt thereof, wherein k is 0, 1, 2, 3 or 4; m is 0, 1 or 2; n is 0, 1, 2, 3, 4 or 5; q is 0, 1, 2, 3, 4, 5 or 6; A is —O— or —S—;

is aryl; $R^1$ is —O—, —C($R^9$)$_2$—, —N($R^{10}$)—, —N($R^{11}$)— or —S(O)$_t$ (where t is 0, 1 or 2); $R^2$ is C($R^9$) or N; $R^3$ is hydrogen, alkyl, haloalkyl, optionally substituted aryl or optionally substituted aralkyl; or $R^3$ is a direct bond to $R^4$; $R^4$ is optionally substituted alkyl, optionally substituted heterocyclyl, optionally substituted heteroaryl, —C(O)N($R^{10}$)$_2$ or —C(=NCN)N($R^{10}$)$_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —O$R^{10}$, —S(O)$_t R^{10}$ (where t is 0, 1 or 2), —C(O)O$R^{10}$, —C(O)$R^{10}$ or —C(O)N($R^{10}$)$_2$; each $R^7$ is independently hydrogen, alkyl, halo, haloalkyl, —O$R^{10}$, —S(O)$_t R^{10}$ (where t is 0, 1 or 2), —C(O)O$R^{10}$, —C(O)$R^{10}$ or —C(O)N($R^{10}$)$_2$; or any two $R^7$'s on the same carbon may form an oxo and the other $R^7$'s, if present, are independently hydrogen, alkyl, halo, haloalkyl, —O$R^{10}$, —S(O)$_t R^{10}$ (where t is 0, 1 or 2), —C(O)O$R^{10}$, —C(O)$R^{10}$ or —C(O)N($R^{10}$)$_2$; or any two $R^7$'s on different carbons may form an optionally substituted straight or branched alkylene chain optionally containing one or more heteroatoms, and the other $R^7$'s, if present, are independently hydrogen, alkyl, halo, haloalkyl, —O$R^{10}$, —S(O)$_t R^{10}$ (where t is 0, 1 or 2), —C(O)O$R^{10}$, —C(O)$R^{10}$ or —C(O)N($R^{10}$)$_2$, $R^8$ is a direct bond or an optionally substituted straight or branched alkylene chain; each $R^9$ is independently hydrogen, alkyl, halo, haloalkyl, —O$R^{10}$, —N($R^{10}$)$_2$, —N($R^{11}$)$_2$, —S(O)$_t R^{10}$ (where t is 0, 1 or 2), —C(O)O$R^{10}$, —C(O)$R^{10}$ or —C(O)N($R^{10}$)$_2$; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each $R^{11}$ is independently —C(O)$R^{10}$; —C(O)O$R^{10}$, —C(O)N($R^{10}$)$_2$, —S(O)$_p R^{10}$ (where p is 1 or 2) or —S(O)$_p$N($R^{10}$)$_2$ (where p is 1 or 2).

Another embodiment is a compound of formula (I), as set forth in the Summary of the Invention, as a stereoisomer, enantiomer or tautomer thereof or mixtures thereof; or a pharmaceutically acceptable salt thereof, wherein k is 0, 1, 2, 3 or 4; m is 0, 1 or 2; n is 0, 1, 2, 3, 4 or 5; q is 0, 1, 2, 3, 4, 5 or 6; A is —O—;

is aryl; $R^1$ is —O—, —C($R^9$)$_2$—, —N($R^{10}$)—, —N($R^{11}$)— or —S(O)$_t$ (where t is 0, 1 or 2); $R^2$ is C($R^9$) or N; $R^3$ is hydrogen, alkyl, haloalkyl, optionally substituted aryl or optionally substituted aralkyl; or $R^3$ is a direct bond to $R^4$; $R^4$ is optionally substituted heterocyclyl, optionally substituted heteroaryl, —C(O)N($R^{10}$)$_2$ or —C(=NCN)N($R^{10}$)$_2$;

or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —$S(O)_tR^{10}$ (where t is 0, 1 or 2), —$C(O)OR^{10}$, —$C(O)R^{10}$ or —$C(O)N(R^{10})_2$; each $R^7$ is independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{10})_2$; or any two $R^7$'s on the same carbon may form an oxo and the other $R^7$'s, if present, are independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{10})_2$; or any two $R^7$'s on different carbons may form an optionally substituted straight or branched alkylene chain optionally containing one or more heteroatoms, and the other $R^7$'s, if present, are independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{16})_2$; $R^8$ is an optionally substituted straight or branched alkylene chain; each $R^9$ is independently hydrogen, alkyl, halo, haloalkyl, —$OR^{10}$, —$N(R^{10})_2$, —$N(R^{11})_2$, —$S(O)_tR^{10}$ (where t is 0, 1 or 2), —$C(O)OR^{10}$, —$C(O)R^{10}$ or —$C(O)N(R^{10})_2$; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each $R^{11}$ is independently —$C(O)R^{10}$; —$C(O)OR^{10}$, —$C(O)N(R^{10})_2$, —$S(O)_pR^{10}$ (where p is 1 or 2) or —$S(O)_pN(R^{10})_2$ (where p is 1 or 2).

Another embodiment is a compound of formula (I) having the following formula (Ia):

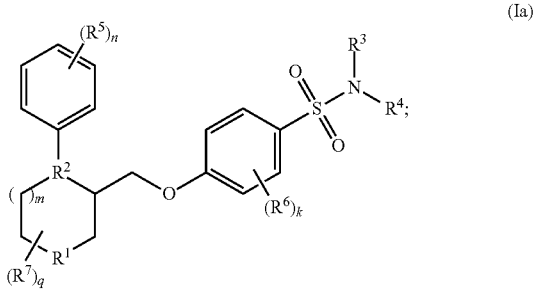

(Ia)

wherein k is 0, 1, 2, 3 or 4; m is 0, 1 or 2; n is 0, 1, 2, 3, 4 or 5; q is 0, 1, 2, 3, 4, 5 or 6; $R^1$ is —O—, —$C(R^9)_2$—, —$N(R^{10})$—, —$N(R^{11})$— or —$S(O)_t$ (where t is 0, 1 or 2); $R^2$ is $C(R^9)$ or N; $R^3$ is hydrogen, alkyl, haloalkyl, optionally substituted aryl or optionally substituted aralkyl; or $R^3$ is a direct bond to $R^4$; $R^4$ is optionally substituted heterocyclyl, optionally substituted heteroaryl, —$C(O)N(R^{10})_2$ or —$C(=NCN)N(R^{10})_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —$S(O)_tR^{10}$ (where t is 0, 1 or 2), —$C(O)OR^{10}$, —$C(O)R^{10}$ or —$C(O)N(R^{10})_2$; each $R^7$ is independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{10})_2$; or any two $R^7$'s on different carbons may form an optionally substituted straight or branched alkylene chain optionally containing one or more heteroatoms, and the other $R^7$'s, if present, are independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{10})_2$; each $R^9$ is independently hydrogen, alkyl, halo, haloalkyl, —$OR^{10}$, —$N(R^{10})_2$, —$N(R^{11})_2$, —$S(O)_tR^{10}$ (where t is 0, 1 or 2), —$C(O)OR^{10}$, —$C(O)R^{10}$ or —$C(O)N(R^{10})_2$; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each $R^{11}$ is independently —$C(O)R^{10}$; —$C(O)OR^{10}$, —$C(O)N(R^{10})_2$, —$S(O)_pR^{10}$ (where p is 1 or 2) or —$S(O)_pN(R^{10})_2$ (where p is 1 or 2).

Another embodiment is a compound of formula (Ia) wherein k is 0, 1, 2, 3 or 4; m is 0 or 1; n is 0, 1, or 2; q is 0, 1 or 2; $R^1$ is —O—, —$C(R^9)_2$—, —$N(R^{10})$—, —$N(R^{11})$— or —$S(O)_t$ (where t is 0, 1 or 2); $R^2$ is $C(R^9)$; $R^3$ is hydrogen, alkyl, haloalkyl, optionally substituted aryl or optionally substituted aralkyl; or $R^3$ is a direct bond to $R^4$; $R^4$ is optionally substituted heterocyclyl, optionally substituted heteroaryl, —$C(O)N(R^{10})_2$ or —$C(=NCN)N(R^{16})_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —$S(O)_tR^{10}$ (where t is 0, 1 or 2), —$C(O)OR^{10}$, —$C(O)R^{10}$ or —$C(O)N(R^{10})_2$; each $R^7$ is independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{16})_2$; each $R^9$ is independently hydrogen, alkyl, halo, haloalkyl, —$OR^{10}$, —$N(R^{10})_2$, —$N(R^{11})_2$, —$S(O)_tR^{10}$ (where t is 0, 1 or 2), —$C(O)OR^{10}$, —$C(O)R^{10}$ or —$C(O)N(R^{10})_2$; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each $R^{11}$ is independently —$C(O)R^{10}$; —$C(O)OR^{10}$, —$C(O)N(R^{10})_2$, —$S(O)_pR^{10}$ (where p is 1 or 2) or —$S(O)_pN(R^{10})_2$ (where p is 1 or 2).

Another embodiment is a compound of formula (Ia) wherein k is 0, 1 or 2; m is 0 or 1; n is 0, 1, or 2; q is 0, 1 or 2; $R^1$ is —$N(R^{10})$— or —$N(R^{11})$—; $R^2$ is $C(R^9)$; $R^3$ is hydrogen, alkyl, haloalkyl, optionally substituted aryl or optionally substituted aralkyl; or $R^3$ is a direct bond to $R^4$; $R^4$ is —$C(O)N(R^{10})_2$, —$C(=NCN)N(R^{10})_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —$S(O)_tR^{10}$ (where t is 0, 1 or 2), —$C(O)OR^{10}$, —$C(O)R^{10}$ or —$C(O)N(R^{10})_2$; each $R^7$ is independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{10})_2$; each $R^9$ is independently hydrogen, alkyl, halo or haloalkyl; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and $R^{11}$ is —C(O)$R^{10}$: —C(O)O$R^{10}$, —C(O)N($R^{10}$)$_2$, —S(O)$_p R^{10}$ (where p is 1 or 2) or —S(O)$_p$N($R^{10}$)$_2$ (where p is 1 or 2).

Another embodiment is a compound of formula (Ia) wherein k is 0, 1 or 2; m is 0 or 1; n is 0, 1, or 2; q is 0, 1 or 2; $R^1$ is —N($R^{10}$)—; $R^2$ is C($R^9$); $R^3$ is hydrogen, alkyl, haloalkyl, optionally substituted aryl or optionally substituted aralkyl; or $R^3$ is a direct bond to $R^4$; $R^4$ is —C(O)N($R^{10}$)$_2$, —C(=NCN)N($R^{10}$)$_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —O$R^{10}$, —S(O)$_t R^{10}$ (where t is 0, 1 or 2), —C(O)O$R^{10}$, —C(O)$R^{10}$ or —C(O)N($R^{10}$)$_2$; each $R^7$ is independently hydrogen, alkyl, halo, haloalkyl, —O$R^{10}$, —S(O)$_t R^{10}$ (where t is 0, 1 or 2), —C(O)O$R^{10}$, —C(O)$R^{10}$ or —C(O)N($R^{10}$)$_2$; each $R^9$ is independently hydrogen, alkyl, halo, haloalkyl or —O$R^{10}$; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1 or 2; $R^1$ is —N($R^{10}$)—; $R^2$ is C($R^9$); $R^3$ is hydrogen, alkyl, haloalkyl, optionally substituted aryl or optionally substituted aralkyl; or $R^3$ is a direct bond to $R^4$; $R^4$ is optionally substituted heterocyclyl selected from N-heterocyclyl, optionally substituted heteroaryl selected from N-heteroaryl, —C(O)N($R^{10}$)$_2$ or —C(=NCN)N($R^{10}$)$_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —O$R^{10}$, —S(O)$_t R^{10}$ (where t is 0, 1 or 2), —C(O)O$R^{10}$, —C(O)$R^{10}$ or —C(O)N($R^{10}$)$_2$; each $R^7$ is independently hydrogen, alkyl, halo, haloalkyl, —O$R^{10}$, —S(O)$_t R^{10}$ (where t is 0, 1 or 2), —C(O)O$R^{10}$, —C(O)$R^{10}$ or —C(O)N($R^{10}$)$_2$; each $R^9$ is independently hydrogen, alkyl, halo, haloalkyl or —O$R^{10}$; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1 or 2; $R^1$ is —N($R^{10}$)—; $R^2$ is C($R^9$); $R^3$ is hydrogen or optionally substituted aralkyl; or $R^3$ is a direct bond to $R^4$; $R^4$ is an optionally substituted N-heteroaryl or an optionally substituted N-heterocyclyl; each $R^5$ is independently hydrogen, halo or haloalkyl; each $R^6$ is independently hydrogen, halo, haloalkyl or cyano; each $R^7$ is independently hydrogen, alkyl, halo or haloalkyl; each $R^9$ is independently hydrogen, alkyl, halo, haloalkyl or —O$R^{10}$; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1 or 2; $R^1$ is —N($R^{10}$)—; $R^2$ is C($R^9$); $R^3$ is hydrogen or a direct bond to $R^4$; $R^4$ is an optionally substituted N-heteroaryl or an optionally substituted N-heterocyclyl; each $R^5$ is independently hydrogen, halo or haloalkyl; each $R^6$ is independently hydrogen, halo or haloalkyl or cyano; each $R^7$ is independently hydrogen, alkyl, halo or haloalkyl; each $R^9$ is independently hydrogen; and each $R^{10}$ is independently hydrogen or alkyl.

Another embodiment is a compound of formula (Ia) wherein k is 0, 1 or 2; m is 1; n is 0, 1, or 2; q is 0, 1 or 2; $R^1$ is —N($R^{10}$)—; $R^2$ is C($R^9$); $R^3$ is hydrogen or a direct bond to $R^4$; $R^4$ is optionally substituted N-heteroaryl selected from optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl; or $R^4$ is optionally substituted 1,2,4-thiadiazol-5(4H)-ylidene; each $R^5$ is independently hydrogen, halo or haloalkyl; each $R^6$ is independently hydrogen, halo or haloalkyl or cyano; each $R^7$ is independently hydrogen, alkyl, halo or haloalkyl; each $R^9$ is independently hydrogen; and each $R^{10}$ is independently hydrogen or alkyl.

Another embodiment is a compound of formula (Ia) selected from:

4-((trans-4-(4-chlorophenyl)piperidin-3-yl)methoxy)-2,5-difluoro-N-(1,2,4-thiadiazol-5-yl)benzenesulfonamide;

4-((trans-4-(4-chlorophenyl)piperidin-3-yl)methoxy)-2,5-difluoro-N-(pyridin-2-yl)benzenesulfonamide;

4-((trans-4-(4-chlorophenyl)piperidin-3-yl)methoxy)-3-cyano-N-(1,2,4-thiadiazol-5-yl)benzenesulfonamide;

4-((trans-4-(4-chlorophenyl)piperidin-3-yl)methoxy)-3-fluoro-N-(1,2,4-thiadiazol-5-yl)benzenesulfonamide;

4-((trans-4-(4-chlorophenyl)-1-methylpiperidin-3-yl)methoxy)-2,5-difluoro-N-(1,2,4-thiadiazol-5-yl)benzenesulfonamide 2,2,2-trifluoroacetate;

2,5-difluoro-4-((trans-4-(4-fluorophenyl)piperidin-3-yl)methoxy)-N-(1,2,4-thiadiazol-5-yl)benzenesulfonamide;

4-((trans-4-(4-chlorophenyl)piperidin-3-yl)methoxy)-2,5-difluoro-N-(3-methyl-1,2,4-thiadiazol-5-yl)benzenesulfonamide;

4-((trans-4-(4-chlorophenyl)piperidin-3-yl)methoxy)-2,5-difluoro-N-(1,3,4-thiadiazol-2-yl)benzenesulfonamide;

4-((trans-4-(4-chlorophenyl)piperidin-3-yl)methoxy)-2,5-difluoro-N-(2-methyl-2H-tetrazol-5-yl)benzenesulfonamide;

4-((trans-4-(4-chlorophenyl)piperidin-3-yl)methoxy)-2,5-difluoro-N-(5-methyl isoxazol-3-yl)benzenesulfonamide;

4-((trans-4-(4-chlorophenyl)piperidin-3-yl)methoxy)-N-(5-chlorothiazol-2-yl)-2,5-difluorobenzenesulfonamide;

4-((trans-4-(4-chlorophenyl)piperidin-3-yl)methoxy)-2,5-difluoro-N-(pyrimidin-2-yl)benzenesulfonamide;

4-((trans-4-(4-chlorophenyl)piperidin-3-yl)methoxy)-2,5-difluoro-N-(5-methylthiazol-2-yl)benzenesulfonamide;

4-((trans-4-(4-chlorophenyl)piperidin-3-yl)methoxy)-2,5-difluoro-N-(5-fluoropyridin-2-yl)benzenesulfonamide;

4-((trans-4-(4-chlorophenyl)piperidin-3-yl)methoxy)-2,5-difluoro-N-(pyrimidin-4-yl)benzenesulfonamide;

4-((trans-4-(3,4-difluorophenyl)piperidin-3-yl)methoxy)-2,5-difluoro-N-(1,2,4-thiadiazol-5-yl)benzenesulfonamide;

4-((trans-4-(4-chlorophenyl)piperidin-3-yl)methoxy)-2,5-difluoro-N-(5-fluoropyrimidin-2-yl)benzenesulfonamide;

4-((trans-4-(4-chlorophenyl)piperidin-3-yl)methoxy)-2,5-difluoro-N-(pyridazin-3-yl)benzenesulfonamide;
2,5-difluoro-4-(((3S,4R)-4-(4-fluorophenyl)piperidin-3-yl)methoxy)-N-(1,2,4-thiadiazol-5-yl)benzenesulfonamide;
4-((cis-4-(4-chlorophenyl)piperidin-3-yl)methoxy)-2,5-difluoro-N-(1,2,4-thiadiazol-5-yl)benzenesulfonamide;
2,5-difluoro-4-((trans-4-(4-fluorophenyl(piperidin-3-yl)methoxy)-N-(pyrimidin-2-yl)benzenesulfonamide;
2,5-difluoro-4((3-fluoro-4-(4-fluorophenyl)piperidin-3-yl)methoxy)-N-(1,2,4-thiadiazol-5-yl)benzenesulfonamide;
N-(5-chlorothiazol-2-yl)-4-(trans-4-(3,4-difluorophenyl)piperidin-3-yl(methoxy)-2,5-difluorobenzenesulfonamide;
4-((trans-4-(4-chlorophenyl)piperidin-3-yl)methoxy)-2,5-difluoro-N-(pyridin-2-yl)benzenesulfonamide;
2,5-difluoro-4-((trans-4-phenylpiperidin-3-yl)methoxy)-N-(1,2,4-thiadiazol-5-yl)benzenesulfonamide;
4-(((3R,4S)-4-(4-chlorophenyl)piperidin-3-yl)methoxy)-2,5-difluoro-N-(1,2,4-thiadiazol-5-yl)benzenesulfonamide;
4-((trans-4-(4-chlorophenyl)piperidin-3-yl(methoxy)-2,5-difluoro-N-(4-methyl-1,2,4-thiadiazol-5(4H)-ylidene)benzenesulfonamide;
4-((trans-4-(4-chlorophenyl)piperidin-3-yl)methoxy)-2,5-difluoro-N-methyl-N-(1,2,4-thiadiazol-5-yl)benzenesulfonamide;
4-((trans-4-(4-chlorophenyl)-1-(2-fluoroethyl)piperidin-3-yl)methoxy)-2,5-difluoro-N-(1,2,4-thiadiazol-5-yl(benzenesulfonamide;
4-((trans-4-(4-chlorophenyl)piperidin-3-yl)methoxy)-3,5-difluoro-N-(1,2,4-thiadiazol-5-yl)benzenesulfonamide;
2,5-difluoro-4-((trans-3-(4-fluorophenyl)piperidin-4-yl)methoxy)-N-(1,2,4-thiadiazol-5-yl)benzenesulfonamide;
4-((trans-4-(4-chlorophenyl)-1-(2,2-difluoroethyl)piperidin-3-yl(methoxy)-2,5-difluoro-N-(1,2,4-thiadiazol-5-yl)benzenesulfonamide;
4-(((3S,4R)-4-(4-chlorophenyl)piperidin-3-yl)methoxy)-2,5-difluoro-N-(1,2,4-thiadiazol-5-yl)benzenesulfonamide;
4-(((3R,4S)-4-(4-chlorophenyl)-1-methylpiperidin-3-yl)methoxy)-2,5-difluoro-N-(1,2,4-thiadiazol-5-yl)benzenesulfonamide;
4-(((3S,4R)-4-(4-chlorophenyl)-1-methylpiperidin-3-yl(methoxy)-2,5-difluoro-N-(1,2,4-thiadiazol-5-yl(benzenesulfonamide;
2,5-difluoro-4-((trans-4-(4-fluorophenyl)-6-oxopiperidin-3-yl)methoxy)-N-(1,2,4-thiadiazol-5-yl)benzenesulfonamide;
4-((trans-4-(4-chlorophenyl)-1-(2,2,2-trifluoroethyl)piperidin-3-yl)methoxy)-2,5-difluoro-N-(1,2,4-thiadiazol-5-yl)benzenesulfonamide;
trans-3-((4(4-(N-(5-chlorothiazol-2-yl)sulfamoyl)-2,5-difluorophenoxy)methyl)-4-(3,4-difluorophenyl)piperidine-1-carboxamide;
4-((trans-4-(4-chlorophenyl)piperidin-3-yl)methoxy)-3-cyano-N-isopropylbenzenesulfonamide;
4-((trans-4-(4-chlorophenyl)piperidin-3-yl)methoxy)-3-cyano-N-(1-cyanocyclopropyl)benzenesulfonamide;
4-((trans-4-(3,4-dichlorophenyl)piperidin-3-yl)methoxy)-2,5-difluoro-N-(1,2,4-thiadiazol-5-yl)benzenesulfonamide;
4-((trans-4-(4-chlorophenyl)piperidin-3-yl)methoxy)-3-cyano-N-(2,2,2-trifluoroethyl)benzenesulfonamide;
2,5-difluoro-4-((trans-4-(4-methoxyphenyl)piperidin-3-yl)methoxy)-N-(1,2,4-thiadiazol-5-yl)benzenesulfonamide;
4-((trans-4-(4-chlorophenyl)piperidin-3-yl)methoxy)-2,5-difluorobenzenesulfonamide;
4-((trans-4-(4-chlorophenyl)piperidin-3-yl)methoxy)-2,5-difluoro-N-isobutylbenzenesulfonamide;
5-difluoro-N-(1,2,4-thiadiazol-5-yl)benzenesulfonamide;
trans-3-((4(4-((1H-pyrazol-1-yl)sulfonyl)-2,5-difluorophenoxy)methyl)-4-(4-fluorophenyl)piperidine;
N-((4-((trans-4-(4-chlorophenyl)piperidin-3-yl)methoxy)-2,5-difluorophenyl)sulfonyl)picolinamide;
2,5-difluoro-N-(1,2,4-thiadiazol-5-yl)-4-((trans-4-(p-tolyl)piperidin-3-yl)methoxy)benzenesulfonamide;
2,5-difluoro-4-((trans-6-oxo-4-(2,4,5-trifluorophenyl)piperidin-3-yl)methoxy)-N-(1,2,4-thiadiazol-5-yl)benzenesulfonamide;
N-((4-((trans-4-(4-chlorophenyl)piperidin-3-yl)methoxy)-2,5-difluorophenyl)sulfonyl)acetamide;
N-((4-((trans-4-(4-chlorophenyl)piperidin-3-yl)methoxy)-2,5-difluorophenyl)sulfonyl)nicotinamide;
N-((4-((trans-4-(4-chlorophenyl)piperidin-3-yl)methoxy)-2,5-difluorophenyl)sulfonyl)benzamide;
4-((trans-4-(4-chlorophenyl)piperidin-3-yl)methoxy)-2,5-difluoro-N-(isopropylcarbamoyl)benzenesulfonamide;
2,5-difluoro-N-(1,2,4-thiadiazol-5-yl)-4-((trans-4-(2,4,5-trifluorophenyl)piperidin-3-yl)methoxy)benzenesulfonamide;
2,5-difluoro-4-((trans-4-(4-fluoro-3-(trifluoromethyl)phenyl)piperidin-3-yl)methoxy)-N-(1,2,4-thiadiazol-5-yl)benzenesulfonamide;
4-((trans-4-(3-(difluoromethyl)-4-fluorophenyl)piperidin-3-yl)methoxy)-2,5-difluoro-N-(1,2,4-thiadiazol-5-yl)benzenesulfonamide;
4-((2-(4-chlorophenyl)-5-oxocyclohexyl)methoxy)-2,5-difluoro-N-(1,2,4-thiadiazol-5-yl)benzenesulfonamide;
4-(((trans-5S)-2-(4-chlorophenyl)-5-hydroxycyclohexyl)methoxy)-2,5-difluoro-N-(1,2,4-thiadiazol-5-yl)benzenesulfonamide;
4-(((trans-5R)-2-(4-chlorophenyl)-5-hydroxycyclohexyl)methoxy)-2,5-difluoro-N-(1,2,4-thiadiazol-5-yl)benzenesulfonamide; and
4-((1-(4-chlorophenyl)piperazin-2-yl)methoxy)-2,5-difluoro-N-(1,2,4-thiadiazol-5-yl)benzenesulfonamide.

Another embodiment is a compound of formula (Ia) wherein k is 0, 1 or 2; m is 0 or 1; n is 0, 1, or 2; q is 0, 1 or 2; $R^1$ is $-N(R^{11})-$; $R^2$ is $C(R^9)$; $R^3$ is hydrogen, alkyl, haloalkyl, optionally substituted aryl or optionally substituted aralkyl; or $R^3$ is a direct bond to $R^4$; $R^4$ is $-C(O)N(R^{10})_2$, $-C(=NCN)N(R^{10})_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, $-OR^{10}$, $-S(O)_tR^{10}$ (where t is 0, 1 or 2), $-C(O)OR^{10}$, $-C(O)R^{10}$ or $-C(O)N(R^{10})_2$; each $R^7$ is independently hydrogen, alkyl, halo, haloalkyl, $-OR^{20}$, $-S(O)_tR^{10}$ (where t is 0, 1 or 2), $-C(O)OR^{10}$, $-C(O)R^{10}$ or $-C(O)N(R^{10})_2$; each $R^9$ is independently hydrogen, alkyl, halo or haloalkyl; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and $R^{11}$ is $-C(O)R^{10}$; $-C(O)OR^{10}$, $-C(O)N(R^{10})_2$, $-S(O)_pR^{10}$ (where p is 1 or 2) or $-S(O)_pN(R^{10})_2$ (where p is 1 or 2).

Another embodiment is a compound of formula (Ia) wherein k is 0, 1 or 2; m is 1; n is 0, 1, or 2; q is 0, 1 or 2; $R^1$ is $-N(R^{11})-$; $R^2$ is $C(R^9)$; $R^3$ is hydrogen, alkyl, haloalkyl, optionally substituted aryl or optionally substituted aralkyl; or $R^3$ is a direct bond to $R^4$; $R^4$ is optionally substituted heterocyclyl selected from N-heterocyclyl, optionally substituted heteroaryl selected from N-heteroaryl, —C(O)N($R^{10}$)$_2$ or —C(=NCN)N($R^{10}$)$_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —S(O)$_t R^{10}$ (where t is 0, 1 or 2), —C(O)$OR^{10}$, —C(O)$R^{10}$ or —C(O)N($R^{10}$)$_2$; each $R^7$ is independently hydrogen, alkyl, halo, haloalkyl, —$OR^{10}$, —S(O)$_t R^{10}$ (where t is 0, 1 or 2), —C(O)$OR^{10}$, —C(O)$R^{10}$ or —C(O)N($R^{10}$)$_2$; each $R^9$ is independently hydrogen, alkyl, halo or haloalkyl; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and $R^{11}$ is —C(O)$R^{10}$; —C(O)$OR^{10}$, —C(O)N($R^{10}$)$_2$, —S(O)$_p R^{10}$ (where p is 1 or 2) or —S(O)$_p$N($R^{10}$)$_2$ (where p is 1 or 2).

Another embodiment is a compound of formula (Ia) wherein k is 0, 1 or 2; m is 1; n is 0, 1, or 2; q is 0, 1 or 2; $R^1$ is —N($R^{11}$)—; $R^2$ is C($R^9$); $R^3$ is hydrogen, optionally substituted aralkyl or a direct bond to $R^4$; $R^4$ is an optionally substituted N-heteroaryl or an optionally substituted N-heterocyclyl; each $R^5$ is independently hydrogen, halo or haloalkyl; each $R^6$ is independently hydrogen, halo, haloalkyl or cyano; each $R^7$ is independently hydrogen, alkyl, halo or haloalkyl; each $R^9$ is independently hydrogen, alkyl, halo or haloalkyl; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and $R^{11}$ is —C(O)$R^{10}$; —C(O)$OR^{10}$, —C(O)N($R^{10}$)$_2$, —S(O)$_p R^{10}$ (where p is 1 or 2) or —S(O)$_p$N($R^{10}$)$_2$ (where p is 1 or 2).

Another embodiment is a compound of formula (Ia) wherein k is 0, 1 or 2; m is 1; n is 0, 1, or 2; q is 0, 1 or 2; $R^1$ is —N($R^{11}$)—; $R^2$ is C($R^9$); $R^3$ is hydrogen or a direct bond to $R^4$; $R^4$ is an optionally substituted N-heteroaryl or an optionally substituted N-heterocyclyl; each $R^5$ is independently hydrogen, halo or haloalkyl; each $R^6$ is independently hydrogen, halo or haloalkyl or cyano; each $R^7$ is independently hydrogen, alkyl, halo or haloalkyl; each $R^9$ is independently hydrogen; each $R^{10}$ is independently hydrogen or alkyl; and $R^{11}$ is —C(O)$R^{10}$; —C(O)$OR^{10}$, —C(O)N($R^{10}$)$_2$, —S(O)$_p R^{10}$ (where p is 1 or 2) or —S(O)$_p$N($R^{10}$)$_2$ (where p is 1 or 2).

Another embodiment is a compound of formula (Ia) wherein k is 0, 1 or 2; m is 1; n is 0, 1, or 2; q is 0, 1 or 2; $R^1$ is —N($R^{11}$)—; $R^2$ is C($R^9$); $R^3$ is hydrogen or a direct bond to $R^4$; $R^4$ is optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl; or $R^4$ is optionally substituted 1,2,4-thiadiazol-5(4H)-ylidene; each $R^5$ is independently hydrogen, halo or haloalkyl; each $R^6$ is independently hydrogen, halo or haloalkyl or cyano; each $R^7$ is independently hydrogen, alkyl, halo or haloalkyl; each $R^9$ is independently hydrogen; each $R^{10}$ is independently hydrogen or alkyl; and $R^{11}$ is —C(O)$OR^{10}$.

Another embodiment is a compound of formula (Ia) which is trans-tert-butyl 3-((4-(N-(1,2,4-thiadiazol-5-yl)sulfamoyl)-2,5-difluorophenoxy)methyl)-4-(4-chlorophenyl)piperidine-1-carboxylate.

Another embodiment is a compound of formula (Ia) wherein k is 0, 1, 2, 3 or 4; m is 0 or 1; n is 0, 1, or 2; q is 0, 1, 2 or 3; $R^1$ is —C($R^9$)$_2$—, —N($R^{10}$)—, —N($R^{11}$)— or —S(O)$_t$ (where t is 0, 1 or 2); $R^2$ is N; $R^3$ is hydrogen, alkyl, haloalkyl, optionally substituted aryl or optionally substituted aralkyl; $R^4$ is optionally substituted heterocyclyl, optionally substituted heteroaryl, —C(O)N($R^{10}$)$_2$ or —C(=NCN)N($R^{10}$)$_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —S(O)$_t R^{10}$ (where t is 0, 1 or 2), —C(O)$OR^{10}$, —C(O)$R^{10}$ or —C(O)N($R^{10}$)$_2$; each $R^7$ is independently hydrogen, alkyl, halo, haloalkyl, —$OR^{10}$, —S(O)$_t R^{10}$ (where t is 0, 1 or 2), —C(O)$OR^{10}$, —C(O)$R^{10}$ or —C(O)N($R^{10}$)$_2$; or any two $R^7$'s on the same carbon may form an oxo and the other $R^7$, if present, is independently hydrogen, alkyl, halo, haloalkyl, —$OR^{10}$, —S(O)$_t R^{10}$ (where t is 0, 1 or 2), —C(O)$OR^{10}$, —C(O)$R^{10}$ or —C(O)N($R^{10}$)$_2$; each $R^9$ is independently hydrogen, alkyl, halo, haloalkyl, —$OR^{10}$, —N($R^{10}$)$_2$, —N($R^{11}$)$_2$, —S(O)$_t R^{10}$ (where t is 0, 1 or 2), —C(O)$OR^{10}$, —C(O)$R^{10}$ or —C(O)N($R^{10}$)$_2$; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each $R^{11}$ is independently —C(O)$R^{10}$; —C(O)$OR^{10}$, —C(O)N($R^{10}$)$_2$, —S(O)$_p R^{10}$ (where p is 1 or 2) or —S(O)$_p$N($R^{10}$)$_2$ (where p is 1 or 2).

Another embodiment is a compound of formula (Ia) wherein k is 0, 1 or 2; m is 0 or 1; n is 0, 1, or 2; q is 0, 1, 2 or 3; $R^1$ is —N($R^{10}$)— or —N($R^{11}$)—; $R^2$ is N; $R^3$ is hydrogen, alkyl, haloalkyl, optionally substituted aryl or optionally substituted aralkyl; $R^4$ is —C(O)N($R^{10}$)$_2$, —C(=NCN)N($R^{10}$)$_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —S(O)$_t R^{10}$ (where t is 0, 1 or 2), —C(O)$OR^{10}$, —C(O)$R^{10}$ or —C(O)N($R^{10}$)$_2$; each $R^7$ is independently hydrogen, alkyl, halo, haloalkyl, —$OR^{10}$, —S(O)$_t R^{10}$ (where t is 0, 1 or 2), —C(O)$OR^{10}$, —C(O)$R^{10}$ or —C(O)N($R^{10}$)$_2$; and or any two $R^7$'s on the same carbon may form an oxo and the other $R^7$, if present, is independently hydrogen, alkyl, halo, haloalkyl, —$OR^{10}$, —S(O)$_t R^{10}$ (where t is 0, 1 or 2), —C(O)$OR^{10}$, —C(O)$R^{10}$ or —C(O)N($R^{10}$)$_2$; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and $R^{11}$ is —C(O)$R^{10}$; —C(O)$OR^{10}$, —C(O)N($R^{10}$)$_2$, —S(O)$_p R^{10}$ (where p is 1 or 2) or —S(O)$_p$N($R^{10}$)$_2$ (where p is 1 or 2).

Another embodiment is a compound of formula (Ia) wherein k is 0, 1 or 2; m is 0 or 1; n is 0, 1, or 2; q is 0, 1, 2 or 3; $R^1$ is —N($R^{10}$)—; $R^2$ is N; $R^3$ is hydrogen, alkyl, haloalkyl, optionally substituted aryl or optionally substituted aralkyl; $R^4$ is —C(O)N($R^{10}$)$_2$, —C(=NCN)N($R^{10}$)$_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —O$R^{10}$, —S(O)$_t$$R^{10}$ (where t is 0, 1 or 2), —C(O)O$R^{10}$, —C(O)$R^{10}$ or —C(O)N($R^{10}$)$_2$; each $R^7$ is independently hydrogen, alkyl, halo, haloalkyl, —O$R^{10}$, —S(O)$_t$$R^{10}$ (where t is 0, 1 or 2), —C(O)O$R^{10}$, —C(O)$R^{10}$ or —C(O)N($R^{10}$)$_2$; or any two $R^7$'s on the same carbon may form an oxo and the other $R^7$, if present, is independently hydrogen, alkyl, halo, haloalkyl, —O$R^{10}$, —S(O)$_t$$R^{10}$ (where t is 0, 1 or 2), —C(O)O$R^{10}$, —C(O)$R^{10}$ or —C(O)N($R^{10}$)$_2$; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1, 2 or 3; $R^1$ is —N($R^{10}$)—; $R^2$ is N; $R^3$ is hydrogen, alkyl, haloalkyl, optionally substituted aryl or optionally substituted aralkyl; $R^4$ is optionally substituted heterocyclyl selected from N-heterocyclyl, optionally substituted heteroaryl selected from N-heteroaryl, —C(O)N($R^{10}$)$_2$ or —C(=NCN)N($R^{10}$)$_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —O$R^{10}$, —S(O)$_t$$R^{10}$ (where t is 0, 1 or 2), —C(O)O$R^{10}$, —C(O)$R^{10}$ or —C(O)N($R^{10}$)$_2$; each $R^7$ is independently hydrogen, alkyl, halo, haloalkyl, —O$R^{10}$, —S(O)$_t$$R^{10}$ (where t is 0, 1 or 2), —C(O)O$R^{10}$, —C(O)$R^{10}$ or —C(O)N($R^{10}$)$_2$; and any two $R^7$'s on the same carbon may form an oxo and the other $R^7$, if present, is independently hydrogen, alkyl, halo, haloalkyl, —O$R^{10}$, —S(O)$_t$$R^{10}$ (where t is 0, 1 or 2), —C(O)O$R^{10}$, —C(O)$R^{10}$ or —C(O)N($R^{10}$)$_2$; and each R is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1, 2 or 3; $R^1$ is —N($R^{10}$)—; $R^2$ is N; $R^3$ is hydrogen or optionally substituted aralkyl; $R^4$ is optionally substituted N-heteroaryl; each $R^5$ is independently hydrogen, halo or haloalkyl; each $R^6$ is independently hydrogen, halo, haloalkyl or cyano; any two $R^7$'s on the same carbon form an oxo and the other $R^7$, if present, is independently hydrogen, alkyl, halo, haloalkyl, —O$R^{10}$, —S(O)$_t$$R^{10}$ (where t is 0, 1 or 2), —C(O)O$R^{10}$, —C(O)$R^{10}$ or —C(O)N($R^{10}$)$_2$; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1, 2 or 3; $R^1$ is —N($R^{10}$)—; $R^2$ is N; $R^3$ is hydrogen; $R^4$ is optionally substituted N-heteroaryl; each $R^5$ is independently hydrogen, halo or haloalkyl; each $R^6$ is independently hydrogen, halo or haloalkyl or cyano; any two $R^7$'s on the same carbon form an oxo and the other $R^7$, if present, is independently hydrogen, alkyl, halo or haloalkyl; and $R^{10}$ is independently hydrogen or alkyl.

Another embodiment is a compound of formula (Ia) wherein k is 0, 1 or 2; m is 1; n is 0, 1, or 2; q is 0, 1, 2 or 3; $R^1$ is —N($R^{10}$)—; $R^2$ is N; $R^3$ is hydrogen; $R^4$ is optionally substituted N-heteroaryl selected from optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl; each $R^5$ is independently hydrogen, halo or haloalkyl; each $R^6$ is independently hydrogen, halo or haloalkyl or cyano; any two $R^7$'s on the same carbon form an oxo and the other $R^7$, if present, is independently hydrogen, alkyl, halo or haloalkyl; and $R^{10}$ is independently hydrogen or alkyl.

Another embodiment is a compound of formula (Ia) selected from:
(R)-4-(1-(4-chlorophenyl)-6-oxopiperazin-2-yl)methoxy)-2,5-difluoro-N-(1,2,4-thiadiazol-5-yl)benzenesulfonamide;
(S)-4-(1-(4-chlorophenyl)-6-oxopiperazin-2-yl)methoxy)-2,5-difluoro-N-(1,2,4-thiadiazol-5-yl)benzenesulfonamide;

Another embodiment is a compound of formula (Ia) wherein: k is 0, 1 or 2; m is 0; n is 0, 1, or 2; q is 0, 1 or 2; $R^1$ is —N($R^{10}$)—; $R^2$ is C($R^9$); $R^3$ is hydrogen, alkyl, haloalkyl, optionally substituted aryl or optionally substituted aralkyl; $R^4$ is optionally substituted heterocyclyl selected from N-heterocyclyl, optionally substituted heteroaryl selected from N-heteroaryl, —C(O)N($R^{10}$)$_2$ or —C(=NCN)N($R^{10}$)$_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —O$R^{10}$, —S(O)$_t$$R^{10}$ (where t is 0, 1 or 2), —C(O)O$R^{10}$, —C(O)$R^{10}$ or —C(O)N($R^{10}$)$_2$; each $R^7$ is independently hydrogen, alkyl, halo, haloalkyl, —O$R^{10}$, —S(O)$_t$$R^{10}$ (where t is 0, 1 or 2), —C(O)O$R^{10}$, —C(O)$R^{10}$ or —C(O)N($R^{10}$)$_2$; each $R^9$ is independently hydrogen, alkyl, halo, haloalkyl; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 0; n is 0, 1, or 2; q is 0, 1 or 2; $R^1$ is —N($R^{10}$)—; $R^2$ is C($R^9$); $R^3$ is hydrogen or optionally substituted aralkyl; $R^4$ is optionally substituted N-heteroaryl; each $R^5$ is independently hydrogen, halo or haloalkyl; each $R^6$ is independently hydrogen, halo, haloalkyl or cyano; each $R^7$ is independently hydrogen, alkyl, halo or haloalkyl; each $R^9$ is independently hydrogen, alkyl, halo, haloalkyl; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 0; n is 0, 1, or 2; q is 0, 1 or 2; $R^1$ is —N($R^{10}$)—; $R^2$ is C($R^9$); $R^3$ is hydrogen; $R^4$ is optionally substituted N-heteroaryl; each $R^5$ is independently hydrogen, halo or haloalkyl; each $R^6$ is independently hydrogen, halo or haloalkyl or cyano; each $R^7$ is independently hydrogen, alkyl, halo or haloalkyl; each $R^9$ is independently hydrogen; and each $R^{10}$ is independently hydrogen, alkyl or optionally substituted aralkyl.

Another embodiment is a compound of formula (Ia) wherein k is 0, 1 or 2; m is 0; n is 0, 1, or 2; q is 0, 1 or 2; $R^1$ is —N($R^{10}$)—; $R^2$ is C($R^9$); $R^3$ is hydrogen; $R^4$ is optionally substituted N-heteroaryl selected from optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl; each $R^5$ is independently hydrogen, halo or haloalkyl; each $R^6$ is independently hydrogen, halo or haloalkyl or cyano; each $R^7$ is independently hydrogen, alkyl, halo or haloalkyl; each $R^9$ is independently hydrogen; and each $R^{10}$ is independently hydrogen, alkyl or optionally substituted aralkyl.

Another embodiment is a compound of formula (Ia) selected from:
4-((trans-1-benzyl-4-(4-chlorophenyl)pyrrolidin-3-yl)methoxy)-2,5-difluoro-N-(1,2,4-thiadiazol-5-yl)benzenesulfonamide; and
4-((trans-4-(4-chlorophenyl)pyrrolidin-3-yl)methoxy)-2,5-difluoro-N-(1,2,4-thiadiazol-5-yl)benzenesulfonamide.

Another embodiment is a compound of formula (Ia) wherein k is 0, 1 or 2; m is 0 or 1; n is 0, 1, or 2; q is 0, 1 or 2; $R^1$ is —C($R^9$)$_2$—; $R^2$ is C($R^9$); $R^3$ is hydrogen, alkyl, haloalkyl, optionally substituted aryl or optionally substituted aralkyl; $R^4$ is —C(O)N($R^{10}$)$_2$, —C(=NCN)N($R^{10}$)$_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —OR$^{10}$, —S(O)$_t$R$^{10}$ (where t is 0, 1 or 2), —C(O)OR$^{10}$, —C(O)R$^{10}$ or —C(O)N($R^{10}$)$_2$; each $R^7$ is independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N($R^{10}$)$_2$; each $R^9$ is independently hydrogen, alkyl, halo, haloalkyl or —OR$^{10}$; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein: k is 0, 1 or 2; m is 1; n is 0, 1, or 2; q is 0, 1 or 2; $R^1$ is —C($R^9$)$_2$—; $R^2$ is C($R^9$); $R^3$ is hydrogen, alkyl, haloalkyl, optionally substituted aryl or optionally substituted aralkyl; $R^4$ is optionally substituted heterocyclyl selected from N-heterocyclyl, optionally substituted heteroaryl selected from N-heteroaryl, —C(O)N($R^{10}$)$_2$ or —C(=NCN)N($R^{10}$)$_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —OR$^{10}$, —S(O)$_t$R$^{10}$ (where t is 0, 1 or 2), —C(O)OR$^{10}$, —C(O)R$^{10}$ or —C(O)N($R^{10}$)$_2$; each $R^7$ is independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N($R^{10}$)$_2$; each $R^9$ is independently hydrogen, alkyl, halo, haloalkyl or —OR$^{10}$; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1 or 2; $R^1$ is —C($R^9$)$_2$—; $R^2$ is C($R^9$); $R^3$ is hydrogen or optionally substituted aralkyl; $R^4$ is optionally substituted N-heteroaryl; each $R^5$ is independently hydrogen, halo or haloalkyl; each $R^6$ is independently hydrogen, halo, haloalkyl or cyano; each $R^7$ is independently hydrogen, alkyl, halo or haloalkyl; each $R^9$ is independently hydrogen, alkyl, halo, haloalkyl or —OR$^{10}$; and $R^{10}$ is hydrogen or alkyl.

Another embodiment is a compound of formula (Ia) wherein k is 0, 1 or 2; m is 1; n is 0, 1, or 2; q is 0, 1 or 2; $R^1$ is —C($R^9$)$_2$—; $R^2$ is C($R^9$); $R^3$ is hydrogen; $R^4$ is optionally substituted N-heteroaryl; each $R^5$ is independently hydrogen, halo or haloalkyl; each $R^6$ is independently hydrogen, halo or haloalkyl or cyano; each $R^7$ is independently hydrogen, alkyl, halo or haloalkyl; and each $R^9$ is hydrogen or —OR$^{10}$; and $R^{10}$ is hydrogen or alkyl.

Another embodiment is a compound of formula (Ia) wherein k is 0, 1 or 2; m is 1; n is 0, 1, or 2; q is 0, 1 or 2; $R^1$ is —C($R^9$)$_2$—; $R^2$ is C($R^9$); $R^3$ is hydrogen; $R^4$ is optionally substituted N-heteroaryl selected from optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl; each $R^5$ is independently hydrogen, halo or haloalkyl; each $R^6$ is independently hydrogen, halo or haloalkyl or cyano; each $R^7$ is independently hydrogen, alkyl, halo or haloalkyl; and each $R^9$ is hydrogen or —OR$^{10}$; and $R^{10}$ is hydrogen or alkyl.

Another embodiment is a compound of formula (Ia) selected from:
2,5-difluoro-4-((trans-2-(4-fluorophenyl)cyclohexyl)methoxy)-N-(1,2,4-thiadiazol-5-yl)benzenesulfonamide; and
2,5-difluoro-4-((trans-2-(4-fluorophenyl)-5-methoxycyclohexyl)methoxy)-N-(1,2,4-thiadiazol-5-yl)benzenesulfonamide.

Another embodiment is a compound of formula (Ia) wherein k is 0, 1 or 2; m is 0 or 1; n is 0, 1, or 2; q is 0, 1 or 2; $R^1$ is —O—; $R^2$ is C($R^9$); $R^3$ is hydrogen, alkyl, haloalkyl, optionally substituted aryl or optionally substituted aralkyl; $R^4$ is —C(O)N($R^{10}$)$_2$, —C(=NCN)N($R^{10}$)$_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —OR$^{10}$, —S(O)$_t$R$^{10}$ (where t is 0, 1 or 2), —C(O)OR$^{10}$, —C(O)R$^{10}$ or —C(O)N($R^{10}$)$_2$; each $R^7$ is independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N($R^{10}$)$_2$; each $R^9$ is independently hydrogen, alkyl, halo or haloalkyl; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1 or 2; $R^1$ is —O—; $R^2$ is $C(R^9)$; $R^3$ is hydrogen, alkyl, haloalkyl, optionally substituted aryl or optionally substituted aralkyl; $R^4$ is optionally substituted heterocyclyl selected from N-heterocyclyl, optionally substituted heteroaryl selected from N-heteroaryl, —$C(O)N(R^{10})_2$ or —$C(=NCN)N(R^{10})_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —$S(O)_tR^{10}$ (where t is 0, 1 or 2), —$C(O)OR^{10}$, —$C(O)R^{10}$ or —$C(O)N(R^{10})_2$; each $R^7$ is independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{10})_2$; each $R^9$ is independently hydrogen, alkyl, halo, haloalkyl; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (Ia) wherein k is 0, 1 or 2; m is 1; n is 0, 1, or 2; q is 0, 1 or 2; $R^1$ is —O—; $R^2$ is $C(R^9)$; $R^3$ is hydrogen or optionally substituted aralkyl; $R^4$ is optionally substituted N-heteroaryl; each $R^5$ is independently hydrogen, halo or haloalkyl; each $R^6$ is independently hydrogen, halo, haloalkyl or cyano; each $R^7$ is independently hydrogen, alkyl, halo or haloalkyl; and $R^9$ is independently hydrogen, alkyl, halo, haloalkyl.

Another embodiment is a compound of formula (Ia) wherein k is 0, 1 or 2; m is 1; n is 0, 1, or 2; q is 0, 1 or 2; $R^1$ is —O—; $R^2$ is $C(R^9)$; $R^3$ is hydrogen; $R^4$ is optionally substituted N-heteroaryl selected from optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl; each $R^5$ is independently hydrogen, halo or haloalkyl; each $R^6$ is independently hydrogen, halo or haloalkyl or cyano; each $R^7$ is independently hydrogen, alkyl, halo or haloalkyl; and $R^9$ is independently hydrogen.

Another embodiment is a compound of formula (Ia) which is 2,5-difluoro-4-((trans-4-(4-fluorophenyl)tetrahydro-2H-pyran-3-yl)methoxy)-N-(1,2,4-thiadiazol-5-yl)benzenesulfonamide.

Another embodiment is a compound of formula (I) wherein k is 0, 1 or 2; m is 0or 1; n is 0, 1, or 2; q is 0, 1 or 2; A is —O—;

is aryl; $R^1$ is —$N(R^{10})$—; $R^2$ is $C(R^9)$; $R^3$ is hydrogen, alkyl, haloalkyl, optionally substituted aryl or optionally substituted aralkyl; $R^4$ is —$C(O)N(R^{10})_2$, —$C(=NCN)N(R^{10})_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —$S(O)_tR^{10}$ (where t is 0, 1 or 2), —$C(O)OR^{10}$, —$C(O)R^{10}$ or —$C(O)N(R^{10})_2$; each $R^7$ is independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{10})_2$; $R^8$ is a direct bond; each $R^9$ is independently hydrogen, alkyl, halo or haloalkyl; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (I) wherein k is 0, 1 or 2; m is 1; n is 0, 1, or 2; q is 0, 1 or 2; A is —O—;

is phenyl; $R^1$ is —$N(R^{10})$—; $R^2$ is $C(R^9)$; $R^3$ is hydrogen, alkyl, haloalkyl, optionally substituted aryl or optionally substituted aralkyl; $R^4$ is —$C(O)N(R^{10})_2$, —$C(=NCN)N(R^{10})_2$, optionally substituted heterocyclyl or optionally substituted heteroaryl, where the heterocyclyl is N-heterocyclyl and the heteroaryl is N-heteroaryl; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —$OR^{10}$, —$S(O)_tR^{10}$ (where t is 0, 1 or 2), —$C(O)OR^{10}$, —$C(O)R^{10}$ or —$C(O)N(R^{10})_2$; each $R^7$ is independently hydrogen, alkyl, halo, haloalkyl, —$OR^{10}$, —$S(O)_tR^{10}$ (where t is 0, 1 or 2), —$C(O)OR^{10}$, —$C(O)R^{10}$ or —$C(O)N(R^{10})_2$; $R^8$ is a direct bond; each $R^9$ is independently hydrogen, alkyl, halo or haloalkyl; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (I) wherein k is 0, 1 or 2; m is 1; n is 0, 1, or 2; q is 0, 1 or 2; A is —O—;

is phenyl; $R^1$ is —$N(R^{10})$—; $R^2$ is $C(R^9)$; $R^3$ is hydrogen or optionally substituted aralkyl; $R^4$ is optionally substituted N-heteroaryl; each $R^5$ is independently hydrogen, halo or haloalkyl; each $R^6$ is independently hydrogen, halo, haloalkyl or cyano; each $R^7$ is independently hydrogen, alkyl, halo or haloalkyl; $R^8$ is a direct bond; each $R^9$ is independently hydrogen, alkyl, halo, haloalkyl; and each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl.

Another embodiment is a compound of formula (I) wherein k is 0, 1 or 2; m is 1; n is 0, 1, or 2; q is 0, 1 or 2; A is —O—;

is phenyl; $R^1$ is —N($R^{10}$)—; $R^2$ is C($R^9$); $R^3$ is hydrogen; $R^4$ is optionally substituted N-heteroaryl selected from optionally substituted thiadiazolyl, optionally substituted tetrazolyl, optionally substituted isoxazolyl, optionally substituted thiazolyl, optionally substituted pyrimidinyl, optionally substituted pyridinyl, CT optionally substituted pyridazinyl; each $R^5$ is independently hydrogen, halo or haloalkyl; each $R^6$ is independently hydrogen, halo or haloalkyl or cyano; each $R^7$ is independently hydrogen, alkyl, halo or haloalkyl; $R^8$ is a direct bond; each $R^9$ is independently hydrogen; and each $R^{10}$ is independently hydrogen or alkyl.

Another embodiment is a compound of formula (I) which is 2,5-difluoro-4-((trans-4-(4-fluorophenyl)piperidin-3-yl)oxy)-N-(1,2,4-thiadiazol-5-yl)benzenesulfonamide.

Another embodiment is a compound of formula (I) wherein k is 0, 1, 2, 3 or 4; m is 0, 1 or 2; n is 0, 1, 2, 3, 4 or 5; q is 0, 1, 2, 3, 4, 5 or 6; A is —O— or —S—;

is heteroaryl; $R^1$ is —O—, —C($R^9$)$_2$—, —C(O$R^{10}$)—, —C($R^9$)[N($R^{10}$)$_2$]-, —C($R^9$)[N($R^{10}$)$_2$]-, —N($R^{10}$)—, —N($R^{11}$)— or —S(O)$_t$ (where t is 0, 1 or 2); $R^2$ is C($R^9$) or N; $R^3$ is hydrogen, alkyl, haloalkyl, optionally substituted aryl or optionally substituted aralkyl; $R^4$ is optionally substituted heterocyclyl, optionally substituted heteroaryl, —C(O)N($R^{10}$)$_2$ or —C(=NCN)N($R^{10}$)$_2$; or $R^3$ and $R^4$, together with the nitrogen to which they are both attached, form an optionally substituted N-heterocyclyl or optionally substituted N-heteroaryl; each $R^5$ and each $R^6$ are independently hydrogen, alkyl, halo, haloalkyl, nitro, cyano, —O$R^{10}$, —S(O)$_t R^{10}$ (where t is 0, 1 or 2), —C(O)O$R^{10}$, —C(O)$R^{10}$ or —C(O)N($R^{10}$)$_2$; each $R^7$ is independently hydrogen, alkyl, halo, haloalkyl, —O$R^{10}$, —S(O)$_t R^{10}$ (where t is 0, 1 or 2), —C(O)O$R^{10}$, —C(O)$R^{10}$ or —C(O)N($R^{16}$)$_2$; or any two $R^7$'s on the same carbon may form an oxo and the other $R^7$'s, if present, are independently hydrogen, alkyl, halo, haloalkyl, —O$R^{10}$, —S(O)$_t R^{10}$ (where t is 0, 1 or 2), —C(O)O$R^{10}$, —C(O)$R^{10}$ or —C(O)N($R^{10}$)$_2$; or any two $R^7$'s on different carbons may form an optionally substituted straight or branched alkylene chain optionally containing one or more heteroatoms, and the other $R^7$'s, if present, are independently hydrogen, alkyl, halo, haloalkyl, —O$R^{10}$, —S(O)$_t R^{10}$ (where t is 0, 1 or 2), —C(O)O$R^{10}$, —C(O)$R^{10}$ or —C(O)N($R^{10}$)$_2$; $R^8$ is a direct bond or an optionally substituted straight or branched alkylene chain; each $R^9$ is independently hydrogen, alkyl, halo, haloalkyl, —O$R^{10}$, —N($R^{10}$)$_2$, —N($R^{11}$)$_2$, —S(O)$_t R^{10}$ (where t is 0, 1 or 2), —C(O)O$R^{10}$, —C(O)$R^{10}$ or —C(O)N($R^{10}$)$_2$; each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each $R^{11}$ is independently —C(O)$R^{10}$; —C(O)O$R^{10}$, —C(O)N($R^{10}$)$_2$, —S(O)$_p R^{10}$ (where p is 1 or 2) or —S(O)$_p$N($R^{10}$)$_2$ (where p is 1 or 2).

Another embodiment of the invention is a compound of formula (I), as described above in the Summary of the Invention and the above embodiments, wherein

and $R^8$ are in the relative trans configuration, which is the preferable configuration for compounds of formula (I) as disclosed herein.

Another embodiment of the invention is a compound of formula (I), as described above in the Summary of the Invention and the above embodiments, wherein

and $R^8$ are in the relative cis configuration.

Another embodiment of the invention is a compound of formula (Ia), as described in the above embodiments, having the following relative trans configuration:

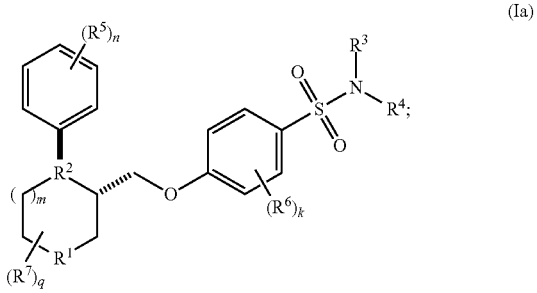

wherein k, m, n, q, $R^1$, $R^2$, $R^3$, $R^4$, $R^5$, $R^6$ and $R^7$ are as described above for compounds of formula (Ia).

Another embodiment of the invention is a compound of formula (I), as described above in the Summary of the Invention and the above embodiments, wherein

is phenyl and at least one $R^5$ is halo, preferably fluoro or chloro, in the para position.

Another embodiment of the invention is a compound of formula (I), wherein:

k is 0, 1, 2, 3 or 4;

m is 0, 1 or 2;

n is 0, 1, 2, 3, 4 or 5;

q is 0, 1, 2, 3, 4, 5 or 6;

A is —O— or —S—;

is aryl or N-heteroaryl;

R$^1$ is —O—, —C(R$^9$)$_2$—, —N(R$^{10}$)—, —N(R$^{11}$)— or —S(O)$_t$ (where t is 0, 1 or 2);

R$^2$ is C(R$^9$) or N;

R$^3$ is hydrogen, alkyl, haloalkyl, optionally substituted aryl or optionally substituted aralkyl;

or R$^3$ is a direct bond to R$^4$;

R$^4$ is optionally substituted alkyl, optionally substituted heterocyclyl, optionally substituted heteroaryl, —C(O)N(R$^{10}$)$_2$ or —C(=NCN)N(R$^{10}$)$_2$;

or R$^3$ and R$^4$, together with the nitrogen to which they are both attached, form an optionally substituted N-heterocyclyl or optionally substituted N-heteroaryl;

each R$^5$ and each R$^6$ are independently hydrogen, alkyl, halo, haloalkyl, nitro, cyano, -OR$^{10}$ —S(O)$_t$R$^{10}$ (where t is 0, 1 or 2), —C(O)OR$^{10}$, —C(O)R$^{10}$ or —C(O)N(R$^{10}$)$_2$;

each R$^7$ is independently hydrogen, alkyl, halo, haloalkyl, OR$^{10}$, —S(O)$_t$R$^{10}$ (where t is 0, 1 or 2), —C(O)OR$^{10}$, —C(O)R$^{10}$ or —C(O)N(R$^{10}$)$_2$;

or any two R$^7$'s on the same carbon may form an oxo and the other R$^7$'s are independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$;

or any two R$^7$'s on different carbons may form an optionally substituted straight or branched alkylene chain optionally containing one or more heteroatoms, and the other R$^7$'s, if present, are independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$, R$^8$ is a direct bond or an optionally substituted straight or branched alkylene chain each R$^9$ is independently hydrogen, alkyl, halo, haloalkyl, —OR$^4$, —N(R$^{10}$)$_2$, —N(R$^{11}$)$_2$, —S(O)$_t$R$^{10}$ (where t is 0, 1 or 2), —C(O)OR$^{10}$, —C(O)R$^{10}$ or —C(O)N(R$^{10}$)$_2$;

each R$^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each R$^{11}$ is independently —C(O)R$^{10}$; —C(O)OR$^{10}$, —C(O)N(R$^{10}$)$_2$, —S(O)$_p$R$^{10}$ (where p is 1 or 2) or —S(O)$_p$N(R$^{10}$)$_2$ (where p is 1 or 2); as individual stereoisomers, enantiomers or tautomers thereof or mixtures thereof; or as pharmaceutically acceptable salts, solvates or prodrugs thereof.

Another embodiment of the invention is a compound of formula (Ia), as described above in the Summary of the Invention and the above embodiments, wherein at least one R$^5$ is halo, preferably fluoro or chloro, in the para position.

Another embodiment of the invention is a compound of formula (I), as described above in the Summary of the Invention and the above embodiments, wherein R$^2$ is C(R$^9$) where R$^9$ is hydrogen.

Another embodiment of the invention is a compound of formula (Ia), as described above in the Summary of the Invention and the above embodiments, wherein R$^1$ is —N(R$^{10}$)— or —N(R$^{11}$)—.

Another embodiment of the invention is a compound of formula (I), as described above in the Summary of the Invention and the above embodiments, wherein R$^8$ is methylene.

Another embodiment of the invention is a compound of formula (I), as described above in the Summary of the Invention and the above embodiments, wherein R$^8$ is a direct bond.

Another embodiment of the invention is a compound of formula (I), as described above in the Summary of the Invention and the above embodiments, wherein A is —O—.

Another embodiment of the invention is a compound of formula (I), as described above in the Summary of the Invention and the above embodiments, wherein A is —S—.

Another embodiment of the invention is a compound of formula (I) or a compound of formula (Ia), as described above in the Summary of the Invention and the above embodiments, wherein R$^4$ is optionally substituted N-heteroaryl selected from optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl.

Another embodiment of the invention is a method of treating a disease or a condition in a mammal, preferably a human, wherein the disease or condition is selected from the group consisting of pain, depression, cardiovascular diseases, respiratory diseases, and psychiatric diseases, and combinations thereof, and wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is wherein the disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, peripheral nerve injury, and combinations thereof.

Another embodiment of this embodiment is wherein the disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke or neural trauma, tachy-arrhythmias, atrial fibrillation and ventricular fibrillation.

Another embodiment of the invention is a method of treating or ameliorating, but not preventing, pain in a mammal, wherein the method comprises administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is a method wherein the pain is selected from the group consisting of neuropathic pain, inflammatory pain, visceral pain, cancer pain, chemotherapy pain, trauma pain, surgical pain, post-surgical pain, childbirth pain, labor pain, dental pain, chronic pain, persistent pain, peripherally mediated pain, centrally mediated pain, chronic headache, migraine headache, sinus headache, tension headache, phantom limb pain, peripheral nerve injury, trigeminal neuralgia, post-herpetic neuralgia, eudynia, familial erythromelalgia, primary erythromelalgia, familial rectal pain or fibromyalgia, and combinations thereof.

Another embodiment of this embodiment is a method wherein the pain is associated with a disease or condition selected from HIV, HIV treatment induced neuropathy, heat sensitivity, tosarcoidosis, irritable bowel syndrome, Crohns disease, multiple sclerosis, amyotrophic lateral sclerosis, diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, neurogenic bladder, ulcerative colitis, cancer, epilepsy, partial and general tonic seizures, restless leg syndrome, arrhythmias, ischaemic conditions caused by stroke or neural trauma, tachy-arrhythmias, atrial fibrillation and ventricular fibrillation.

Another embodiment of the invention is the method of treating pain in a mammal, preferably a human, by the inhibition of ion flux through a voltage-dependent sodium channel in the mammal, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating pruritus in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating cancer in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of decreasing ion flux through a voltage-dependent sodium channel in a cell in a mammal, wherein the method comprises contacting the cell with an embodiment of a compound of the invention, as set forth above, as a stereoisomer, enantiomer or tautomer thereof or mixtures thereof, or a pharmaceutically acceptable salt, solvate or prodrug thereof.

Another embodiment of the invention is the method of selectively inhibiting a first voltage-gated sodium channel over a second voltage-gated sodium channel in a mammal, wherein the method comprises administering to the mammal an inhibitory amount of a compound of formula (I), as described above in the Summary of the Invention, or an embodiment of a compound of formula (I), as described above, as a stereoisomer, enantiomer or tautomer thereof or mixtures thereof; or a pharmaceutically acceptable salt, solvate or prodrug thereof.

Another embodiment of the invention is the method of selectively inhibiting $Na_v1.7$ in a mammal or a mammalian cell as compared to $Na_v1.5$, wherein the method comprises administering to the mammal in need thereof an inhibitory amount of a compound of formula (I), as described above in the Summary of the Inveniton, or an embodiment of a compound of formula (I), as described above, as a stereoisomer, enantiomer or tautomer thereof or mixtures thereof, or a pharmaceutically acceptable salt, solvate or prodrug thereof, or a pharmaceutical composition comprising an inhibitory amount of a compound of formula (I), as described above in the Summary of the Invention, as a stereoisomer, enantiomer or tautomer thereof or mixtures thereof, or a pharmaceutically acceptable salt, solvate or prodrug thereof, and a pharmaceutically acceptable excipient.

Another embodiment of the invention is a method of using the compounds of formula (I) as standards or controls in in vitro or in vivo assays in determining the efficacy of test compounds in modulating voltage-dependent sodium channels.

In another embodiment of the invention, the compounds of formula (I) are isotopically-labeled by having one or more atoms therein replaced by an atom having a different atomic mass or mass number. Such isotopically-labeled (i.e., radiolabelled) compounds of formula (I) are considered to be within the scope of this invention. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the sodium channels, or binding affinity to pharmacologically important site of action on the sodium channels, particularly $Na_v1.7$. Certain isotopically-labeled compounds of formula (I), for example, those incorporating a radioactive isotope, are useful in drug and/or substrate tissue distribution studies. The radioactive isotopes tritium, i.e. $^3H$, and carbon-14, i.e., $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Specific embodiments of the compounds of the invention are described in more detail below in the Preparation of the Compounds of the Invention.

Utility and Testing of the Compounds of the Invention

The compounds of the invention modulate, preferably inhibit, ion flux through a voltage-dependent sodium channel in a mammal, especially in a human. Any such modulation, whether it be partial or complete inhibition or prevention of ion flux, is sometimes referred to herein as "blocking" and corresponding compounds as "blockers" or "inhibitors". In general, the compounds of the invention modulate the activity of a sodium channel downwards by inhibiting the voltage-dependent activity of the sodium channel, and/or reduce or prevent sodium ion flux across a cell membrane by preventing sodium channel activity such as ion flux.

The compounds of the invention inhibit the ion flux through a voltage-dependent sodium channel. Preferably, the compounds are state or frequency dependent modifers of the sodium channels, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestèle, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention are sodium channel blockers and are therefore useful for treating diseases and conditions in mammals, preferably humans, and other organisms, including all those human diseases and conditions which are the result of aberrant voltage-dependent sodium channel biological activity or which may be ameliorated by modulation of voltage-dependent sodium channel biological activity. In particular, the compounds of the invention, i.e., the compounds of formula (I), as set forth above in the Summary of the Invention, as individual stereoisomers, enantiomers or tautomers thereof or mixtures thereof; or as pharmaceutically acceptable salts, solvates or prodrugs thereof, are useful for treating diseases and conditions in mammals, preferably humans, which are the result of aberrant voltage-dependent $Na_v1.7$ biological activity or which may be ameliorated by the modulation, preferably the inhibition, of $Na_v1.7$ biological activity. Preferably the compounds of the invention selectively inhibit $Na_v1.7$ over $Na_v1.5$.

As defined herein, a sodium channel-mediated disease or condition refers to a disease or condition in a mammal, preferably a human, which is ameliorated upon modulation of the sodium channel and includes, but is not limited to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

The present invention therefore relates to compounds, pharmaceutical compositions and methods of using the compounds and pharmaceutical compositions for the treatment of sodium channel-mediated diseases in mammals, preferably humans and preferably diseases and conditions related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome, by administering to a mammal, preferably a human, in need of such treatment an effective amount of a sodium channel blocker modulating, especially inhibiting, agent.

Accordingly, the present invention provides a method for treating a mammal for, or protecting a mammal from developing, a sodium channel-mediated disease, especially pain, comprising administering to the mammal, especially a human, in need thereof, a therapeutically effective amount of a compound of the invention or a pharmaceutical composition comprising a therapeutically effective amount of a compound of the invention wherein the compound modulates the activity of one or more voltage-dependent sodium channels.

The general value of the compounds of the invention in mediating, especially inhibiting, the sodium channel ion flux can be determined using the assays described below in the Biological Assays section. Alternatively, the general value of the compounds in treating conditions and diseases in humans may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physiopathological conditions observed in humans can be modeled allowing the evaluation of pharmacotherapies.

In rat models of peripheral nerve injury, ectopic activity in the injured nerve corresponds to the behavioural signs of pain. In these models, intravenous application of the sodium channel blocker and local anesthetic lidocaine can suppress the ectopic activity and reverse the tactile allodynia at concentrations that do not affect general behaviour and motor function (Mao, J. and Chen, L. L, *Pain* (2000), 87:7-17). Allimetric scaling of the doses effective in these rat models, translates into doses similar to those shown to be efficacious in humans (Tanelian, D. L. and Brose, W. G., *Anesthesiology* (1991), 74(5):949-951). Furthermore, Lidoderm®, lidocaine applied in the form of a dermal patch, is currently an FDA approved treatment for post-herpetic neuralgia (Devers, A. and Glaler, B. S., *Clin. J. Pain* (2000), 16(3):205-8).

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g., opiate, benzodiazepine, amphetamine, cocaine, alcohol, butane inhalation), Alzheimer, dementia, age-related memory impairment, Korsakoff syndrome, restenosis, urinary dysfunction, incontinence, Parkinson's disease, cerebrovascular ischemia, neurosis, gastrointestinal disease, sickle cell anemia, transplant rejection, heart failure, myocardial infarction, reperfusion injury, intermittant claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congentia, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, hypothyroidism, bipolar depression, anxiety, schizophrenia, sodium channel toxin related illnesses, familial erythromelalgia, primary erythromelalgia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), multiresistant seizures, seizure prophylaxis (antiepileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, reflex sympathetic dystrophy, brachial plexus avulsion, neurogenic bladder, acute pain (e.g., musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

Sodium channel blockers have clinical uses in addition to pain. The present invention therefore also relates to compounds, pharmaceutical compositions and methods of using the compounds and pharmaceutical compositions for the treatment of diseases or conditions such as cancer and pruritus (itch).

Pruritus, commonly known as itch, is a common dermatological condition. While the exact causes of pruritus are complex and incompletely understood, there has long been evidence that itch involves sensory neurons, especially C fibers, similar to those that mediate pain (Schmelz, M., et al., *J. Neurosci*. (1997), 17: 8003-8). In particular, it is believed that sodium influx through voltage-gated sodium channels is essential for the propagation of itch sensation from the skin. Transmission of the itch impulses results in the unpleasant sensation that elicits the desire or reflex to scratch.

Multiple causes and electrical pathways for eliciting itch are known. In humans, pruritis can be elicited by histamine or PAR-2 agonists such as mucunain that activate distinct populations of C fibers (Namer, B., et al., *J. Neurophysiol*. (2008), 100: 2062-9). A variety of neurotrophic peptides are known to mediate itch in animal models (Wang, H., and Yosipovitch, G., International Journal of Dermatology (2010), 49: 1-11). Itch can also be elicited by opioids, evidence of distinct pharmacology from that of pain responses.

There exists a complex interaction between itch and pain responses that arises in part from the overlapping sensory input from the skin (Ikoma, A., et al., *Arch. Dermatol*. (2003), 139: 1475-8) and also from the diverse etiology of both pain and pruritis. Pain responses can exacerbate itching by enhancing central sensitization or lead to inhibition of painful scratching. Particularly severe forms of chronic itch occur when pain responses are absent, as in the case of post-herpetic itch (Oaklander, A. L., et al., *Pain* (2002), 96: 9-12).

The compounds of the invention can also be useful for treating pruritus. The rationale for treating itch with inhibitors of voltage-gated sodium channels, especially $Na_v1.7$, is as follows:

1) The propagation of electrical activity in the C fibers that sense pruritinergic stimulants requires sodium entry through voltage-gated sodium channels.

2) $Na_v1.7$ is expressed in the C fibers and kerotinocytes in human skin (Zhao, P., et al., *Pain* (2008), 139: 90-105).

3) A gain of function mutation of $Na_v1.7$ (L858F) that causes erythromelalgia also causes chronic itch (Li, Y., et al., *Clinical and Experimental Dermatology* (2009), 34: e313-e4).

4) Chronic itch can be alleviated with treatment by sodium channel blockers, such as the local anesthetic lidocaine (Oaklander, A. L., et al., *Pain* (2002), 96: 9-12; Villamil, A. G., et al., *The American Journal of Medicine* (2005), 118: 1160-3). In these reports, lidocaine was effective when administered either intravenously or topically (a Lidoderm patch). Lidocaine can have multiple activities at the plasma concentrations achieved when administered systemically, but when administered topically, the plasma concentrations are only about 1 μM (Center for Drug Evaluation and Research NDA 20-612). At these concentrations, lidocaine is selective for sodium channel block and inhibits spontaneous electrical activity in C fibers and pain responses in animal models (Xiao, W. H., and Bennett, G. J. *Pain* (2008), 137: 218-28).

The types of itch or skin irritation, include, but are not limited to:

a) psoriatic pruritus, itch due to hemodyalisis, aguagenic pruritus, and itching caused by skin disorders (e.g., contact dermatitis), systemic disorders, neuropathy, psychogenic factors or a mixture thereof;

b) itch caused by allergic reactions, insect bites, hypersensitivity (e.g., dry skin, acne, eczema, psoriasis), inflammatory conditions or injury;

c) itch associated with vulvar vestibulitis; and d) skin irritation or inflammatory effect from administration of another therapeutic such as, for example, antibiotics, antivirals and antihistamines.

The compounds of the invention are also useful in treating certain cancers, such as hormone sensitive cancers, such as prostate cancer (adenocarcinoma), breast cancer, ovarian cancer, testicular cancer and thyroid neoplasia, in a mammal, preferably a human. The voltage gated sodium channels have been demonstrated to be expressed in prostate and breast cancer cells. Up-regulation of neonatal $Na_v1.5$ occurs as an integral part of the metastatic process in human breast cancer and could serve both as a novel marker of the metastatic phenotype and a therapeutic target (*Clin. Cancer Res.* (2005), August 1; 11(15): 5381-9). Functional expression of voltage-gated sodium channel alpha-subunits, specifically $Na_v1.7$, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (*Prostate Cancer Prostatic Dis.*, 2005; 8(3):266-73). See also Diss, J. K. J., et al., *Mol. Cell. Neurosci.* (2008), 37:537-547 and Kis-Toth, K., et al., *The Journal of Immunology* (2011), 187:1273-1280.

The present invention readily affords many different means for identification of sodium channel modulating agents that are useful as therapeutic agents. Identification of modulators of sodium channel can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., *J. General Physiology* (1983), 83:613-642, and Leuwer, M., et al., *Br. J. Pharmacol* (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they alleviate pain, especially chronic pain or other conditions such as cancer and pruritus (itch) with minimal adverse events. The assays described below in the Biological Assays Section are useful in assessing the biological activity of the instant compounds.

Typically, the efficacy of a compound of the invention is expressed by its $IC_{50}$ value ("Inhibitory Concentration—50%"), which is the measure of the amount of compound required to achieve 50% inhibition of the activity of the target sodium channel over a specific time period. For example, representative compounds of the present invention have demonstrated $IC_{50}$'s ranging from less than 100 nanomolar to less than 10 micromolar in the patch voltage clamp $Na_v1.7$ electrophysiology assay described herein.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity, preferably $Na_v1.7$ activity, in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention, as set forth above in the Summary of the Invention, as stereoisomers, enantiomers, tautomers thereof or mixtures thereof, or pharmaceutically acceptable salts, solvates or prodrugs thereof, and/or the pharmaceutical compositions described herein which comprise a pharmaceutically acceptable excipient and one or more compounds of the invention, as set forth above in the Summary of the Invention, as a stereoisomer, enantiomer or tautomer thereof or mixtures thereof, or a pharmaceutically acceptable salt, solvate or prodrug thereof, can be used in the preparation of a medicament for the treatment of sodium channel-mediated disease or condition in a mammal.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier, excipient or diluent and in an amount effective to modulate, preferably inhibit, ion flux through a voltage-dependent sodium channel to treat sodium channel mediated diseases, such as pain, when administered to an animal, preferably a mammal, most preferably a human patient.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer.

In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., *The Merck Manual*, 16$^{th}$ edition, Merck and Co., Rahway, N.J., 1992; Goodmanetna., eds., *Goodman and Cilman's The Pharmacological Basis of Therapeutics*, 10$^{th}$ edition, Pergamon Press, Inc., Elmsford, N.Y., (2001); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985); Osolci al., eds., *Remington's Pharmaceutical Sciences*, 18$^{th}$ edition, Mack Publishing Co., Easton, Pa. (1990); Katzung, *Basic and Clinical Pharmacology*, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as desscribed in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transportionized drugs into and through body tissues). Those skilled in the art would combine the best suited excipients with the compound for safe and effective intra-occular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the invention may be usefully combined with one or more other compounds of the invention or one or more other therapeutic agent or as any combination thereof, in the treatment of sodium channel-mediated diseases and conditions. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetomeniphen, salicylates (e.g., aspirin);

nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (αR,9R)-7-[3,5-bis(trifluoromethyl)benzyl)]-8,9,10,11-tetrahydro-9-methyl-5-(4-methylphenyl)-7H-[1,4]diazocino[2,1g][1,7]-naphthyridine-6-13-dione (TAK-637), 5-[[2R,3S)-2-[(1R)-1-[3,5-bis(trifluoromethylphenyl)ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buproprion, buprorion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT$_3$ antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenyloin;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressants such as mirtazapine, topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotinc) analgesics;

alpha-2-delta ligands;

prostaglandin E2 subtype antagonists;

leukotriene B4 antagonists;

5-lipoxygenase inhibitors; and

5-HT$_3$ antagonists.

Sodium channel-mediated diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

Kits-of-Parts

The present invention also provides kits that contain a pharmaceutical composition which includes one or more compounds of the invention. The kit also includes instructions for the use of the pharmaceutical composition for modulating the activity of ion channels, for the treatment of pain, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds of the Invention

The following Reaction Schemes illustrate methods to make compounds of this invention, i.e., compounds of formula (I):

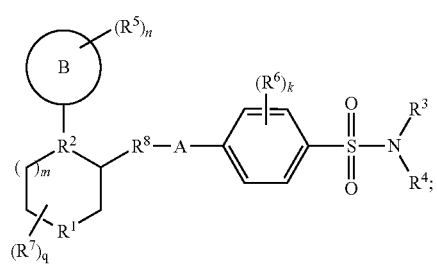

(I)

wherein k, m, n, q, A, $R^1$, $R^2$, $R^3$, $R^4$, $R^5$, $R^6$, $R^7$ and $R^8$ are as described above for compounds of formula (I) in the Summary of the Invention, as a stereoisomer, enantiomer or tautomer thereof or mixtures thereof; or a pharmaceutically acceptable salt, solvate or prodrug thereof.

It is also understood that one skilled in the art would be able to make the compounds of the invention by similar methods or by methods known to one skilled in the art. It is also understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure*, 6th edition (Wiley, 2007)) or prepared as described herein.

It is also understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Greene's Protective Groups in Organic Synthesis* (2006), 4$^{th}$ Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The compounds of formula (I) contain at least one asymmetric carbon atom and thus can exist as racemates, enantiomers and/or diastereoisomers. Specific enantiomers or diastereoisomers may be prepared by utilizing the appropriate chiral starting material. Alternatively, diastereoisomeric mixtures or racemic mixtures of compounds of formula (I) may be resolved into their respective enantiomers or diastereoisomers. Methods for resolution of diastereoisomeric mixtures or racemic mixtures of the compounds of formula (I), as described herein, or intermediates prepared herein, are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g., preferential crystallization, preferential crystallization in the presence of additives), asymmetric transformation of racemates, chemical separation (e.g., formation and separation of diastereomers such as diastereomeric salt mixtures or the use of other resolving agents; separation via complexes and inclusion compounds), kinetic resolution (e.g., with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, *Analytical Chemistry*, 2002, 2863-2872).

The following Reaction Schemes illustrates methods to make compounds of this invention. It is understood that one skilled in the art would be able to make these compounds by similar methods or by methods known to one skilled in the art. It is also understood that one skilled in the art would be able to make in a similar manner as described below other compounds of formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *March's Advanced*

*Organic Chemistry: Reactions, Mechanisms, and Structure,* 6th edition (Wiley, 2007)) or prepared as described herein.

Preparation of Compounds of Formula (I)

In general, compounds of formula (I), as described above in the Summary of the Invention, can be can be synthesized following the general procedure described below in Reaction Scheme 1 where k, m, n, q, A, $R^1$, $R^2$, $R^3$, $R^4$, $R^5$, $R^6$, $R^7$ and $R^8$ are as described above for compounds of formula (I) in the Summary of the Invention, $R^{12}$ is alkyl and X is halo:

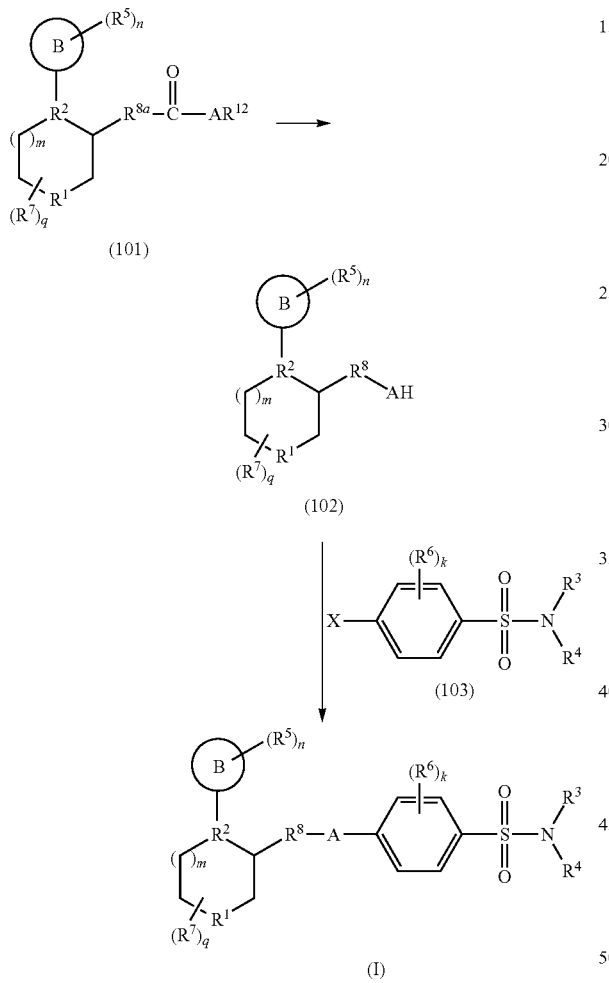

Compounds of formula (101), formula (102) and formula (103) are commercially available or can be prepared according to methods known to one skilled in the art or by the methods disclosed herein.

In general, compounds of formula (I) are prepared as described above in Reaction Scheme 1 by first reducing the ester or thioester compound of formula (101) by an appropriating reducing agent, such as, but not limited to, $LiBH_4$, under standard reaction conditions, such as, but not limited to, at a temperature of between about 0° C. and ambient temperature in a polar aprotic solvent, such as, but not limited to, tetrahydrofuran, to produce the compound of formula (102). The compound of formula (102) is then treated with a compound of formula (103) under standard reaction conditions, such as, but not limited to, the use of a polar aprotic solvent, such as, but not limited to, tetrahydrofuran, in the presence of a base, such as, but not limited to, lithium bis(trimethylsilyl)amide, at a temperature of between about –78° C. and ambient temperature, for about 10 to 20 hours, to produce the compound of formula (I), which can be isolated from the reaction mixture by standard isolation techniques.

A specific method of preparing the compounds of formula (I) as set forth above in Reaction Scheme 1 is illustrated below in Reaction Scheme 1A for the preparation of compounds of formula (Ia), which are compounds of formula (I) where

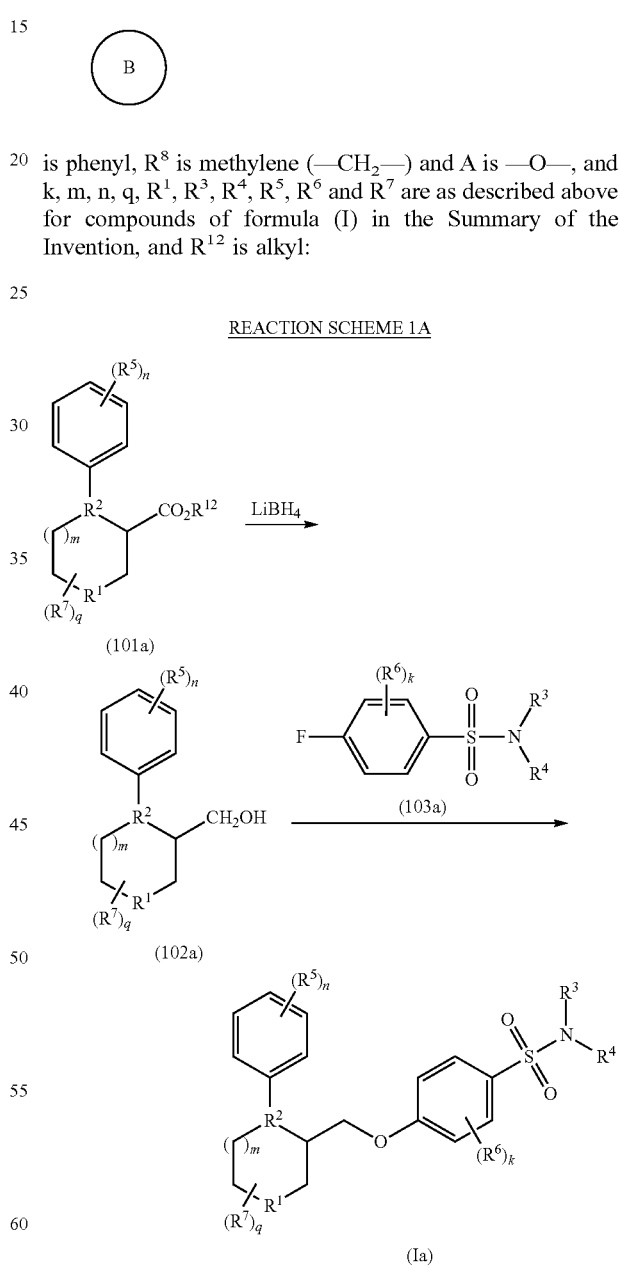

is phenyl, $R^8$ is methylene (—$CH_2$—) and A is —O—, and k, m, n, q, $R^1$, $R^3$, $R^4$, $R^5$, $R^6$ and $R^7$ are as described above for compounds of formula (I) in the Summary of the Invention, and $R^{12}$ is alkyl:

Compounds of formula (101a), formula (102a) and formula (103a) are commercially available or can be prepared according to methods known to one skilled in the art or by the methods disclosed herein.

The following Examples, which are directed to the synthesis of intermediates or starting materials used in the synthesis of the compounds of the invention and to the synthesis of the compounds of the invention; and the following Biological Examples are provided as a guide to assist in the practice of the invention, and are not intended as a limitation on the scope of the invention.

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

EXAMPLE 1

Synthesis of trans-tert-butyl 4-(4-chlorophenyl)-3-(hydroxymethyl)piperidine-1-carboxylate

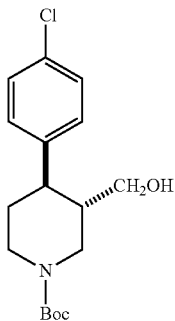

A. To a stirred solution of trans-methyl 4-(4-chlorophenyl)-1-methylpiperidine-3-carboxylate (2.70 g, 10.1 mmol, prepared according to Kozikowski, A. P. et. al. *J. Med. Chem.* 1998, 41, 1962) in 1,2-dichloroethane (50 mL) was added 1-chloroethyl chloroformate (1.4 mL, 13 mmol) at 0° C. The reaction mixture was stirred for 30 minutes at 0° C., and then heated at reflux for 4 h. The residue obtained after concentration in vacuo was dissolved in methanol (50 mL), and the resulting mixture was heated at reflux for 18 h and concentrated in vacuo. The residue was dissolved in methylene chloride (50 mL), and triethylamine (7.0 mL, 50 mmol) and di-tert-butyl dicarbonate (3.30 g, 15.1 mmol) were added. The reaction mixture was stirred at ambient temperature for 20 h and concentrated in vacuo. The residue was diluted with ethyl acetate (200 mL) and washed with saturated sodium bicarbonate solution (50 mL) and brine (50 mL), dried over anhydrous sodium sulfate and filtered. The filtrate was concentrated in vacuo, and the residue was purified by column chromatography (20% ethyl acetate in hexanes) to afford trans-1-tert-butyl 3-methyl 4-(4-chlorophenyl)piperidine-1,3-dicarboxylate in 40% yield (1.40 g) as a colorless oil: $^1$H NMR (300 MHz, CDCl$_3$) δ 7.22 (d, J=8.4 Hz, 2H), 7.08 (d, J=8.4 Hz, 2H), 4.50-4.15 (m, 2H), 3.43 (s, 3H), 2.95-2.58 (m, 4H), 1.80-1.49 (m, 2H), 1.49 (s, 9H).

B. To a stirred solution of trans-1-tert-butyl 3-methyl 4-(4-chlorophenyl)piperidine-1,3-dicarboxylate (1.40 g, 4.0 mmol) in tetrahydrofuran (30 mL) was added methanol (0.24 mL, 5.9 mmol), followed by the addition of lithium borohydride solution (2.0 M in tetrahydrofuran, 5.0 mL, 10.0 mmol) at 0° C. The reaction mixture was stirred at 0° C. for 10 minutes, and then at ambient temperature for 20 h. Saturated ammonium chloride solution (10 mL) was added to the reaction mixture, followed by the addition of ethyl acetate (200 mL). The mixture was washed with brine and concentrated in vacuo. The residue was purified by column chromatography (40% ethyl acetate in hexanes) to afford trans-tert-butyl 4-(4-chlorophenyl)-3-(hydroxymethyl)piperidine-1-carboxylate in 99% yield (1.28 g) as a colorless solid: $^1$H NMR (300 MHz, CDCl$_3$) δ 7.25 (d, J=8.4 Hz, 2H), 7.10 (d, J=8.4 Hz, 2H), 4.40-4.28 (m, 1H), 4.25-4.13 (m, 1H), 3.45-3.37 (m, 1H), 3.29-3.20 (m, 1H), 2.83-2.64 (m, 2H), 2.57-2.46 (m 1H), 1.85-1.53 (m, 3H), 1.46 (s, 9H), 1.11 (br s, 1H).

EXAMPLE 2

Synthesis of trans-tert-butyl 4-(4-fluorophenyl)-3-(hydroxymethyl)piperidine-1-carboxylate

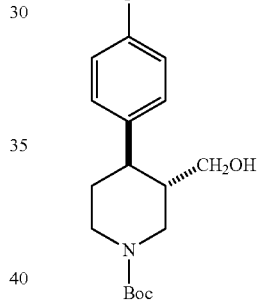

A. Following the procedure as described in Step A of EXAMPLE 1 and making non-critical variations to replace trans-methyl 4-(4-chlorophenyl)-1-methylpiperidine-3-carboxylate with trans-methyl 4-(4-fluorophenyl)-1-methylpiperidine-3-carboxylate (prepared according to the methods disclosed in U.S. Pat. No. 4,007,196), trans-1-tert-butyl 3-methyl 4-(4-fluorophenyl)piperidine-1,3-dicarboxylate was obtained in 62% yield (8.40 g) as a colorless oil: $^1$H NMR (300 MHz, CDCl$_3$) δ 7.16-7.07 (m, 2H), 6.99-6.91 (m, 2H), 4.45-4.12 (m, 2H), 3.42 (s, 3H), 2.95-2.55 (m, 4H), 1.84-1.52 (m, 2H), 1.46 (s, 9H).

B. Following the procedure as described in Step B of EXAMPLE 1 and making non-critical variations to replace trans-1-tert-butyl 3-methyl 4-(4-chlorophenyl)piperidine-1,3-dicarboxylate with trans-1-tert-butyl 3-methyl 4-(4-fluorophenyl)piperidine-1,3-dicarboxylate, trans-tert-butyl 4-(4-fluorophenyl)-3-(hydroxymethyl)piperidine-1-carboxylate was obtained in 65% yield (2.84 g) as a colorless solid: $^1$H NMR (300 MHz, CDCl$_3$) δ 7.15-7.09 (m, 2H), 7.01-6.93 (m, 2H), 4.40-4.08 (m, 2H), 3.45-3.37 (m, 1H), 3.28-3.19 (m, 1H), 2.80-2.63 (m, 2H), 2.57-2.46 (m, 1H), 1.84-1.59 (m, 3H), 1.46 (s, 9H), 1.31 (br s, 1H).

EXAMPLE 3

Synthesis of (3S,4R)-tert-butyl 4-(4-fluorophenyl)-3-(hydroxymethyl)piperidine-1-carboxylate

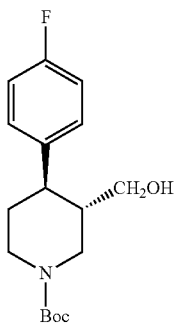 [SMILES: CC(C)(C)OC(=O)N1CC[C@@H](c2ccc(F)cc2)[C@H](CO)C1]

To a stirred solution of ((3S,4R)-4-(4-fluorophenyl)piperidin-3-yl)methanol (1.00 g, 4.8 mmol) in methylene chloride (20 mL), was added triethylamine (1.30 mL, 9.3 mmol) and di-tert-butyl dicarbonate (1.50 g, 6.9 mmol). The resulting reaction mixture was stirred at ambient temperature for 20 h and concentrated in vacuo. The residue was dissolved in ethyl acetate (200 mL) and washed with saturated sodium bicarbonate solution (50 mL) and brine (50 mL); dried over anhydrous sodium sulfate and filtered. The filtrate was concentrated in vacuo, and the residue was purified by column chromatography (30% ethyl acetate in hexanes) to afford (3S,4R)-tert-butyl 4-(4-fluorophenyl)-3-(hydroxymethyl)piperidine-1-carboxylate in 92% yield (1.36 g) as a colorless solid: $^1$H NMR (300 MHz, CDCl$_3$) δ 7.22 (d, J=8.4 Hz, 2H), 7.08 (d, J=8.4 Hz, 2H), 4.50-4.15 (m, 2H), 3.43 (s, 3H), 2.95-2.58 (m, 4H), 1.80-1.49 (m, 2H), 1.49 (s, 9H).

EXAMPLE 4

Synthesis of tert-butyl 3-fluoro-4-(4-fluorophenyl)-3-(hydroxymethyl)piperidine-1-carboxylate

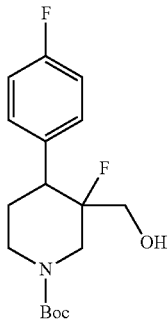

A. To a stirred solution of trans-1-tert-butyl 3-methyl 4-(4-fluorophenyl)piperidine-1,3-dicarboxylate (3.37 g, 10.0 mmol) in tetrahydrofuran (100 mL) was added lithium bis(trimethylsilyl)amide solution (1.0 M in tetrahydrofuran, 12.0 mL, 12.0 mmoL) at 0° C. The reaction mixture was allowed to stir for 1 h at 0° C., followed by the addition of N-fluorobenzenesulfonamide (4.00 g, 12.7 mmol). The stirring was continued for 5 minutes. The cooling bath was removed and the mixture was stirred at ambient temperature for 23 h and concentrated to a volume of about 30 mL. The mixture was diluted with ethyl acetate (300 mL), washed with 10% citric acid solution, water and brine, then concentrated in vacuo. The residue was purified by column chromatography (20% ethyl acetate in hexanes) to afford 1-tert-butyl 3-methyl 3-fluoro-4-(4-fluorophenyl)piperidine-1,3-dicarboxylate in 17% yield (0.61 g) as a colorless oil: $^1$H NMR (300 MHz, CDCl$_3$) δ 7.12-7.08 (m, 2H), 6.91-6.83 (m, 2H), 4.42-4.16 (m, 2H), 3.48 (s, 3H), 3.21-3.04 (m, 2H), 2.85-2.74 (m, 1H), 2.15-2.01 (m, 1H), 1.64-1.57 (m, 1H), 1.39 (s, 9H).

B. Following the procedure as described Step B of EXAMPLE 1 and making non-critical variations to replace trans-1-tert-butyl 3-methyl 4-(4-chlorophenyl)piperidine-1,3-dicarboxylate with 1-tert-butyl 3-methyl 3-fluoro-4-(4-fluorophenyl)piperidine-1,3-dicarboxylate, tert-butyl 3-fluoro-4-(4-fluorophenyl)-3-(hydroxymethyl)piperidine-1-carboxylate was obtained in 66% yield (0.37 g) as a colorless solid: $^1$H NMR (300 MHz, CDCl$_3$) δ 7.23-7.16 (m, 2H), 6.98-6.89 (m, 2H), 4.52-4.17 (m, 2H), 3.45-3.20 (m, 2H), 3.00-2.67 (m, 3H), 2.19-2.07 (m, 1H), 1.66-1.54 (m, 1H), 1.43 (s, 9H).

EXAMPLE 5

Synthesis of trans-tert-butyl 4-(3,4-difluorophenyl)-3-(hydroxymethyl)piperidine-1-carboxylate

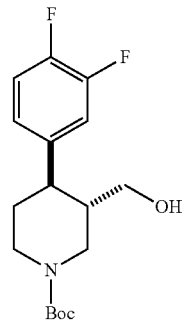

A. To a cooled (−20° C.) solution of 3,4-difluorophenylmagnesium bromide (0.5 M solution in diethyl ether, 179 mL, 89.5 mmol) was added a solution of arecoline (9.85 g, 63.5 mmol) in anhydrous diethyl ether (75 mL) dropwise over 1 h, while maintaining the temperature below −5° C. The reaction mixture was stirred for further 2 h, and poured into saturated ammonium chloride solution (100 mL). The organic layer was separated and the aqueous layer was extracted with diethyl ether (200 mL). The combined organic solution was washed with water and brine, dried over anhydrous sodium sulfate and filtered. The filtrate was concentrated in vacuo. The residue was dissolved in methanol (100 mL), and sodium methoxide (3.10 g, 57.4 mmol) was added. The reaction mixture was heated at reflux for 18 h and concentrated in vacuo. 200 mL of 2.5% hydrochloric acid solution was added to the residue at 0° C. The mixture was extracted with diethyl ether (3×100 mL). The aqueous layer was basified with sodium bicarbonate to pH 9-10 and extracted with diethyl ether (3×200 mL). The combined organic extracts was washed with water, brine, and concentrated in vacuo to afford trans-methyl 4-(3,4-difluorophenyl)-1-methylpiperidine-3-carboxylate in 65% yield (11.10 g) as a colorless oil: MS (ES+) m/z 270.0 (M+1).

B. Following the procedure as described in Step A of EXAMPLE 1 and making non-critical variations to replace trans-methyl 4-(4-chlorophenyl)-1-methylpiperidine-3-carboxylate with trans-methyl 4-(3,4-difluorophenyl)-1-methylpiperidine-3-carboxylate, trans-1-tert-butyl 3-methyl 4-(3,4-difluorophenyl)piperidine-1,3-dicarboxylate was obtained in 31% yield (4.40 g) as a colorless oil: $^1$H NMR (300 MHz, CDCl$_3$) δ 7.09-6.87 (m, 3H), 4.37-4.08 (m, 2H), 3.45 (s, 3H), 3.02-2.56 (m, 4H), 1.82-1.50 (m, 2H), 1.46 (s, 9H).

C. Following the procedure as described in Step B of EXAMPLE 1 and making non-critical variations to replace trans-1-tert-butyl 3-methyl 4-(4-chlorophenyl)piperidine-1,3-dicarboxylate with trans-1-tert-butyl 3-methyl 4-(3,4-difluorophenyl)piperidine-1,3-dicarboxylate, trans-tert-butyl 4-(3,4-difluorophenyl)-3-(hydroxymethyl)piperidine-1-carboxylate was obtained in 61% yield (1.18 g) as a colorless solid: $^1$H NMR (300 MHz, CDCl$_3$) δ 7.11-6.85 (m, 3H), 4.40-4.05 (m, 2H), 3.46-3.37 (m, 1H), 3.28-3.17 (m, 1H), 2.79-2.63 (m, 2H), 2.57-2.46 (m, 1H), 1.80-1.56 (m, 4H), 1.45 (s, 9H).

EXAMPLE 5.1

Synthesis of cis-tert-butyl 4-(4-chlorophenyl)-3-(hydroxymethyl)piperidine-1-carboxylate

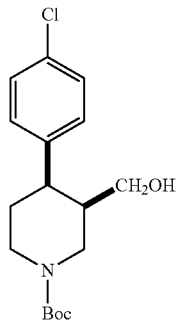

A. To a stirred solution of cis-methyl 4-(4-chlorophenyl)-1-methylpiperidine-3-carboxylate (5.50 g, 20.5 mmol, prepared according to Mobele, Bingidimi I. et al. *Organic Process Research & Development*, 10(5), 914-920; 2006) in 1,2-dichloroethane (50 mL) was added 1-chloroethyl chloroformate (3.4 mL, 31 mmol) at 0° C. The reaction mixture was stirred for 30 minutes at 0° C., and then heated at reflux for 4 h. The residue obtained after concentration in vacuo was dissolved in methanol (50 mL), and the resulting mixture was heated at reflux for 18 h and concentrated in vacuo. The residue was dissolved in methylene chloride (50 mL), followed by the addition of triethylamine (7.0 mL, 50 mmol) and di-tert-butyl dicarbonate (5.90 g, 27.0 mmol). The reaction mixture was stirred at ambient temperature for 20 h and concentrated in vacuo. The residue was diluted with ethyl acetate (200 mL) and washed with saturated sodium bicarbonate solution (50 mL) and brine (50 mL), dried over anhydrous sodium sulfate and filtered. The filtrate was concentrated in vacuo, and the residue was purified by column chromatography (20% ethyl acetate in hexanes) to afford cis-1-tert-butyl 3-methyl 4-(4-chlorophenyl)piperidine-1,3-dicarboxylate in 66% yield (4.40 g) as a colorless solid: MS (ES+) m/z 354.5 (M+1).

B. To a stirred solution of cis-1-tert-butyl 3-methyl 4-(4-chlorophenyl)piperidine-1,3-dicarboxylate (4.40 g, 12.4 mmol) in tetrahydrofuran (50 mL) was added methanol (0.47 mL, 15 mmol), followed by the addition of lithium borohydride solution (4.0 M in tetrahydrofuran, 12.5 mL, 50 mmol) at 0° C. The reaction mixture was stirred at 0° C. for 10 minutes, and then at ambient temperature for 20 h. Saturated ammonium chloride solution (20 mL) was added to the reaction mixture, followed by the addition of ethyl acetate (200 mL). The mixture was washed with brine, and concentrated in vacuo. The residue was purified by column chromatography (40% ethyl acetate in hexanes) to afford cis-tert-butyl 4-(4-chlorophenyl)-3-(hydroxymethyl)piperidine-1-carboxylate in 77% yield (3.10 g) as a colorless solid: $^1$H NMR (300 MHz, CDCl$_3$) δ 7.33-7.20 (m, 2H), 7.12-7.02 (m, 2H), 4.45-4.13 (m, 2H), 3.47-2.73 (m, 6H), 2.21-2.03 (m, 1H), 1.96-1.82 (m, 1H), 1.68-1.57 (m, 1H), 1.46 (s, 9H); MS (ES+) m/z 326.5 (M+1).

EXAMPLE 5.2

Synthesis of methyl 4-(4-fluorophenyl)-5,6-dihydro-2H-pyran-3-carboxylate

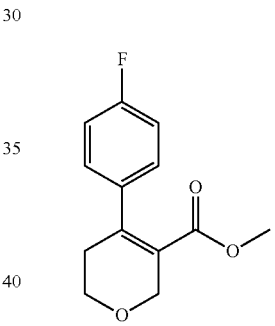

A stirred mixture of methyl 4-(((trifluoromethyl)sulfonyl)oxy)-5,6-dihydro-2H-pyran-3-carboxylate (1.73 g, 5.96 mmol, prepared according to methods disclosed in PCT Published Patent Application No. WO 2008/120093), (4-fluorophenyl)boronic acid (1.25 g, 8.9 mmol), sodium carbonate (1.26 g, 11.9 mmol), triphenylphosphine (0.234 g, 0.89 mmol), and palladium(II) acetate (0.067 g, 0.30 mmol) in benzene (35 mL) and ethanol (15 mL) was purged with nitrogen at ambient temperature for 20 min and then heated at 65° C. for 16 h. The mixture was cooled down to ambient temperature, filtered, and concentrated in vacuo. The residue was diluted with water (30 mL), and extracted with ethyl acetate (3×70 mL). The combined organic layer was washed with brine (80 mL), dried over anhydrous magnesium sulfate, filtered and concentrated in vacuo. The residue was purified by column chromatography eluted with a 10 to 20% gradient of ethyl acetate in hexanes to afford methyl 4-(4-fluorophenyl)-5,6-dihydro-2H-pyran-3-carboxylate in 71% yield (1.00 g) as a colorless oil: $^1$H NMR (300 MHz, CDCl$_3$) δ 7.20-6.98 (m, 4H), 4.49-4.39 (m, 2H), 3.96-3.84 (m, 2H), 3.51 (s, 3H), 2.53-2.45 (m, 2H).

EXAMPLE 5.3

Synthesis of cis-methyl 4-(4-fluorophenyl)tetrahydro-2H-pyran-3-carboxylate

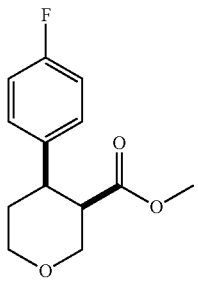

A 250 mL Parr bottle was charged with methyl 4-(4-fluorophenyl)-5,6-dihydro-2H-pyran-3-carboxylate (1.14 g, 4.8 mmol), ethyl acetate (7 mL), absolute ethanol (35 mL), and 10% wt. palladium on carbon (0.285 g) and was shaken under an atmosphere of hydrogen (55 psi) for 3 h. The mixture was filtered through a pad of diatomaceous earth and concentrated in vacuo to dryness to afford cis-methyl 4-(4-fluorophenyl)tetrahydro-2H-pyran-3-carboxylate in 78% yield (0.9 g) as a colorless solid: $^1$H NMR (300 MHz, CDCl$_3$) δ 7.30-7.19 (m, 2H), 7.07-6.94 (m, 2H), 4.37-4.11 (m, 2H), 3.82-3.70 (m, 1H), 3.64-3.41 (m, 4H), 3.12-2.99 (m, 1H), 2.92-2.63 (m, 2H), 1.79-1.63 (m, 1H); MS (ES+) m/z 239.0 (M+1).

EXAMPLE 5.4

Synthesis of trans-methyl 4-(4-fluorophenyl)tetrahydro-2H-pyran-3-carboxylate

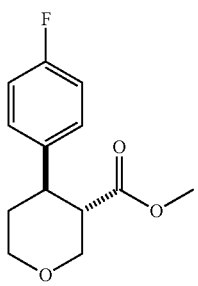

A stirred mixture of methyl 4-(4-fluorophenyl)tetrahydro-2H-pyran-3-carboxylate (1.11 g, 4.7 mmol) and sodium methoxide (0.266 g, 4.7 mmol) in anhydrous methanol (47 mL) was heated at reflux for 16 h. The mixture was allowed to cool to ambient temperature and concentrated in vacuo. The residue was diluted with saturated aqueous ammonium chloride solution (50 mL) and extracted with ethyl acetate (3×80 mL). The combined organic layer was washed with brine (100 mL), dried over anhydrous magnesium sulfate, filtered and concentrated in vacuo to afford trans-methyl 4-(4-fluorophenyl)tetrahydro-2H-pyran-3-carboxylate in 97% yield (1.08 g) as a colorless oil: $^1$H NMR (300 MHz, CDCl$_3$) δ 7.24-7.12 (m, 2H), 7.05-6.93 (m, 2H), 4.24-4.01 (m, 2H), 3.63-3.40 (m, 5H), 3.12-2.80 (m, 2H), 1.95-1.67 (m, 2H); MS (ES+) m/z 239.0 (M+1).

EXAMPLE 5.5

Synthesis of trans-4-(4-fluorophenyl)tetrahydro-2H-pyran-3-yl)methanol

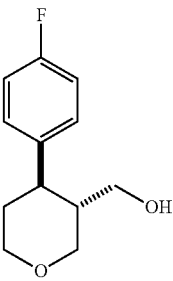

Following the procedure as described in Step B of EXAMPLE 1, making non-critical variations to replace trans-1-tert-butyl 3-methyl 4-(4-chlorophenyl)piperidine-1,3-dicarboxylate with trans-methyl 4-(4-fluorophenyl)tetrahydro-2H-pyran-3-carboxylate, trans-4-(4-fluorophenyl)tetrahydro-2H-pyran-3-yl)methanol was obtained in 47% yield (0.45 g) as a colorless oil: $^1$H NMR (300 MHz, CDCl$_3$) δ 7.23-7.13 (m, 2H), 7.07-6.95 (m, 2H), 4.27-4.15 (m, 1H), 4.12-3.99 (m, 1H), 3.57-3.19 (m, 4H), 2.69-2.53 (m, 1H), 2.10-1.66 (m, 3H), 1.13-1.02 (m, 1H); MS (ES+) m/z 211.1 (M+1).

EXAMPLE 5.6

Synthesis of methyl 8-(4-fluorophenyl)-1,4-dioxaspiro[4.5]dec-7-ene-7-carboxylate

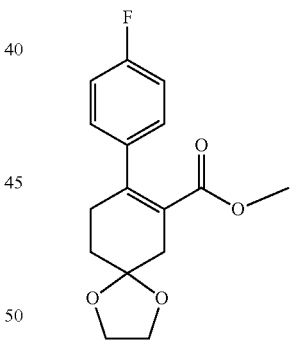

To a solution of methyl 8-(((trifluoromethyl)sulfonyl)oxy)-1,4-dioxaspiro[4.5]dec-7-ene-7-carboxylate (19.0 g, 54.8 mmol), (prepared according to Hue, B. T. Buu et al.; European Journal of Organic Chemistry, (1), 127-137; 2006) in N,N-dimethylformamide (590 mL) was added a 2M solution of sodium carbonate in water (62.5 mL, 125 mmol), followed by (4-fluorophenyl)boronic acid (10.2 g, 73.25 mmol) and 1,1'-bis(diphenylphosphino)ferrocene]dichloropalladium, complex with dichloromethane 1:1 (3.9 g, 5.3 mmol). The reaction mixture was degassed with nitrogen and was stirred at ambient temperature for 20 h. After completion of the reaction, the reaction mixture was filtered through a layer of diatomaceous earth, diluted with ethyl acetate (1 L) and extracted with water (2×500 mL). The organic layer was dried over magnesium sulfate, filtered and the filtrate was concentrated in vacuo to provide a residue which was purified by column chromatography, eluting with ethyl acetate/hexanes (1:4-1:3) to afford methyl 8-(4-fluorophenyl)-1,4-dioxaspiro[4.5]dec-7-ene-7-carboxylate in 79% yield (12.7 g) as a colorless oil; MS (ES+) m/z 292.9 (M+1).

EXAMPLE 5.7

Synthesis of cis-methyl 2-(4-fluorophenyl)-5-methoxycyclohexanecarboxylate

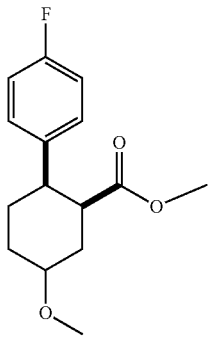

A solution of methyl 8-(4-fluorophenyl)-1,4-dioxaspiro [4.5]dec-7-ene-7-carboxylate (5.84 g, 20.0 mmol) in methanol (150 mL) and acetic acid (5.0 mL) was hydrogenated in a Parr apparatus over 1.0 g of 10% palladium on actived carbon at ambient temperature at 60 psi for 56 h. The reaction mixture was filtered, the filtrate was evaporated and the residue thus obtained was subjected to column chromatography, eluting with ethyl acetate/hexanes (1:5-1:3) to afford cis-methyl 2-(4-fluorophenyl)-5-methoxycyclohexanecarboxylate in 73% yield (3.89 g) as a colorless solid: $^1$H NMR (300 MHz, CDCl$_3$) δ 7.41-7.15 (m, 2H), 7.04-6.84 (m, 2H), 3.48 (s, 3H), 3.42-3.33 (m, 1H), 3.30 (s, 3H), 3.16-3.08 (m, 1H), 2.89-2.79 (m, 2H), 2.41-2.19 (m, 1H), 2.11-1.98 (m, 1H), 1.83-1.63 (m, 3H); MS (ES$^+$) ink 266.9 (M+1).

EXAMPLE 5.8

Synthesis of trans-methyl 2-(4-fluorophenyl)-5-methoxycyclohexanecarboxylate

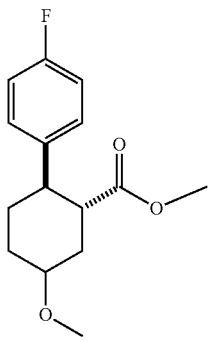

A solution of cis-methyl 2-(4-fluorophenyl)-5-methoxycyclohexanecarboxylate (3.89 g, 14.6 mmol) and sodium methoxide (1.02 g, 18.9 mmol) in methanol (50 mL) was stirred at reflux under nitrogen for 16 h. The mixture was allowed to cool to ambient temperature and a saturated solution of ammonium chloride (10 mL) was added. The mixture was filtered through a pad of diatomaceous earth and the filtrate was concentrated in vacuo. The residue thus obtained was subjected to column chromatography, eluting with ethyl acetate/hexanes (1:5-1:3) to afford trans-methyl 2-(4-fluorophenyl)-5-methoxycyclohexanecarboxylate in 75% yield (2.93 g) as a colorless oil: MS (ES+) m/z 266.9 (M+1).

EXAMPLE 5.9

Synthesis of trans-2-(4-fluorophenyl)-5-methoxycyclohexyl)methanol

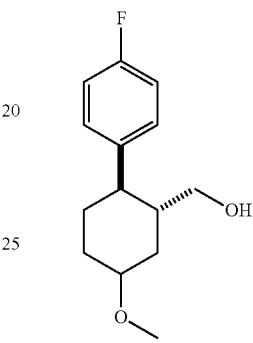

A solution of trans-methyl 2-(4-fluorophenyl)-5-methoxycyclohexanecarboxylate (2.93 g, 11.0 mmol) in tetrahydrofuran (50 mL) was treated with 4M solution of lithium borohydryde (6.25 mL, 4.0 mmol) and methanol (0.6 mL, 17.0 mmol). The reaction mixture was stirred under nitrogen at 30° C. for 16 h and heated at reflux for 2 h. The reaction mixture was allowed to cool to ambient temperature and a saturated aqueous solution of ammonium chloride (5 mL) was added and the mixture was diluted with ethyl acetate (100 mL). The organic layer was separated and dried over magnesium sulfate and filtered. The filtrate was evaporated and the residue thus obtained was subjected to column chromatography, eluting with ethyl acetate/hexanes (1:2-3:1) to afford trans-2-(4-fluorophenyl)-5-methoxycyclohexyl) methanol in 65% yield (1.71 g) as a colorless oil: MS (ES+) m/z 238.9 (M+1).

EXAMPLE 5.10

Synthesis of trans-tert-butyl 4-(4-fluorophenyl)-3-hydroxypiperidine-1-carboxylate

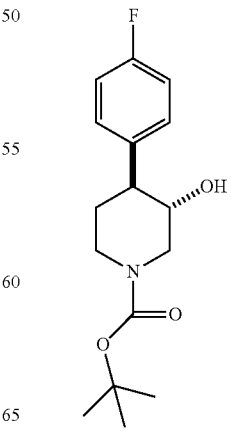

To a solution of trans-tert-butyl 4-(4-fluorophenyl)-5,6-dihydropyridine-1(2H)-carboxylate (4.28 g, 15.2 mmol, prepared according to L. Zhang et al., *Journal of Medicinal Chemistry,* 54(6), 1724-1739; 2011) in diglyme (14 mL) was added sodium borohydride (1.14 g, 30.1 mmol), boron trifluoride-diethyl ether complex (4.41 mL, 31.0 mmol) and diglyme (3.5 mL) at ambient temperature. The reaction mixture was stirred for 4 h at ambient temperature and cooled with an ice bath. Water (1.7 mL) was added, followed by 6 N aqueous sodium hyroxide (5.0 mL) and 30% w/v aqueous hydrogen peroxide (4.5 mL). After stirring at 50° C. for 2 h, the mixture was extracted with ethyl acetate (2×30 mL). The organic layer was washed with brine, dried over magnesium sulfate, filtered, and concentrated in vacuo. The residue was subjected to column chromatography, eluting with methanol/dichloromethane (1:20) to afford trans-tert-butyl 4-(4-fluorophenyl)-3-hydroxypiperidine-1-carboxylate in 54% yield (2.43 g) as a colorless solid: MS (ES+) m/z 295.9 (M+1).

EXAMPLE 5.11

Synthesis of trans-tert-butyl 3-(hydroxymethyl)-4-phenylpiperidine-1-carboxylate

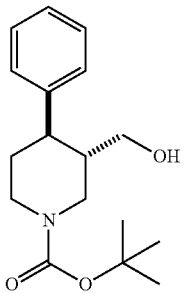

To a stirred solution of trans-tert-butyl 4-(4-chlorophenyl)-3-(hydroxymethyl)piperidine-1-carboxylate (0.70 g, 2.2 mmol) in methanol (100 mL) was added palladium on carbon (20 wt %). The mixture was stirred for 16 h under an atmosphere of hydrogen gas (1 atm). The reaction was filtered through a pad of diatomaceous earth and washed with methanol. The filtrate was concentrated and the residue was disolved in dichloromethane (60 mL) followed by the addition of triethylamine (0.9 mL, 6.0 mmol) and di-tert-butyl dicarbonate (0.43 g, 1.9 mmol). The reaction mixture was stirred at ambient temperature for 16 h, saturated aqueous sodium bicarbonate was added and the mixture was extracted with dichloromethane. The organic layer was dried over anhydrous sodium sulfate and filtered. The filtrate was concentrated in vacuo to afford trans-tert-butyl 3-(hydroxymethyl)-4-phenylpiperidine-1-carboxylate as a light yellow oil in quantitative yield (0.67 g): $^1$H NMR (300 MHz, DMSO-$d_6$) δ 7.26-7.12 (m, 5H), 4.35-4.13 (m, 2H), 3.37-3.33 (m, 1H), 3.19-3.12 (m, 1H), 2.72-2.42 (m, 4H), 1.82-1.60 (m, 3H), 1.43 (s, 9H); MS (ES+) m/z 292.0 (M+1).

EXAMPLE 5.12

Synthesis of N-(4-chlorophenyl)-2-((2,4-dimethoxybenzyl)amino)acetamide

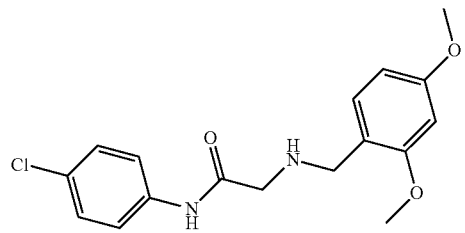 [SMILES: COc1ccc(CNCC(=O)Nc2ccc(Cl)cc2)c(OC)c1]

To a solution of 2-chloro-N-(4-chlorophenyl)acetamide (10.2 g, 0.05 mol) in tetrahydrofuran (200 mL) was added 2,4-dimethoxybenzylamine (16.00 mL, 0.106 mol) and the reaction mixture was heated at reflux for 22 h, allowed to cool to ambient temperature and filtered. The filtrate was concentrated in vacuo. The residue was recrystallized from diethyl ether to afford N-(4-chlorophenyl)-2-((2,4-dimethoxybenzyl)amino)acetamide as a colorless solid in 65% yield (11.0 g): $^1$H NMR (300 MHz, CDCl$_3$) δ 9.90 (br s, 1H), 7.60 (d, J=8.7 Hz, 2H), 7.31 (d, J=8.7 Hz, 2H), 7.15 (d, J=8.1 Hz, 2H), 6.50-6.42 (m, 2H), 3.71 (s, 3H), 3.69 (s, 3H), 3.58 (s, 2H), 3.20 (s, 2H).

EXAMPLE 5.13

Synthesis of (R)-1-(4-chlorophenyl)-4-(2,4-dimethoxybenzyl)-6-(hydroxymethyl)piperazin-2-one

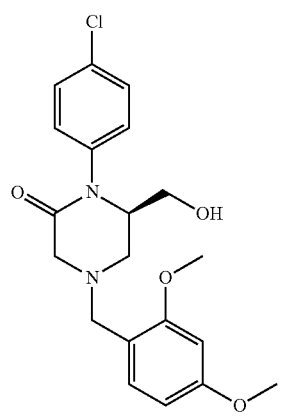 [SMILES: COc1ccc(CN2CC(=O)N(c3ccc(Cl)cc3)[C@@H](CO)C2)c(OC)c1]

To a solution of N-(4-chlorophenyl)-2-((2,4-dimethoxybenzyl)amino)acetamide (5.0 g, 15 mmol) in methanol (100 mL) and methylene chloride (35 mL) was added anhydrous magnesium sulfate (5.0 g, 41 mmol), followed by (S)-(+)-epichlorohydrin (3.0 mL, 38 mmol). Once the addition was complete, the reaction mixture was heated at 40° C., and stirred for 60 h. The mixture was allowed to cool to ambient temperature and was filtered through a pad of diatomaceous earth. The pad was washed with ethyl acetate and the filtrate concentrated in vacuo. The residue was dissolved in tetrahydrofuran (100 mL) and methanol (100 mL), a 5% w/v aqueous solution of sodium hydroxide (100 mL) was added dropwise and the mixture stirred for 50 h at ambient temperature. The reaction mixture was poured into brine (200 mL) and extracted with ethyl acetate (3 200 mL). The organic layer was washed with water and brine, dried over anhydrous sodium sulfate and concentrated in vacuo to afford (R)-1-(4-chlorophenyl)-4-(2,4-dimethoxybenzyl)-6-(hydroxymethyl)piperazin-2-one in 78% yield (4.60 g) as a colorless solid: $^1$H NMR (300 MHz, CDCl$_3$) δ 7.39-7.32 (m, 2H), 7.22-7.16 (m, 2H), 7.08-7.04 (m, 1H), 6.48-6.40 (m, 2H), 3.81 (s, 3H), 3.79 (s, 3H), 3.67-3.50 (m, 6H), 3.33-3.26 (m, 1H), 3.02-2.90 (m, 2H).

EXAMPLE 5.14

Synthesis of (R)-tert-butyl 4-(4-chlorophenyl)-3-(hydroxymethyl)-5-oxopiperazine-1-carboxylate

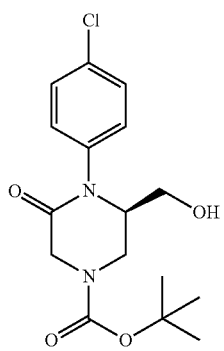 [SMILES: CC(C)(C)OC(=O)N1CC(=O)N(c2ccc(Cl)cc2)[C@@H](CO)C1]

To a stirred solution of (R)-1-(4-chlorophenyl)-4-(2,4-dimethoxybenzyl)-6-(hydroxymethyl)piperazin-2-one (4.60 g, 11.8 mmol) in methylene chloride (50 mL), was added trifluoroacetic acid (50 mL) and trfluoromethanesulfonic acid (5.0 mL). The resulting reaction mixture was stirred at ambient temperature for 4 h and concentrated in vacuo. The residue was dissolved in ethyl acetate (300 mL), basified with sodium bicarbonate to pH 9-10 and filtered. The filtrate was concentrated in vacuo, the residue was dissolved in tetrahydrofuran (150 mL) and triethylamine (10.0 mL, 71.7 mmol) and di-tert-butyl dicarbonate (3.90 g, 33.2 mmol). The reaction mixture was stirred at ambient temperature for 20 h and concentrated in vacuo. The residue was dissolved in ethyl acetate (300 mL) and washed with saturated aqueous sodium bicarbonate (50 mL) and brine (50 mL), dried over anhydrous sodium sulfate and filtered. The filtrate was concentrated in vacuo and the residue was purified by column chromatography, eluting with 40% ethyl acetate in hexanes, to afford (R)-tert-butyl 4-(4-chlorophenyl)-3-(hydroxymethyl)-5-oxopiperazine-1-carboxylate in 27% yield (1.10 g) as a colorless solid: $^1$H NMR (300 MHz, CDCl$_3$) δ 7.36 (d, J=8.7 Hz, 2H), 7.12 (d, J=8.7 Hz, 2H), 4.53 (d, J=18.6 Hz, 1H), 4.44-4.38 (m, 1H), 3.94 (d, J=18.6 Hz, 1H), 3.82-3.74 (m, 1H), 3.64-3.56 (m, 1H), 3.46-3.35 (m, 2H), 1.47 (s, 9H).

EXAMPLE 5.15

Synthesis of (S)-1-(4-chlorophenyl)-4-(2,4-dimethoxybenzyl)-6-(hydroxymethyl)piperazin-2-one

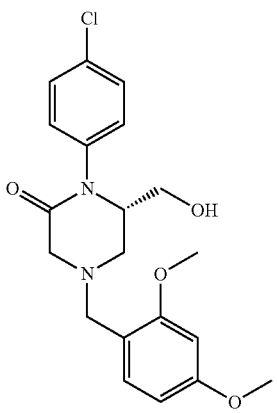 [SMILES: COc1ccc(CN2CC(=O)N(c3ccc(Cl)cc3)[C@H](CO)C2)c(OC)c1]

Following the procedure as described above in EXAMPLE 5.13 and making non-critical variations to replace (S)-(+)-epichlorohydrin with (R)-(−)-epichlorohydrin, (S)-1-(4-chlorophenyl)-4-(2,4-dimethoxybenzyl)-6-(hydroxymethyl)piperazin-2-one was obtained in 83% yield (4.90 g) as a colorless solid: $^1$H NMR (300 MHz, CDCl$_3$) δ 7.39-7.32 (m, 2H), 7.22-7.16 (m, 2H), 7.08-7.04 (m, 1H), 6.48-6.40 (m, 2H), 3.81 (s, 3H), 3.79 (s, 3H), 3.67-3.50 (m, 6H), 3.33-3.26 (m, 1H), 3.02-2.90 (m, 2H).

EXAMPLE 5.16

Synthesis of (S)-tert-butyl 4-(4-chlorophenyl)-3-(hydroxymethyl)-5-oxopiperazine-1-carboxylate

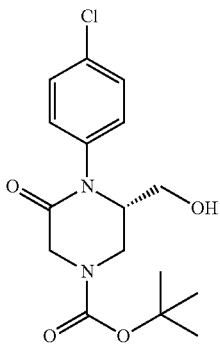 [SMILES: CC(C)(C)OC(=O)N1CC(=O)N(c2ccc(Cl)cc2)[C@H](CO)C1]

Following the procedure as described as described above in EXAMPLE 5.14 and making non-critical variations to replace (R)-1-(4-chlorophenyl)-4-(2,4-dimethoxybenzyl)-6-(hydroxymethyl)piperazin-2-one with (S)-1-(4-chlorophenyl)-4-(2,4-dimethoxybenzyl)-6-(hydroxymethyl)piperazin-2-one, (S)-tert-butyl 4-(4-chlorophenyl)-3-(hydroxymethyl)-5-oxopiperazine-1-carboxylate was obtained in 19% yield (0.84 g) as a colorless solid: $^1$H NMR (300 MHz, CDCl$_3$) δ 7.36 (d, J=8.7 Hz, 2H), 7.12 (d, J=8.7 Hz, 2H), 4.53 (d, J=18.6 Hz, 1H), 4.44-4.38 (m, 1H), 3.94 (d, J=18.6 Hz, 1H), 3.82-74 (m, 1H), 3.64-3.56 (m, 1H), 3.46-3.35 (m, 2H), 1.47 (s, 9H).

EXAMPLE 6

Synthesis of N-(2,4-dimethoxybenzyl)-2,4,5-trifluoro-N-(pyrimidin-2-yl)benzenesulfonamide

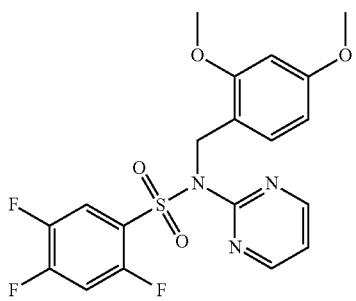 [SMILES: COc1ccc(CN(c2ncccn2)S(=O)(=O)c2cc(F)c(F)cc2F)c(OC)c1]

A. To a suspension of 2,4-dimethoxybenzaldehyde (22.0 g, 130 mmol) and 2-aminopyrimidine (11.4 g, 120 mmol) in toluene (200 mL) was added acetic acid (0.50 mL). The reaction mixture was heated at reflux for 48 h in a Dean-Stark apparatus and was allowed to cool to ambient temperature. The reaction mixture was concentrated in vacuo and the residue diluted with methanol (200 mL). Sodium tetrahydroborate (6.84 g, 180.0 mmol) was added in portions over 30 minutes at ambient temperature. The reaction mixture was stirred for further 4 h at ambient temperature, cooled to 0° C. and 10% w/v aqueous sodium hydroxide (50 mL) was added. The resulting mixture was extracted with ethyl acetate and the organic phase was washed with water and brine, dried over anhydrous sodium sulfate, filtered and concentrated in vacuo. The residue was purified by column chromatography eluting with 50% ethyl acetate in hexanes to afford N-(2,4-dimethoxybenzyl)pyrimidin-2-amine in 25% yield (7.57 g) as a pale yellow solid: $^1$H NMR (300 MHz, DMSO-d$_6$) δ 8.27-8.19 (m, 2H), 7.34-7.29 (m, 1H), 7.04-7.01 (m, 1H), 6.53-6.48 (m, 2H), 6.42-6.37 (m, 1H), 4.34 (d, J=6.3 Hz, 2H), 3.75 (s, 3H), 3.68 (s, 3H).

B. To a solution of N-(2,4-dimethoxybenzyl)pyrimidin-2-amine (2.66 g, 10.8 mmol) in tetrahydrofuran (40 mL) was added sodium hydride (60% in mineral oil, 0.48 g, 12 mmol) at 0° C. The reaction mixture was allowed to stir for 30 minutes at 0° C., and then the cooling bath was removed. The reaction mixture was stirred at ambient temperature for 1 h and 2,4,5-trifluorobenzenesulfonyl chloride (2.50 g, 10.8 mmol) was added dropwise at 0° C. After the addition was complete, the cooling bath was removed. The reaction mixture was stirred for 1 h and saturated aqueous ammonium chloride was added. The resulting mixture was extracted with ethyl acetate. The organic layer was washed with water and brine, dried over anhydrous sodium sulfate and filtered. The filtrate was concentrated in vacuo and the residue was purified by column chromatography eluting with 30% ethyl acetate in hexanes to afford N-(2,4-dimethoxybenzyl)-2,4,5-trifluoro-N-(pyrimidin-2-yl)benzenesulfonamide in 22% yield (1.07 g) as a pale yellow solid: $^1$H NMR (300 MHz, DMSO-d$_6$) δ 8.55-8.51 (m, 2H), 8.14-8.03 (m, 1H), 7.88-7.77 (m, 1H), 7.18-7.11 (m, 1H), 6.99-6.94 (m, 1H), 6.57-6.52 (m, 1H), 6.47-6.42 (m, 1H), 5.22 (s, 2H), 3.75 (s, 3H), 3.69 (s, 3H).

EXAMPLE 6.1

Synthesis of N-(2,4-dimethoxybenzyl)-2,4,5-trifluoro-N-(pyrimidin-4-yl)benzenesulfonamide

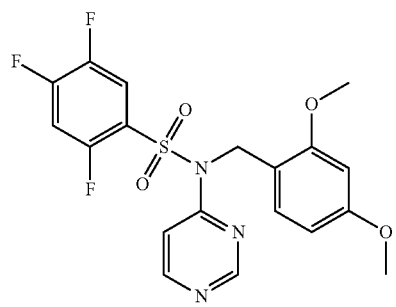 [SMILES: COc1ccc(CN(c2ccncn2)S(=O)(=O)c2cc(F)c(F)cc2F)c(OC)c1]

A. Following the procedure as described in Step A of EXAMPLE 6 and making non-critical variations to replace 2-aminopyrimidine with 4-aminopyrimidine, N-(2,4-dimethoxybenzyl)pyrimidin-4-amine was obtained in 17% yield (1.30 g) as a pale yellow solid: MS (ES+) m/z 246.1 (M+1).

B. Following the procedure as described in Step B of EXAMPLE 6 and making non-critical variations to replace N-(2,4-dimethoxybenzyl)-2-methyl-2H-tetrazol-5-amine with N-(2,4-dimethoxybenzyl)pyrimidin-4-amine, N-(2,4-dimethoxybenzyl)-2,4,5-trifluoro-N-(pyrimidin-4-yl)benzenesulfonamide was obtained as as a pale yellow solid in 10% yield (0.23 g): $^1$H NMR (300 MHz, CDCl$_3$) δ 8.85 (s, 1H), 8.60-8.45 (m, 1H), 7.99-7.81 (m, 1H), 7.38-7.28 (m, 1H), 7.23-7.15 (m, 1H), 7.10-6.97 (m, 1H), 6.54-6.33 (m, 2H), 5.28 (s, 2H), 3.83-3.73 (m, 6H); MS (ES+) m/z 439.8 (M+1).

EXAMPLE 7

Synthesis of N-(2,4-dimethoxybenzyl)-2,4,5-trifluoro-N-(1,3,4-thiadiazol-2-yl)benzenesulfonamide

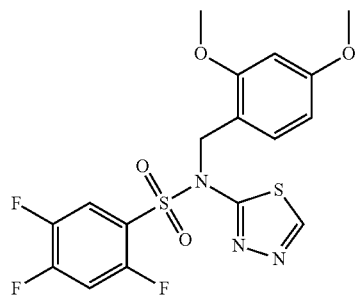 [SMILES: COc1ccc(CN(c2nncs2)S(=O)(=O)c2cc(F)c(F)cc2F)c(OC)c1]

A. To a suspension of 2,4-dimethoxybenzaldehyde (7.50 g, 45.0 mmol) and 1,3,4-thiadiazol-2-amine (4.35 g, 43.0 mmol) in toluene (100 mL) was added acetic acid (0.25 mL). The reaction mixture was heated at reflux for 48 h in a Dean-Stark apparatus and was allowed to cool to ambient temperature. The reaction mixture was concentrated in vacuo and the residue diluted with methanol (100 mL). Sodium tetrahydroborate (3.42 g, 90.0 mmol) was added in portions over 30 minutes at ambient temperature. After completion of the addition, the reaction mixture was stirred for 4 h at ambient temperature, cooled to 0° C. and 10% w/v aqueous sodium hydroxide solution (25 mL) was added. The mixture was extracted with ethyl acetate (2×100 mL). The organic layer was washed with water and brine, dried over anhydrous sodium sulfate and filtered. The filtrate was concentrated in vacuo, and the residue was purified by column chromatography eluting with 50% ethyl acetate in hexanes to afford N-(2,4-dimethoxybenzyl)-1,3,4-thiadiazol-2-amine as a colorless solid in 37% yield (4.00 g): MS (ES+) 251.8 (M+1).

B. To a solution of N-(2,4-dimethoxybenzyl)-1,3,4-thiadiazol-2-amine (1.09 g, 4.30 mmol) in tetrahydrofuran (20 mL) was added lithium bis(trimethylsilyl)amide (4.3 mL of a 1 M solution in tetrahydrofuran, 4.3 mmol) at −78° C. The reaction mixture was allowed to stir for 30 minutes at 0° C. and a solution of 2,4,5-trifluorobenzenesulfonyl chloride (0.99 g, 4.3 mmol) in tetrahydrofuran (10 mL) was added dropwise at −78° C. After the addition was complete, the cooling bath was removed. The reaction mixture was stirred for 3 h at ambient temperature and saturated aqueous ammonium chloride (10 mL) was added. The resulting mixture was extracted with ethyl acetate (2×30 mL). The organic layer was washed with water and brine, dried over anhydrous sodium sulfate and filtered. The filtrate was concentrated in vacuo and the residue was purified by column chromatography eluting with 30% ethyl acetate in hexanes to afford N-(2,4-dimethoxybenzyl)-2,4,5-trifluoro-N-(1,3,4-thiadiazol-2-yl)benzenesulfonamide in 57% yield (1.10 g) as a colorless solid: MS (ES+) m/z 446.0 (M+1).

EXAMPLE 8

Synthesis of N-(2,4-dimethoxybenzyl)-2,4,5-trifluoro-N-(3-methyl-1,2,4-thiadiazol-5-y)benzenesulfonamide

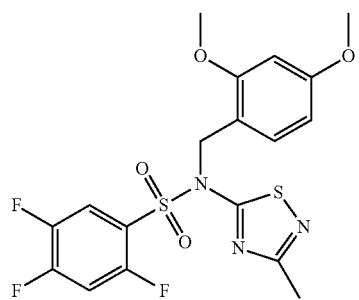 [SMILES: COc1ccc(CN(c2nc(C)ns2)S(=O)(=O)c2cc(F)c(F)cc2F)c(OC)c1]

A. To a suspension of 2,4-dimethoxybenzaldehyde (7.50 g, 45.0 mmol) and 1,3,4-thiadiazol-2-amine (5.00 g, 43.0 mmol) in toluene (100 mL) was added acetic acid (0.25 mL). The reaction mixture was heated at reflux for 40 h in a Dean-Stark apparatus and was allowed to cool to ambient temperature. The reaction mixture was concentrated in vacuo and the residue was diluted with methanol (50 mL) and tetrahydrofuran (50 mL). Sodium tetrahydroborate (2.50 g, 66.0 mmol) was added in portions over 30 minutes at ambient temperature. After the addition was complete, the reaction mixture was stirred for a further 5 h at ambient temperature and 10% w/v aqueous sodium hydroxide (50 mL) was added at 0° C. The mixture was extracted with ethyl acetate (2×100 mL). The combined organic extracts were washed with water and brine, dried over anhydrous sodium sulfate and filtered. The filtrate was concentrated in vacuo, and the residue was purified by column chromatography eluting with 50% ethyl acetate in hexanes to afford N-(2,4-dimethoxybenzyl)-3-methyl-1,2,4-thiadiazol-5-amine as a colorless solid in 41% yield (4.70 g): MS (ES+) m/z 265.9 (M+1).

B. To a solution of N-(2,4-dimethoxybenzyl)-3-methyl-1,2,4-thiadiazol-5-amine (1.14 g, 4.30 mmol) in tetrahydrofuran (20 mL) was added lithium bis(trimethylsilyl)amide (1 M solution in tetrahydrofuran, 4.3 mL, 4.3 mmol) at −78° C. The reaction mixture was stirred for 30 minutes at 0° C. and a solution of 2,4,5-trifluorobenzenesulfonyl chloride (0.99 g, 4.30 mmol) in tetrahydrofuran (10 mL) was added dropwise at −78° C. After the addition was complete, the cooling bath was removed. The reaction mixture was stirred for 3 h at ambient temperature and saturated aqueous ammonium chloride (10 mL) was added. The mixture was extracted with ethyl acetate (2×30 mL). The organic layer was washed with water and brine, dried over anhydrous sodium sulfate and filtered. The filtrate was concentrated in vacuo and the residue was purified by column chromatography eluting with 30% ethyl acetate in hexanes to afford N-(2,4-dimethoxybenzyl)-2,4,5-trifluoro-N-(3-methyl-1,2,4-thiadiazol-5-yl)benzenesulfonamide in 42% yield (0.83 g) as a colorless solid: MS (ES+) m/z 459.8 (M+1).

EXAMPLE 9

Synthesis of N-(2,4-dimethoxybenzyl)-2,4,5-trifluoro-N-(5-methylisoxazol-3-yl)benzenesulfonamide

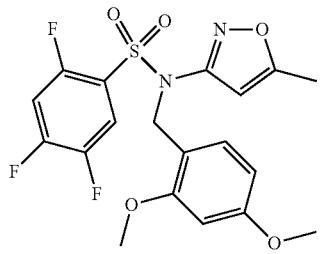 [SMILES: COc1ccc(CN(c2cc(C)on2)S(=O)(=O)c2cc(F)c(F)cc2F)c(OC)c1]

Following the procedure as described in Step B of EXAMPLE 8 and making non-critical variations to replace N-(2,4-dimethoxybenzyl)-3-methyl-1,2,4-thiadiazol-5-amine with N-(2,4-dimethoxybenzyl)-5-methylisoxazol-3-amine (prepared according to Smith, Clive A. et al, Tetrahedron Letters, 2009, 50, 4906-4911), N-(2,4-dimethoxybenzyl)-2,4,5-trifluoro-N-(5-methylisoxazol-3-yl)benzenesulfonamide was obtained as a colorless solid in 24% yield (0.46 g): MS (ES+) m/z 442.9 (M+1).

EXAMPLE 10

Synthesis of N-(2,4-dimethoxybenzyl)-2,4,5-trifluoro-N-(2-methyl-2H-tetrazol-5-yl)benzenesulfonamide

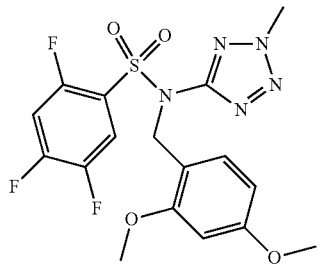 [SMILES: COc1ccc(CN(c2nnn(C)n2)S(=O)(=O)c2cc(F)c(F)cc2F)c(OC)c1]

Following the procedure as described in Step B of EXAMPLE 8 and making non-critical variations to replace N-(2,4-dimethoxybenzyl)-3-methyl-1,2,4-thiadiazol-5-amine with N-(2,4-dimethoxybenzyl)-2-methyl-2H-tetrazol-5-amine, N-(2,4-dimethoxybenzyl)-2,4,5-trifluoro-N-(2-methyl-2H-tetrazol-5-yl(benzenesulfonamide was obtained as a colorless solid in 61% yield (1.18 g): $^1$H NMR (300 MHz, CDCl$_3$) δ 7.87-7.75 (m, 1H), 7.23-7.15 (m, 1H), 7.09-6.99 (m, 1H), 6.42-6.33 (m, 2H), 5.11 (s, 2H), 4.22 (s, 3H), 3.76 (s, 3H), 3.70 (s, 3H); MS (ES+) m/z 443.9 (M+1).

EXAMPLE 11

Synthesis of N-(2,4-dimethoxybenzyl)-2,4,5-trifluoro-N-(5-methylthiazol-2-yl(benzenesulfonamide

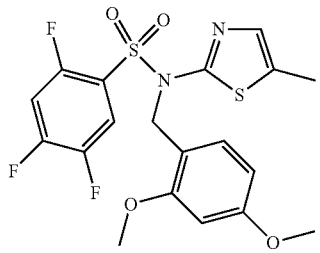 [SMILES: COc1ccc(CN(c2ncc(C)s2)S(=O)(=O)c2cc(F)c(F)cc2F)c(OC)c1]

Following the procedure as described in Step B of EXAMPLE 8 and making non-critical variations to replace N-(2,4-dimethoxybenzyl)-3-methyl-1,2,4-thiadiazol-5-amine with N-(2,4-dimethoxybenzyl)-5-methylthiazol-2-amine, N-(2,4-dimethoxybenzyl)-2,4,5-trifluoro-N-(5-methylthiazol-2-yl)benzenesulfonamide was obtained as a colorless solid in 30% yield (0.54 g): MS (ES+) m/z 458.8 (M+1).

EXAMPLE 12

Synthesis of N-(5-chlorothiazol-2-yl)-N-(2,4-dimethoxybenzyl)-2,4,5-trifluorobenzenesulfonamide

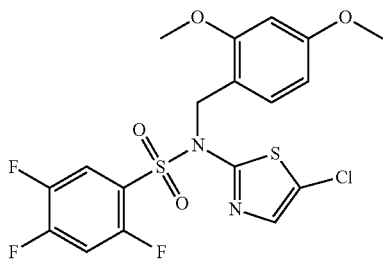 [SMILES: COc1ccc(CN(c2ncc(Cl)s2)S(=O)(=O)c2cc(F)c(F)cc2F)c(OC)c1]

Following the procedure as described in Step B of EXAMPLE 8 and making non-critical variations to replace N-(2,4-dimethoxybenzyl)-3-methyl-1,2,4-thiadiazol-5-amine with 5-chloro-N-(2,4-dimethoxybenzypthiazol-2-amine (prepared according to PCT Published Patent Application No. WO 2010/079443), N-(5-chlorothiazol-2-yl)-N-(2,4-dimethoxybenzyl)-2,4,5-trifluorobenzene-sulfonamide was obtained as a yellow solid in 53% yield (3.1 g): $^1$H NMR (300 MHz, CDCl$_3$) δ 7.74-7.66 (m, 1H), 7.26-7.26 (m, 2H), 7.09-7.00 (m, 1H), 6.40-6.34 (m, 2H), 5.12 (s, 2H), 3.77 (s, 3H), 3.73 (s, 3H); MS (ES+) m/z 478.8 (M+1), 480.8 (M+1).

EXAMPLE 13

Synthesis of N-(2,4-dimethoxybenzyl)-2,4,5-trifluoro-N-(5-fluoropyrimidin-2-yl)benzenesulfonamide

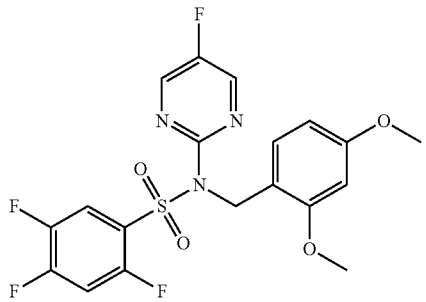 [SMILES: COc1ccc(CN(c2ncc(F)cn2)S(=O)(=O)c2cc(F)c(F)cc2F)c(OC)c1]

A. Following the procedure as described in Step A of EXAMPLE 8 and making non-critical variations to replace 1,3,4-thiadiazol-2-amine with 5-fluoropyrimidin-2-amine, N-(2,4-dimethoxybenzyl)-5-fluoropyrimidin-2-amine was obtained in 41% yield (1.7 g) as a colorless solid: MS (ES+) m/z 264.1 (M+1).

B. Following the procedure as described in Step B of EXAMPLE 8 and making non-critical variations to replace N-(2,4-dimethoxybenzyl)-3-methyl-1,2,4-thiadiazol-5-amine with N-(2,4-dimethoxybenzyl)-5-fluoropyrimidin-2-amine, N-(2,4-dimethoxybenzyl)-2,4,5-trifluoro-N-(5-fluoropyrimidin-2-yl)benzenesulfonamide was obtained as a colorless solid in 24% yield (0.21 g): $^1$H NMR (300 MHz, CDCl$_3$) δ 8.27 (s, 2H), 7.89-7.90 (m, 1H), 7.17-7.14 (m, 1H), 7.02-6.94 (m, 1H), 6.44-6.38 (m, 2H), 5.36 (m, 2H), 3.78 (s, 3H), 3.76 (s, 3H); MS (ES$^+$) m/z 457.5 (M+1).

EXAMPLE 14

Synthesis of N-(2,4-dimethoxybenzyl)-2,4,5-trifluoro-N-(pyridazin-3-yl)benzenesulfonamide

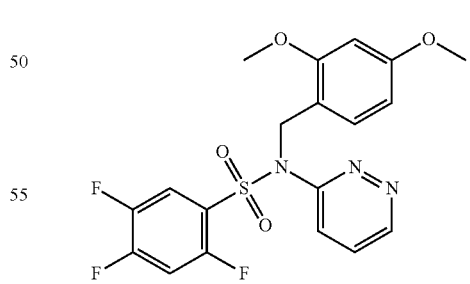

A. To a suspension of 2,4-dimethoxybenzaldehyde (0.87 g, 5.3 mmol), ytterbium (III) trifluoromethanesulfonate (0.33 g, 0.5 mmol) and pyridazin-3-amine (0.50 g, 5.3 mmol) in dichloromethane (40 mL) was added sodium triacetoxyborohydride (2.23 g, 10.5 mmol). The reaction mixture was stirred at ambient temperature for 16 h and saturated aqueous sodium bicarbonate (50 mL) was added.

The mixture was extracted with dichloromethane (2×100 mL). The combined organic extracts were washed with brine, dried over anhydrous sodium sulfate and filtered. The filtrate was concentrated in vacuo and the residue was purified by column chromatography eluting with 10% to 50% ethyl acetate in hexanes to obtain N-(2,4-dimethoxybenzyl)pyridazin-3-amine as an off-white solid in 62% yield (0.80 g): $^1$H NMR (300 MHz, CDCl$_3$) δ 8.51-8.49 (m, 1H), 7.24-7.08 (m, 2H), 6.61-6.58 (m, 1H), 6.45-6.39 (m, 2H), 5.19 (br s, 1H), 4.50-4.48 (m, 2H), 3.81-3.77 (m, 6H).

B. Following the procedure as described in Step B of EXAMPLE 8 and making non-critical variations to replace N-(2,4-dimethoxybenzyl)-3-methyl-1,2,4-thiadiazol-5-amine with N-(2,4-dimethoxybenzyl)pyridazin-3-amine, N-(2,4-dimethoxybenzyl)-2,4,5-trifluoro-N-(pyridazin-3-yl)benzenesulfonamide was obtained as an off-white solid in 19% yield (0.25 g): $^1$H NMR (300 MHz, CDCl$_3$) δ 8.96-8.94 (m, 1H), 7.71-7.63 (m, 1H), 7.54-7.50 (m, 1H), 7.40-7.36 (m, 1H), 7.16-7.13 (m, 1H), 7.02-6.94 (m, 1H), 6.31-6.28 (m, 2H), 5.14 (s, 2H), 3.70 (s, 3H), 3.61 (s, 3H); MS (ES+) m/z 439.5 (M+1).

EXAMPLE 15

Synthesis of N-(2,4-dimethoxybenzyl)-2,4,5-trifluoro-N-(pyridin-2-yl)benzenesulfonamide

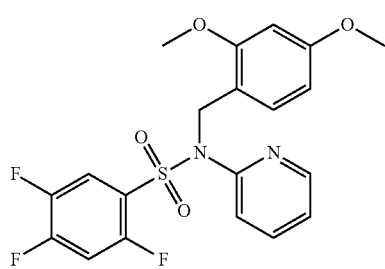 [SMILES: COc1ccc(CN(c2ccccn2)S(=O)(=O)c2cc(F)c(F)cc2F)c(OC)c1]

A. Following the procedure as described in Step A of EXAMPLE 8 and making non-critical variations to replace 1,3,4-thiadiazol-2-amine with pyridin-2-amine, N-(2,4-dimethoxybenzyl)pyridin-2-amine was obtained as a colorless solid in 56% yield (7.26 g): MS (ES+) m/z 245.1 (M+1).

B. Following the procedure as described in Step B of EXAMPLE 8 and making non-critical variations to replace N-(2,4-dimethoxybenzyl)-3-methyl-1,2,4-thiadiazol-5-amine with N-(2,4-dimethoxybenzyl)pyridin-2-amine, N-(2,4-dimethoxybenzyl)-2,4,5-trifluoro-N-(pyridin-2-yl)benzenesulfonamide was obtained as an off-white solid in 19% yield (0.37 g): $^1$H NMR (300 MHz, CDCl$_3$) δ 8.27-8.26 (m, 1H), 7.74-7.56 (m, 2H), 7.27-7.17 (m, 2H), 7.08-6.95 (m, 2H), 6.36-6.33 (m, 2H), 5.06 (s, 2H), 3.73 (s, 3H), 3.66 (s, 3H).

EXAMPLE 16

Synthesis of trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate

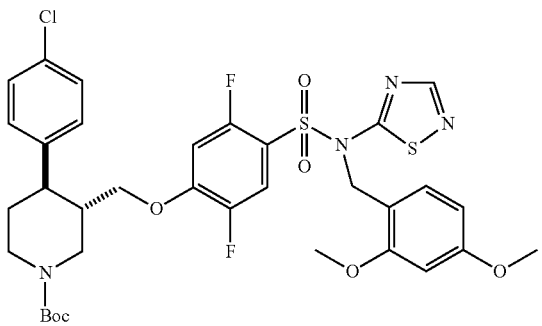

To a stirred solution of trans-tert-butyl 4-(4-chlorophenyl)-3-(hydroxymethyl)piperidine-1-carboxylate (1.75 g, 5.37 mmol) in tetrahydrofuran (60 mL) was added lithium bis(trimethylsilyl)amide (1.0 M solution in tetrahydrofuran, 5.9 mL, 5.9 mmol) at −78° C. The reaction mixture was stirred for 30 minutes at −78° C. and at ambient temperature for 1 h. N-(2,4-dimethoxybenzyl)-2,4,5-trifluoro-N-(1,2,4-thiadiazol-5-yl(benzenesulfonamide (2.39 g, 5.37 mmol, prepared according to PCT Published Patent Application No. WO 2010/079443) was added, and the stirring was continued for 20 h at ambient temperature. Saturated aqueous ammonium chloride (20 mL) was added at 0° C., followed by ethyl acetate (300 mL). The mixture was washed with brine and concentrated in vacuo. The residue was purified by column chromatography eluting with 30% ethyl acetate in hexanes to afford trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)-piperidine-1-carboxylate in 91% yield (3.70 g) as a colorless solid: $^1$H NMR (300 MHz, CDCl$_3$) δ 8.14 (s, 1H), 7.53-7.43 (m, 1H), 7.30-7.23 (m, 2H), 7.15-7.07 (m, 3H), 6.35-6.29 (m, 2H), 6.20 (br s, 1H), 5.24 (s, 2H), 4.42-4.18 (m, 2H), 3.71-3.64 (m, 7H), 3.60-3.52 (m, 1H), 2.90-2.59 (m, 3H), 2.13-2.05 (m, 1H), 1.83-1.64 (m, 2H), 1.46 (s, 9H); MS (ES+) m/z 750.9 (M+1), 752.9 (M+1).

EXAMPLE 17

Synthesis of trans-tert-butyl 4-(4-fluorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate

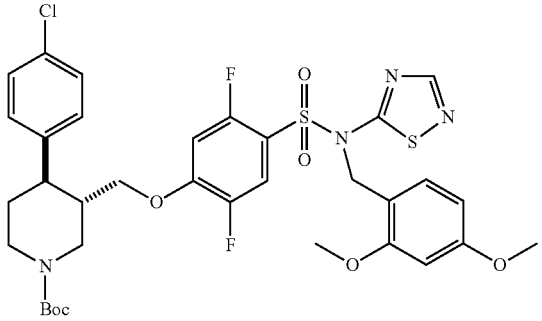

Following the procedure as described in EXAMPLE 16 and making non-critical variations to replace trans-tert-butyl 4-(4-chlorophenyl)-3-(hydroxymethyl)piperidine-1-carboxylate with trans-tert-butyl 4-(4-fluorophenyl)-3-(hydroxymethyl)piperidine-1-carboxylate, trans-tert-butyl 4-(4-fluorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate was obtained in 52% yield (0.68 g) as a colorless solid: $^1$H NMR (300 MHz, CDCl$_3$)δ 8.14 (s, 1H), 7.52-7.44 (m, 1H), 7.16-7.09 (m, 3H), 7.01-6.94 (m, 2H), 6.34-6.27 (m, 2H), 6.21 (br s, 1H), 5.24 (br s, 2H), 4.47-4.11 (m, 2H), 3.78-3.53 (m, 8H), 2.88-2.61 (m, 3H), 2.12-2.03 (m, 1H), 1.84-1.60 (m, 2H), 1.47 (s, 9H); MS (ES+) m/z 734.8 (M+1).

EXAMPLE 18

Synthesis of (3S,4R)-tert-butyl 4-(4-fluorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate

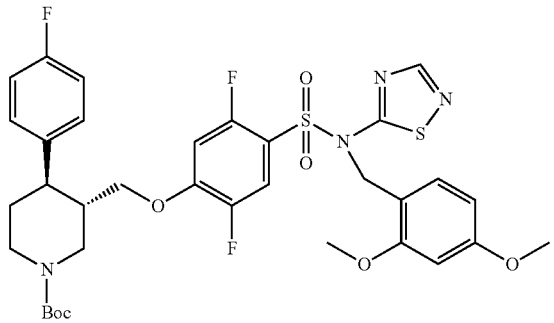 [SMILES: COc1ccc(CN(c2ncns2)S(=O)(=O)c2cc(F)c(OC[C@@H]3CN(C(=O)OC(C)(C)C)CC[C@H]3c3ccc(F)cc3)cc2F)c(OC)c1]

Following the procedure as described in EXAMPLE 16 and making non-critical variations to replace trans-tert-butyl 4-(4-chlorophenyl)-3-(hydroxymethyl)piperidine-1-carboxylate with (3S,4R)-tert-butyl 4-(4-fluorophenyl)-3-(hydroxymethyl)piperidine-1-carboxylate, (3S,4R)-tert-butyl 4-(4-fluorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate was obtained in 44% yield (0.37 g) as a colorless solid: $^1$H NMR (300 MHz, CDCl$_3$) δ 8.14 (s, 1H), 7.52-7.44 (m, 1H), 7.16-7.09 (m, 3H), 7.01-6.94 (m, 2H), 6.34-6.27 (m, 2H), 6.21 (br s, 1H), 5.24 (br s, 2H), 4.47-4.11 (m, 2H), 3.78-3.53 (m, 8H), 2.88-2.61 (m, 3H), 2.12-2.03 (m, 1H), 1.84-1.60 (m, 2H), 1.47 (s, 9H); MS (ES+) m/z 734.9 (M+1).

EXAMPLE 19

Synthesis of tert-butyl 3-((4(4-(N-(2,4-dimethoxybenzyl)-N-(1,2,4-thiadiazol-5-yl)sulfamoyl)-2,5-difluorophenoxy)methyl)-3-fluoro-4-(4-fluorophenyl)piperidine-1-carboxylate

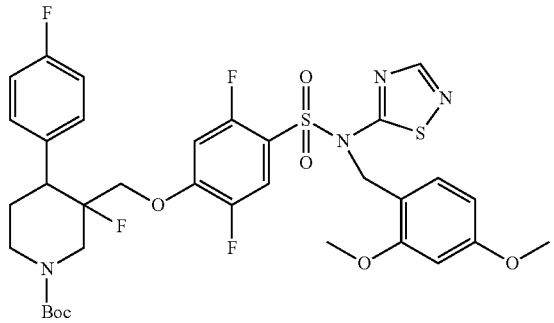 [SMILES: COc1ccc(CN(c2ncns2)S(=O)(=O)c2cc(F)c(OCC3(F)CN(C(=O)OC(C)(C)C)CCC3c3ccc(F)cc3)cc2F)c(OC)c1]

Following the procedure as described in EXAMPLE 16 and making non-critical variations to replace trans-tert-butyl 4-(4-chlorophenyl)-3-(hydroxymethyl)piperidine-1-carboxylate with tert-butyl 3-fluoro-4-(4-fluorophenyl)-3-(hydroxymethyl)piperidine-1-carboxylate, tert-butyl 3-((4(4-(N-(2,4-dimethoxybenzyl)-N-(1,2,4-thiadiazol-5-yl)sulfamoyl)-2,5-difluorophenoxy)methyl)-3-fluoro-4-(4-fluorophenyl)piperidine-1-carboxylate was obtained in 84% yield (0.19 g) as a colorless solid: $^1$H NMR (300 MHz, CDCl$_3$) δ 8.13 (s, 1H), 7.54-7.43 (m, 1H), 7.24-7.09 (m, 3H), 7.00-6.89 (m, 2H), 6.40-6.27 (m, 2H), 6.18 (br s, 1H), 5.24 (br s, 2H), 4.60-4.22 (m, 3H), 3.70 (s, 3H), 3.05 (s, 3H), 3.44-3.22 (m, 1H), 3.22-2.68 (m, 3H), 2.50-2.11 (m, 1H), 1.72-1.57 (m, 1H), 1.45 (s, 9H); MS (ES+) m/z 752.9 (M+1).

EXAMPLE 20

Synthesis of trans-tert-butyl 4-(3,4-difluorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate

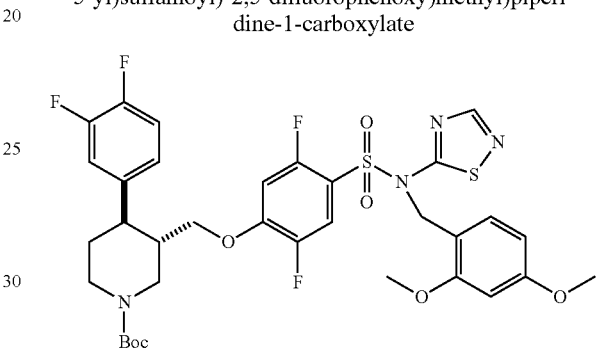

Following the procedure as described in EXAMPLE 16 and making non-critical variations to replace trans-tert-butyl 4-(4-chlorophenyl)-3-(hydroxymethyl)piperidine-1-carboxylate with trans-tert-butyl 4-(3,4-difluorophenyl)-3-(hydroxymethyl)piperidine-1-carboxylate, trans-tert-butyl 4-(3,4-difluorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate was obtained in 82% yield (0.87 g) as a colorless solid: $^1$H NMR (300 MHz, CDCl$_3$) δ 8.09 (s, 1H), 7.49-7.37 (m, 1H), 7.10-6.82 (m, 4H), 6.37-6.15 (m, 3H), 5.19 (br s, 2H), 4.42-4.11 (m, 2H), 3.74-3.52 (m, 8H), 2.82-2.60 (m, 3H), 2.12-2.01 (m, 1H), 1.82-1.57 (m, 2H), 1.46 (s, 9H); MS (ES+) m/z 752.9 (M+1).

EXAMPLE 21

Synthesis of trans-tert-butyl 4-(4-chlorophenyl)-3-((4-(N-(2,4-dimethoxybenzyl)-N-(pyrimidin-2-yl)sulfamoyl)-2,5-difluorophenoxy)methyl)piperidine-1-carboxylate

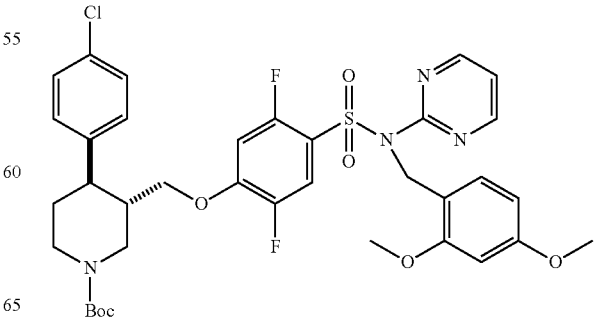

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-2,4,5-trifluoro-N-(pyrimidin-2-yl)benzenesulfonamide, trans-tert-butyl 4-(4-chlorophenyl)-3-((4-(N-(2,4-dimethoxybenzyl)-N-(pyrimidin-2-yl)sulfamoyl)-2,5-difluorophenoxy)methyl)piperidine-1-carboxylate was obtained in 86% yield (0.38 g) as a colorless solid: $^1$H NMR (300 MHz, CDCl$_3$) δ 8.32-8.29 (m, 2H), 7.80-7.74 (m, 1H), 7.19-7.02 (m, 5H), 6.80-6.75 (m, 1H), 6.40-6.29 (m, 3H), 5.34 (s, 2H), 4.42-4.15 (m, 2H), 3.78-3.51 (m, 8H), 2.87-2.59 (m, 3H), 2.12-2.03 (m, 1H), 1.78-1.56 (m, 2H), 1.43 (s, 9H); MS (ES+) m/z 744.8 (M+1), 746.8 (M+1).

EXAMPLE 22

Synthesis of trans-tert-butyl 3-((4(4-(N-(2,4-dimethoxybenzyl)-N-(pyrimidin-2-yl)sulfamoyl)-2,5-difluorophenoxy)methyl)-4-(4-fluorophenyl)piperidine-1-carboxylate

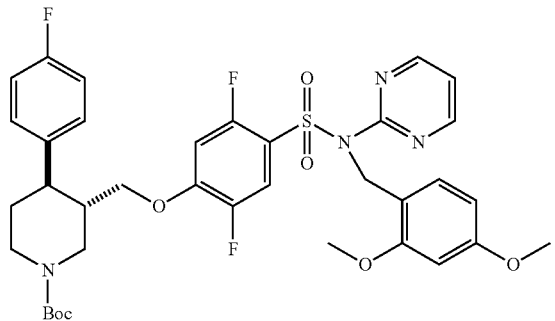

Following the procedure as described in EXAMPLE 16 making non-critical variations to replace trans-tert-butyl 4-(4-chlorophenyl)-3-(hydroxymethyl)piperidine-1-carboxylate with trans-tert-butyl 4-(4-fluorophenyl)-3-(hydroxymethyl)piperidine-1-carboxylate and to replace N-(2,4-dimethoxybenzyl)-2,4,5-trifluoro-N-(1,2,4-thiadiazol-5-yl)benzenesulfonamide with N-(2,4-dimethoxybenzyl)-2,4,5-trifluoro-N-(pyrimidin-2-yl)benzenesulfonamide, trans-tert-butyl 3-((4-(N-(2,4-dimethoxybenzyl)-N-(pyrimidin-2-yl)sulfamoyl)-2,5-difluorophenoxy)methyl)-4-(4-fluorophenyl(piperidine-1-carboxylate was obtained in 34% yield (0.32 g) as a colorless solid: $^1$H NMR (300 MHz, CDCl$_3$)δ 8.35-8.32 (m, 2H), 7.83-7.74 (m, 1H), 7.18-7.06 (m, 4H), 6.96-6.77 (m, 3H), 6.42-6.33 (m, 2H), 5.36 (s, 2H), 4.50-4.15 (m, 2H), 3.87-3.52 (m, 8H), 2.91-2.52 (m, 3H), 2.06-1.58 (m, 3H), 1.45 (s, 9H); MS (ES+) m/z 728.9 (M+1).

EXAMPLE 23

Synthesis of trans-tert-butyl 4-(4-chlorophenyl)-3-((4-(N-(2,4-dimethoxybenzyl)-N-(1,3,4-thiadiazol-2-yl)sulfamoyl)-2,5-difluorophenoxy)methyl)piperidine-1-carboxylate

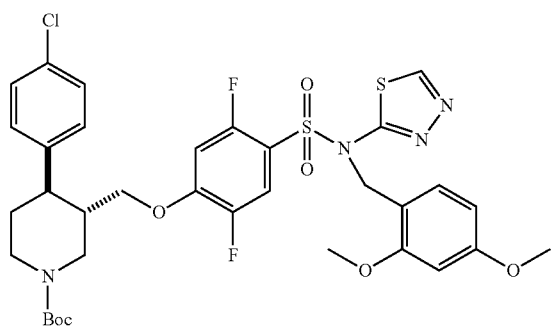

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-2,4,5-trifluoro-N-(1,3,4-thiadiazol-2-yl)benzenesulfonamide, trans-tert-butyl 4-(4-chlorophenyl)-3-((4-(N-(2,4-dimethoxybenzyl)-N-(1,3,4-thiadiazol-2-yl)sulfamoyl)-2,5-difluorophenoxy)methyl)piperidine-1-carboxylate was obtained in 86% yield (0.24 g) as a colorless solid: MS (ES+) m/z 750.7 (M+1), 752.7 (M+1).

EXAMPLE 24

Synthesis of trans-tert-butyl 4-(4-chlorophenyl)-3-((4-(N-(2,4-dimethoxybenzyl)-N-(3-methyl-1,2,4-thiadiazol-5-yl)sulfamoyl)-2,5-difluorophenoxy)methyl)piperidine-1-carboxylate

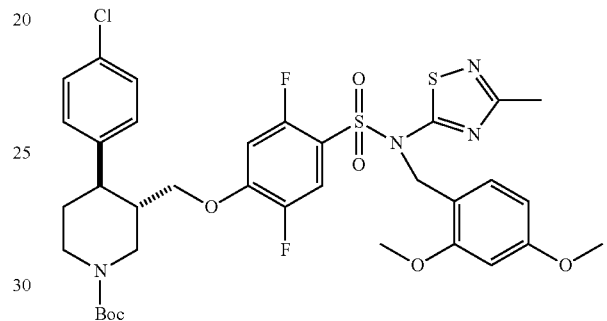

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-2,4,5-trifluoro-N-(3-methyl-1,2,4-thiadiazol-5-yl)benzenesulfonamide, trans-tert-butyl 4-(4-chlorophenyl)-3-((4-(N-(2,4-dimethoxybenzyl)-N-(3-methyl-1,2,4-thiadiazol-5-yl)sulfamoyl)-2,5-difluorophenoxy)methylypiperidine-1-carboxylate was obtained in 71% yield (0.20 g) as a colorless solid: MS (ES+) m/z 764.8 (M+1), 766.8 (M+1).

EXAMPLE 25

Synthesis of trans-tert-butyl 4-(4-chlorophenyl)-3-((4-(N-(2,4-dimethoxybenzyl)-N-(5-methylisoxazol-3-yl)sulfamoyl)-2,5-difluorophenoxy)methyl)piperidine-1-carboxylate

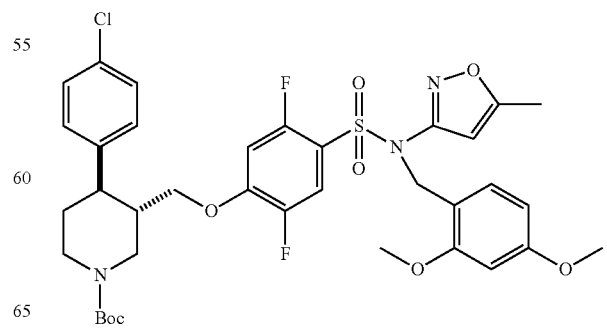

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-2,4,5-trifluoro-N-(5-methylisoxazol-3-yl(benzenesulfonamide, trans-tert-butyl 4-(4-chlorophenyl)-3-((4-(N-(2,4-dimethoxybenzyl)-N-(5-methylisoxazol-3-yl)sulfamoyl)-2,5-difluorophenoxy)methyl)piperidine-1-carboxylate was obtained as a colorless solid in 75% yield (0.34 g): MS (ES$^+$) m/z 747.8 (M+1), 749.7 (M+1).

EXAMPLE 26

Synthesis of trans-tert-butyl 4-(4-chlorophenyl)-3-(4-(N-(2,4-dimethoxybenzyl)-N-(2-methyl-2H-tetrazol-5-yl)sulfamoyl)-2,5-difluorophenoxy)methyl)piperidine-1-carboxylate

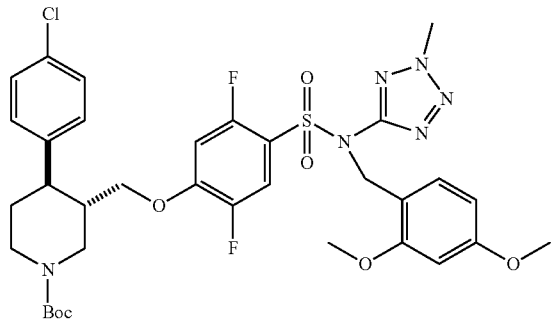

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-2-methyl-2H-tetrazol-5-amine, trans-tert-butyl 4-(4-chlorophenyl)-3-(4-(N-(2,4-dimethoxybenzyl)-N-(2-methyl-2H-tetrazol-5-yl(sulfamoyl)-2,5-difluorophenoxy)methyl)piperidine-1-carboxylate was obtained as a colorless solid in 57% yield (0.26 g): MS (ES+) m/z 772.8 (M+23).

EXAMPLE 27

Synthesis of trans-tert-butyl 4-(4-chlorophenyl)-3-((4-(N-(2,4-dimethoxybenzyl)-N-(5-methylthiazol-2-yl)sulfamoyl)-2,5-difluorophenoxy)methyl)piperidine-1-carboxylate

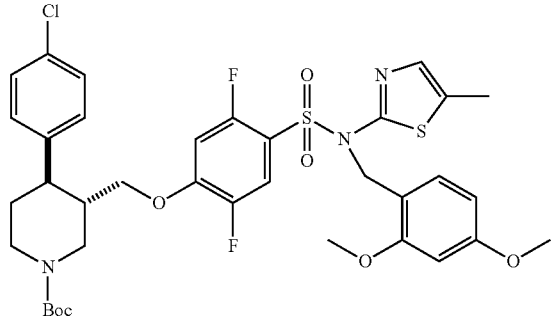

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-2,4,5-trifluoro-N-(5-methylthiazol-2-yl)benzenesulfonamide, trans-tert-butyl 4-(4-chlorophenyl)-3-((4-(N-(2,4-dimethoxybenzyl)-N-(5-methylthiazol-2-yl)sulfamoyl)-2,5-difluorophenoxy)methyl)piperidine-1-carboxylate was obtained as a colorless solid in 71% yield (0.33 g): MS (ES+) m/z 763.9 (M+1).

EXAMPLE 28

Synthesis of trans-tert-butyl 4-(4-chlorophenyl)-3-((2-cyano-4-(N-(2,4-dimethoxybenzyl)-N-(1,2,4-thiadiazol-5-yl)sulfamoyl)phenoxy)methyl)piperidine-1-carboxylate

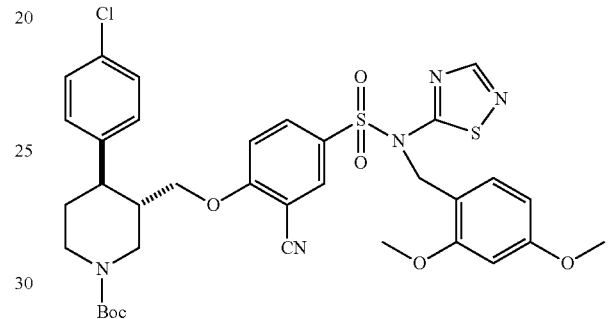

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with 3-cyano-N-(2,4-dimethoxybenzyl)-4-fluoro-N-(1,2,4-thiadiazol-5-yl)benzenesulfonamide (prepared according to Beaudoin, S. et al. WO 2010/079443 A1), trans-tert-butyl 4-(4-chlorophenyl)-3-(2-cyano-4-(N-(2,4-dimethoxybenzyl)-N-(1,2,4-thiadiazol-5-yl)sulfamoyl)phenoxy)methyl)piperidine-1-carboxylate was obtained in 14% yield (0.051 g): MS (ES+) m/z 761.7 (M+23), 763.7 (M+23).

EXAMPLE 29

Synthesis of trans-tert-butyl 4-(4-chlorophenyl)-3-(4-(N-(2,4-dimethoxybenzyl)-N-(1,2,4-thiadiazol-5-yl)sulfamoyl)-2-fluorophenoxy)methyl)piperidine-1-carboxylate

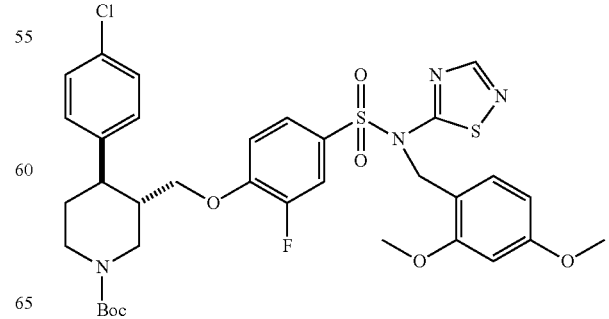

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-3,4-difluoro-N-(1,2,4-thiadiazol-5-yl)benzenesulfonamide (prepared according to Beaudoin, S. at al. WO 2010/079443 A1), trans-tert-butyl 4-(4-chlorophenyl)-3-((4-(N-(2,4-dimethoxybenzyl)-N-(1,2,4-thiadiazol-5-yl)sulfamoyl)-2-fluorophenoxy)methyl)piperidine-1-carboxylate was obtained in 42% yield (0.25 g) as a colorless solid: MS (ES+) m/z 732.7 (M+1).

EXAMPLE 30

Synthesis of trans-tert-butyl 3-((4-(N-(5-chlorothiazol-2-yl)-N-(2,4-dimethoxybenzyl(sulfamoyl)-2,5-difluorophenoxy)methyl)-4-(3,4-difluorophenyl)piperidine-1-carboxylate

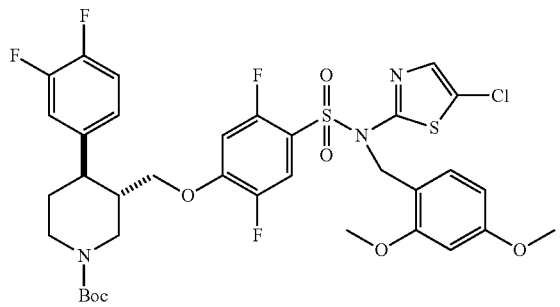

Following the procedure as described in EXAMPLE 16 and making non-critical variations to replace trans-cert-butyl 4-(4-chlorophenyl)-3-(hydroxymethyl)piperidine-1-carboxylate with trans-tert-butyl 4-(3,4-difluorophenyl)-3-(hydroxymethyl)piperidine-1-carboxylate and to replace N-(2,4-dimethoxybenzyl)-2,4,5-trifluoro-N-(1,2,4-thiadiazol-5-yl)benzenesulfonamide with N-(5-chlorothiazol-2-yl)-N-(2,4-dimethoxybenzyl)-2,4,5-trifluorobenzenesulfonamide, trans-tert-butyl 3-((4(4-(N-(5-chlorothiazol-2-yl)-N-(2,4-dimethoxybenzyl)sulfamoyl)-2,5-difluorophenoxy)methyl)-4-(3,4-difluorophenyl)piperidine-1-carboxylate was obtained in 69% yield (1.09 g) as a colorless solid: $^1$H NMR (300 MHz, CDCl$_3$) δ 7.59-7.47 (m, 2H), 7.28-6.94 (m, 4H), 6.90-6.83 (m, 1H), 6.49-6.30 (m, 2H), 5.06 (s, 2H), 4.49-4.12 (m, 2H), 3.78-3.67 (m, 7H), 3.64-3.55 (m, 1H), 2.92-2.60 (m, 3H), 2.12-1.95 (m, 1H), 185-1.61 (m, 2H), 1.47 (s, 9H); MS (ES+) m/z 785.7 (M+1).

EXAMPLE 31

Synthesis of trans-tert-butyl 4-(4-chlorophenyl)-3-(4-(N-(5-chlorothiazol-2-yl)-N-(2,4-dimethoxybenzyl)sulfamoyl)-2,5-difluorophenoxy)methyl)piperidine-1-carboxylate

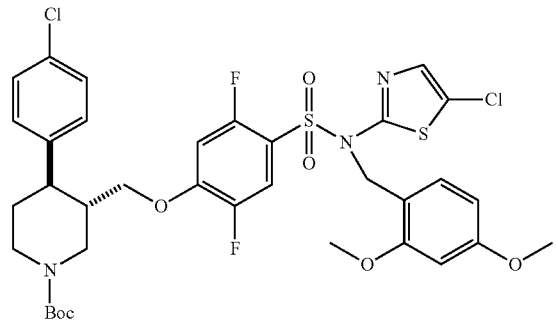

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(5-chlorothiazol-2-yl)-N-(2,4-dimethoxybenzyl)-2,4,5-trifluorobenzenesulfonamide, trans-tert-butyl 4-(4-chlorophenyl)-3-(4-(N-(5-chlorothiazol-2-yl)-N-(2,4-dimethoxybenzyl)sulfamoyl)-2,5-difluorophenoxy)methyl)piperidine-1-carboxylate was obtained as a clear oil in 41% yield (0.30 g): $^1$H NMR (300 MHz, CDCl$_3$) δ 7.57-7.52 (m, 1H), 7.30-7.28 (m, 2H), 7.19-7.11 (m, 4H), 6.49-6.35 (m, 3H), 5.09 (s, 2H), 4.47-4.43 (m, 1H), 4.29-4.23 (m, 1H), 3.76-3.73 (m, 7H), 3.64-3.59 (m, 1H), 2.88-2.68 (m, 3H), 2.18-2.11 (m, 1H), 1.86-1.70 (m, 2H), 1.50 (s, 9H).

EXAMPLE 32

Synthesis of trans-tert-butyl 4-(4-chlorophenyl)-3-(4-(N-(2,4-dimethoxybenzyl)-N-(5-fluoropyrimidin-2-yl)sulfamoyl)-2,5-difluorophenoxy)methyl)piperidine-1-carboxylate

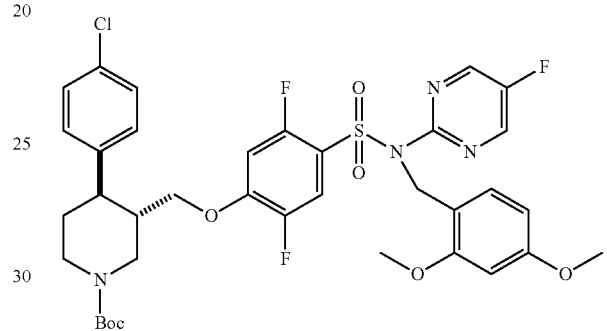

Following the procedure as described in EXAMPLE 16 and making non-critical variations to replace N-(2,4-dimethoxybenzyl)-2,4,5-trifluoro-N-(1,2,4-thiadiazol-5-yl(benzenesulfonamide with N-(2,4-dimethoxybenzyl)-2,4,5-trifluoro-N-(5-fluoropyrimidin-2-yl)benzenesulfonamide, trans-tert-butyl 4-(4-chlorophenyl)-3-(4-(N-(2,4-dimethoxybenzyl)-N-(5-fluoropyrimidin-2-Asulfamoyl)-2,5-difluorophenoxy)methyl)piperidine-1-carboxylate was obtained as a clear oil in 68% yield (0.25 g): $^1$H NMR (300 MHz, CDCl$_3$) δ 8.23 (s, 2H), 7.78-7.73 (m, 1H), 7.24-7.05 (m, 5H), 6.41-6.35 (m, 3H), 5.32 (s, 2H), 4.43-4.20 (m, 2H), 3.77-3.69 (m, 7H), 3.59-3.54 (m, 1H), 2.83-2.63 (m, 3H), 2.08-2.06 (m, 1H), 1.87-1.61 (m, 2H), 1.45 (s, 9H); MS (ES+) m/z 762.9 (M+1), 764.0 (M+1).

EXAMPLE 33

Synthesis of trans-tert-butyl 4-(4-chlorophenyl)-3-(4-(N-(2,4-dimethoxybenzyl)-N-(pyridazin-3-yl)sulfamoyl)-2,5-difluorophenoxy)methyl)piperidine-1-carboxylate

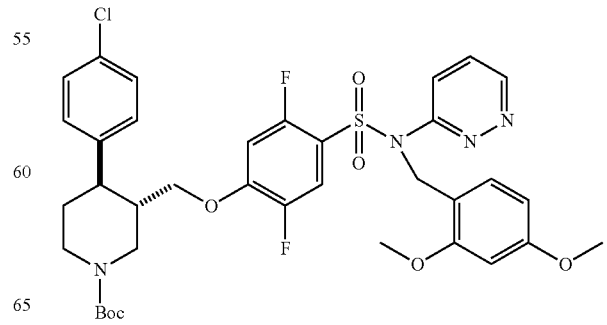

Following the procedure as described in EXAMPLE 16 and making non-critical variations to replace N-(2,4-dimethoxybenzyl)-2,4,5-trifluoro-N-(1,2,4-thiadiazol-5-yl(benzenesulfonamide with N-(2,4-dimethoxybenzyl)-2,4,5-trifluoro-N-(pyridazin-3-yl)benzenesulfonamide, trans-tert-butyl 4-(4-chlorophenyl)-3-((4-(N-(2,4-dimethoxybenzyl)-N-(pyridazin-3-yl)sulfamoyl)-2,5-difluorophenoxy)methyl)piperidine-1-carboxylate was obtained as a clear oil in 70% yield (0.25 g):$^1$H NMR (300 MHz, CDCl$_3$) δ 8.94-8.93 (m, 1H), 7.60-7.35 (m, 3H), 7.28-7.24 (m, 2H), 7.17-7.07 (m, 3H), 6.42-6.29 (m, 3H), 5.12 (s, 2H), 4.44-4.22 (m, 2H), 3.71-3.55 (m, 8H), 2.84-2.64 (m, 3H), 2.12-2.07 (m, 1H), 1.84-1.65 (m, 2H), 1.47 (s, 9H); MS (ES$^+$) m/z 745.0 (M+1), 747.0 (M+1).

EXAMPLE 34

Synthesis of trans-tert-butyl 4-(4-chlorophenyl)-3-(4-(N-(2,4-dimethoxybenzyl)-N-(pyridin-2-yl)sulfamoyl)-2,5-difluorophenoxy)methyl)piperidine-1-carboxylate

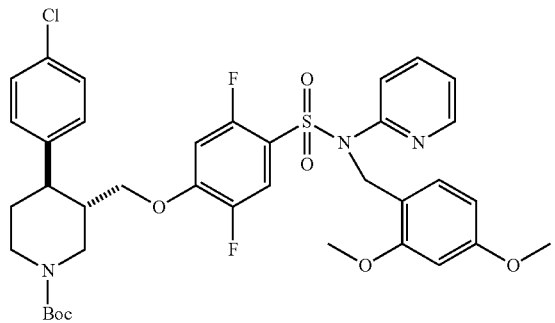

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-2,4,5-trifluoro-N-(pyridin-2-yl)benzene-sulfonamide, trans-tert-butyl 4-(4-chlorophenyl)-3-((4-(N-(2,4-dimethoxybenzyl)-N-(pyridin-2-yl)sulfamoyl)-2,5-difluorophenoxy)methyl)piperidine-1-carboxylate was obtained as an off-white solid in 66% yield (0.30 g): MS (ES+) m/z 744.0 (M+1), 746.0 (M+1).

EXAMPLE 35

Synthesis of cis-tert-butyl 4-(4-chlorophenyl)-3-(4-(N-(2,4-dimethoxybenzyl)-N-(1,2,4-thiadiazol-5-Asulfamoyl)-2,5-difluorophenoxy)methyl)piperidine-1-carboxylate

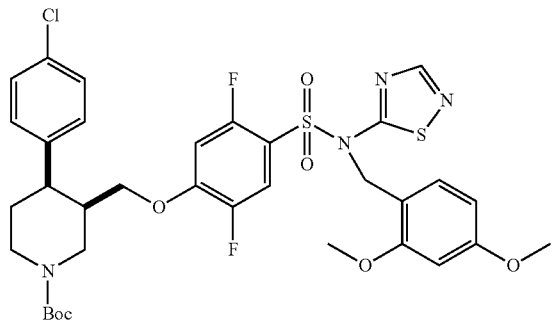

Following the procedure as described in EXAMPLE 16 and making non-critical variations to replace trans-tert-butyl 4-(4-chlorophenyl)-3-(hydroxymethyl)piperidine-1-carboxylate with cis-tert-butyl 4-(4-chlorophenyl)-3-(hydroxymethyl)piperidine-1-carboxylate (prepared according to Kozikowski, A. P. et. al. *J. Med. Chem.* 1998, 41, 1962), cis-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate was obtained as a colorless solid in 65% yield (0.30 g): MS (ES+) m/z 750.9 (M+1), 752.8 (M+1).

EXAMPLE 36

Synthesis of trans-4-((-1-benzyl-4-(4-chlorophenyl)pyrrolidin-3-yl)methoxy)-N-(2,4-dimethoxybenzyl)-2,5-difluoro-N-(1,2,4-thiadiazol-5-yl)benzenesulfonamide

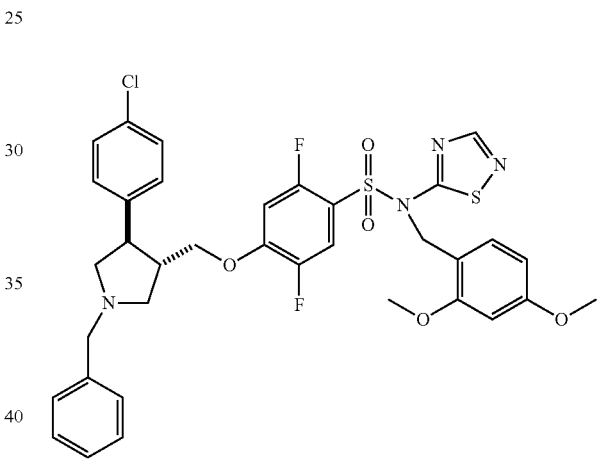

To a stirred solution of (trans-1-benzyl-4-(4-chlorophenyl)pyrrolidin-3-yl)methanol (0.81 g, 2.7 mmol, prepared according to Knust, Henner et al.; U.S. Pat. Appl. Publ., 2010/0210659) in tetrahydrofuran (30 mL) was added lithium bis(trimethylsilyl)amide (1.0 M solution in tetrahydrofuran, 2.95 mL, 2.95 mmol) at −78° C. The reaction mixture was allowed to stir for 30 minutes at −78° C. and the cooling bath was removed. The reaction mixture was stirred at ambient temperature for 1 h and N-(2,4-dimethoxybenzyl)-2,4,5-trifluoro-N-(1,2,4-thiadiazol-5-yl)benzenesulfonamide (1.19 g, 2.69 mmol) was added. The stirring was continued at ambient temperature for 20 h. Saturated aqueous ammonium chloride (10 mL) was added at 0° C., followed by ethyl acetate (200 mL). The organic layer was separated, washed with brine and concentrated in vacuo. The residue was purified by column chromatography eluting with 30% ethyl acetate in hexanes to afford trans-4-((-1-benzyl-4-(4-chlorophenyl)pyrrolidin-3-yl(methoxy)-N-(2, 4-dimethoxybenzyl)-2,5-difluoro-N-(1,2,4-thiadiazol-5-yl (benzenesulfonamide in 59% yield (1.15 g) as a colorless solid: MS (ES+) m/z 726.8 (M+1), 728.8 (M+1).

EXAMPLE 37

Synthesis of trans-tert-butyl 3-(4-chlorophenyl)-4-(4-(N-(2,4-dimethoxybenzyl)-N-(1,2,4-thiadiazol-5-yl)sulfamoyl)-2,5-difluorophenoxy)methyl)pyrrolidine-1-carboxylate

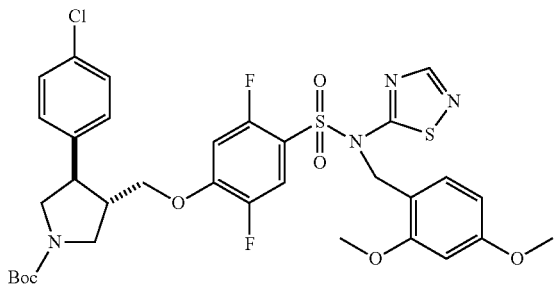

A. To a stirred solution of trans-1-tert-butyl 3-methyl 4-(4-chlorophenyl)pyrrolidine-1,3-dicarboxylate (1.00 g, 2.9 mmol, prepared according to U.S. Published Patent Application No. 2005/0176772) in tetrahydrofuran (30 mL) was added lithium borohydride (4 M solution in tetrahydrofuran, 2.0 mL, 8.0 mmol). The reaction mixture was heated at to reflux and methanol (0.25 mL, 8.0 mmol) was added dropwise. The mixture was heated at reflux for 16 h and was allowed to cool to ambient temperature. Saturated aqueous ammonium chloride (10 mL) and ethyl acetate (30 mL) were added and the phases were separated. The organic layer was washed with brine (20 mL), dried over magnesium sulfate and filtered. The filtrate was concentrated in vacuo and the residue was purified by column chromatography eluting with 50% ethyl acetate in hexanes to afford trans-tert-butyl 3-(4-chlorophenyl)-4-(hydroxymethyl)pyrrolidine-1-carboxylate in 35% yield (0.32 g) as a colorless solid: MS (ES+) m/z 311.8 (M+1), 313.8 (M+1).

B. Following the procedure as described in EXAMPLE 35 and making non-critical variations to replace (trans-1-benzyl-4-(4-chlorophenyl)pyrrolidin-3-yl)methanol with trans-tert-butyl 3-(4-chlorophenyl)-4-(hydroxymethyl)pyrrolidine-1-carboxylate, trans-tert-butyl 3-(4-chlorophenyl)-4-(4-(N-(2,4-dimethoxybenzyl)-N-(1,2,4-thiadiazol-5-yl)sulfamoyl)-2,5-difluorophenoxy)methyl)pyrrolidine-1-carboxylate was obtained in 95% yield (0.51 g) as a colorless solid: MS (ES+) m/z 736.8 (M+1), 738.8 (M+1).

EXAMPLE 38

Synthesis of (trans-2-(4-fluorophenyl)cyclohexyl)methanol

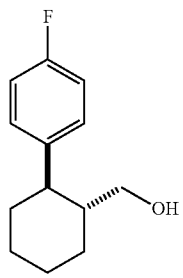

A. To a suspension of (E)-3-(4-fluorophenyl)acrylic acid (21.0 g, 125 mmol) in toluene (90 mL) in a stainless steel bomb were added buta-1,3-diene (40.0 g, 740 mmol) and hydroquinone (0.2 g). The reaction mixture was heated at 260° C. for 56 h, allowed to cool to ambient temperature and concentrated in vacuo. The residue was dissolved in methanol (200 mL) and filtered through a pad of diatomaceous earth. The filtrate was concentrated in vacuo and the residue was purified by column chromatography eluting with a gradient of ethyl acetate in hexanes (10-50%) to afford trans-4'-fluoro-1,2,3,6-tetrahydro-[1,1'-biphenyl]-2-carboxylic acid as a colorless solid in 76% yield (15.0 g): MS (ES−) m/z 219.3 (M−1).

B. To a solution of trans-4'-fluoro-1,2,3,6-tetrahydro-[1,1-biphenyl]-2-carboxylic acid (4.50 g, 20.4 mmol) in methanol (50 mL) was added 5% w/w palladium on activated carbon (0.50 g) and the reaction mixture was stirred under an atmosphere of hydrogen gas (1 atm) for 16 h at ambient temperature. The reaction mixture was filtered through a pad of diatomaceous earth and the filtrate was concentrated in vacuo. The residue was purified by column chromatography eluting with 30% ethyl acetate in hexanes to afford trans-2-(4-fluorophenyl)-cyclohexanecarboxylic acid in 97% yield (4.40 g) as a colorless oil: MS (ES−) m/z 221.1 (M−1).

C. A suspension of trans-2-(4-fluorophenyl)cyclohexanecarboxylic acid (4.40 g, 19.8 mmol), cesium carbonate (6.52 g, 20.0 mmol) and dimethyl sulfate (2.53 g, 20.0 mmol) in acetone (20 mL) was stirred at ambient temperature for 16 h. The reaction mixture was filtered, and the filtrate was concentrated in vacuo. The residue was dissolved in tetrahydrofuran (50 mL) and lithium borohydride (4 M solution in terahydrofuran, 20.0 mL, 80.0 mmol) and methanol (0.8 mL, 20.0 mmol) were added. The reaction mixture was heated at reflux for 16 h and allowed to cool to ambient temperature. Saturated aqueous ammonium chloride (20 mL) and ethyl acetate (200 mL) were added. The organic phase was separated, dried over magnesium sulfate, filtered and concentrated in vacuo. The residue was purified by column chromatography eluting 30% ethyl acetate in hexanes to afford (trans-2-(4-fluorophenyl)cyclohexyl)methanol as a colorless oil in 73% yield (3.01 g): MS (ES+) m/z 208.8 (M+1).

EXAMPLE 39

Synthesis of N-(2,4-dimethoxybenzyl)-2,5-difluoro-4-((trans-4-(4-fluorophenyl)tetrahydro-2H-pyran-3-yl)methoxy)-N-(1,2,4-thiadiazol-5-yl)benzenesulfonamide

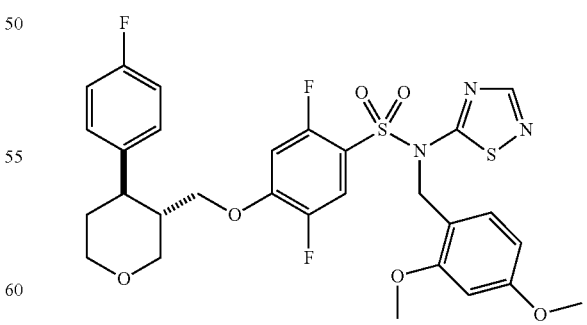

Following the procedure as described in EXAMPLE 16 and making non-critical variations to replace trans-tert-butyl 4-(4-chlorophenyl)-3-(hydroxymethyl)piperidine-1-carboxylate with trans-4-(4-fluorophenyl)tetrahydro-2H-pyran-3-yl)methanol, N-(2,4-dimethoxybenzyl)-2,5-difluoro-4-

((trans-4-(4-fluorophenyptetrahydro-2H-pyran-3-yl)methoxy)-N-(1,2,4-thiadiazol-5-yl)benzenesulfonamide was obtained as a colorless solid in 35% yield (0.34 g): MS (ES+) m/z 635.7 (M+1), 637.8 (M+1).

EXAMPLE 40

Synthesis of trans-tert-butyl 3-(4-(N-(2,4-dimethoxybenzyl)-N-(1,2,4-thiadiazol-5-yl)sulfamoyl)-2,5-difluorophenoxy)-4-(4-fluorophenyl)piperidine-1-carboxylate

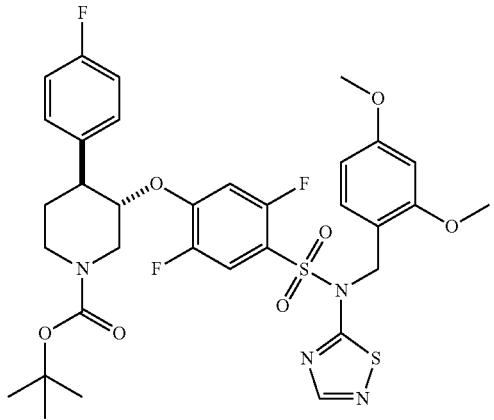

To a solution of trans-tert-butyl 4-(4-fluorophenyl)-3-hydroxypiperidine-1-carboxylate (0.30 g, 1.0 mmol) in tetrahydrofuran (5 mL) was added sodium hydride (60% dispersion in mineral oil, 0.05 g, 1.1 mmol). After stirring for 10 minutes, a solution of N-(2,4-dimethoxybenzyl)-2,4,5-trifluoro-N-(1,2,4-thiadiazol-5-yl)benzenesulfonamide (0.45 g, 1.0 mmol, prepared according to PCT Published Patent Application No. WO 2010/079443) in tetrahydrofuran (2 mL) was added and the reaction mixture was stirred at ambient temperature for 56 h. The reaction mixture was filtered, the filtrate was concentrated in vacuo and the residue was subjected to column chromatography eluting with 50% ethyl acetate in hexanes to afford trans-tert-butyl 3-(4-(N-(2,4-dimethoxybenzyl)-N-(1,2,4-thiadiazol-5-yl)sulfamoyl)-2,5-difluorophenoxy)-4-(4-fluorophenyl)piperidine-1-carboxylate as a colorless solid in 37% yield (0.27 g): MS (ES+) m/z 721.4 (M+1).

EXAMPLE 41

Synthesis of trans-tert-butyl 3-((4(4-(N-(2,4-dimethoxybenzyl)-N-(1,2,4-thiadiazol-5-yl)sulfamoyl)-2,5-difluorophenoxy)methyl)-4-phenylpiperidine-1-carboxylate

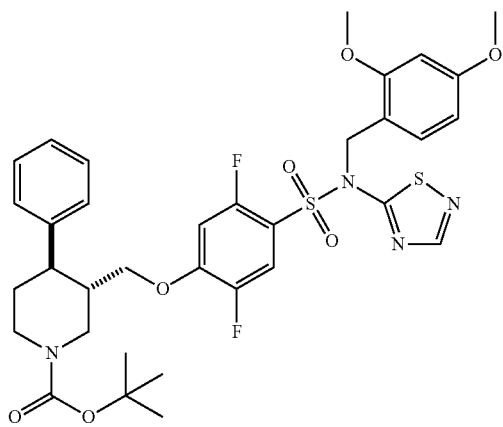

Following the procedure as described above in EXAMPLE 16 and making non-critical variations to replace trans-tert-butyl 4-(4-chlorophenyl)-3-(hydroxymethyl)piperidine-1-carboxylate with trans-tert-butyl 3-(hydroxymethyl)-4-phenylpiperidine-1-carboxylate, trans-tert-butyl 3-((4(4-(N-(2,4-dimethoxybenzyl)-N-(1,2,4-thiadiazol-5-yl)sulfamoyl)-2,5-difluorophenoxy)methyl)-4-phenylpiperidine-1-carboxylate was obtained as a colorless oil in 18% yield (0.17 g): MS (ES+) m/z 716.9 (M+1).

EXAMPLE 42

Synthesis of (R)-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)-5-oxopiperazine-1-carboxylate

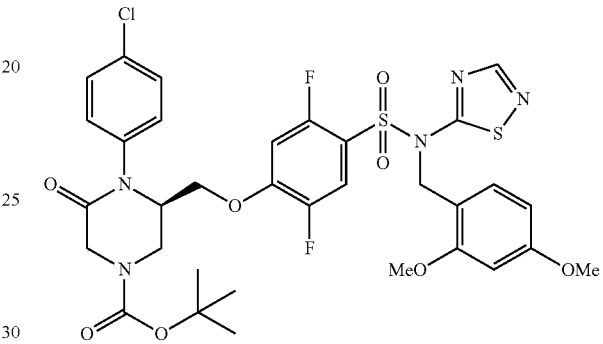

Following the procedure as described above in EXAMPLE 16 and making non-critical variations to replace trans-tert-butyl 4-(4-chlorophenyl)-3-(hydroxymethyl)piperidine-1-carboxylate with (R)-tert-butyl 4-(4-chlorophenyl)-3-(hydroxymethyl)-5-oxopiperazine-1-carboxylate, (R)-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)-5-oxopiperazine-1-carboxylate was obtained in 22% yield (0.21 g) as a colorless solid: $^1$H NMR (300 MHz, CDCl$_3$) δ 8.10 (s, 1H), 7.56-7.42 (m, 1H), 7.38-7.30 (m, 2H), 7.15-7.07 (m, 3H), 6.55-6.45 (m, 1H), 6.37-6.32 (m, 1H), 6.22-6.18 (m, 1H), 5.20 (br s, 2H), 4.40-4.31 (m, 1H), 4.10-3.88 (m, 4H), 3.78-3.53 (m, 8H), 1.44 (s, 9H).

EXAMPLE 43

Synthesis of (S)-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)-5-oxopiperazine-1-carboxylate

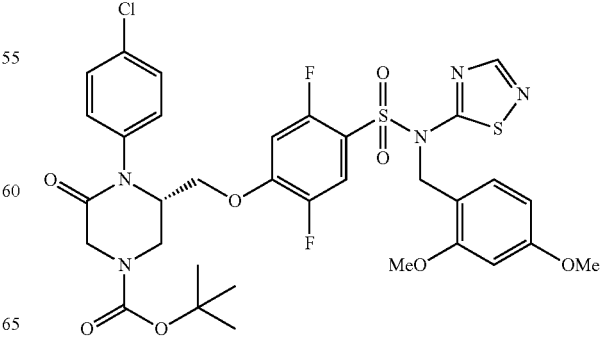

Following the procedure as described above in EXAMPLE 16 and making non-critical variations to replace trans-tert-butyl 4-(4-chlorophenyl)-3-(hydroxymethyl)piperidine-1-carboxylate with (S)-tert-butyl 4-(4-chlorophenyl)-3-(hydroxymethyl)-5-oxopiperazine-1-carboxylate, (S)-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)-5-oxopiperazine-1-carboxylate was obtained in 61% yield (0.76 g) as a colorless solid: $^1$H NMR (300 MHz, CDCl$_3$) δ 8.13 (s, 1H), 7.59-7.41 (m, 1H), 7.41-7.36 (m, 2H), 7.18-7.10 (m, 3H), 6.52-6.45 (m, 1H), 6.35-6.30 (m, 1H), 6.24-6.18 (m, 1H), 5.22 (br s, 2H), 4.43-4.30 (m, 1H), 4.15-3.88 (m, 4H), 3.74-3.58 (m, 8H), 1.42 (s, 9H).

EXAMPLE 44

Synthesis of 4-((trans-4-(4-chlorophenyl)piperidin-3-yl)methoxy)-2,5-difluoro-N-(1,2,4-thiadiazol-5-yl)benzenesulfonamide

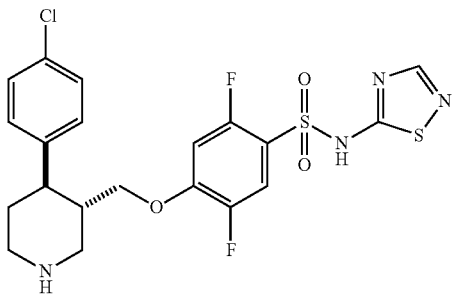

To a stirred solution of trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate (3.70 g, 4.9 mmol) in methylene chloride (30 mL) was added trifluoroacetic acid (30 mL) at 0° C. The reaction mixture was stirred at 0° C. for 10 minutes and at ambient temperature for 4 h. The mixture was concentrated in vacuo to a volume of about 10 mL and methanol (50 mL) was added, causing a precipitate to be deposited. The resultant suspension was filtered and the filtrate was concentrated in vacuo to afford. The residue was purified by trituration in methanol (20 mL), followed by titration in ethyl acetate (20 mL) to afford 4-((trans-4-(4-chlorophenyl)piperidin-3-yl)methoxy)-2,5-difluoro-N-(1,2,4-thiadiazol-5-yl(benzenesulfonamide as the corresponding trifluoroacetic acid salt in 64% yield (1.96 g) as a colorless solid: $^1$H NMR (300 MHz, DMSO-d$_6$) δ 8.87 (br s, 1H), 8.68 (br s, 1H), 8.39 (s, 1H), 7.60-7.52 (m, 1H), 7.39-7.32 (m, 2H), 7.23-7.04 (m, 3H), 3.86-3.65 (m, 2H), 3.55-3.32 (m, 2H), 3.07-2.73 (m, 3H), 2.36-3.44 (m, 1H), 1.92-1.65 (m, 2H); MS (ES+) m/z 500.8 (M+1), 502.8 (M+1).

EXAMPLE 45

Synthesis of 2,5-difluoro-4-((trans-4-(4-fluorophenyl)piperidin-3-yl)methoxy)-N-(1,2,4-thiadiazol-5-yl)benzenesulfonamide

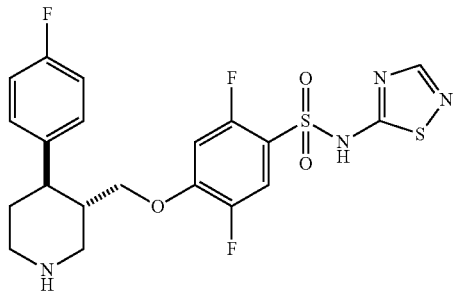

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-fluorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate, 2,5-difluoro-4-((trans-4-(4-fluorophenyl)piperidin-3-yl(methoxy)-N-(1,2,4-thiadiazol-5-yl)benzenesulfonamide was obtained as the corresponding trifluoroacetic acid salt in 90% yield (0.50 g) as a colorless solid: $^1$H NMR (300 MHz, DMSO-d$_6$) δ 9.00-8.82 (m, 1H), 8.80-8.65 (m, 1H), 8.39 (s, 1H), 7.62-7.50 (m, 1H), 7.27-7.02 (m, 5H), 3.86-3.65 (m, 2H), 3.55-3.32 (m, 2H), 3.07-2.73 (m, 3H), 2.47-2.42 (m, 1H), 1.97-1.82 (m, 2H); MS (ES+) m/z 484.7 (M+1).

EXAMPLE 46

Synthesis of 2,5-difluoro-4-(((3S,4R)-4-(4-fluorophenyl)piperidin-3-yl)methoxy)-N-(1,2,4-thiadiazol-5-yl)benzenesulfonamide

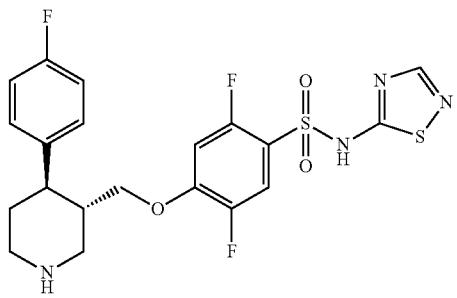 [SMILES: O=S(=O)(Nc1ncns1)c1cc(F)c(OC[C@@H]2CNCC[C@H]2c2ccc(F)cc2)cc1F]

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with (3S,4R)-tert-butyl 4-(4-fluorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate, 2,5-difluoro-4-(((3S,4R)-4-(4-fluorophenyl)piperidin-3-yl)methoxy)-N-(1,2,4-thiadiazol- 5-yl)benzenesulfonamide was obtained as the corresponding trifluoroacetic acid salt in 78% yield (0.50 g) as a colorless solid: $^1$H NMR (300 MHz, DMSO-d$_6$) δ 9.00-8.82 (m, 1H), 8.80-8.65 (m, 1H), 8.39 (s, 1H), 7.62-7.50 (m, 1H), 7.27-7.02 (m, 5H), 3.86-3.65 (m, 2H), 3.55-3.32 (m, 2H), 3.07-2.73 (m, 3H), 2.47-2.42 (m, 1H), 1.97-1.82 (m, 2H); MS (ES$^+$) m/z 484.8 (M+1).

EXAMPLE 47

Synthesis of 2,5-difluoro-4-((3-fluoro-4-(4-fluorophenyl)piperidin-3-yl)methoxy)-N-(1,2,4-thiadiazol-5-yl)benzenesulfonamide

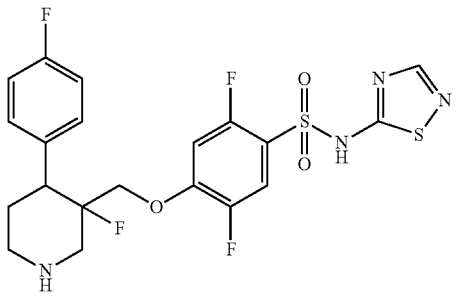 [SMILES: O=S(=O)(Nc1ncns1)c1cc(F)c(OCC2(F)CNCCC2c2ccc(F)cc2)cc1F]

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with tert-butyl 3-((4(4-(N-(2,4-dimethoxybenzyl)-N-(1,2,4-thiadiazol-5-yl)sulfamoyl)-2,5-difluorophenoxy)methyl)-3-fluoro-4-(4-fluorophenyl)piperidine-1-carboxylate, 2,5-difluoro-4-((3-fluoro-4-(4-fluorophenyl)piperidin-3-yl)methoxy)-N-(1,2,4-thiadiazol-5-yl)benzenesulfonamide was obtained as the corresponding trifluoroacetic acid salt in 28% yield (0.04 g) as a colorless solid: $^1$H NMR (300 MHz, DMSO-d$_6$) δ 9.12 (br s, 1H), 8.80 (br s, 1H), 8.35 (s, 1H), 7.62-7.55 (m, 1H), 7.28-7.11 (m, 5H), 4.17-4.02 (m, 1H), 3.95-3.84 (m, 2H), 3.43-3.06 (m, 4H), 2.31-2.15 (m, 1H), 1.89-1.77 (m, 1H); MS (ES$^+$) m/z 502.8 (M+1).

EXAMPLE 48

Synthesis of 4-((trans-4-(3,4-difluorophenyl)piperidin-3-yl)methoxy)-2,5-difluoro-N-(1,2,4-thiadiazol-5-yl)benzenesulfonamide

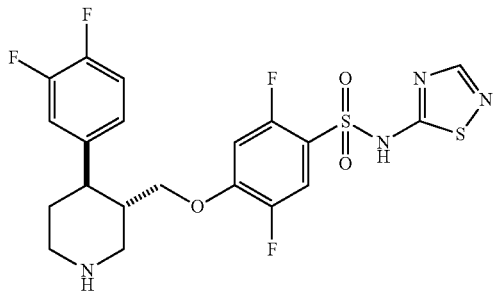

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(3,4-difluorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate, 4-((trans-4-(3,4-difluorophenyl)piperidin-3-yl)methoxy)-2,5-difluoro-N-(1,2,4-thiadiazol-5-yl)benzenesulfonamide was obtained as the corresponding trifluoroacetic acid salt in 73% yield (0.52 g) as a colorless solid: $^1$H NMR (300 MHz, DMSO-d$_5$) δ 88.87 (br s, 1H), 8.65 (br s, 1H), 8.39 (s, 1H), 7.60-7.51 (m, 1H), 7.40-7.30 (m, 1H), 7.26-7.17 (m, 1H), 7.15-7.06 (m, 1H), 7.03-6.86 (m, 1H), 3.87-3.70 (m, 2H), 3.55-3.32 (m, 2H), 3.02-2.75 (m, 3H), 2.50-2.42 (m, 1H), 1.95-1.78 (m, 2H); MS (ES$^+$) ink 502.8 (M+1).

EXAMPLE 49

Synthesis of 4-((trans-4-(4-chlorophenyl)piperidin-3-yl)methoxy)-2,5-difluoro-N-(pyrimidin-2-yl)benzenesulfonamide

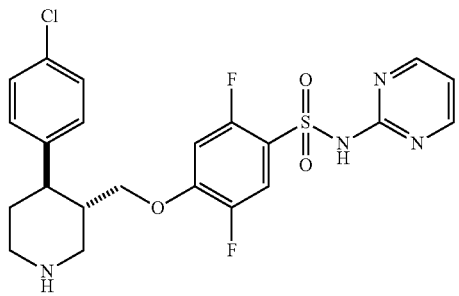

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-((4-(N-(2,4-dimethoxybenzyl)-N-(pyrimidin-2-yl)sulfamoyl)-2,5-difluorophenoxy)-methyl)piperidine-1-carboxylate, 4-((trans-4-(4-chlorophenyl)piperidin-3-yl)methoxy)-2,5-difluoro-N-(pyrimidin-2-yl)benzenesulfonamide was obtained as the corresponding trifluoroacetic acid salt in 28% yield (0.09 g) as a colorless solid: $^1$H NMR (300 MHz, DMSO-d$_6$) δ 8.78 (br s, 1H), 8.55 (br s, 1H), 8.41-8.45 (m, 2H), 7.69-7.62 (m, 1H), 7.33-7.29 (m, 2H), 7.16-7.12 (m, 2H), 7.07-7.97 (m, 2H), 3.81-3.64 (m, 2H), 3.50-3.30 (m, 2H), 3.03-2.72 (m, 3H), 2.51-2.68 (m, 1H), 1.75-1.90 (m, 2H); MS (ES$^+$) ink 494.8 (M+1), 496.8 (M+1).

EXAMPLE 50

Synthesis of 2,5-difluoro-4-((trans-4-(4-fluorophenyl)piperidin-3-yl)methoxy)-N-(pyrimidin-2-yl)benzenesulfonamide

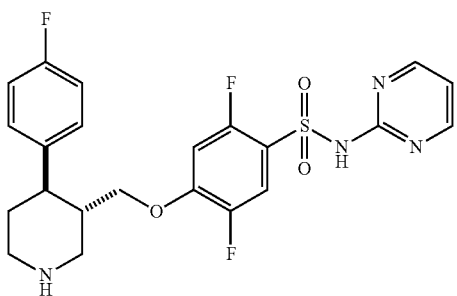

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl(sulfamoyl)-2,5-difluorophenoxy)methyl)piperidine-1-carboxylate with trans-tert-butyl 3-((4(4-(N-(2,4-dimethoxybenzyl)-N-(pyrimidin-2-yl)sulfamoyl)-2,5-difluorophenoxy)methyl)-4-(4-fluorophenyl)piperidine-1-carboxylate, 2,5-difluoro-4-((trans-4-(4-fluorophenyl(piperidin-3-yl)methoxy)-N-(pyrimidin-2-yl)benzenesulfonamide was obtained as the corresponding trifluoroacetic acid salt in 33% yield (0.09 g) as a colorless solid: $^1$H NMR (300 MHz, DMSO-$d_6$) δ 8.81-8.42 (m, 4H), 7.73-7.62 (m, 1H), 7.25-6.99 (m, 6H), 3.83-3.63 (m, 2H), 3.53-3.30 (m, 2H), 3.07-2.72 (m, 3H), 2.51-2.68 (m, 1H), 1.75-1.90 (m, 2H); MS (ES$^+$) m/z 478.9 (M+1).

EXAMPLE 51

Synthesis of 4-((trans-4-(4-chlorophenyl)piperidin-3-yl(methoxy)-2,5-difluoro-N-(1,3,4-thiadiazol-2-yl)benzenesulfonamide

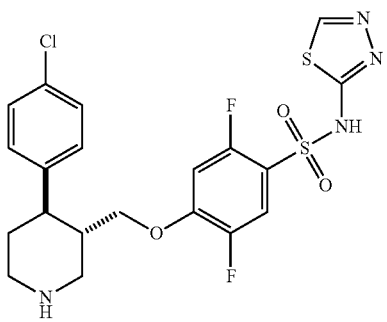

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-(4-(N-(2,4-dimethoxybenzyl)-N-(1,3,4-thiadiazol-2-yl)sulfamoyl)-2,5-difluorophenoxy)methyl)piperidine-1-carboxylate, 4-((trans-4-(4-chlorophenyl)piperidin-3-yl)methoxy)-2,5-difluoro-N-(1,3,4-thiadiazol-2-yl(benzenesulfonamide was obtained as the corresponding trifluoroacetic acid salt in 50% yield (0.05 g) as a colorless solid: $^1$H NMR (300 MHz, DMSO-$d_6$) δ 9.05-8.57 (m, 3H), 7.44-7.28 (m, 4H), 7.22-7.14 (m, 2H), 3.86-3.66 (m, 2H), 3.55-3.29 (m, 3H), 3.07-2.75 (m, 3H), 1.96-1.77 (m, 2H); MS (ES+) m/z 500.9 (M+1), 502.9 (M+1).

EXAMPLE 52

Synthesis of 4-((trans-4-(4-chlorophenyl)piperidin-3-yl)methoxy)-2,5-difluoro-N-(3-methyl-1,2,4-thiadiazol-5-yl)benzenesulfonamide

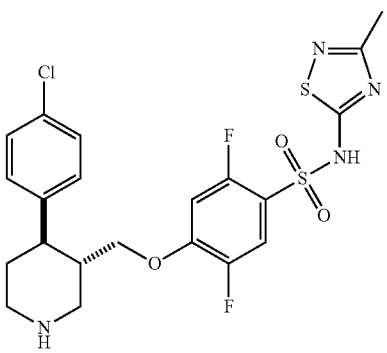

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-((4-(N-(2,4-dimethoxybenzyl)-N-(3-methyl-1,2,4-thiadiazol-5-yl)sulfamoyl)-2,5-difluorophenoxy)methyl)piperidine-1-carboxylate, 4-((trans-4-(4-chlorophenyl)piperidin-3-yl)methoxy)-2,5-difluoro-N-(3-methyl-1,2,4-thiadiazol-5-yl)benzenesulfonamide was obtained as the corresponding trifluoroacetic acid salt in 44% yield (0.057 g) as a colorless solid: $^1$H NMR (300 MHz, DMSO-$d_6$)δ 9.01-8.53 (m, 2H), 7.63-7.06 (m, 6H), 3.89-3.31 (m, 5H), 3.10-2.77 (m, 3H), 2.26 (s, 3H), 1.95-1.78 (m, 2H); MS (ES+) m/z 514.8 (M+1), 516.8 (M+1).

EXAMPLE 53

Synthesis of 4-((trans-1-benzyl-4-(4-chlorophenyl(pyrrolidin-3-yl(methoxy)-2,5-difluoro-N-(1,2,4-thiadiazol-5-yl)benzenesulfonamide

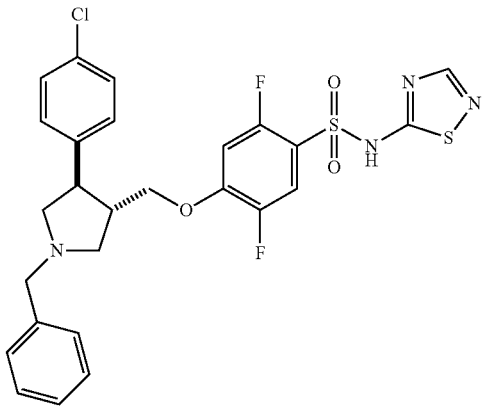

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-4-((-1-benzyl-4-(4-chlorophenyl(pyrrolidin-3-yl)methoxy)-N-(2,4-dimethoxybenzyl)-2,5-difluoro-N-(1,2,4-thiadiazol-5-yl) benzenesulfonamide, 4-((trans-1-benzyl-4-(4-chlorophenyl) pyrrolidin-3-yl(methoxy)-2,5-difluoro-N-(1,2,4-thiadiazol-5-yl(benzenesulfonamide was obtained as a colorless solid in 39% yield (0.36 g): $^1$H NMR (300 MHz, DMSO-d$_6$) δ 10.50 (s, 1H), 8.35 (s, 1H), 7.65-7.15 (m, 11H), 4.46 (s, 2H), 4.21-4.00 (m, 2H), 3.81-3.61 (m, 2H), 3.52-3.21 (m, 3H), 3.10-2.85 (m, 1H); MS (ES+) m/z 576.8 (M+1), 578.8 (M+1).

EXAMPLE 54

Synthesis of 4-((trans-4-(4-chlorophenyl)pyrrolidin-3-yl)methoxy)-2,5-difluoro-N-(1,2,4-thiadiazol-5-yl)benzenesulfonamide

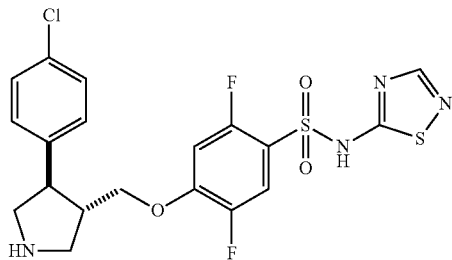

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-(4-chlorophenyl)-4-(4-(N-(2,4-dimethoxybenzyl)-N-(1,2,4-thiadiazol-5-yl)sulfamoyl)-2,5-difluorophenoxy)methyl)pyrrolidine-1-carboxylate and to replace trifluoroacetic acid with 30% w/v hydrogen bromide in acetic acid, 4-((trans-4-(4-chlorophenyl)pyrrolidin-3-yl)methoxy)-2,5-difluoro-N-(1,2,4-thiadiazol-5-yl(benzenesulfonamide was obtained as the corresponding hydrobromide salt in 71% yield (0.057 g) as a colorless solid: $^1$H NMR (300 MHz, DMSO-d$_6$) δ 9.31-8.92 (m, 2H), 8.50 (s, 1H), 7.61-7.50 (m, 1H), 7.49-7.23 (m, 5H), 4.21-3.99 (m, 1H), 3.76-3.49 (m, 3H), 3.35-3.05 (m, 3H), 2.93-2.65 (m, 1H); MS (ES$^+$) m/z 486.8 (M+1), 488.8 (M+1).

EXAMPLE 55

Synthesis of 4-((trans-4-(4-chlorophenyl)piperidin-3-yl)methoxy)-2,5-difluoro-N-(2-methyl-2H-tetrazol-5-yl)benzenesulfonamide

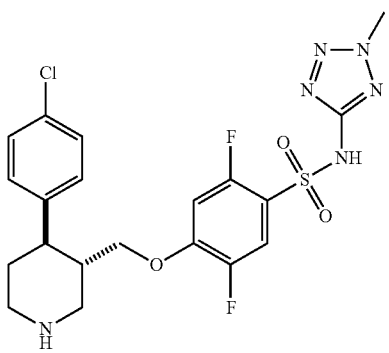

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl(sulfamoyl)-2,5-difluorophenoxy)methyl)piperidine-1-carboxylate with trans-tert-butyl 4-(4-chlorophenyl)-3-((4-(N-(2,4-dimethoxybenzyl)-N-(2-methyl-2H-tetrazol-5-yl(sulfamoyl)-2,5-difluorophenoxy)methyl)piperidine-1-carboxylate, 4-((trans-4-(4-chlorophenyl)piperidin-3-yl)methoxy)-2,5-difluoro-N-(2-methyl-2H-tetrazol-5-yl)benzenesulfonamide was obtained as a colorless solid in 71% yield (0.13 g): $^1$H NMR (300 MHz, DMSO-d$_6$) δ 8.76 (s, 2H), 7.56-7.45 (m, 1H), 7.44-7.35 (m, 2H), 7.27-7.17 (m, 2H), 6.89-6.77 (m, 1H), 3.97 (s, 3H), 3.84-3.64 (m, 2H), 3.61-3.50 (m, 1H), 3.46-3.36 (m, 1H), 3.11-2.78 (m, 3H), 2.47-2.37 (m, 1H), 2.01-1.84 (m, 2H); MS (ES$^+$) m/z 498.9 (M+1), 500.9 (M+1).

EXAMPLE 56

Synthesis of 4-((trans-4-(4-chlorophenyl)piperidin-3-yl)methoxy)-2,5-difluoro-N-(5-methylisoxazol-3-yl)benzenesulfonamide

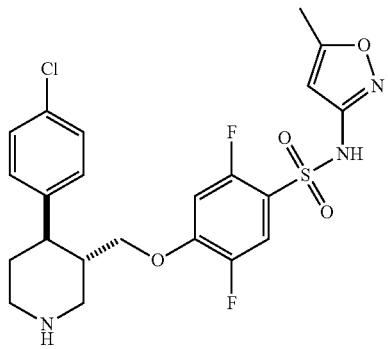

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-(4-(N-(2,4-dimethoxybenzyl)-N-(5-methylisoxazol-3-yl)sulfamoyl)-2,5-difluorophenoxy)methyl)piperidine-1-carboxylate, 4-((trans-4-(4-chlorophenyl)piperidin-3-yl)methoxy)-2,5-difluoro-N-(5-methylisoxazol-3-yl)benzenesulfonamide was obtained as a colorless solid in 80% yield (0.18 g): $^1$H NMR (300 MHz, DMSO-d$_6$) δ 8.60 (s, 2H), 7.47-7.33 (m, 3H), 7.28-7.16 (m, 2H), 6.91-6.80 (m, 1H), 5.76 (s, 1H), 3.84-3.63 (m, 2H), 3.55-3.47 (m, 2H), 3.06-2.76 (m, 3H), 2.46-2.35 (m, 1H), 2.13 (s, 3H), 1.96-1.79 (m, 2H); MS (ES$^+$) ink 497.8 (M+1), 499.8 (M+1).

EXAMPLE 57

Synthesis of 4-((trans-4-(4-chlorophenyl)piperidin-3-yl)methoxy)-2,5-difluoro-N-(5-methylthiazol-2-yl)benzenesulfonamide

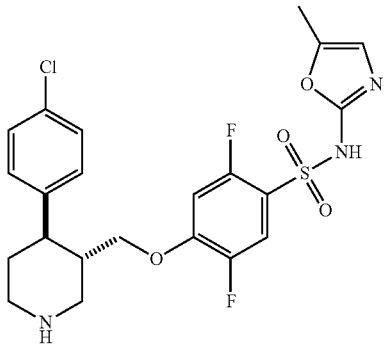

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-(4-(N-(2,4-dimethoxybenzyl)-N-(5-methylthiazol-2-yl)sulfamoyl)-2,5-difluorophenoxy)methyl)piperidine-1-carboxylate, 4-((trans-4-(4-chlorophenyl)piperidin-3-yl)methoxy)-2,5-difluoro-N-(5-methylthiazol-2-yl)benzenesulfonamide was obtained as a colorless solid in 71% yield (0.14 g): $^1$H NMR (300 MHz, DMSO-$d_6$+1 drop of $D_2O$) δ 7.47-7.28 (m, 3H), 7.24-7.14 (m, 2H), 6.92-6.80 (m, 1H), 6.67-6.59 (m, 1H), 3.81-3.59 (m, 2H), 3.35-3.15 (m, 2H), 2.98-2.64 (m, 3H), 2.41-2.22 (m, 1H), 2.09 (s, 3H), 1.90-1.66 (m, 2H); MS (ES+) m/z 513.8 (M+1), 515.8 (M+1).

EXAMPLE 58

Synthesis of 4-((trans-4-(4-chlorophenyl)piperidin-3-yl)methoxy)-3-cyano-N-(1,2,4-thiadiazol-5-yl)benzenesulfonamide

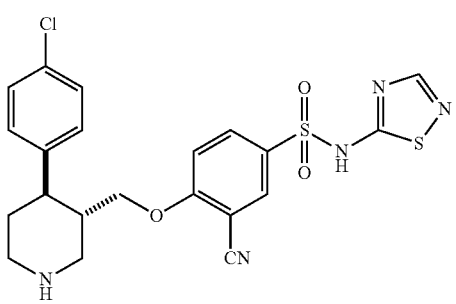

Following the procedure as described in EXAMPLE 44, making non-critical variations to replace trans-tent-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-((2-cyano-4-(N-(2,4-dimethoxybenzyl)-N-(1,2,4-thiadiazol-5-yl)sulfamoyl)-phenoxy)methyl)piperidine-1-carboxylate, 4-((trans-4-(4-chlorophenyl)piperidin-3-yl)methoxy)-3-cyano-N-(1,2,4-thiadiazol-5-yl)benzenesulfonamide was obtained as a colorless solid in 47% yield (0.016 g): $^1$H NMR (300 MHz, DMSO-$d_6$) δ 8.75-8.45 (m, 2H), 8.00-7.83 (m, 3H), 7.46-7.35 (m, 2H), 7.29-7.18 (m, 2H), 7.09-7.00 (m, 1H), 3.98-3.70 (m, 2H), 3.63-3.35 (m, 3H), 3.09-2.76 (m, 3H), 2.04-1.76 (m, 2H); MS (ES+) m/z 489.8 (M+1), 491.8 (M+1).

EXAMPLE 59

Synthesis of 4-((trans-4-(4-chlorophenyl)piperidin-3-yl)methoxy)-3-fluoro-N-(1,2,4-thiadiazol-5-yl)benzenesulfonamide

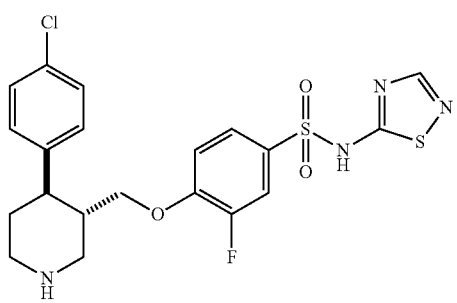

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl) piperidine-1-carboxylate with trans-tert-butyl 4-(4-chlorophenyl)-3-((4-(N-(2,4-dimethoxybenzyl)-N-(1,2,4-thiadiazol-5-yl)sulfamoyl)-2-fluorophenoxy)methyl)piperidine-1-carboxylate, 4-((trans-4-(4-chlorophenyl)piperidin-3-yl)methoxy)-3-fluoro-N-(1,2,4-thiadiazol-5-yl)benzenesulfonamide was obtained as a colorless solid in 31% yield (0.051 g): $^1$H NMR (300 MHz, DMSO-$d_6$) δ 8.70-8.50 (m, 2H), 7.84 (s, 1H), 7.55-7.33 (m, 4H), 7.30-7.14 (m, 2H), 7.03-6.88 (m, 1H), 3.87-3.63 (m, 2H), 3.61-3.26 (m, 2H), 3.10-2.77 (m, 3H), 2.46-2.36 (m, 1H), 1.97-1.76 (m, 2H); MS (ES$^+$) m/z 482.8 (M+1), 484.8 (M+1).

EXAMPLE 60

Synthesis of 4-((trans-4-(4-chlorophenyl)piperidin-3-yl)methoxy)-2,5-difluoro-N-(pyrimidin-4-yl)benzenesulfonamide

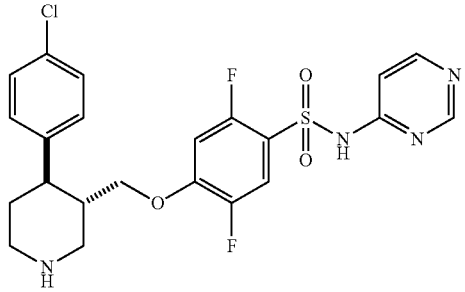

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-(4-(N-(2,4-dimethoxybenzyl)-N-(pyrimidin-4-yl)sulfamoyl)-2,5-difluorophenethyl)piperidine-1-carboxylate, 4-((trans-4-(4-chlorophenyl)piperidin-3-yl)methoxy)-2,5-difluoro-N-(pyrimidin-4-yl)benzenesulfonamide was obtained as a colorless solid in 68% yield (0.12 g):$^1$H NMR (300 MHz, DMSO-d$_6$) δ 8.70 (s, 2H), 8.26 (s, 1H), 8.02-7.85 (m, 1H), 7.62-7.11 (m, 5H), 6.96-6.76 (m, 1H), 6.63-6.42 (m, 1H), 3.92-3.45 (m, 4H), 3.11-2.71 (m, 3H), 2.45-2.36 (m, 1H), 1.96-1.80 (m, 2H); MS (ES$^+$) m/z 494.9 (M+1), 496.9 (M+1).

EXAMPLE 61

Synthesis of N-(5-chlorothiazol-2-yl)-4-(trans-4-(3,4-difluorophenyl)piperidin-3-yl)methoxy)-2,5-difluorobenzenesulfonamide

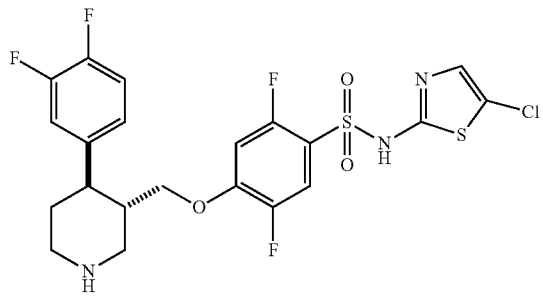

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-((4(4-(N-(5-chlorothiazol-2-yl)-N-(2,4-dimethoxybenzyl(sulfamoyl)-2,5-difluorophenoxy)methyl)-4-(3,4-difluorophenyl)piperidine-1-carboxylate, N-(5-chlorothiazol-2-yl)-4-((trans-4-(3,4-difluorophenyl)piperidin-3-yl)methoxy)-2,5-difluorobenzenesulfonamide was obtained as the corresponding trifluoroacetic acid salt in 40% yield (0.17 g) as a colorless solid: $^1$H NMR (300 MHz, DMSO-d$_6$) δ 9.00-8.54 (m, 2H), 7.59-7.52 (m, 2H), 7.41-7.30 (m, 1H), 7.25-7.08 (m, 2H), 7.04-6.97 (m, 1H), 3.87-3.72 (m, 2H), 3.53-3.34 (m, 2H), 3.01-2.75 (m, 3H), 2.50-2.42 (m, 1H), 1.95-1.78 (m, 2H); MS (ES+) m/z 535.7 (M+1).

EXAMPLE 62

Synthesis of 4-((trans-4-(4-chlorophenyl)piperidin-3-yl)methoxy)-N-(5-chlorothiazol-2-yl)-2,5-difluorobenzenesulfonamide

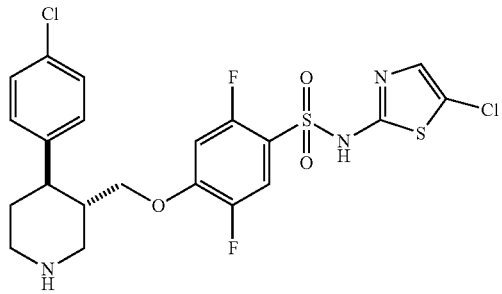

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl(sulfamoyl)-2,5-difluorophenoxy)methyl)piperidine-1-carboxylate with trans-tert-butyl 4-(4-chlorophenyl)-3-((4-(N-(5-chlorothiazol-2-yl)-N-(2,4-dimethoxybenzyl)sulfamoyl)-2,5-difluorophenoxy)methyl)piperidine-1-carboxylate, 4-((trans 4-(4-chlorophenyl)piperidin-3-yl)methoxy)-N-(5-chlorothiazol-2-yl)-2,5-difluorobenzenesulfonamide was obtained as the corresponding trifluoroacetic acid salt in 46% yield (0.095 g) as a colorless solid: $^1$H NMR (300 MHz, CDCl$_3$) δ 9.57 (br s, 1H), 8.83 (br s, 1H), 7.62-7.57 (m, 1H), 7.30-7.27 (m, 2H), 7.18-7.16 (m, 2H), 6.94 (s, 1H), 6.49-6.44 (m, 1H), 3.79-3.61 (m, 4H), 3.21-3.17 (m, 2H), 2.98-2.94 (m, 1H), 2.69-2.62 (m, 1H), 2.30-2.25 (m, 1H), 2.12-2.06 (m, 1H); MS (ES−) m/z 531.6 (M−1), 533.6 (M−1).

EXAMPLE 63

Synthesis of 4-((trans-4-(4-chlorophenyl)piperidin-3-yl)methoxy)-2,5-difluoro-N-(5-fluoropyridin-2-yl)benzenesulfonamide

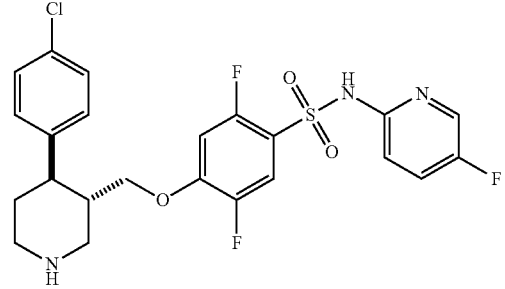

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-((2,5-difluoro-4-(N-(5-fluoropyridin-2-yl)-N-(methoxymethyl)sulfamoyl)-phenoxy)methyl)piperidine-1-carboxylate, 4-((trans-4-(4-chlorophenyl)piperidin-3-yl)methoxy)-2,5-difluoro-N-(5-fluoropyridin-2-yl)benzenesulfonamide was obtained as the corresponding trifluoroacetic acid salt in 49% yield (0.03 g) as a colorless solid: $^1$H NMR (300 MHz, CDCl$_3$) δ 9.93 (br s, 1H), 9.39 (br s, 1H), 8.27 (s, 1H), 7.50-7.45 (m, 3H), 7.31-7.29 (m, 2H), 7.15-7.13 (m, 2H), 6.44-6.39 (m, 1H), 3.76-3.56 (m, 4H), 3.08-3.01 (m, 2H), 2.85-2.78 (m, 1H), 2.70-2.63 (m, 1H), 2.31-2.04 (m, 2H); MS (ES−) m/z 509.7 (M−1), 511.8 (M−1).

EXAMPLE 64

Synthesis of 4-((trans-4-(4-chlorophenyl)piperidin-3-yl)methoxy)-2,5-difluoro-N-(5-fluoropyrimidin-2-yl)benzenesulfonamide

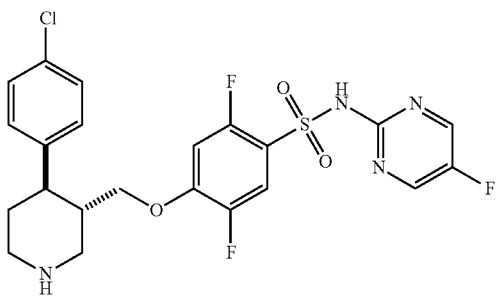

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-((4-(N-(2,4-dimethoxybenzyl)-N-(5-fluoropyrimidin-2-yl)sulfamoyl)-2,5-difluorophenoxy)methyl)piperidine-1-carboxylate, 4-((trans-4-(4-chlorophenyl)piperidin-3-yl)methoxy)-2,5-difluoro-N-(5-fluoropyrimidin-2-yl)benzenesulfonamide was obtained as the corresponding trifluoroacetic acid salt in 39% yield (0.065 g) as a colorless solid: $^1$H NMR (300 MHz, DMSO-$d_6$) δ 12.31 (s, 1H), 8.91-8.86 (m, 1H), 8.68-8.61 (m, 3H), 7.75-7.70 (m, 1H), 7.39-7.36 (m, 2H), 7.22-7.10 (m, 3H), 3.87-3.71 (m, 2H), 3.56-3.38 (m, 2H), 3.02-2.81 (m, 3H), 2.49-2.44 (m, 1H), 1.92-1.90 (m, 2H); MS (ES+) m/z 512.9 (M+1), 514.9 (M+1).

EXAMPLE 65

Synthesis of 4-((trans-4-(4-chlorophenyl)piperidin-3-yl)methoxy)-2,5-difluoro-N-(pyridazin-3-yl)benzenesulfonamide

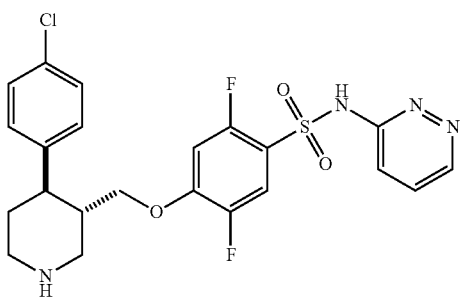

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-(4-(N-(2,4-dimethoxybenzyl)-N-(pyridazin-3-yl)sulfamoyl)-2,5-difluorophenoxy)-methyl)piperidine-1-carboxylate, 4-((trans-4-(4-chlorophenyl)piperidin-3-yl(methoxy)-2,5-difluoro-N-(pyridazin-3-yl)benzenesulfonamide was obtained as the corresponding trifluoroacetic acid salt in 65% yield (0.09 g) as a colorless solid: $^1$H NMR (300 MHz, DMSO-$d_6$) δ 8.85-8.64 (m, 2H), 8.33-8.32 (m, 2H), 7.90-7.86 (m, 1H), 7.71-7.62 (m, 2H), 7.36-7.34 (m, 1H), 7.19-7.16 (m, 1H), 7.08-7.02 (m, 1H), 3.82-3.66 (m, 2H), 3.53-3.35 (m, 2H), 3.03-2.77 (m, 3H), 2.46-2.37 (m, 1H), 1.87-1.85 (m, 2H); MS (ES+) m/z 494.8 (M+1), 496.8 (M+1).

EXAMPLE 66

Synthesis of 4-((cis-4-(4-chlorophenyl)piperidin-3-yl(methoxy)-2,5-difluoro-N-(1,2,4-thiadiazol-5-yl)benzenesulfonamide

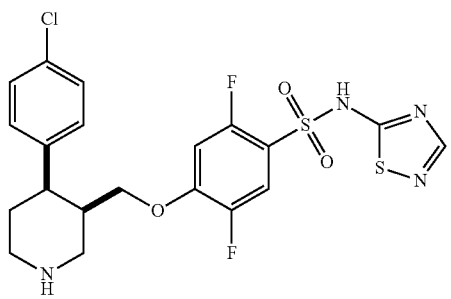

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with cis-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate, 4-((cis-4-(4-chlorophenyl)piperidin-3-yl)methoxy)-2,5-difluoro-N-(1,2,4-thiadiazol-5-yl)benzenesulfonamide was obtained as the corresponding trifluoroacetic acid salt in 78% yield (0.13 g) as a colorless solid: $^1$H NMR (300 MHz, DMSO-$d_6$) δ 9.08-8.48 (m, 3H), 7.59-7.71 (m, 6H), 4.42-4.25 (m, 1H), 3.68-3.65 (m, 1H), 3.50-3.06 (m, 5H), 2.71-2.68 (m, 1H), 2.21-2.08 (m, 1H), 1.92-1.87 (m, 1H); MS (ES−) m/z 498.6 (M−1), 500.5 (M−1).

EXAMPLE 67

Synthesis of 4-((trans-4-(4-chlorophenyl)piperidin-3-yl)methoxy)-2,5-difluoro-N-(pyridin-2-yl)benzenesulfonamide

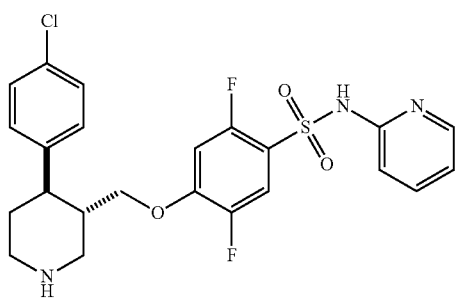

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl) piperidine-1-carboxylate with trans-tert-butyl 4-(4-chlorophenyl)-3-((4-(N-(2,4-dimethoxybenzyl)-N-(pyridin-2-yl) sulfamoyl)-2,5-difluorophenoxy)-methyl)piperidine-1-carboxylate, 4-((trans-4-(4-chlorophenyl)piperidin-3-yl)methoxy)-2,5-difluoro-N-(pyridin-2-yl) benzenesulfonamide was obtained as the corresponding trifluoroacetic acid salt in 17% yield (0.033 g) as a colorless solid: $^1$H NMR (300 MHz, DMSO-$d_6$) δ 8.81 (br s, 1H), 8.61 (br s, 1H), 7.89 (br s, 1H), 7.78-7.73 (m, 1H), 7.66-7.60 (m, 1H), 7.35-7.30 (m, 2H), 7.18-6.99 (m, 4H), 6.83-6.79 (m, 1H), 3.82-3.66 (m, 2H), 3.52-3.48 (m, 2H), 3.08-2.77 (m, 3H), 2.49-2.44 (m, 1H), 1.87-1.85 (m, 2H); MS (ES+) m/z 493.4 (M+1), 495.3 (M+1).

EXAMPLE 68

Synthesis of 2,5-difluoro-4-((trans-2-(4-fluorophenyl)cyclohexyl)methoxy)-N-(1,2,4-thiadiazol-5-yl)benzenesulfonamide

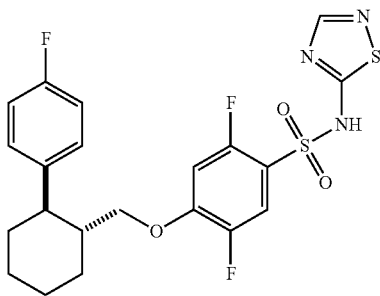

To a solution of (trans-2-(4-fluorophenyl)cyclohexyl) methanol (0.113 g, 0.50 mmol) in tetrahydrofuran (10 mL) was added lithium bis(trimethylsilyl)amide (1 M solution in tetrahydrofuran, 0.6 mL, 0.6 mmol) at 0° C. The reaction mixture was cooled to −78° C. and a solution of N-(2,4-dimethoxybenzyl)-2,4,5-trifluoro-N-(1,2,4-thiadiazol-5-yl)benzenesulfonamide (0.233 g, 0.50 mmol, prepared according to PCT Published Patent Applicatin No. WO 2010/079443) in tetrahydrofuran (5 mL) was added to the reaction mixture. The reaction mixture was stirred at ambient temperature for 16 h and saturated aqueous ammonium chloride (2 mL) was added at 0° C., followed by ethyl acetate (30 mL). The mixture was washed with brine (50 mL) and concentrated in vacuo. The residue was dissolved in trifluoroacetic acid (5 mL) and stirred for 5 h at ambient temperature. The mixture was concentrated in vacuo and the residue was purified by column chromatography eluting with 30% ethyl acetate in hexanes to afford 2,5-difluoro-4-((trans-2-(4-fluorophenyl)cyclohexyl)methoxy)-N-(1,2,4-thiadiazol-5-yl)benzenesulfonamide as an off-white solid in 17% yield (0.041 g): $^1$H NMR (300 MHz, CDCl$_3$) δ 8.03 (s, 1H), 7.71-7.51 (m, 1H), 7.32-6.85 (m, 4H), 6.51-6.34 (m, 1H), 3.80-3.35 (m, 2H), 2.55-2.43 (m, 1H), 2.10-1.13 (m, 10H); MS (ES+) m/z 483.9 (M+1).

EXAMPLE 69

Synthesis of trans-tert-butyl 3-((4-(N-(1,2,4-thiadiazol-5-yl)sulfamoyl)-2,5-difluorophenoxy)methyl)-4-(4-chlorophenyl)piperidine-1-carboxylate

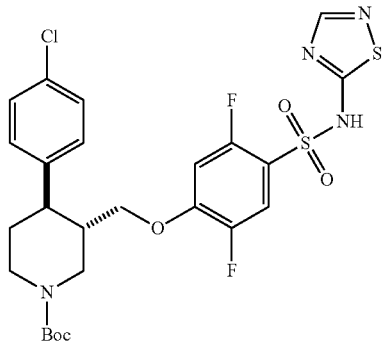

To a stirred suspension of 4-((trans-4-(4-chlorophenyl)piperidin-3-yl(methoxy)-2,5-difluoro-N-(1,2,4-thiadiazol-5-yl)benzenesulfonamide (0.085 g, 0.17 mmol) in dichloromethane (6 mL) at ambient temperature was added triethylamine (24 µL, 0.2 mmol). The reaction mixture was stirred for 5 minutes at ambient temperature and cooled to 0° C. A solution of di-tert-butyl dicarbonate (0.037 g. 0.2 mmol) in dichloromethane (2 mL) was added dropwise. The mixture was stirred at ambient temperature for 16 h, diluted with water (40 mL) and extracted with dichloromethane (2×50 mL). The combined organic extracts were washed with brine (100 mL), dried over anhydrous magnesium sulfate, filtered and concentrated in vacuo. The residue was purified by column chromatography eluting with a 0 to 10% gradient of methanol in dichloromethane to afford a colorless solid. The solid was dissolved in dichloromethane, washed with 7% w/v aqueous citric acid and brine, dried over anhydrous magnesium sulfate, filtered and concentrated in vacuo to afford trans-tert-butyl 3-((4(4-(N-(1,2,4-thiadiazol-5-yl)sulfamoyl)-2,5-difluorophenoxy)methyl)-4-(4-chlorophenyl)piperidine-1-carboxylate as a colorless solid (0.020 g, 20%): $^1$H NMR (300 MHz, CDCl$_3$) δ 8.06 (s, 1H), 7.69-7.57 (m, 1H), 7.31-7.20 (m, 2H), 7.15-7.04 (m, 2H), 6.53-6.40 (m, 1H), 4.48-4.34 (m, 1H), 4.33-4.16 (m, 1H), 3.81-3.67 (m, 1H), 3.64-3.53 (m, 1H), 2.92-2.63 (m, 3H), 2.20-2.01 (m, 1H), 1.88-1.63 (m, 2H), 1.48 (s, 9H); MS (ES+) m/z 622.8 (M+23), 624.7 (M+23).

EXAMPLE 70

Synthesis of 4-((trans-4-(4-chlorophenyl)-1-methylpiperidin-3-yl)methoxy)-2,5-difluoro-N-(1,2,4-thiadiazol-5-yl)benzenesulfonamide

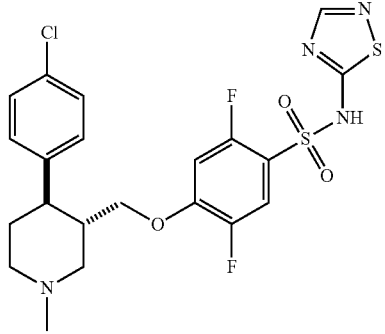

To a stirred suspension of 4-((trans-4-(4-chlorophenyl)piperidin-3-yl)methoxy)-2,5-difluoro-N-(1,2,4-thiadiazol-5-yl)benzenesulfonamide (0.11 g, 0.22 mmol) in dichloromethane (7 mL) and methanol (4 mL) was added 37% w/v aqueous formaldehyde (0.09 mL, 1.2 mmol). The mixture was stirred at ambient temperature for 30 minutes and sodium triacetoxyborohydride (0.24 g, 1.15 mmol) was added. The mixture was stirred for 3 h and concentrated to dryness in vacuo. The residue was diluted with ethyl acetate (100 mL), washed with saturated aqueous sodium bicarbonate (2×40 mL) and brine (2×40 mL), dried over anhydrous magnesium sulfate, filtered and concentrated in vacuo. The residue was purified by preparative HPLC to afford 4-((trans-4-(4-chlorophenyl)-1-methylpiperidin-3-yl)methoxy)-2,5-difluoro-N-(1,2,4-thiadiazol-5-yl)benzenesulfonamide as the corresponding colorless trifluoroacetic acid salt (0.009 g, 8%): $^1$H NMR (300 MHz, DMSO-$d_6$+1 drop of $D_2O$) δ 8.41 (s, 1H), 7.63-7.54 (m, 1H), 7.43-7.35 (m, 2H), 7.25-7.18 (m, 2H), 7.17-7.07 (m, 1H), 4.17-4.08 (m, 1H), 3.91-3.80 (m, 1H), 3.79-3.59 (m, 3H), 3.19-3.00 (m, 2H), 2.95-2.74 (m, 4H), 2.04-1.86 (m, 2H); MS (ES+) m/z 514.7 (M+1), 516.7 (M+1).

EXAMPLE 71

Synthesis of 2,5-difluoro-4-((trans-4-(4-fluorophenyl)tetrahydro-2H-pyran-3-yl)methoxy)-N-(1,2,4-thiadiazol-5-yl(benzenesulfonamide

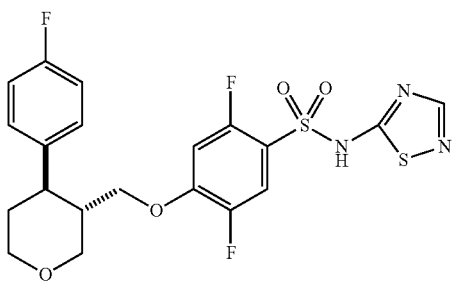

Following the procedure as described in EXAMPLE 44, making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with N-(2,4-dimethoxybenzyl)-2,5-difluoro-4-((trans-4-(4-fluorophenyl)tetrahydro-2H-pyran-3-yl)methoxy)-N-(1,2,4-thiadiazol-5-yl)benzenesulfonamide, 2,5-difluoro-4-Wrans-4-(4-fluorophenyl)tetrahydro-2H-pyran-3-yl)methoxy)-N-(1,2,4-thiadiazol-5-yl)benzenesulfonamide was obtained as a colorless solid in 32% yield (0.084 g): $^1$H NMR (300 MHz, CDCl$_3$) δ 8.12-7.99 (m, 1H), 7.72-7.59 (m, 1H), 7.22-7.09 (m, 2H), 7.07-6.89 (m, 2H), 6.54-6.37 (m, 1H), 4.35-4.00 (m, 2H), 3.84-3.37 (m, 4H), 2.88-2.69 (m, 1H), 2.41-2.17 (m, 1H), 2.05-1.69 (m, 2H); MS (ES+) m/z 485.9 (M+1).

EXAMPLE 72

Synthesis of 2,5-difluoro-4-((trans-2-(4-fluorophenyl)-5-methoxycyclohexyl)methoxy)-N-(1,2,4-thiadiazol-5-yl)benzenesulfonamide

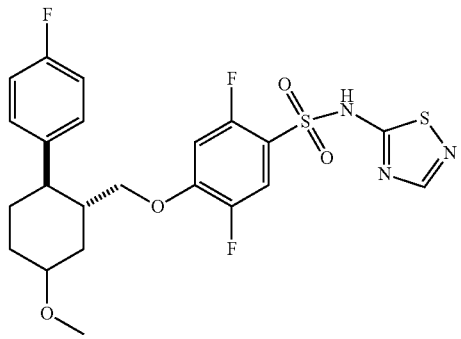

A solution of trans-2-(4-fluorophenyl)-5-methoxycyclohexyl)methanol (0.48 g, 2.0 mmol) in tetrahydrofuran (10 mL) was treated with lithium bis(trimethylsilyl)amide (1 M solution in tetrahydrofuran, 2.0 mL, 2.0 mmol) at 0° C. The reaction mixture was cooled to −78° C. and a solution of N-(2,4-dimethoxybenzyl)-2,4,5-trifluoro-N-(1,2,4-thiadiazol-5-yl)benzenesulfonamide (0.89 g, 2.0 mmol, prepared according to PCT Published Patent Application No. WO 2010/079443) in tetrahydrofuran (5 mL) was added to the reaction mixture. The reaction mixture was allowed to warm to ambient temperature and was stirred for 5 h. Saturated aqueous ammonium chloride (2 mL) was added at 0° C., followed by ethyl acetate (30 mL). The mixture was washed with brine (50 mL) and concentrated in vacuo. The residue was dissolved in trifluoroacetic acid (10 mL) and stirred for 3 h at ambient temperature. The mixture was concentrated in vacuo and the residue purified by column chromatography eluting with 5% methanol in dichloromethane to afford 2,5-difluoro-4-((trans-2-(4-fluorophenyl)-5-methoxycyclohexyl)methoxy)-N-(1,2,4-thiadiazol-5-yl)benzenesulfonamide as an off-white solid in 17% yield (0.17 g): $^1$H NMR (300 MHz, CDCl$_3$) δ 8.47 (s, 1H), 7.61-7.48 (m, 1H), 7.21-6.96 (m, 5H), 3.80-3.42 (m, 3H), 3.22 (s, 3H), 2.52-2.39 (m, 2H), 2.23-1.62 (m, 4H), 1.55-1.36 (m, 3H); MS (ES+) m/z 514.0 (M+1).

EXAMPLE 73

Synthesis of 2,5-difluoro-4-((trans-4-(4-fluorophenyl)piperidin-3-yl(oxy)-N-(1,2,4-thiadiazol-5-yl)benzenesulfonamide

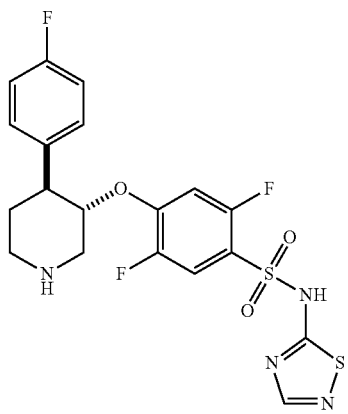

A solution of tert-butyl 3-(4-(N-(2,4-dimethoxybenzyl)-N-(1,2,4-thiadiazol-5-yl)sulfamoyl)-2,5-difluorophenoxy)-4-(4-fluorophenyl)piperidine-1-carboxylate (0.27 g, 0.38 mmol) in trifluoroacetic acid (2 mL) was stirred at ambient temperature for 16 h. The mixture was concentrated in vacuo and the residue was purified by preparative reverse phase HPLC to afford 2,5-difluoro-4-((trans-4-(4-fluorophenyl)piperidin-3-yl)oxy)-N-(1,2,4-thiadiazol-5-yl)benzenesulfonamide as the corresponding trifluoroacetic acid salt in 28% yield (0.047 g) as a colorless solid: $^1$H NMR (300 MHz, DMSO-$d_6$) δ 9.34 (s, 1H), 8.63 (s, 1H), 8.35 (s, 1H), 7.53-7.02 (m, 6H), 3.75-3.66 (m, 1H), 3.46-3.13 (m, 3H), 3.11-2.94 (m, 2H), 2.08-1.82 (m, 2H); MS (ES+) m/z 470.7 (M+1).

EXAMPLE 74

Synthesis of 2,5-difluoro-4-((trans-4-phenylpiperidin-3-yl)methoxy)-N-(1,2,4-thiadiazol-5-yl)benzenesulfonamide

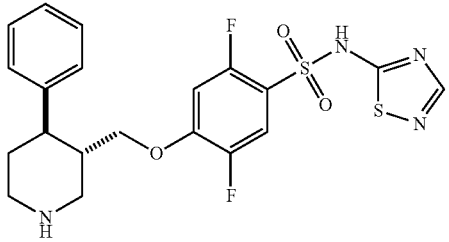

Following the procedure as described above in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-((4-(N-(2,4-dimethoxybenzyl)-N-(1,2,4-thiadiazol-5-yl)sulfamoyl)-2,5-difluorophenoxy)methyl)-4-phenylpiperidine-1-carboxylate, 2,5-difluoro-4-((trans-4-phenylpiperidin-3-yl(methoxy)-N-(1,2,4-thiadiazol-5-yl)benzenesulfonamide was obtained as a colorless solid in 34% yield (0.03 g): $^1$H NMR (300 MHz, DMSO-$d_6$) δ 8.95-8.71 (m, 2H), 8.47 (s, 1H), 7.63-7.53 (m, 1H), 7.36-7.07 (m, 6H), 3.87-3.72 (m, 2H), 3.57-3.39 (m, 2H), 3.04-2.82 (m, 3H), 2.50-2.40 (m, 1H), 1.97-1.85 (m, 2H); $^{19}$F NMR (282 MHz, DMSO-$d_6$) δ −76.6 (s), −113.2 (d, J=15 Hz), −141.0 (d, J=15 Hz); MS (ES+) m/z 466.9 (M+1).

EXAMPLE 75

Synthesis of (R)-4-((1-(4-chlorophenyl)-6-oxopiperazin-2-yl)methoxy)-2,5-difluoro-N-(1,2,4-thiadiazol-5-yl)benzenesulfonamide

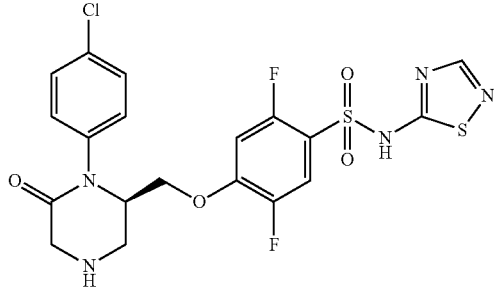 [SMILES: O=C1CNC[C@H](COc2cc(F)c(S(=O)(=O)Nc3ncns3)cc2F)N1c1ccc(Cl)cc1]

Following the procedure as described above in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-((4-(N-(2,4-dimethoxybenzyl)-N-(1,2,4-thiadiazol-5-yl)sulfamoyl)-2,5-difluorophenoxy)methyl)-4-(4-fluorophenyl)piperidine-1-carboxylate, (R)-4-(1-(4-chlorophenyl)-6-oxopiperazin-2-yl)methoxy)-2,5-difluoro-N-(1,2,4-thiadiazol-5-yl)benzenesulfonamide was obtained after purification by preparative HPLC as the corresponding trifluoroacetic acid salt in 48% yield (0.08 g) as a colorless solid: $^1$H NMR (300 MHz, DMSO-$d_6$) δ 9.50 (br s, 2H), 8.43 (s, 1H), 7.62-7.55 (m, 1H), 7.50-7.43 (m, 2H), 7.26-7.20 (m, 2H), 7.19-7.14 (m, 1H), 4.55-4.43 (br s, 1H), 4.19-3.75 (m, 5H), 3.57-3.49 (m, 1H); MS (ES+) m/z 515.7 (M+1), 517.7 (M+1).

EXAMPLE 76

Synthesis of (S)-4-((1-(4-chlorophenyl)-6-oxopiperazin-2-yl)methoxy)-2,5-difluoro-N-(1,2,4-thiadiazol-5-yl)benzenesulfonamide

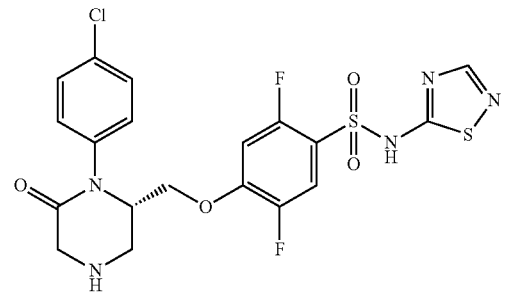 [SMILES: O=C1CNC[C@@H](COc2cc(F)c(S(=O)(=O)Nc3ncns3)cc2F)N1c1ccc(Cl)cc1]

Following the procedure as described above in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with (S)-tert-butyl 4-(4-chlorophenyl)-3-((4(4-(N-(2,4-dimethoxybenzyl)-N-(1,2,4-thiadiazol-5-yl)sulfamoyl)-2,5-difluorophenoxy)methyl)-5-oxopiperazine-1-carboxylate, (S)-4-((1-(4-chlorophenyl)-6-oxopiperazin-2-yl)methoxy)-2,5-difluoro-N-(1,2,4-thiadiazol-5-yl)benzenesulfonamide was obtained as the corresponding trifluoroacetic acid salt in 99% yield (0.61 g) as a colorless solid: $^1$H NMR (300 MHz, DMSO-$d_6$) δ 9.70 (br s, 1H), 8.43 (s, 1H), 7.62-7.55 (m, 1H), 7.50-7.43 (m, 2H), 7.26-7.20 (m, 2H), 7.19-7.14 (m, 1H), 4.51 (br s, 1H), 4.19-3.75 (m, 5H), 3.57-3.49 (m, 1H); MS (ES$^+$) m/z 515.7, 517.7 (M+1).

EXAMPLE 77.1

Synthesis of (3R,4S)-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate

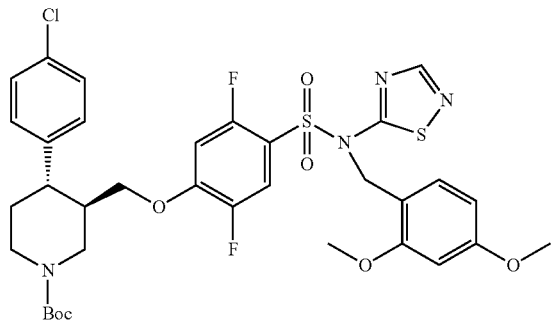 [SMILES: COc1ccc(CN(c2ncns2)S(=O)(=O)c2cc(F)c(OC[C@H]3CN(C(=O)OC(C)(C)C)CC[C@@H]3c3ccc(Cl)cc3)cc2F)c(OC)c1]

Following the procedure as described in EXAMPLE 16 and making non-critical variations to replace tert-butyl trans-4-(4-chlorophenyl)-3-(hydroxymethyl)piperidine-1-carboxylate with (3R,4S)-tert-butyl 4-(4-chlorophenyl)-3-(hydroxymethyl)piperidine-1-carboxylate, (3R,4S)-tert-butyl 4-(4-chlorophenyl)-3-((4-(N-(2,4-dimethoxybenzyl)-N-(1,2,4-thiadiazol-5-yl(sulfamoyl)-2,5-difluorophenoxy)methyl)piperidine-1-carboxylate was obtained as a colorless solid in 65% yield (0.90 g): MS (ES+) m/z 751.0, 753.0 (M+1).

EXAMPLE 77

Synthesis of 4-(((3R,4S)-4-(4-chlorophenyl)piperidin-3-yl)methoxy)-2,5-difluoro-N-(1,2,4-thiadiazol-5-yl)benzenesulfonamide

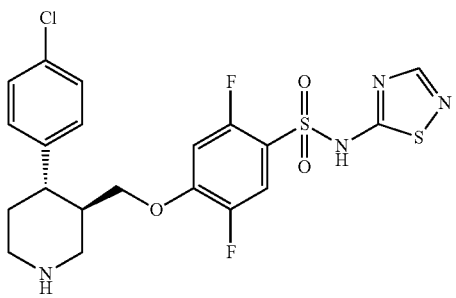 [SMILES: O=S(=O)(Nc1ncns1)c1cc(F)c(OC[C@H]2CNCC[C@@H]2c2ccc(Cl)cc2)cc1F]

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with (3R,4S)-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate, 4-(((3R,4S)-4-(4-chlorophenyl)piperidin-3-yl)methoxy)-2,5-difluoro-N-(1,2,4-thiadiazol-5-yl)benzenesulfonamide was obtained as the corresponding trifluoroacetic acid salt in 25% yield (0.14 g): $^1$H NMR (300 MHz, DMSO-d$_6$) δ 8.81-8.75 (m, 1H), 8.56-8.47 (m, 2H), 7.63-7.57 (m, 1H), 7.41-7.38 (m, 2H), 7.22-7.11 (m, 3H), 3.88-3.72 (m, 2H), 3.55-3.38 (m, 2H), 3.03-2.81 (m, 3H), 2.48-2.41 (m, 1H), 1.91-1.89 (m, 2H); MS (ES+) m/z 501.0, 503.0 (M+1).

EXAMPLE 78.1

Synthesis of trans-tert-butyl 4-(4-chlorophenyl)-3-((2,5-difluoro-4-(N-methyl-N-(1,2,4-thiadiazol-5-yl)sulfamoyl)phenoxy)methyl)piperidine-1-carboxylate and trans-tert-butyl 4-(4-chlorophenyl)-3((2,5-difluoro-4-((E)-N-(4-methyl-1,2,4-thiadiazol-5(4H)-ylidene)sulfamoyl)phenoxy)methyl)piperidine-1-carboxylate

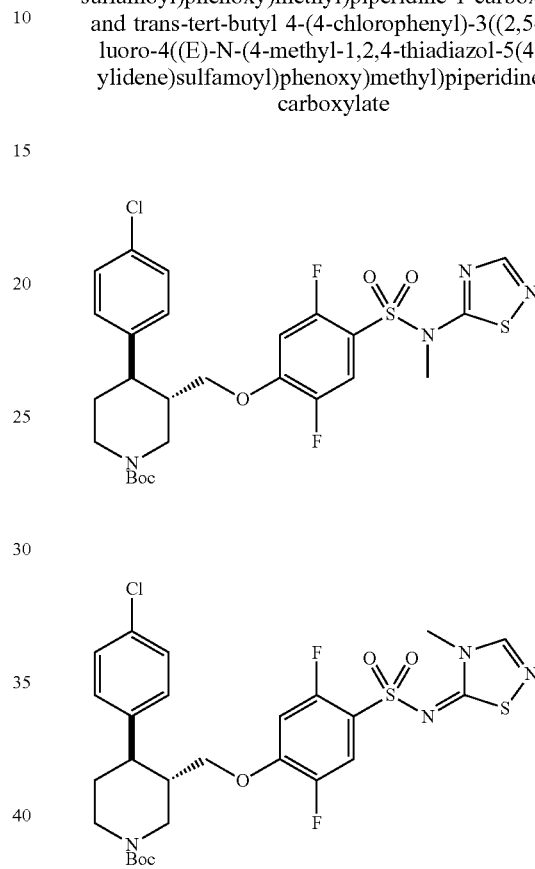

Step A: To a stirred mixture of the trifluoroacetic acid salt of 4-(trans-4-(4-chlorophenyl)piperidin-3-yl(methoxy)-2,5-difluoro-N-(1,2,4-thiadiazol-5-yl)benzenesulfonamide (0.3 g, 0.49 mmol) in methylene chloride (10 mL) was added triethylamine (0.14 mL, 0.98 mmol). The mixture was cooled to 0° C. and a solution of di-tert-butyl dicarbonate (0.11 g, 0.49 mmol) in methylene chloride (5 mL) was added dropwise. The reaction mixture was stirred at ambient temperature for 16 h, diluted with water (25 mL) and extracted with methylene chloride (3×70 mL). The combined organic extracts were washed with brine (100 mL), dried over anhydrous magnesium sulfate, filtered, and concentrated in vacuo. The residue was purified by column chromatography (2% to 10% gradient of methanol in methylene chloride) to afford trans-tert-butyl 3-((4-(4-N-(1,2,4-thiadiazol-5-yl)sulfamoyl)-2,5-difluorophenoxy)methyl)-4-(4-chlorophenyl)piperidine-1-carboxylate in 92% yield (0.27 g) as a colorless solid: MS (ES+) m/z 600.7, 602.7 (M+1).

Step B: To a stirred solution of trans-tert-butyl 3-((4-(N-(1,2,4-thiadiazol-5-yl)sulfamoyl)-2,5-difluorophenoxy)methyl)-4-(4-chlorophenyl)piperidine-1-carboxylate (0.27 g, 0.45 mmol) in N,N-dimethylformamide (5 mL) at ambient temperature was added cesium carbonate (0.146 g, 0.45 mmol), followed by iodomethane (0.042 mL, 0.67 mmol). The reaction mixture was stirred for 2 h, and further iodomethane (0.028 mL, 0.45 mmol) was added. The mixture was stirred at ambient temperature for 64 h, diluted with water (30 mL) and extracted with ethyl acetate (3×70 mL). The combined organic extracts were washed with brine (100 mL), dried over anhydrous magnesium sulfate, filtered, and concentrated in vacuo. The residue was purified by column chromatography (30% to 50% gradient of ethyl acetate in hexanes) to afford trans-ted-butyl 4-(4-chlorophenyl)-3-(2,5-difluoro-4-(N-methyl-N-(1,2,4-thiadiazol-5-yl)sulfamoyl)phenoxy)methyl)piperidine-1-carboxylate in 22% yield (0.06 g) as a colorless solid and trans-tert-butyl 4-(4-chlorophenyl)-3-((2,5-difluoro-4((E)-N-(4-methyl-1,2,4-thiadiazol-5(4H)-ylidene)sulfamoyl)phenoxy)methyl)piperidine-1-carboxylate in 65% yield (0.18 g) as a colorless solid. Analytical data for trans-tert-butyl 4-(4-chlorophenyl)-3-((2,5-difluoro-4-(N-methyl-N-(1,2,4-thiadiazol-5-yl)sulfamoyl)phenoxy)methyl)piperidine-1-carboxylate: $^1$H NMR (300 MHz, CDCl$_3$) δ 8.21-8.16 (m, 1H), 7.73-7.61 (m, 1H), 7.31-7.20 (m, 2H), 7.15-7.04 (m, 2H), 6.57-6.45 (m, 1H), 4.51-4.35 (m, 1H), 4.35-4.14 (m, 1H), 3.82-3.70 (m, 1H), 3.68-3.57 (m, 1H), 3.58-3.49 (m, 3H), 2.93-2.60 (m, 3H), 2.21-2.03 (m, 1H), 1.91-1.66 (m, 2H), 1.48 (s, 9H); MS (ES+) m/z 614.7, 616.8 (M+1). Analytical data for trans-tert-butyl 4-(4-chlorophenyl)-3-((2,5-difluoro-4-(N-methyl-N-(1,2,4-thiadiazol-5-yl)sulfamoyl)phenoxy)methyl)piperidine-1-carboxylate: $^1$H NMR (300 MHz, CDCl$_3$) δ 7.92-7.85 (m, 1H), 7.74-7.62 (m, 1H), 7.31-7.22 (m, 2H), 7.16-7.06 (m, 2H), 6.53-6.40 (m, 1H), 4.54-4.15 (m, 2H), 3.81-3.67 (m, 1H), 3.67-3.46 (m, 4H), 2.98-2.62 (m, 3H), 2.20-1.98 (m, 1H), 1.90-1.63 (m, 2H), 1.58-1.28 (m, 9H); MS (ES+) m/z 514.8, 516.8 (M+1).

EXAMPLE 78

Synthesis of (E)-4-((trans-4-(4-chlorophenyl)piperidin-3-yl)methoxy)-2,5-difluoro-N-(4-methyl-1,2,4-thiadiazol-5(4H)-ylidene)benzenesulfonamide

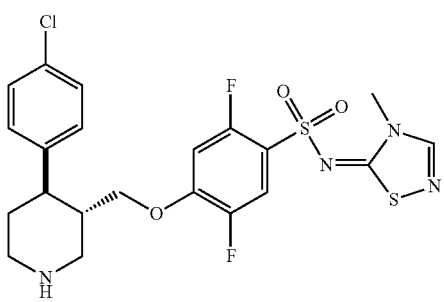

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl(sulfamoyl)-2,5-difluorophenoxy)methyl)piperidine-1-carboxylate with trans-tert-butyl 4-(4-chlorophenyl)-3-(2,5-difluoro-4-((E)-N-(4-methyl-1,2,4-thiadiazol-5(4H)-ylidene)sulfamoyl)phenoxy)methyl)piperidine-1-carboxylate, (E)-4-((trans-4-(4-chlorophenyl)piperidin-3-yl)methoxy)-2,5-difluoro-N-(4-methyl-1,2,4-thiadiazol-5(4H)-ylidene)benzenesulfonamide was obtained as the corresponding trifluoroacetic acid salt in 79% yield (0.11 g) as a colorless solid: $^1$H NMR (300 MHz, DMSO-d$_6$) δ 8.72 (s, 2H), 8.64-8.54 (m, 1H), 7.72-7.58 (m, 1H), 7.49-7.34 (m, 2H), 7.30-7.09 (m, 3H), 3.92-3.69 (m, 2H), 3.61-3.38 (m, 6H), 3.12-2.77 (m, 3H), 1.98-1.81 (m, 2H); (ES+) m/z 514.9, 516.9 (M+1).

EXAMPLE 79

Synthesis of 4-((trans-4-(4-chlorophenyl)piperidin-3-yl)methoxy)-2,5-difluoro-N-methyl-N-(1,2,4-thiadiazol-5-yl)benzenesulfonamide

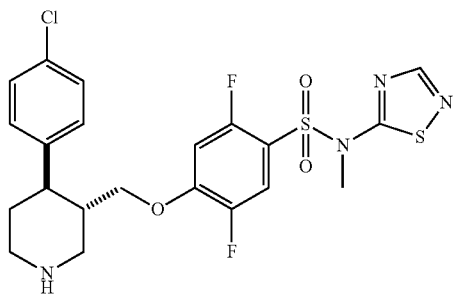

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-(2,5-difluoro-4-(N-methyl-N-(1,2,4-thiadiazol-5-yl)sulfamoyl)phenoxy)methyl)piperidine-1-carboxylate, 4-((trans-4-(4-chlorophenyl)-10 piperidin-3-yl)methoxy)-2,5-difluoro-N-methyl-N-(1,2,4-thiadiazol-5-yl)-benzenesulfonamide was obtained as the corresponding trifluoroacetic acid salt in 57% yield (0.026 g) as a colorless solid: $^1$H NMR (300 MHz, CDCl$_3$) δ 8.18 (s, 1H), 7.74-7.65 (m, 1H), 7.35-7.27 (m, 2H), 7.19-7.09 (m, 2H), 6.57-6.46 (m, 1H), 3.84-3.45 (m, 7H), 3.17-2.96 (m, 2H), 2.95-2.81 (m, 1H), 2.72-2.57 (m, 1H), 2.31-2.13 (m, 1H), 2.12-2.01 (m, 1H); (ES+) m/z 515.0, 516.9 (M+1).

EXAMPLE 80.1

Synthesis of trans-methyl 4-(4-chlorophenyl)-1-(2-fluoroethyl)piperidine-3-carboxylate

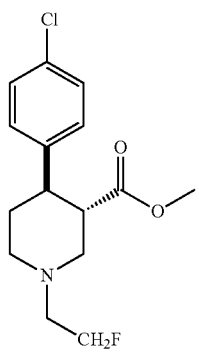

To a stirred solution of trans-methyl 4-(4-chlorophenyl)piperidine-3-carboxylate (0.61 g, 2.38 mmol) in tetrahydrofuran (24 mL) was added N,N-diisopropylethylamine (0.83 mL, 4.77 mmol), followed by 1-iodo-2-fluoroethane (0.38 mL, 4.77 mmol). The reaction mixture was stirred at 55-60° C. for 16 h, cooled to ambient temperature and 1-iodo-2-fluoroethane (0.19 mL, 2.38 mmol) was added. The reaction mixture was stirred at 55-60° C. for 72 h, cooled to ambient temperature, and concentrated in vacuo. The residue was diluted with saturated aqueous sodium bicarbonate (80 mL) and extracted with ethyl acetate (3×80 mL). The combined organic extracts were washed with brine (100 mL), dried over anhydrous magnesium sulfate, filtered, and concentrated in vacuo. This procedure was repeated once on a 1.18 mmol scale. The residues were combined and purified by column chromatography (30% to 50% gradient of ethyl acetate in hexanes) to afford trans-methyl 4-(4-chlorophenyl)-1-(2-fluoroethyl)piperidine-3-carboxylate in 80% yield (0.85 g) as a colorless oil: MS (ES+) m/z 300.0 (M+1), 302.0 (M+1).

EXAMPLE 80.2

Synthesis of (trans-4-(4-chlorophenyl)-1-(2-fluoroethyl)piperidin-3-yl)methanol

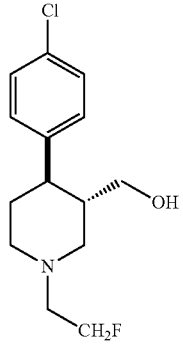

Following the procedure as described in Step B of EXAMPLE 1, making non-critical variations to replace trans-1-tert-butyl 3-methyl 4-(4-chlorophenyl)piperidine-1,3-dicarboxylate with trans-methyl 4-(4-chlorophenyl)-1-(2-fluoroethyl)piperidine-3-carboxylate, (trans-4-(4-chlorophenyl)-1-(2-fluoroethyl)piperidin-3-yl)methanol was obtained in 35% yield (0.27 g) as a colorless oil: MS (ES+) m/z 272.1, 274.1 (M+1).

EXAMPLE 80.3

Synthesis of 4-((trans-4-(4-chlorophenyl)-1-(2-fluoroethyl)piperidin-3-yl)methoxy)-N-(2,4-dimethoxybenzyl)-2,5-difluoro-N-(1,2,4-thiadiazol-5-yl)benzenesulfonamide

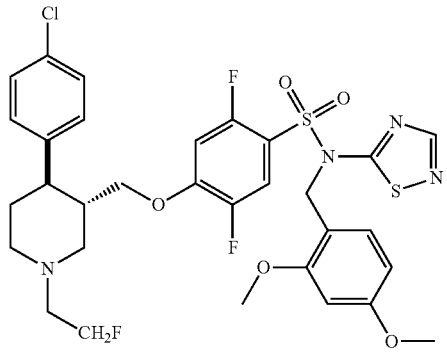

Following the procedure as described in EXAMPLE 16 and making non-critical variations to replace trans-tert-butyl 4-(4-chlorophenyl)-3-(hydroxymethyl)piperidine-1-carboxylate with (trans-4-(4-chlorophenyl)-1-(2-fluoroethyl)piperidin-3-yl)methanol, 4-((trans-4-(4-chlorophenyl)-1-(2-fluoroethyl)piperidin-3-yl)methoxy)-N-(2,4-dimethoxybenzyl)-2,5-difluoro-N-(1,2,4-thiadiazol-5-yl)benzenesulfonamide was obtained as a colorless solid in 33% yield (0.23 g): MS (ES−) m/z 695.6 (M−1).

EXAMPLE 80

Synthesis of 4-((trans-4-(4-chlorophenyl)-1-(2-fluoroethyl)piperidin-3-yl)methoxy)-2,5-difluoro-N-(1,2,4-thiadiazol-5-yl)benzenesulfonamide

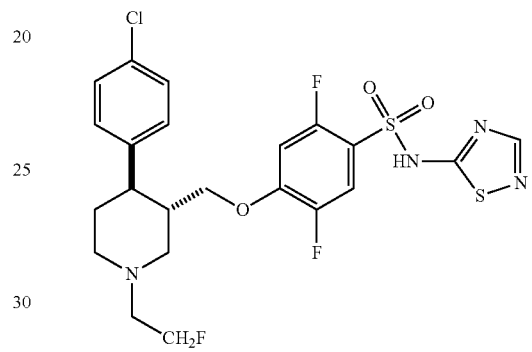

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with 4-((trans-4-(4-chlorophenyl)-1-(2-fluoroethyl)piperidin-3-yl)methoxy)-N-(2,4-dimethoxybenzyl)-2,5-difluoro-N-(1,2,4-thiadiazol-5-yl)benzenesulfonamide, 4-((trans-4-(4-chlorophenyl)-1-(2-fluoroethyl)piperidin-3-Arnethoxy)-2,5-difluoro-N-(1,2,4-thiadiazol-5-yl)benzenesulfonamide was obtained as the corresponding trifluoroacetic acid salt in 62% yield (0.11 g) as a colorless solid: $^1$H NMR (300 MHz, DMSO-$d_6$) δ 10.08 (br.s, 1H), 7.94 (s, 1H), 7.52-7.33 (m, 3H), 7.29-7.16 (m, 2H), 7.05-6.94 (m, 1H), 4.94-4.70 (m, 2H), 3.93-3.41 (m, 7H), 3.14-2.88 (m, 2H), 2.89-2.68 (m, 1H), 2.09-1.84 (m, 2H); (ES+) m/z 546.8, 548.8 (M+1).

EXAMPLE 81.1

Synthesis of N-(2,4-dimethoxybenzyl)-3,4,5-trifluoro-N-(1,2,4-thiadiazol-5-yl)benzenesulfonamide

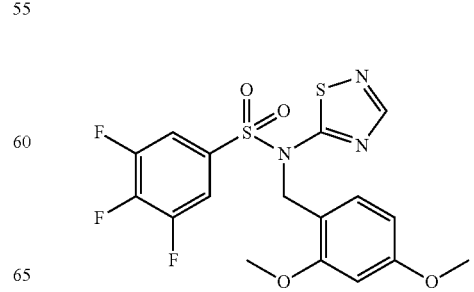

Following the procedure as described in Step B of EXAMPLE 8 and making non-critical variations to replace 2,4,5-trifluorobenzene-1-sulfonyl chloride with 3,4,5-trifluorobenzene-1-sulfonyl chloride and to replace N-(2,4-dimethoxybenzyl)-3-methyl-1,2,4-thiadiazol-5-amine with N-(2,4-dimethoxybenzyl)-1,2,4-thiadiazol-5-amine (prepared according to PCT Published Patent Application No. WO 2010/079443), N-(2,4-dimethoxybenzyl)-3,4,5-trifluoro-N-(1,2,4-thiadiazol-5-yl)benzenesulfonamide was obtained as a colorless solid in 53% yield (3.10 g): $^1$H NMR (300 MHz, CDCl$_3$) δ 7.37-7.28 (m, 1H), 7.26-7.22 (m, 1H), 7.07 (d, J=8.1 Hz, 1H), 6.39-6.32 (m, 1H), 6.29-6.24 (m, 1H), 5.27 (s, 2H), 3.75 (s, 3H), 3.65 (s, 3H).

EXAMPLE 81.2

Synthesis of trans-tert-butyl 4-(4-chlorophenyl)-3-(4-(N-(2,4-dimethoxybenzyl)-N-(1,2,4-thiadiazol-5-yl)sulfamoyl)-2,6-difluorophenoxy)methyl)piperidine-1-carboxylate

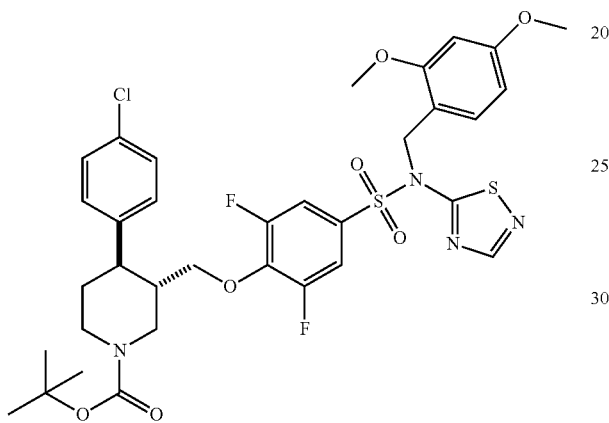

Following the procedure as described in EXAMPLE 16 and making non-critical variations to replace N-(2,4-dimethoxybenzyl)-2,4,5-trifluoro-N-(1,2,4-thiadiazol-5-yl)benzenesulfonamide with N-(2,4-dimethoxybenzyl)-3,4,5-trifluoro-N-(1,2,4-thiadiazol-5-yl)benzenesulfonamide, trans-tert-butyl 4-(4-chlorophenyl)-3-((4-(N-(2,4-dimethoxybenzyl)-N-(1,2,4-thiadiazol-5-yl)sulfamoyl)-2,6-difluorophenoxy)methyl)piperidine-1-carboxylate was obtained in 33% yield (0.20 g) as pale yellow solid: $^1$H NMR (300 MHz, CDCl$_3$) δ 8.20 (s, 1H), 7.44-7.05 (m, 7H), 6.39-6.31 (m, 1H), 6.27-6.21 (m, 1H), 5.3-5.21 (m, 2H), 4.54-4.44 (m, 1H), 4.33-4.20 (m, 1H), 4.18-4.10 (m, 2H), 4.01-3.94 (m, 2H), 3.84-3.62 (m, 8H), 2.95-2.62 (m, 2H), 1.55-1.45 (m, 9H).

EXAMPLE 81

Synthesis of 4-((trans-4-(4-chlorophenyl)piperidin-3-yl)methoxy)-3,5-difluoro-N-(1,2,4-thiadiazol-5-yl)benzenesulfonamide

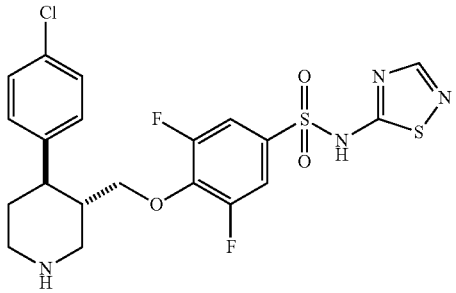

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-(4-chlorophenyl)-3-(4-(N-(2,4-dimethoxybenzyl)-N-(1,2,4-thiadiazol-5-yl)sulfamoyl)-2,6-difluorophenoxy)methyppiperidine-1-carboxylate, 4-((trans-4-(4-chlorophenyl)piperidin-3-yl)methoxy)-3,5-difluoro-N-(1,2,4-thiadiazol-5-yl(benzenesulfonamide was obtained as the corresponding trifluoroacetic acid salt in 88% yield (0.15 g) as a colorless solid: $^1$H NMR (300 MHz, DMSO-d$_6$) δ 8.86-8.50 (m, 2H), 8.33 (s, 1H), 7.53-7.13 (m, 6H), 3.91-3.77 (m, 2H), 3.61-3.52 (m, 1H), 3.41-3.31 (m, 1H), 3.09-2.92 (m, 2H), 2.88-2.77 (m, 1H), 2.43-2.31 (m, 1H), 1.91-1.77 (m, 2H); MS (ES+) m/z 500.8, 502.9 (M+1)

EXAMPLE 82.1

Synthesis of 1-tert-butyl 4-ethyl 3-(4-fluorophenyl)-5,6-dihydropyridine-1,4(2H)-dicarboxylate

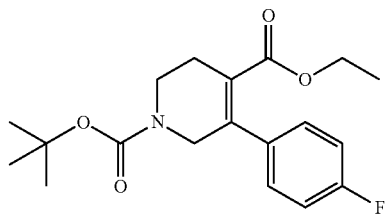 [SMILES: CCOC(=O)C1=C(c2ccc(F)cc2)CN(C(=O)OC(C)(C)C)CC1]

Following the procedure as described in EXAMPLE 5.2 and making non-critical variations to replace methyl 4-(((trifluoromethyl)sulfonyl)oxy)-5,6-dihydro-2H-pyran-3-carboxylate with 1-tert-butyl 4-ethyl 3-(((trifluoromethyl)sulfonyl)oxy)-5,6-dihydropyridine-1,4(2H)-dicarboxylate (prepared according to methods disclosed in PCT Published Patent Application No. WO 2007/015162), 1-tert-butyl 4-ethyl 3-(4-fluorophenyl)-5,6-dihydropyridine-1,4(2H)-dicarboxylate was obtained in quantitative yield (1.05 g) as a pale yellow oil: MS (ES+) m/z 350.1 (M+1).

EXAMPLE 82.2

Synthesis of cis-1-tert-butyl 4-ethyl 3-(4-fluorophenyl)piperidine-1,4-dicarboxylate

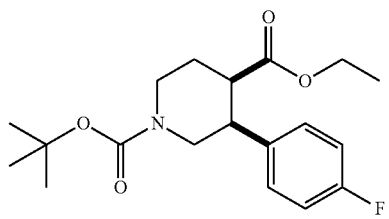 [SMILES: CCOC(=O)[C@@H]1CCN(C(=O)OC(C)(C)C)C[C@@H]1c1ccc(F)cc1]

Following the procedure as described in EXAMPLE 5.3 and making non-critical variations to replace methyl 4-(4- fluorophenyl)-5,6-dihydro-2H-pyran-3-carboxylate with 1-tert-butyl 4-ethyl 3-(4-fluorophenyl)-5,6-dihydropyridine-1,4(2H)dicarboxylate, cis-1-tert-butyl 4-ethyl 3-(4-fluorophenyl)piperidine-1,4-dicarboxylate was obtained in 87% yield (0.9 g) as a pale yellow oil: MS (ES+) m/z 352.0 (M+1).

EXAMPLE 82.3

Synthesis of trans-1-tert-butyl 4-ethyl 3-(4-fluorophenyl)piperidine-1,4-dicarboxylate

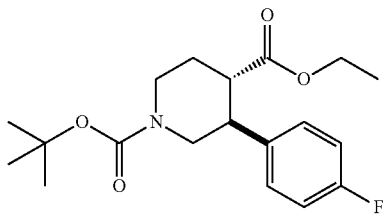 [SMILES: CCOC(=O)[C@H]1CCN(C(=O)OC(C)(C)C)C[C@@H]1c1ccc(F)cc1]

Following the procedure as described in EXAMPLE 5.4 and making non-critical variations to replace cis-methyl 4-(4-fluorophenyl)tetrahydro-2H-pyran-3-carboxylate with cis-1-tert-butyl 4-ethyl 3-(4-fluorophenyl)piperidine-1,4-dicarboxylate, and to replace sodium methoxide in methanol with sodium ethoxide in ethanol, trans-1-tert-butyl 4-ethyl 3-(4-fluorophenyl)piperidine-1,4-dicarboxylate was obtained as a pale yellow oil in 51% yield (0.46 g): MS (ES$^+$) m/z 352.1 (M+1).

EXAMPLE 82.4

Synthesis of trans-tert-butyl 3-(4-fluorophenyl)-4-(hydroxymethyl)piperidine-1-carboxylate

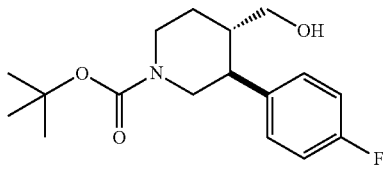 [SMILES: CC(C)(C)OC(=O)N1CC[C@H](CO)[C@@H](c2ccc(F)cc2)C1]

Following the procedure as described in Step B of EXAMPLE 1, making non-critical variations to replace trans-1-tert-butyl 3-methyl 4-(4-chlorophenyl)piperidine-1,3-dicarboxylate with trans-1-tert-butyl 4-ethyl 3-(4-fluorophenyl)piperidine-1,4-dicarboxylate, trans-tert-butyl 3-(4-fluorophenyl)-4-(hydroxymethyl)piperidine-1-carboxylate was obtained in 72% yield (0.29 g) as a colorless oil: MS (ES$^+$) ink 210.1 (M−99).

EXAMPLE 82.5

Synthesis of trans-tert-butyl 4-((4-(N-(2,4-dimethoxybenzyl)-N-(1,2,4-thiadiazol-5-yl)sulfamoyl)-2,5-difluorophenoxy)methyl)-3-(4-fluorophenyl)piperidine-1-carboxylate

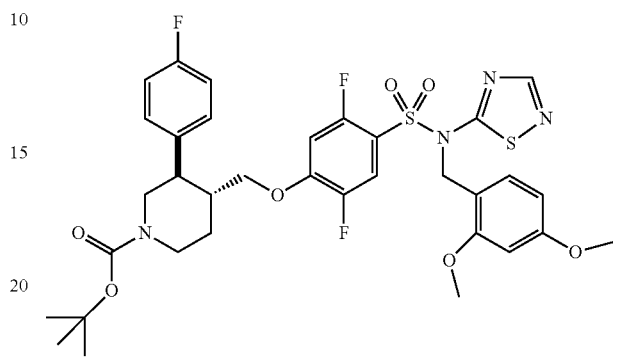

Following the procedure as described in EXAMPLE 16 and making non-critical variations to replace trans-tert-butyl 4-(4-chlorophenyl)-3-(hydroxymethyl)piperidine-1-carboxylate with trans-tert-butyl 3-(4-fluorophenyl)-4-(hydroxymethyl)piperidine-1-carboxylate, trans-tert-butyl 4-((4-(N-(2,4-dimethoxybenzyl)-N-(1,2,4-thiadiazol-5-yl)sulfamoyl)-2,5-difluorophenoxy)methyl)-3-(4-fluorophenyl)piperidine-1-carboxylate was obtained in 33% yield (0.19 g) as a colorless solid: MS (ES+) m/z 734.9 (M+1).

EXAMPLE 82

Synthesis of 2,5-difluoro-4-((trans-3-(4-fluorophenyl)piperidin-4-yl)methoxy)-N-(1,2,4-thiadiazol-5-yl)benzenesulfonamide

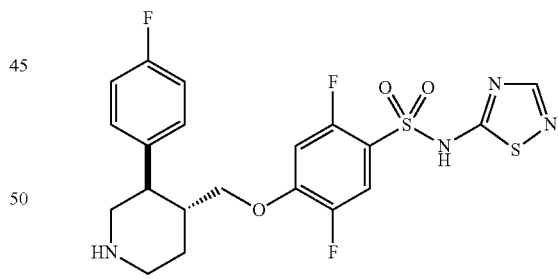

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 4-((4-(N-(2,4-dimethoxybenzyl)-N-(1,2,4-thiadiazol-5-yl)sulfamoyl)-2,5-difluorophenoxy)methyl)-3-(4-fluorophenyl)piperidine-1-carboxylate, 2,5-difluoro-4-((trans-3-(4-fluorophenyl)piperidin-4-yl)methoxy)-N-(1,2,4-thiadiazol-5-yl)benzenesulfonamide was obtained in 52% yield (0.066 g) as a colorless solid: $^1$H NMR (300 MHz, DMSO-d$_6$) δ 8.82 (s, 1H), 8.44 (s, 1H), 7.89 (s, 1H), 7.49-7.39 (m, 1H), 7.36-7.26 (m, 2H), 7.23-7.11 (m, 2H), 7.01-6.90 (m, 1H), 3.86-3.77

(m, 1H), 3.70-3.58 (m, 1H); 3.31-2.88 (m, 5H); 2.41-2.25 (m, 1H), 2.11-1.99 (m, 1H), 1.87-1.68 (m, 1H); (ES+) ink 485.1 (M+1).

Although not a compound of formula (I), the compound of Example 82 and the intermediate compounds identified in Examples 82.1 through 82.5, and salts thereof represent compounds of the invention.

EXAMPLE 83.1

Synthesis of (trans-methyl 4-(4-chlorophenyl)-1-(2,2-difluoroethyl)piperidine-3-carboxylate

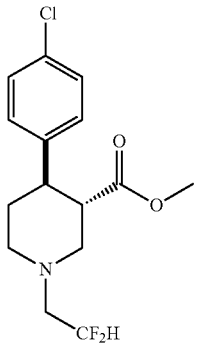

Following the procedure as described in EXAMPLE 80.1, making non-critical variations to replace 1-iodo-2-fluoroethane with 1-iodo-2,2-difluoroethane, (trans-methyl 4-(4-chlorophenyl)-1-(2,2-difluoroethyl)piperidine-3-carboxylate was obtained in 57% yield (0.71 g) as a colorless oil: MS (ES+) m/z 318.1 (M+1), 320.1 (M+1).

EXAMPLE 83.2

Synthesis of (trans-4-(4-chlorophenyl)-1-(2,2-difluoroethyl)piperidin-3-yl)methanol

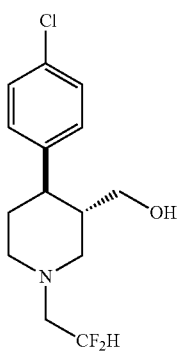

Following the procedure as described in Step B of EXAMPLE 1, making non-critical variations to replace trans-1-tert-butyl 3-methyl 4-(4-chlorophenyl)piperidine-1,3-dicarboxylate with (trans-methyl 4-(4-chlorophenyl)-1-(2,2-difluoroethyl)piperidine-3-carboxylate, (trans-4-(4-chlorophenyl)-1-(2,2-difluoroethyl)piperidin-3-yl)methanol was obtained in 80% yield (0.51 g) as a colorless oil: MS (ES+) m/z 290.1 (M+1), 292.1 (M+1).

EXAMPLE 83.3

Synthesis of 4-((trans-4-(4-chlorophenyl)-1-(2,2-difluoroethyl)piperidin-3-yl)methoxy)-N-(2,4-dimethoxybenzyl)-2,5-difluoro-N-(1,2,4-thiadiazol-5-yl)benzenesulfonamide

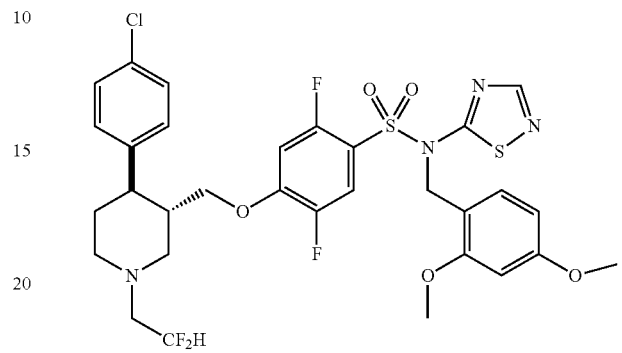

Following the procedure as described in EXAMPLE 16 and making non-critical variations to replace trans-tert-butyl 4-(4-chlorophenyl)-3-(hydroxymethyl)piperidine-1-carboxylate with (trans-4-(4-chlorophenyl)-1-(2,2-difluoroethyl)piperidin-3-yl)methanol, 4-((trans-4-(4-chlorophenyl)-1-(2,2-difluoroethyl)piperidin-3-yl)methoxy)-N-(2,4-dimethoxybenzyl)-2,5-difluoro-N-(1,2,4-thiadiazol-5-yl)benzenesulfonamide was obtained in 20% yield (0.25 g) as a colorless solid: MS (ES+) m/z 714.9 (M+1).

EXAMPLE 83

Synthesis of 4-((trans-4-(4-chlorophenyl)-1-(2,2-difluoroethyl)piperidin-3-yl)methoxy)-2,5-difluoro-N-(1,2,4-thiadiazol-5-yl)benzenesulfonamide

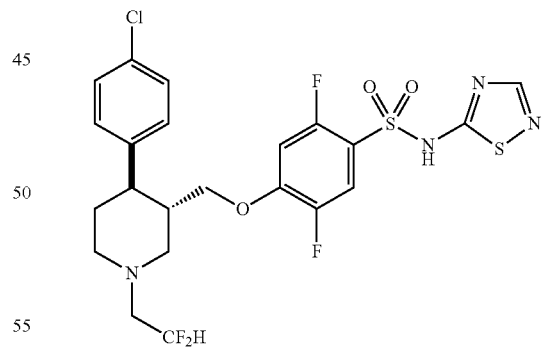

Following the procedure as described in EXAMPLE 44 and making non-critical variations to replace trans-tert-butyl 4-(4-chlorophenyl)-3-((4-(N-(2,4-dimethoxybenzyl) -N-(1,2,4-thiadiazol-5-yl)sulfamoyl)-2,5-difluorophenoxy)methyl)piperidine-1-carboxylate with 4-((trans-4-(4-chlorophenyl)-1-(2,2-difluoroethyl)piperidin-3-yl)methoxy)-N-(2,4-dimethoxybenzyl)-2,5-difluoro-N-(1,2,4-thiadiazol-5-yl)benzenesulfonamide, 4-((trans-4-(4-chlorophenyl)-1-(2,2-difluoroethyl)piperidin-3-yl)methoxy)-2,5-difluoro-N-(1,2,4-thiadiazol-5-yl)benzenesulfonamide was obtained in 7% yield (0.02 g) as a colorless solid: ¹H NMR (300 MHz, DMSO-d₆+1 drop of D₂O) δ 8.43 (s, 1H), 7.64-7.54 (m, 1H), 7.42-7.33 (m, 2H), 7.28-7.19 (m, 2H), 7.16-7.04 (m, 1H), 6.70-6.27 (m, 1H), 3.89-3.79 (m, 1H), 3.77-3.55 (m, 6H), 3.12-2.91 (m, 2H), 2.85-2.70 (m, 1H), 2.04-1.86 (m, 2H); (ES⁺) m/z 564.9 (M+1), 566.9 (M+1).

EXAMPLE 84.1

Synthesis of (3S,4R)-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate

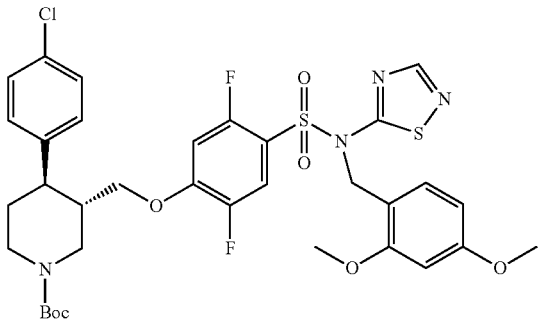 [SMILES: COc1ccc(CN(c2ncns2)S(=O)(=O)c2cc(F)c(OC[C@@H]3CN(C(=O)OC(C)(C)C)CC[C@H]3c3ccc(Cl)cc3)cc2F)c(OC)c1]

Following the procedure as described in EXAMPLE 16 and making non-critical variations to replace tert-butyl trans-4-(4-chlorophenyl)-3-(hydroxymethyl)piperidine-1-carboxylate with (3S,4R)-tert-butyl 4-(4-chlorophenyl)-3-(hydroxymethyl)piperidine-1-carboxylate, (3S,4R)-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate was obtained in 43% yield (0.45 g) as a colorless solid: MS (ES+) m/z 750.9 (M+1), 752.9 (M+1).

EXAMPLE 84

Synthesis of 4-(((3S,4R)-4-(4-chlorophenyl)piperidin-3-yl)methoxy)-2,5-difluoro-N-(1,2,4-thiadiazol-5-yl)benzenesulfonamide

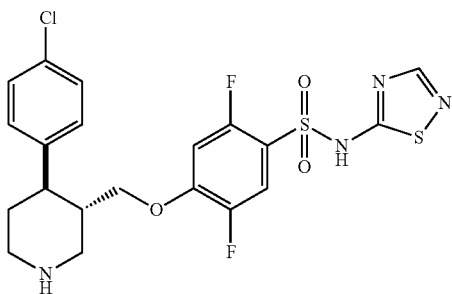

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with (3S,4R)-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl) piperidine-1-carboxylate, 4-(((3S,4R)-4-(4-chlorophenyl)piperidin-3-yl)methoxy)-2,5-difluoro-N-(1,2,4-thiadiazol-5-yl)benzenesulfonamide was obtained as the corresponding trifluoroacetic acid salt in 92% yield (0.29 g) as colorless solid: ¹H NMR (300 MHz, DMSO-d₆) δ 8.88-8.63 (m, 2H), 8.39 (s, 1H), 7.61-7.55 (m, 1H), 7.40 (d, J=8.4 Hz, 2H), 7.21 (d, J=8.4 Hz, 2H), 7.15-7.09 (m, 1H), 3.88-3.83 (m, 1H), 3.77-3.72 (m, 1H), 3.55-3.51 (m, 1H), 3.42-3.38 (m, 1H), 3.05-2.80 (m, 3H), 2.49-2.42 (m, 1H), 1.91-1.87 (m, 2H); MS (ES+) m/z 500.8, 502.8 (M+1).

EXAMPLE 85

Synthesis of 4-(((3R,4S)-4-(4-chlorophenyl)-1-methylpiperidin-3-yl)methoxy)-2,5-difluoro-N-(1,2,4-thiadiazol-5-yl)benzenesulfonamide

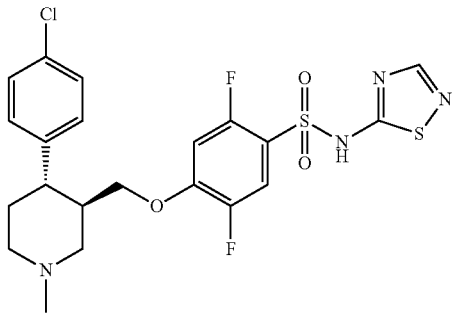 [SMILES: CN1CC[C@H](c2ccc(Cl)cc2)[C@@H](COc2cc(F)c(S(=O)(=O)Nc3ncns3)cc2F)C1]

Following the procedure as described in EXAMPLE 70 and making non-critical variations to replace 4-((trans-4-(4-chlorophenyl)piperidin-3-yl)methoxy)-2,5-difluoro-N-(1,2,4-thiadiazol-5-yl)benzenesulfonamide with 4-(((3R,4S)-4-(4-chlorophenyl)piperidin-3-yl)methoxy)-2,5-difluoro-N-(1,2,4-thiadiazol-5-yl)benzenesulfonamide, 4-(((3R,4S)-4-(4-chlorophenyl)-1-methylpiperidin-3-yl)methoxy)-2,5-difluoro-N-(1,2,4-thiadiazol-5-yl)benzenesulfonamide was obtained as the corresponding trifluoroacetic acid salt in 56% yield (0.03 g) as a colorless solid: ¹H NMR (300 MHz, DMSO-d₆) δ 9.58 (br s, 1H), 7.90 (s, 1H), 7.48-7.38 (m, 3H), 7.23-7.21 (m, 2H), 7.01-6.95 (m, 1H), 3.82-3.61 (m, 3H), 3.52-3.48 (m, 1H), 3.06-3.03 (m, 2H), 2.88 (s, 3H), 2.79-2.75 (m, 1H), 2.46-2.43 (m, 1H), 1.95-1.89 (m, 2H); MS (ES+) m/z 514.9 (M+1), 516.9 (M+1).

EXAMPLE 86

Synthesis of 4-(((3S,4R)-4-(4-chlorophenyl)-1-methylpiperidin-3-yl)methoxy)-2,5-difluoro-N-(1,2,4-thiadiazol-5-yl)benzenesulfonamide

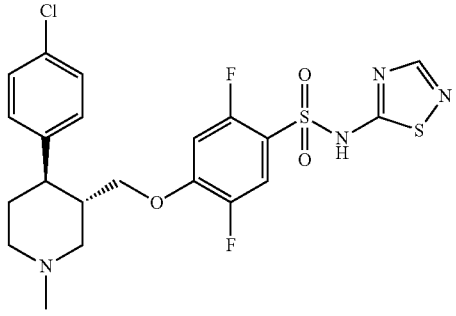 [SMILES: CN1CC[C@@H](c2ccc(Cl)cc2)[C@H](COc2cc(F)c(S(=O)(=O)Nc3ncns3)cc2F)C1]

Following the procedure as described in EXAMPLE 70 and making non-critical variations to replace 4-((trans-4-(4- chlorophenyl)piperidin-3-yl)methoxy)-2,5-difluoro-N-(1,2,4-thiadiazol-5-yl)benzenesulfonamide with 4-(((3S,4R)-4-(4-chlorophenyl)piperidin-3-yl)methoxy)-2,5-difluoro-N-(1,2,4-thiadiazol-5-yl)benzenesulfonamide, 4-(((3S,4R)-4-(4-chlorophenyl)-1-methylpiperidin-3-yl)methoxy)-2,5-difluoro-N-(1,2,4-thiadiazol-5-yl)benzenesulfonamide was obtained as the corresponding trifluoroacetic acid salt in 57% yield (0.04 g) as a colorless solid: $^1$H NMR (300 MHz, DMSO-$d_6$) δ 9.63 (br s, 1H), 7.90 (s, 1H), 7.49-7.37 (m, 3H), 7.23-7.20 (m, 2H), 7.01-6.95 (m, 1H), 3.82-3.48 (m, 4H), 3.11-3.03 (m, 2H), 2.88 (s, 3H), 2.79-2.75 (m, 1H), 2.46-2.43 (m, 1H), 1.94-1.89 (m, 2H); MS (ES+) m/z 514.8 (M+1), 516.7 (M+1).

EXAMPLE 87.1

Synthesis of methyl trans-4-(4-fluorophenyl)-1-(4-methoxybenzyl)-6-oxopiperidine-3-carboxylate

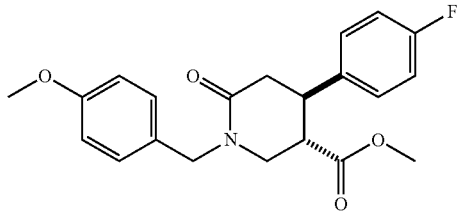 [SMILES: COC(=O)[C@@H]1CN(Cc2ccc(OC)cc2)C(=O)C[C@H]1c1ccc(F)cc1]

To a stirred solution of methyl trans-4-(4-fluorophenyl)-6-oxopiperidine-3-carboxylate (1.00 g, 4.0 mmol, prepared according to Sugi, Kiyoshi et al.; Eur. Pat. Appl., 1384720, 28 Jan. 2004) in anhydrous N,N-dimethylformamide (50 mL) was added sodium hydride (0.21 g, 5.2 mmol, 60% w/w dispersion in mineral oil) at 0° C. The reaction mixture was stirred at ambient temperature for 1 h. p-Methoxybenzyl-bromide (0.7 mL, 4.8 mmol) was added to the reaction mixture at 0° C. and the mixture was stirred at ambient temperature for 48 h. Saturated ammonium chloride (50 mL) was added to the reaction mixture, followed by ethyl acetate (200 mL). The organic layer was washed with brine, dried over anhydrous magnesium sulfate, filtered, and concentrated in vacuo. The residue was purified by column chromatography (40%-100% ethyl acetate in hexanes) to afford methyl trans-4-(4-fluorophenyl)-1-(4-methoxybenzyl)-6-oxopiperidine-3-carboxylate as a clear oil in 60% yield (0.9 g): MS (ES+) m/z 372.2 (M+1).

EXAMPLE 87.2

Synthesis of trans-4-(4-fluorophenyl)-5-(hydroxymethyl)-1-(4-methoxybenzyl)piperidin-2-one

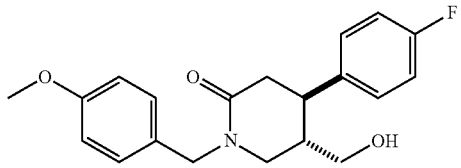 [SMILES: COc1ccc(CN2C[C@@H](CO)[C@H](c3ccc(F)cc3)CC2=O)cc1]

Following the procedure as described in Step B of EXAMPLE 1, making non-critical variations to replace 1-tert-butyl trans-3-methyl 4-(4-chlorophenyl)piperidine-1,3-dicarboxylate with methyl trans-4-(4-fluorophenyl)-1-(4-methoxybenzyl)-6-oxopiperidine-3-carboxylate, trans-4-(4-fluorophenyl)-5-(hydroxymethyl)-1-(4-methoxybenzyl)piperidin-2-one was obtained in 63% yield (0.35 g) as a colorless solid: MS (ES+) m/z 344.1 (M+1).

EXAMPLE 87.3

Synthesis of N-(2,4-dimethoxybenzyl)-2,5-difluoro-4-((trans-4-(4-fluorophenyl)-1-(4-methoxybenzyl)-6-oxopiperidin-3-yl)methoxy)-N-(1,2,4-thiadiazol-5-yl)benzenesulfonamide

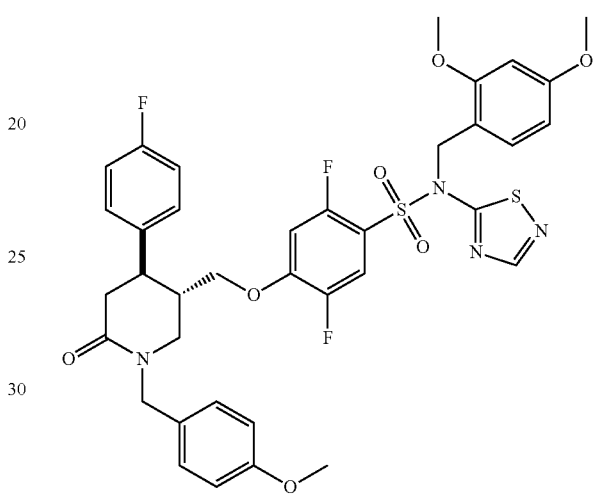

Following the procedure as described in EXAMPLE 16 and making non-critical variations to replace tert-butyl trans-4-(4-chlorophenyl)-3-(hydroxymethyl)piperidine-1-carboxylate with trans-4-(4-fluorophenyl)-5-(hydroxymethyl)-1-(4-methoxybenzyl)piperidin-2-one, N-(2,4-dimethoxybenzyl)-2,5-difluoro-4-((trans-4-(4-fluorophenyl)-1-(4-methoxybenzyl)-6-oxopiperidin-3-yl)methoxy)-N-(1,2,4-thiadiazol-5-yl)benzenesulfonamide was obtained as an off-white solid in 60% yield (0.35 g): MS (ES$^+$) ink 769.0 (M+1).

EXAMPLE 87

Synthesis of 2,5-difluoro-4-((trans-4-(4-fluorophenyl)-6-oxopiperidin-3-yl)methoxy)-N-(1,2,4-thiadiazol-5-yl)benzenesulfonamide

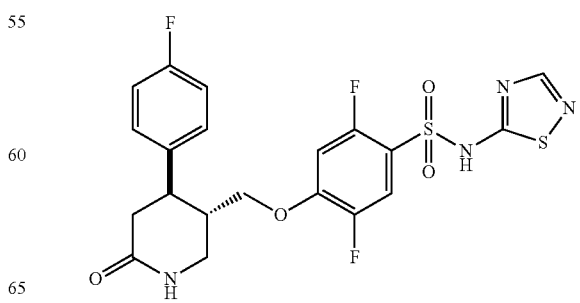

A mixture of N-(2,4-dimethoxybenzyl)-2,5-difluoro-4-((trans-4-(4-fluorophenyl)-1-(4-methoxybenzyl)-6-oxopiperidin-3-yl)methoxy)-N-(1,2,4-thiadiazol-5-yl)benzenesulfonamide (0.16 g, 0.21 mmol), anisole (1.0 mL) and trifluoroacetic acid (15 mL) was heated at reflux for 72 h. The mixture was concentrated in vacuo and the residue was triturated with ethyl acetate. The solid was filtered and washed with methanol and water to afford 2,5-difluoro-4-((trans-4-(4-fluorophenyl)-6-oxopiperidin-3-yl(methoxy)-N-(1,2,4-thiadiazol-5-yl(benzenesulfonamide in 48% yield (0.05 g) as a colorless solid: $^1$H NMR (300 MHz, DMSO-d$_6$) δ 8.53 (s, 1H), 7.67-7.57 (m, 2H), 7.35-7.09 (m, 5H), 3.90-3.76 (m, 2H), 3.39-3.04 (m, 3H), 2.50-2.31 (m, 3H); MS (ES+) m/z 498.7 (M+1).

EXAMPLE 88.1

Synthesis of trans-ethyl 4-(4-chlorophenyl)-1-(2,2,2-trifluoroethyl)piperidine-3-carboxylate

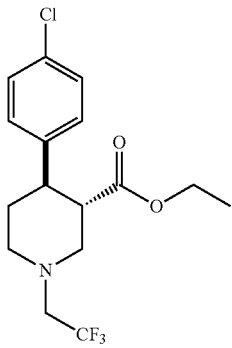

Step A: To a stirred solution of trans-1-tert-butyl 3-ethyl 4-(4-chlorophenyl)piperidine-1,3-dicarboxylate (1.49 g, 4.05 mmol) in methylene chloride (90 mL) was added trifluoroacetic acid (10 mL) at 0° C. The reaction mixture was stirred at 0° C. for 1 h and at ambient temperature for 2 h. The mixture was concentrated in vacuo. The residue was dissolved in methylene chloride (100 mL), washed with saturated aqueous sodium bicarbonate (50 mL) and brine (50 mL), dried over anhydrous magnesium sulfate, filtered, and concentrated in vacuo to afford trans-ethyl 4-(4-chlorophenyl)piperidine-3-carboxylate in quantitative yield (1.08 g) as a pale yellow oil: MS (ES+) m/z 268.1 (M+1), 270.1 (M+1).

Step B: To a stirred solution of trans-ethyl 4-(4-chlorophenyl)piperidine-3-carboxylate (1.08 g, 4.05 mmol) in acetone (20 mL) was added triethylamine (2.8 mL, 20.3 mmol), followed by 2,2,2-trifluoroethyl trifluoromethanesulfonate (0.7 mL, 4.9 mmol). The reaction mixture was stirred at reflux for 16 h, cooled to ambient temperature, and concentrated in vacuo. The residue was diluted with methylene chloride (70 mL) and washed with saturated aqueous sodium bicarbonate (50 mL). The aqueous layer was extracted with methylene chloride (2×70 mL). The combined organic extracts were dried over anhydrous magnesium sulfate, filtered, and concentrated in vacuo to afford trans-ethyl 4-(4-chlorophenyl)-1-(2,2,2-trifluoroethyl)piperidine-3-carboxylate in quantitative yield (1.42 g) as a colorless oil: MS (ES+) m/z 350.0 (M+1), 352.0 (M+1).

EXAMPLE 88.2

Synthesis of (trans-4-(4-chlorophenyl)-1-(2,2,2-trifluoroethyl)piperidin-3-yl)methanol

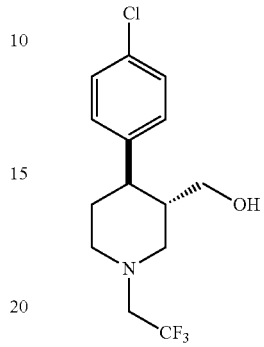

Following the procedure as described in Step B of EXAMPLE 1, making non-critical variations to replace trans-1-tert-butyl 3-methyl 4-(4-chlorophenyl)piperidine-1,3-dicarboxylate with trans-ethyl 4-(4-chlorophenyl)-1-(2,2,2-trifluoroethyl)piperidine-3-carboxylate, (trans-4-(4-chlorophenyl)-1-(2,2,2-trifluoroethyl)piperidin-3-yl)methanol was obtained in 73% yield (0.91 g) as a colorless oil: MS (ES+) m/z 308.1 (M+1), 310.1 (M+1).

EXAMPLE 88.3

Synthesis of N-(2,4-dimethoxybenzyl)-2,5-difluoro-4-((trans-3-(4-fluorophenyl)piperidin-4-yl)methoxy)-N-(1,2,4-thiadiazol-5-yl)benzenesulfonamide

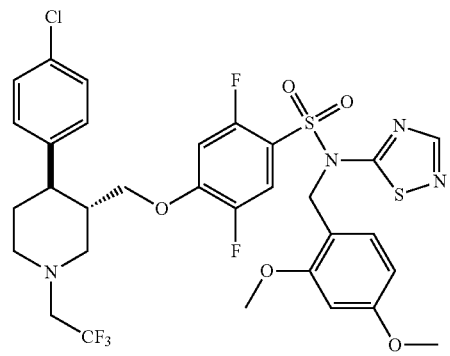

Following the procedure as described in EXAMPLE 16 and making non-critical variations to replace trans-tert-butyl 4-(4-chlorophenyl)-3-(hydroxymethyl)piperidine-1-carboxylate with (trans-4-(4-chlorophenyl)-1-(2,2,2-trifluoroethyl)piperidin-3-yl)methanol, N-(2,4-dimethoxybenzyl)-2,5-difluoro-4-((trans-3-(4-fluorophenyl)piperidin-4-yl)methoxy)-N-(1,2,4-thiadiazol-5-yl)benzenesulfonamide was obtained as a colorless solid in 20% yield (0.22 g): MS (ES+) m/z 732.8 (M+1), 734.8 (M+1).

EXAMPLE 88

Synthesis of 4-((trans-4-(4-chlorophenyl)-1-(2,2,2-trifluoroethyl)piperidin-3-yl)methoxy)-2,5-difluoro-N-(1,2,4-thiadiazol-5-yl)benzenesulfonamide

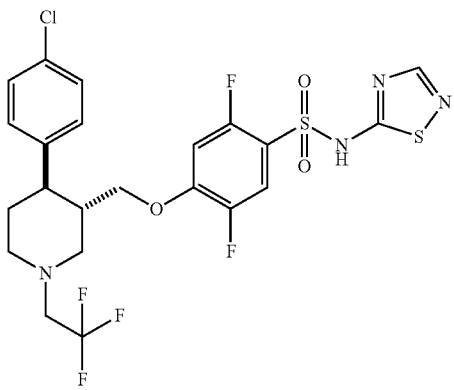

Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with 4-((trans-4-(4-chlorophenyl)-1-(2,2,2-trifluoroethyl)piperidin-3-yl)methoxy)-N-(2,4-dimethoxybenzyl)-2,5-difluoro-N-(1,2,4-thiadiazol-5-yl)benzenesulfonamide, 4-((trans-4-(4-chlorophenyl)-1-(2,2,2-trifluoroethyl)piperidin-3-yl)methoxy)-2,5-difluoro-N-(1,2,4-thiadiazol-5-yl)benzenesulfonamide was obtained in 14% yield (0.011 g) as a colorless solid: $^1$H NMR (300 MHz, DMSO-$d_6$+1 drop of $D_2O$) δ 8.48 (s, 1H), 7.63-7.52 (m, 1H), 7.38-7.21 (m, 4H), 7.13-7.01 (m, 1H), 3.81-3.64 (m, 2H), 3.41-3.14 (m, 4H), 3.08-2.96 (m, 1H), 2.48-2.37 (m, 2H), 2.33-2.20 (m, 1H), 1.84-1.64 (m, 2H); (ES+) m/z 582.8 (M+1), 584.8 (M+1).

EXAMPLE 89

Synthesis of trans-3-((4(4-(N-(5-chlorothiazol-2-yl)sulfamoyl)-2,5-difluorophenoxy)methyl)-4-(3,4-difluorophenyl)piperidine-1-carboxamide

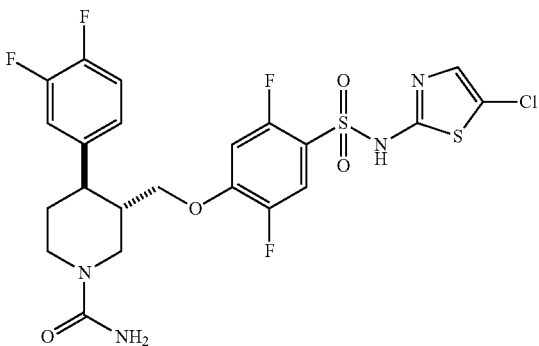

To a stirred solution of N-(5-chlorothiazol-2-yl)-4-(trans-4-(3,4-difluorophenyl)piperidin-3-yl(methoxy)-2,5-difluorobenzenesulfonamide (0.47 g, 0.72 mmol) in dichloromethane (50 mL) was added N,N-diisopropylethylamine (0.5 mL, 2.87 mmol) and triethyllsilylisocyanate (0.2 mL, 1.3 mmol) at ambient temperature. The reaction mixture was stirred at ambient temperature for 18 h and 5% hydrochloric acid (10 mL) was added. The mixture was diluted with ethyl acetate (200 mL), washed with water and brine and concentrated in vacuo. The residue was purified by column chromatography (1% methanol in dichloromethane) to afford trans-3-((4-(N-(5-chlorothiazol-2-yl)sulfamoyl)-2,5-difluorophenoxy)methyl)-4-(3,4-difluorophenyl)piperidine-1-carboxamide in 40% yield (0.17 g) as a colorless solid: $^1$H NMR (300 MHz, DMSO-$d_6$) δ 13.13 (br s, 1H), 7.62-7.53 (m, 2H), 7.41-7.24 (m, 2H), 7.15-7.05 (m, 2H), 6.03 (s 2H), 4.35-4.29 (m, 1H), 4.04-3.98 (m, 1H), 3.84-3.71 (m, 2H), 2.80-2.56 (m, 3H), 2.03-2.17 (m, 1H), 1.72-1.54 (m, 2H); (ES+) m/z 578.7 (M+1), 580.7 (M+1).

EXAMPLE 90.1

Synthesis of tert-butyl trans-4-(4-chlorophenyl)-3-((2-cyano-4-iodophenoxy)methyl)piperidine-1-carboxylate

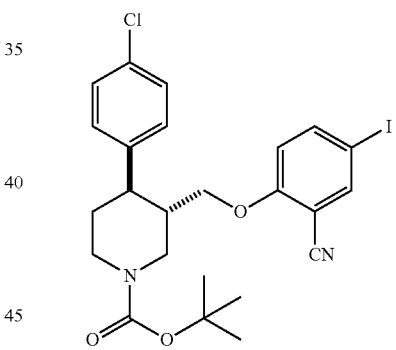

To a stirred solution of tert-butyl trans-4-(4-chlorophenyl)-3-(hydroxymethyl)piperidine-1-carboxylate (2.20 g, 6.75 mmol) in anhydrous N,N-dimethylformamide (100 mL) was added sodium hydride (0.35 g, 8.8 mmol, 60% w/w dispersion in mineral oil) at 0° C. The reaction mixture was stirred at ambient temperature for 30 minutes. 2-Fluoro-5-iodobenzonitrile (1.83 g, 7.40 mmol) was added at 0° C. and the reaction mixture was stirred at ambient temperature for 16 h. Saturated ammonium chloride (50 mL) was added, followed by ethyl acetate (200 mL). The organic layer was washed with brine, dried over anhydrous sodium sulfate and filtered. The filtrate was concentrated in vacuo. The residue was purified by column chromatography (5%-50% gradient of ethyl acetate in hexanes) to afford tert-butyl trans-4-(4-chlorophenyl)-3-((2-cyano-4-iodophenoxy)methyl)piperidine-1-carboxylate in 88% yield (3.30 g) as a colorless solid: MS (ES+) m/z 552.8 (M+1), 554.8 (M+1).

EXAMPLE 90.2

Synthesis of tert-butyl trans-3-((4-(benzylthio)-2-cyanophenoxy)methyl)-4-(4-chlorophenyl)piperidine-1-carboxylate

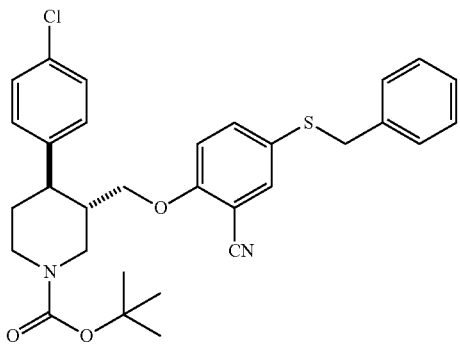

A mixture of tert-butyl trans-4-(4-chlorophenyl)-3-((2-cyano-4-iodophenoxy)methyl)piperidine-1-carboxylate (1.66 g, 3.00 mmol), benzylmercaptan (0.37 g, 3.00 mmol), copper(I) iodide (0.03 g, 0.15 mmol), ethylene glycol (0.37 g, 6.00 mmol) and potassium carbonate (0.83 g, 6.00 mmol) in 2-propanol (5 mL) was stirred at 80° C. for 16 h, filtered and the solid was washed with ethyl acetate (50 mL). The filtrate was diluted with ethyl acetate (100 mL) and washed with 25% aqueous ammonium chloride and brine, dried over anhydrous sodium sulfate and filtered. The filtrate was concentrated in vacuo and the residue was purified by column chromatography (5% to 50% gradient of ethyl acetate in hexanes) to obtain tert-butyl trans-3-((4-(benzylthio)-2-cyanophenoxy)methyl)-4-(4-chlorophenyl)piperidine-1-carboxylate as a colorless solid in 42% yield (0.70 g): MS (ES+) m/z 548.9 (M+1), 550.9 (M+1).

EXAMPLE 90.3

Synthesis of tert-butyl trans-4-(4-chlorophenyl)-3-((4-(chlorosulfonyl)-2-cyanophenoxy)methyl)piperidine-1-carboxylate

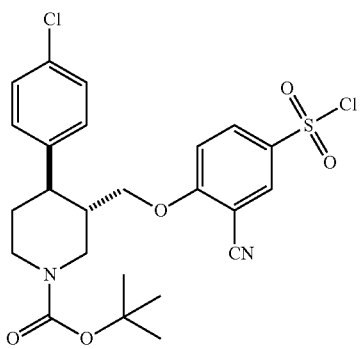

To a mixture of tert-butyl trans-3-((4-(benzylthio)-2-cyanophenoxy)methyl)-4-(4-chlorophenyl)piperidine-1-carboxylate (0.70 g, 1.27 mmol) in acetonitrile (25 mL), acetic acid (1 mL) and water (0.6 mL) was slowly added 1,3-dichloro-5,5-dimethylhydantoin (1.00 g, 5.10 mmol) at 0-5° C. and stirred at this temperature for 2 h. Ice-cold water was added and the mixture was extracted with diethyl ether (200 mL), dried over anhydrous sodium sulfate and filtered. The filtrate was concentrated in vacuo and the residue was titrated in hexanes to obtain tert-butyl trans-4-(4-chlorophenyl)-3-((4-(chlorosulfonyl)-2-cyanophenoxy)methyl)piperidine-1-carboxylate as a light yellow gummy solid. This material was used in the next step without further purification.

EXAMPLE 90.4

Synthesis of tert-butyl trans-4-(4-chlorophenyl)-3-((2-cyano-4-(N-isopropylsulfamoyl)phenoxy)methyl)piperidine-1-carboxylate

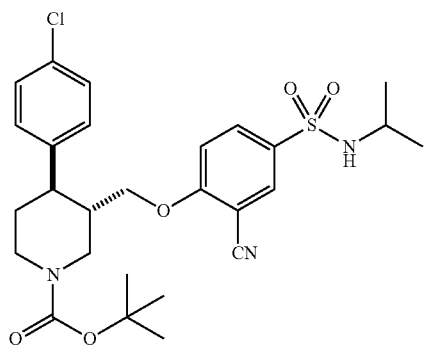

To a solution of tert-butyl trans-4-(4-chlorophenyl)-3-((4-(chlorosulfonyl)-2-cyanophenoxy)methyl)piperidine-1-carboxylate (0.36 g, 0.69 mmol), pyridine (0.22 mL, 2.74 mmol) in dichloromethane (10 mL) was added isopropylamine (0.50 g, 0.82 mmol). The reaction mixture was stirred at ambient temperature for 4 h. The mixture was diluted with ethyl acetate (100 mL), washed with 1 N hydrochloric acid, 25% aqueous ammonium chloride and brine, dried over anhydrous sodium sulfate and filtered. The filtrate was concentrated in vacuo and the residue was purified by column chromatography (5% to 60% gradient of ethyl acetate in hexanes) to obtain tert-butyl trans-4-(4-chlorophenyl)-3-(4-(chlorosulfonyl)-2-cyanophenoxy)methyl)piperidine-1-carboxylate in 19% yield (0.07 g) as a colorless oil: $^1$H NMR (300 MHz, CDCl$_3$) δ 8.04 (d, J=2.3 Hz, 1H), 7.91 (dd, J=2.3 Hz, 8.9 Hz, 1H), 7.23 (d, J=8.0 Hz, 2H), 7.11 (d, J=8.0 Hz, 2H), 6.77 (d, J=8.9 Hz, 1H), 4.70 (d, J=7.7 Hz, 1H), 4.42-4.38 (m, 1H), 4.25 (br s, 1H), 3.90-3.87 (m, 1H), 3.71-3.67 (m, 1H), 3.47-3.36 (m, 1H), 2.97-2.84 (m, 3H), 2.15-2.09 (m, 1H), 1.84-1.71 (m, 2H), 1.47 (s, 9H), 1.07 (d, J=6.5 Hz, 6H); MS (ES+) m/z 547.9 (M+1), 549.8 (M+1).

EXAMPLE 90

Synthesis of 4-((trans-4-(4-chlorophenyl)piperidin-3-yl)methoxy)-3-cyano-N-isopropylbenzenesulfonamide

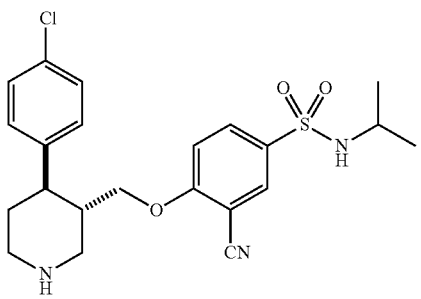

To a stirred solution of trans-tert-butyl 4-(4-chlorophenyl)-3-(4-(chlorosulfonyl)-2-cyanophenoxy)methyl)piperidine-1-carboxylate (0.07 g, 0.14 mmol) in methylene chloride (3 mL) was added trifluoroacetic acid (1 mL) at 0° C. The reaction mixture was stirred at 0° C. for 10 minutes and at ambient temperature for 0.5 h and concentrated in vacuo. The residue was purified by column chromatography (0% to 15% gradient of methanol in dichloromethane) to obtain 4-((trans-4-(4-chlorophenyl)piperidin-3-yl)methoxy)-3-cyano-N-isopropylbenzenesulfonamide as the corresponding trifluoroacetic acid salt in 61% yield (0.04 g): $^1$H NMR (300 MHz, DMSO-$d_6$) δ 8.77 (br s, 2H), 8.10 (d, J=2.3 Hz, 1H), 7.95 (dd, J=2.3 Hz, 8.9 Hz, 1H), 7.66 (d, J=7.2 Hz, 1H), 7.40 (d, J=8.3 Hz, 2H), 7.26-7.18 (m, 3H), 4.00-3.96 (m, 1H), 3.86-3.80 (m, 1H), 3.62-3.57 (m, 1H), 3.45-3.40 (m, 1H), 3.27-3.16 (m, 1H), 3.02-2.82 (m, 3H), 2.57-2.53 (m, 1H), 1.94-1.92 (m, 2H), 0.92 (d, J=6.5 Hz, 6H); MS (ES+) m/z 447.8 (M+1), 449.8 (M+1).

EXAMPLE 91.1

Synthesis of tert-butyl trans-4-(4-chlorophenyl)-3-((2-cyano-4-(N-(1-cyanocyclopropyl)sulfamoyl)phenoxy)methyl)piperidine-1-carboxylate

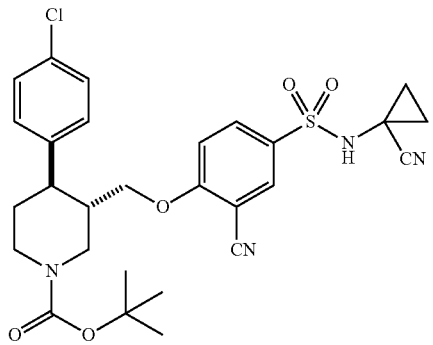

Following the procedure as described in EXAMPLE 90.4 and making non-critical variations to replace isopropylamine with 1-aminocyclopropanecarbonitrile, tert-butyl trans-4-(4-chlorophenyl)-3-((2-cyano-4-(N-(1-cyanocyclopropyl)sulfamoyl)phenoxy)methyl)piperidine-1-carboxylate was obtained in 18% yield (0.08 g) as a clear oil: MS (ES+) m/z 592.9 (M+1), 594.9 (M+1).

EXAMPLE 91

Synthesis of 4-((trans-4-(4-chlorophenyl)piperidin-3-yl)methoxy)-3-cyano-N-(1-cyanocyclopropyl)benzenesulfonamide

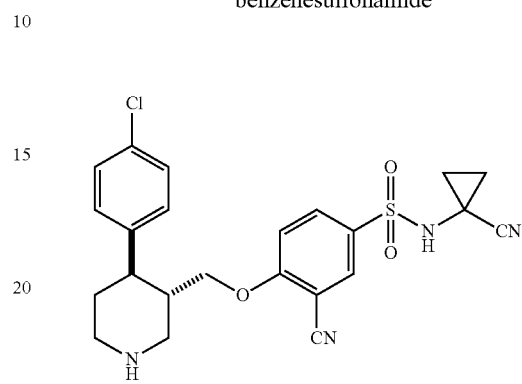

Following the procedure as described in EXAMPLE 90 and making non-critical variations to replace trans-tert-butyl 4-(4-chlorophenyl)-3-((4-(chlorosulfonyl)-2-cyanophenoxy)methyl)piperidine-1-carboxylate with tert-butyl trans-4-(4-chlorophenyl)-3-((2-cyano-4-(N-(1-cyanocyclopropyl)sulfamoyl)phenoxy)methyl)piperidine-1-carboxylate, 4-((trans-4-(4-chlorophenyl)piperidin-3-yl)methoxy)-3-cyano-N-(1-cyanocyclopropyl)benzenesulfonamide was obtained as the corresponding trifluoroacetic acid salt in 38% yield (0.03 g): $^1$H NMR (300 MHz, DMSO-$d_5$) δ 8.14-8.13 (m, 1H), 8.07 (br s, 1H), 8.00-7.98 (m, 1H), 7.37-7.22 (m, 5H), 3.97-3.93 (m, 1H), 3.84-3.78 (m, 1H), 3.50-3.44 (m, 1H), 3.28-3.24 (m, 1H), 2.85-2.73 (m, 3H), 2.44-2.35 (m, 1H), 1.83-1.77 (m, 2H), 1.44-1.40 (m, 2H), 1.28-1.23 (m, 2H); MS (ES+) m/z 470.8 (M+1), 472.8 (M+1).

EXAMPLE 92.1

Synthesis of tert-butyl trans-4-(3,4-dichlorophenyl)-3-(hydroxymethyl)piperidine-1-carboxylate

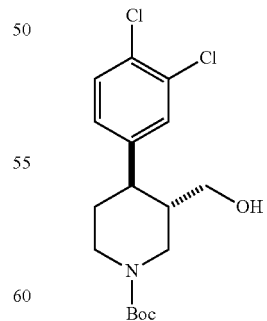

Following the procedure as described in EXAMPLE 5, making non-critical variations to replace 3,4-difluorophenylmagnesium bromide with 3,4-dichlorophenylmagnesium bromide, tert-butyl trans-4-(3,4-dichlorophenyl)-3-(hydroxymethyl)piperidine-1-carboxylate was obtained in 2% yield over 3 steps (0.35 g) as a colorless solid: $^1$H NMR (300 MHz, CDCl$_3$) δ 7.49-7.32 (m, 1H), 7.29-7.25 (m, 1H), 7.05-6.97 (m, 1H), 4.42-4.25 (m, 1H), 3.49-3.35 (m, 1H), 3.31-3.19 (m, 1H), 2.82-2.62 (m, 2H), 2.61-2.45 (m, 1H), 1.87-1.69 (m, 5H), 1.51-1.41 (m, 9H); MS (ES+) m/z 359.8 (M+1), 361.8 (M+1).

EXAMPLE 92.1

Synthesis of tert-butyl trans-4-(3,4-dichlorophenyl)-3-(4-(N-(3,4-dimethoxybenzyl)-N-(1,2,4-thiadiazol-5-yl)sulfamoyl)-2,5-difluorophenoxy)methyl)piperidine-1-carboxylate

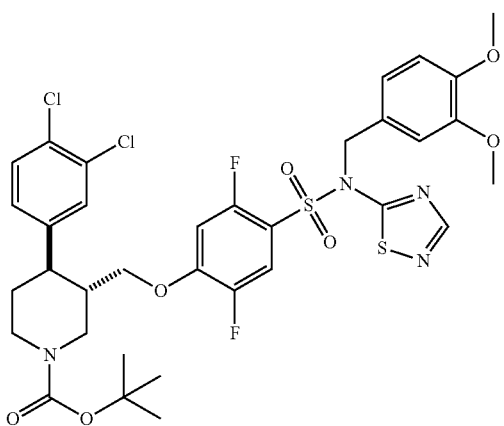

Following the procedure as described in EXAMPLE 16 and making non-critical variations to replace tert-butyl trans-4-(4-chlorophenyl)-3-(hydroxymethyl)piperidine-1-carboxylate with tert-butyl trans-4-(3,4-dichlorophenyl)-3-(hydroxymethyl)piperidine-1-carboxylate, tert-butyl trans-4-(3,4-dichlorophenyl)-3-((4-(N-(3,4-dimethoxybenzyl)-N-(1,2,4-thiadiazol-5-yl)sulfamoyl)-2,5-difluorophenoxy)methyl)piperidine-1-carboxylate was obtained in 76% yield (0.58 g) as a colorless solid: $^1$H NMR (300 MHz, CDCl$_3$) δ 8.15 (s, 1H), 7.56-7.46 (m, 1H), 7.40-7.33 (m, 1H), 7.28-7.22 (m, 3H), 7.17-7.10 (m, 1H), 7.04-6.96 (m, 1H), 6.41-6.29 (m, 2H), 6.28-6.18 (m, 1H), 5.24 (br s, 2H), 3.76-3.62 (m, 9H), 2.90-2.62 (m, 3H), 1.86-1.76 (m, 2H), 1.51-1.43 (m, 9H); MS (ES+) m/z 784.8 (M+1), 786.8 (M+1).

EXAMPLE 92

Synthesis of 4-((trans-4-(3,4-dichlorophenyl)piperidin-3-yl)methoxy)-2,5-difluoro-N-(1,2,4-thiadiazol-5-yl)benzenesulfonamide

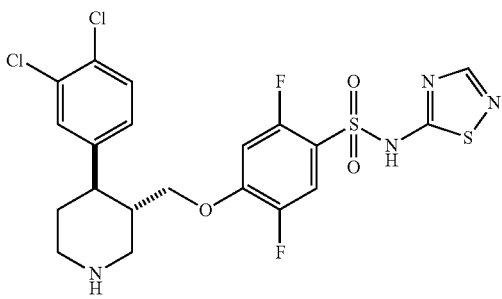

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy) methyl)piperidine-1-carboxylate with tert-butyl trans-4-(3,4-dichlorophenyl)-3-(4-(N-(3,4-dimethoxybenzyl)-N-(1,2,4-thiadiazol-5-yl)sulfamoyl)-2,5-difluorophenoxy)methyl) piperidine-1-carboxylate, 4-((trans-4-(3,4-dichlorophenyl)piperidin-3-yl)methoxy)-2,5-difluoro-N-(1,2,4-thiadiazol-5-yl)benzenesulfonamide was obtained as the corresponding trifluoroacetic acid salt in 2% yield (0.01 g) as a colorless solid: $^1$H NMR (300 MHz, DMSO-d$_6$) δ 8.83-8.65 (m, 1H), 8.56-8.35 (m, 1H), 8.25 (s, 1H), 7.62-7.57 (m, 1H), 7.57-7.49 (m, 1H), 7.44-7.39 (m, 1H), 7.21-7.15 (m, 1H), 7.15-7.06 (m, 1H), 3.97-3.70 (m, 2H), 3.47-3.28 (m, 2H), 3.08-2.78 (m, 3H), 2.44-2.40 (m, 1H), 1.99-1.85 (m. 2H); MS (ES+) m/z 534.7 (M+1), 536.7 (M+1).

EXAMPLE 93.1

Synthesis of tert-butyl trans-4-(4-chlorophenyl)-3-((2-cyano-4-(N-(2,2,2-trifluoroethyl)sulfamoyl)phenoxy)methyl)piperidine-1-carboxylate

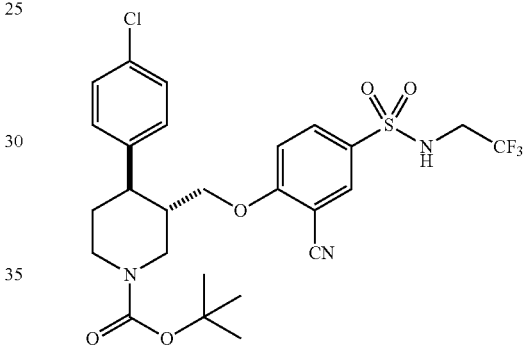

Following the procedure as described in EXAMPLE 90.4 and making non-critical variations to replace isopropyl amine with 2,2,2-trifluoroethanamine, tert-butyl trans-4-(4-chlorophenyl)-3-((2-cyano-4-(N-(2,2,2-trifluoroethyl)sulfamoyl)-phenoxy)methyl)piperidine-1-carboxylate was obtained as a clear oil in 21% yield (0.12 g): MS (ES+) m/z 609.8 (M+23), 611.7 (M+23).

EXAMPLE 93

Synthesis of 4-((trans-4-(4-chlorophenyl)piperidin-3-yl)methoxy)-3-cyano-N-(2,2,2-trifluoroethyl)benzenesulfonamide

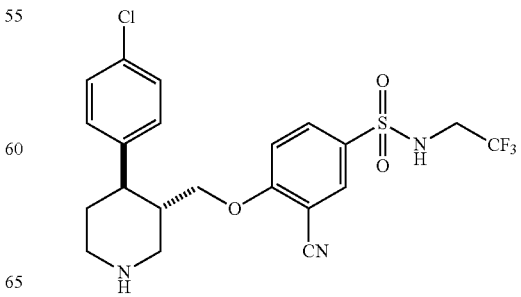

Following the procedure as described in EXAMPLE 90 and making non-critical variations to replace trans-tert-butyl 4-(4-chlorophenyl)-3-((4-(chlorosulfonyl)-2-cyanophenoxy)methyl)piperidine-1-carboxylate with trans-tert-butyl 4-(4-chlorophenyl)-3-(2-cyano-4-(N-(2,2,2-trifluoroethyl)sulfamoyl)phenoxy)methyl)piperidine-1-carboxylate, 4-((trans-4-(4-chlorophenyl)piperidin-3-yl)methoxy)-3-cyano-N-(2,2,2-trifluoroethyl)benzenesulfonamide was obtained as the corresponding trifluoroacetic acid salt in 73% yield (0.07 g) as a colorless solid: $^1$H NMR (300 MHz, DMSO-d$_6$) δ 8.61 (br s, 3H), 8.17 (d, J=2.3 Hz, 1H), 7.97 (dd, J=2.3 Hz, 9.0 Hz, 1H), 7.40 (d, J=8.3 Hz, 2H), 2.27-2.19 (m, 3H), 4.00-3.96 (m, 1H), 3.86-3.80 (m, 1H), 3.76-3.67 (m, 2H), 3.59-3.54 (m, 1H), 3.42-3.38 (m, 1H), 2.98-2.81 (m, 3H), 2.57-2.52 (m, 1H), 1.92-1.90 (m, 2H); MS (ES+) m/z 487.8 (M+1), 489.7 (M+1).

EXAMPLE 94.1

Synthesis of 1-tert-butyl 3-ethyl 4-(4-methoxyphenyl)-5,6-dihydropyridine-1,3(2H)-dicarboxylate

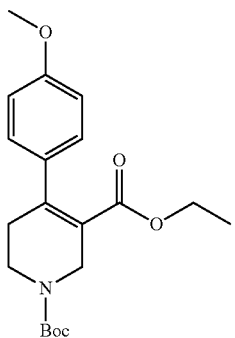 [SMILES: CCOC(=O)C1=C(c2ccc(OC)cc2)CCN(C(=O)OC(C)(C)C)C1]

To a degassed mixture of 1-tert-butyl 3-ethyl 4-(((trifluoromethyl)sulfonyl)oxy)-5,6-dihydropyridine-1,3(2H)-dicarboxylate (14.9 g, 36.9 mmol), (4-methoxyphenyl)boronic acid (6.7 g, 44.3 mmol) and 2.0 M aqueous sodium carbonate (73.8 mL, 147.6 mmol) in dimethoxyethane (360 mL) was added tetrakis(triphenylphosphine)palladium (2.71 g, 2.35 mmol). The resulting mixture was heated at reflux under nitrogen for 4 h. The reaction mixture was diluted with ethyl acetate (400 mL), washed with saturated ammonium chloride (4×200 mL) and brine (200 mL), dried over anhydrous sodium sulfate and filtered. The filtrate was concentrated in vacuo and the residue was purified by column chromatography eluting with ethyl acetate in hexanes to afford 1-tert-butyl 3-ethyl 4-(4-methoxyphenyl)-5,6-dihydropyridine-1,3(2H)-dicarboxylate in 67% yield (8.9 g) as a colorless oil: $^1$H NMR (300 MHz, CDCl$_3$) δ 7.08-7.02 (m, 2H), 6.86-6.80 (m, 2H), 4.24-4.18 (m, 2H), 3.95 (q, J=7.2 Hz, 2H), 3.78 (s, 3H), 3.60-3.53 (m, 2H), 2.50-2.42 (m, 2H), 1.47 (s, 9H), 1.00-0.90 (m, 3H); MS (ES$^+$) ink 362.0 (M+1).

EXAMPLE 94.2

Synthesis of trans-1-tert-butyl 3-ethyl 4-(4-methoxyphenyl)piperidine-1,3-dicarboxylate

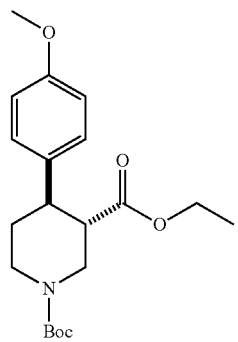

A solution of 1-tert-butyl 3-ethyl 4-(4-methoxyphenyl)-5,6-dihydropyridine-1,3(2H)-dicarboxylate (8.9 g, 24.6 mmol) in anhydrous methanol (200 mL) was treated portionwise with magnesium turnings (2.4 g, 98.3 mmol). The resulting mixture was stirred under nitrogen for 18 h. The reaction mixture was concentrated in vacuo to a volume of ~50 mL. The residue was diluted with ethyl acetate (400 mL), washed with 1.0 M hydrochloric acid (2×200 mL) and brine (2×150 mL), dried over anhydrous sodium sulfate and filtered. The filtrate was concentrated in vacuo and the residue was dissolved in absolute ethanol (50 mL) and added to a solution of sodium (1.1 g, 46.8 mmol) in absolute ethanol (50 mL). The resulting mixture was heated at reflux for 3 h and allowed to cool to ambient temperature. Saturated aqueous ammonium chloride (100 mL) was added and the mixture was concentrated in vacuo to half volume and diluted with ethyl acetate (400 mL). The layers were separated; the organic layer was washed with saturated aqueous ammonium chloride (100 mL) and brine (2×150 mL), dried over anhydrous sodium sulfate and filtered. The filtrate was concentrated in vacuo and the residue was purified by column chromatography eluting with a gradient of ethyl acetate in hexanes to afford trans-1-tert-butyl 3-ethyl 4-(4-methoxyphenyl)piperidine-1,3-dicarboxylate as in 58% yield (4.9 g) as a colorless oil: MS (ES+) m/z 386.0 (M+23).

EXAMPLE 94.3

Synthesis of trans-tertbutyl 3-(hydroxymethyl)-4-(4-methoxyphenyl)piperidine-1-carboxylate

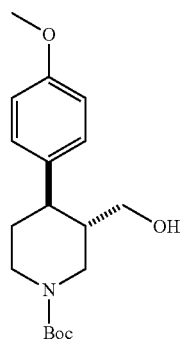

Following the procedure as described in Step B of EXAMPLE 1 and making non-critical variations to replace trans-1-tert-butyl 3-methyl 4-(4-chlorophenyl)piperidine-1,3-dicarboxylate with trans-1-tert-butyl 3-ethyl 4-(4-methoxyphenyl)piperidine-1,3-dicarboxylate, trans-tert-butyl 3-(hydroxymethyl)-4-(4-methoxyphenyl)piperidine-1-carboxylate was obtained in 99% yield (4.30 g) as a colorless oil: $^1$H NMR (300 MHz, CDCl$_3$) δ 7.08 (d, J=8.6 Hz, 2H), 6.82 (d, J=8.6 Hz, 2H), 4.37-4.28 (m, 1H), 4.21-4.12 (m, 1H), 3.76 (s, 3H), 3.41 (dd, J=11.1, 3.4 Hz, 1H), 3.23 (dd, J=11.1, 6.6 Hz, 1H), 2.78-2.70 (m, 1H), 2.69-2.59 (m, 1H), 2.49-2.38 (m, 1H), 1.84-1.57 (m, 4H), 1.46 (s, 9H); MS (ES+) m/z 321.9 (M+1).

EXAMPLE 94.4

Synthesis of trans-tert-butyl 3-((4(4-(N-(2,4-dimethoxybenzyl)-N-(1,2,4-thiadiazol-5-yl)sulfamoyl)-2,5-difluorophenoxy)methyl)-4-(4-methoxyphenyl)piperidine-1-carboxylate

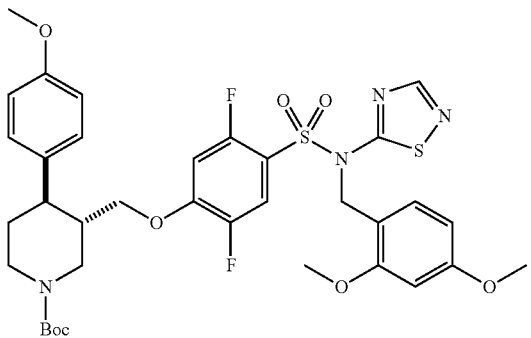

Following the procedure as described in EXAMPLE 16 and making non-critical variations to replace trans-tert-butyl 4-(4-chlorophenyl)-3-(hydroxymethyl)piperidine-1-carboxylate with trans-tert-butyl 3-(hydroxymethyl)-4-(4-methoxyphenyl)piperidine-1-carboxylate, trans-tert-butyl 3-((4(4-(N-(2,4-dimethoxybenzyl)-N-(1,2,4-thiadiazol-5-yl)sulfamoyl)-2,5-difluorophenoxy)methyl)-4-(4-methoxyphenyl)piperidine-1-carboxylate was obtained in 19% yield (0.2 g) as a colorless solid: MS (ES+) m/z 746.8 (M+1).

EXAMPLE 94

Synthesis of 2,5-difluoro-4-((trans-4-(4-methoxyphenyl)piperidin-3-yl)methoxy)-N-(1,2,4-thiadiazol-5-yl)benzenesulfonamide

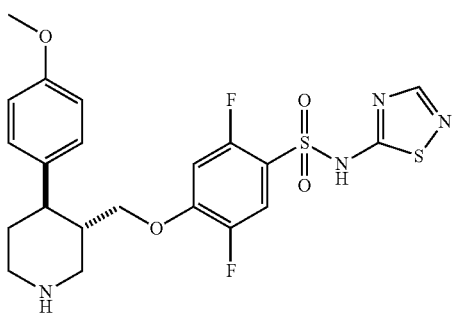

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-((4(4-(N-(2,4-dimethoxybenzyl)-N-(1,2,4-thiadiazol-5-yl)sulfamoyl)-2,5-difluorophenoxy)methyl)-4-(4-methoxyphenyl)piperidine-1-carboxylate, 2,5-difluoro-4-((trans-4-(4-methoxyphenyl)piperidin-3-yl)methoxy)-N-(1,2,4-thiadiazol-5-yl)benzenesulfonamide was obtained as the corresponding trifluoroacetic acid salt in 66% yield (0.11 g) as a colorless solid: $^1$H NMR (300 MHz, DMSO-d$_6$) δ 8.96-8.84 (m, 1H), 8.77-8.61 (m, 1H), 8.40 (s, 1H), 7.56 (dd, J=10.4, 6.7 Hz, 1H), 7.11-7.02 (m, 3H), 6.88-6.82 (m, 2H), 3.85-3.78 (m, 1H), 3.76-3.69 (m, 1H), 3.66 (s, 3H), 3.54-3.45 (m, 1H), 3.40-3.31 (m, 1H), 3.05-2.85 (m, 2H), 2.79-2.67 (m, 1H), 2.44-2.31 (m, 1H), 1.93-1.79 (m, 2H); MS (ES+) m/z 496.7 (M+1).

EXAMPLE 95.1

Synthesis of tert-butyl trans-4-(4-chlorophenyl)-3-(2,5-difluoro-4-sulfamoylphenoxy)methyl)piperidine-1-carboxylate

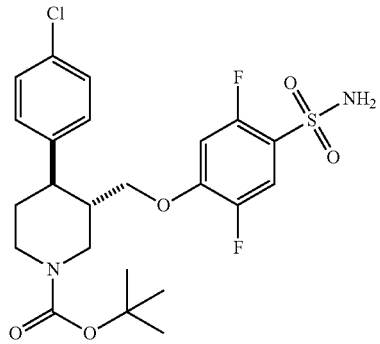

Following the procedure as described in EXAMPLE 90.1 and making non-critical variations to replace 2-fluoro-5-iodobenzonitrile with 2,4,5-trifluorobenzenesulfonamide, tert-butyl trans-4-(4-chlorophenyl)-3-((2,5-difluoro-4-sulfamoylphenoxy)methyl)piperidine-1-carboxylate was obtained as a colorless solid in 27% yield (0.19 g): $^1$H NMR (300 MHz, CDCl$_3$) δ 7.57-7.51 (m, 1H), 7.26-7.24 (m, 2H), 7.25 (d, J=8.3 Hz, 2H), 7.09 (d, J=8.3 Hz, 2H), 6.53-6.48 (m, 1H), 5.21 (s, 2H), 4.42-4.39 (m, 1H), 4.23-4.20 (m, 1H), 3.77-3.73 (m, 1H), 3.61-3.56 (m, 1H), 2.86-2.67 (m, 3H), 2.14-2.07 (m, 1H), 1.83-1.69 (m, 2H), 1.46 (s, 9H); MS (ES+) m/z 538.8 (M+23), 540.7 (M+23).

EXAMPLE 95

Synthesis of 4-((trans-4-(4-chlorophenyl)piperidin-3-yl)methoxy)-2,5-difluorobenzenesulfonamide

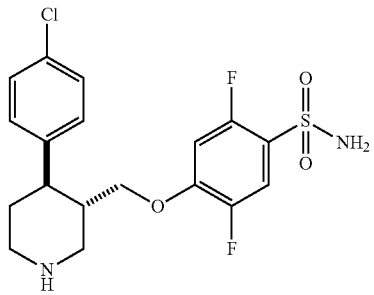

Following the procedure as described above in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with tert-butyl trans-4-(4-chlorophenyl)-3-((2,5-difluoro-4-sulfamoylphenoxy)methyl)piperidine-1-carboxylate, 4-((trans-4-(4-chlorophenyl)piperidin-3-yl)methoxy)-2,5-difluorobenzenesulfonamide was obtained as the corresponding trifluoroacetic acid salt in 79% yield (0.03 g) as a colorless solid: $^1$H NMR (300 MHz, DMSO-$d_6$) δ 7.64 (br s, 2H), 7.52-7.46 (m, 1H), 7.35 (d, J=8.4 Hz, 2H), 7.20 (d, J=8.5 Hz, 2H), 7.14-7.08 (m, 1H), 3.82-3.68 (m, 2H), 3.44-3.23 (m, 3H), 2.90-2.70 (m, 3H), 2.40-2.33 (m, 1H), 1.84-1.78 (m, 2H); MS (ES$^+$) m/z 416.8 (M+1), 418.7 (M+1).

EXAMPLE 96.1

Synthesis of N-(2,4-dimethoxybenzyl)-2,4,5-trifluorobenzenesulfonamide

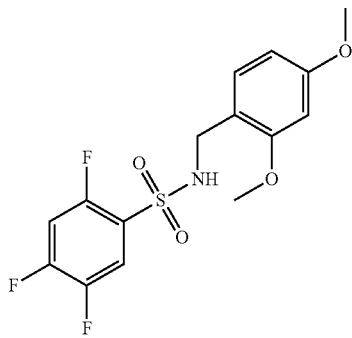 [SMILES: COc1ccc(CNS(=O)(=O)c2cc(F)c(F)cc2F)c(OC)c1]

A mixture of 2,4,5-trifluorobenzene-1-sulfonyl chloride (5.00 g, 21.7 mmol), 2,4-dimethoxybenzylamine (3.63 g, 21.7 mmol), diethylpropylethylamine (3.36 g, 26.0 mmol) in dichloromethane (100 mL) was stirred at ambient temperature for 16 h. The mixture was diluted in dichloromethane (100 mL), washed with 1N hydrochloric acid, 25% aqueous ammonium chloride and brine, dried over anhydrous sodium sulfate and filtered. The filtrate was concentrated in vacuo and the residue was crystallized from dichloromethane/hexanes to obtain N-(2,4-dimethoxybenzyl)-2,4,5-trifluorobenzenesulfonamide as a cream solid in 95% yield (7.5 g): $^1$H NMR (300 MHz, CDCl$_3$) δ 7.55-7.47 (m, 1H), 6.81-6.76 (m, 2H), 6.25-6.20 (m, 2H), 5.50 (s, 1H), 4.18 (s, 2H), 3.76-3.73 (m, 6H).

EXAMPLE 96.2

Synthesis of N-(2,4-dimethoxybenzyl)-2,4,5-trifluoro-N-isobutylbenzenesulfonamide

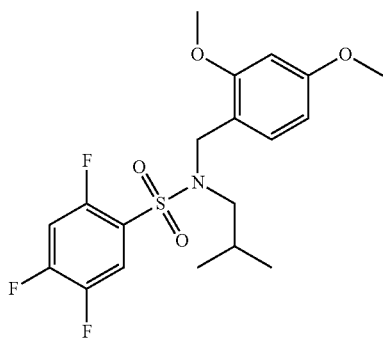 [SMILES: COc1ccc(CN(CC(C)C)S(=O)(=O)c2cc(F)c(F)cc2F)c(OC)c1]

A mixture of N-(2,4-dimethoxybenzyl)-2,4,5-trifluorobenzenesulfonamide (0.50 g, 1.38 mmol), 1-iodo-2-methylpropane (0.38 g, 2.08 mmol), potassium carbonate (0.38 g, 2.77 mmol) and tetra-n-butylammonium iodide (0.01 g) in acetonitrile (7 mL) was stirred at 78° C. for 16 h and allowed to cool to ambient temperature. The mixture was diluted with ethyl acetate (100 mL), washed with 1 N hydrochloric acid, 25% aqueous ammonium chloride and brine, dried over anhydrous sodium sulfate and filtered. The filtrate was concentrated in vacuo and the residue was purified by column chromatography (0% to 55% gradient of ethyl acetate in hexanes) to afford N-(2,4-dimethoxybenzyl)-2,4,5-trifluoro-N-isobutylbenzenesulfonamide in 95% yield (0.45 g) as a clear oil: $^1$H NMR (300 MHz, CDCl$_3$) δ 7.45-7.36 (m, 1H), 7.13 (d, J=8.3 Hz, 1H), 6.97-6.89 (m, 1H), 6.39-6.36 (m, 1H), 6.19-6.18 (m, 1H), 4.36 (s, 2H), 3.76 (s, 3H), 3.65 (s, 3H), 3.19 (d, J=7.5 Hz, 2H), 1.95-1.81 (m, 1H), 0.87 (d, J=6.7 Hz, 6H).

EXAMPLE 96.3

Synthesis of tert-butyl trans-4-(4-chlorophenyl)-3-((4-(N-(2,4-dimethoxybenzyl)-N-isobutylsulfamoyl)-2,5-difluorophenoxy)methyl)piperidine-1-carboxylate

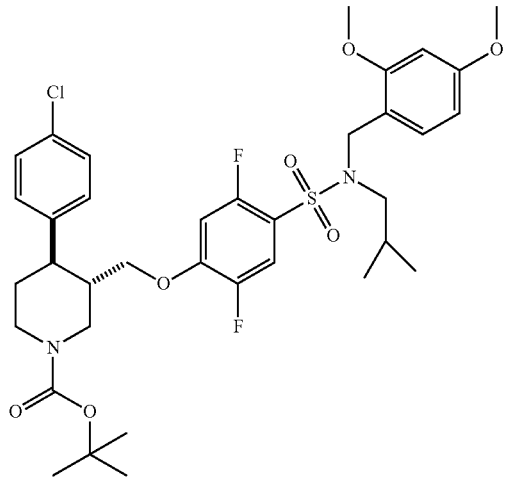 [SMILES: COc1ccc(CN(CC(C)C)S(=O)(=O)c2cc(F)c(OC[C@@H]3CN(C(=O)OC(C)(C)C)CC[C@H]3c3ccc(Cl)cc3)cc2F)c(OC)c1]

Following the procedure as described in EXAMPLE 90.1 and making non-critical variations to replace 2-fluoro-5-iodobenzonitrile with N-(2,4-dimethoxybenzyl)-2,4,5-trifluoro-N-isobutylbenzenesulfonamide, tert-butyl trans-4-(4-chlorophenyl)-3-((4-(N-(2,4-dimethoxybenzyl)-N-isobutylsulfamoyl)-2,5-difluorophenoxy)methyl)piperidine-1-carboxylate was obtained in 74% yield (0.55 g) as a colorless solid: $^1$H NMR (300 MHz, CDCl$_3$) δ 7.14-7.08 (m, 3H), 6.40-6.32 (m, 2H), 6.19-6.18 (m, 1H), 4.43-4.39 (m, 1H), 4.30 (s, 2H), 4.23 (br s, 1H), 3.73-3.69 (m, 4H), 3.60-3.53 (m, 4H), 3.04 (d, J=7.5 Hz, 2H), 2.86-2.67 (m, 3H), 2.10-2.04 (m, 1H), 1.82-1.66 (m, 3H), 1.46 (s, 9H), 0.78 (d, J=6.6 Hz, 6H); MS (ES+) m/z 744.9 (M+23), 746.9 (M+23).

EXAMPLE 96

Synthesis of 4-((trans-4-(4-chlorophenyl)piperidin-3-yl)methoxy)-2,5-difluoro-N-isobutylbenzenesulfonamide

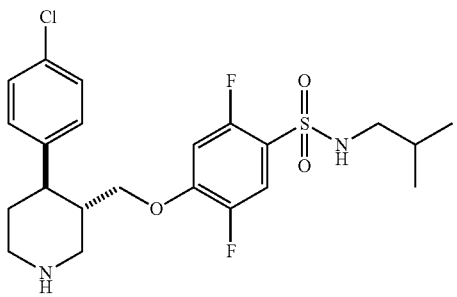 [SMILES: CC(C)CNS(=O)(=O)c1cc(F)c(OC[C@@H]2CNCC[C@H]2c2ccc(Cl)cc2)cc1F]

Following the procedure as described above in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with tert-butyl trans-4-(4-chlorophenyl)-3-((4-(N-(2,4-dimethoxybenzyl)-N-isobutylsulfamoyl)-2,5-difluorophenoxy)methyl)piperidine-1-carboxylate, 4-((trans-4-(4-chlorophenyl)piperidin-3-yl)methoxy)-2,5-difluoro-N-isobutylbenzenesulfonamide was obtained as the corresponding trifluoroacetic acid salt in 56% yield (0.20 g) as a colorless solid: $^1$H NMR (300 MHz, DMSO-d$_6$) δ 8.98-8.78 (m, 2H), 7.93-7.89 (m, 1H), 7.56-7.50 (m, 1H), 7.41-7.39 (m, 2H), 7.24-7.15 (m, 3H), 3.90-3.74 (m, 2H), 3.58-3.54 (m, 1H), 3.44-3.39 (m, 1H), 3.03-2.82 (m, 3H), 2.61 (t, J=6.4 Hz, 2H), 1.92-1.89 (m, 2H), 1.67-1.54 (m, 1H), 0.79 (d, J=6.7 Hz, 6H); MS (ES+) m/z 472.8 (M+1), 474.8 (M+1).

EXAMPLE 97.1

Synthesis of tert-butyl trans-4-(4-chloro-3-fluorophenyl)-3-(hydroxymethyl)piperidine-1-carboxylate

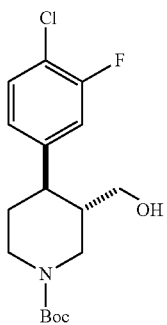

Following the procedure as described in EXAMPLE 5, making non-critical variations to replace 3,4-difluorophenylmagnesium bromide with 4-chloro-3-fluorophenylmagnesium bromide, tert-butyl trans-4-(4-chloro-3-fluorophenyl)-3-(hydroxymethyl)piperidine-1-carboxylate was obtained in 4% yield over 3 steps (0.85 g) as a colorless solid: MS (ES$^+$) m/z 343.9 (M+1), 345.9 (M+1).

EXAMPLE 97.2

Synthesis of tert-butyl trans-4-(4-chloro-3-fluorophenyl)-3-(4-(N-(3,4-dimethoxybenzyl)-N-(1,2,4-thiadiazol-5-yl)sulfamoyl)-2,5-difluorophenoxy)methyl)piperidine-1-carboxylate

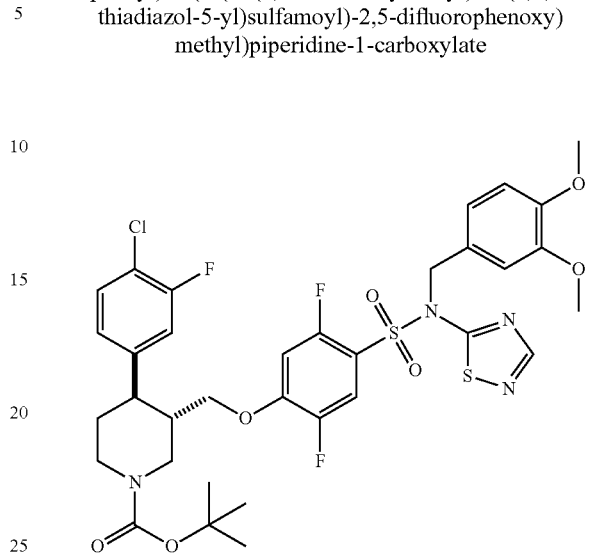

Following the procedure as described in EXAMPLE 16 and making non-critical variations to replace tert-butyl trans-4-(4-chlorophenyl)-3-(hydroxymethyl)piperidine-1-carboxylate with tert-butyl trans-4-(4-chloro-3-fluorophenyl)-3-(hydroxymethyl)piperidine-1-carboxylate, tert-butyl trans-4-(4-chloro-3-fluorophenyl)-3-((4-(N-(3,4-dimethoxybenzyl)-N-(1,2,4-thiadiazol-5-yl)sulfamoyl)-2,5-difluorophenoxy)methyl)piperidine-1-carboxylate was obtained as a colorless solid in 64% yield (0.43 g): MS (ES+) m/z 768.8, 770.8 (M+1).

EXAMPLE 97

Synthesis of 4-((trans-4-(4-chloro-3-fluorophenyl(piperidin-3-yl)methoxy)-2,5-difluoro-N-(1,2,4-thiadiazol-5-yl)benzenesulfonamide

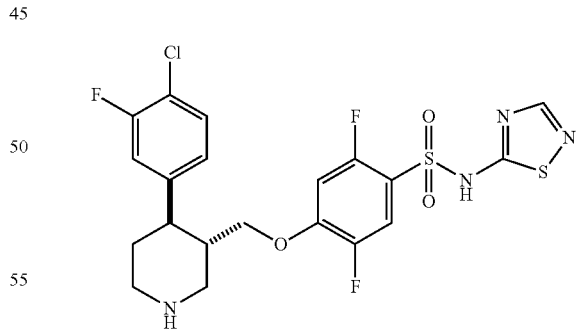

Following the procedure as described in EXAMPLE 44 and making non-critical variations to replace trans-tert-butyl 4-(4-chlorophenyl)-3-((4-(N-(2,4-dimethoxybenzyl) -N-(1,2,4-thiadiazol-5-yl)sulfamoyl)-2,5-difluorophenoxy)methyl)piperidine-1-carboxylate with tert-butyl trans-4-(4-chloro-3-fluorophenyl)-3-((4-(N-(3,4-dimethoxybenzyl)-N-(1,2,4-thiadiazol-5-yl)sulfamoyl)-2,5-difluorophenoxy)methyl)piperidine-1-carboxylate, 4-((trans-4-(4-chloro-3-fluorophenyl)piperidin-3-yl)methoxy)-2,5-difluoro-N-(1,2, 4-thiadiazol-5-yl)benzenesulfonamide was obtained as the corresponding trifluoroacetic acid salt in 36% yield (0.10 g) as a colorless solid: $^1$H NMR (300 MHz, DMSO-d$_6$) δ 8.80 (br s, 1H), 8.55 (br s, 1H), 8.41-8.33 (s, 1H), 7.61-7.46 (m, 2H), 7.25-7.16 (m, 1H), 7.15-7.07 (m, 1H), 7.06-6.90 (m, 1H), 3.90-3.80 (m, 1H), 3.80-3.69 (m, 1H), 3.56-3.44 (m, 1H), 3.42-3.28 (m, 1H), 3.08-2.76 (m, 3H), 2.43-2.37 (m, 1H), 1.94-1.75 (m, 2H); (ES+) m/z 518.7 (M+1), 520.7 (M+1);

EXAMPLE 98.1

Synthesis of 1-((2,4,5-trifluorophenyl)sulfonyl)-1H-pyrazole

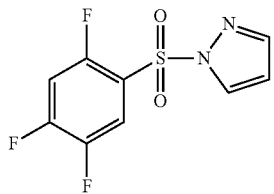 [SMILES: O=S(=O)(c1cc(F)c(F)cc1F)n1cccn1]

Following the procedure as described in step B of EXAMPLE 7 and making non-critical variations to replace N-(2,4-dimethoxybenzyl)-1,3,4-thiadiazol-2-amine with 1H-pyrazole, 1-((2,4,5-trifluorophenyl)sulfonyl)-1H-pyrazole was obtained as a colorless solid in 89% yield (1.06 g): $^1$H NMR (300 MHz, CDCl$_3$) δ 8.19-8.18 (m, 1H), 8.02-7.94 (m, 1H), 7.56-7.55 (m, 1H), 7.08-7.00 (m, 1H), 6.45 (dd, J=2.8, 1.6 Hz, 1H; MS (ES+) m/z 262.9 (M+1).

EXAMPLE 98.2

Synthesis of trans-tert-butyl 3-((4-((1H-pyrazol-1-yl)sulfonyl)-2,5-difluorophenoxy)methyl)-4-(4-fluorophenyl)piperidine-1-carboxylate

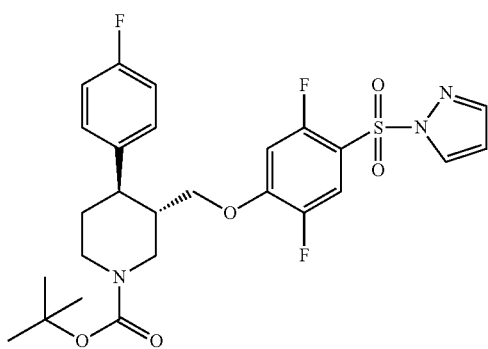 [SMILES: CC(C)(C)OC(=O)N1CC[C@@H](c2ccc(F)cc2)[C@H](COc2cc(F)c(S(=O)(=O)n3cccn3)cc2F)C1]

Following the procedure as described in EXAMPLE 40 and making non-critical variations to replace N-(2,4-dimethoxybenzyl)-2,4,5-trifluoro-N-(1,2,4-thiadiazol-5-yl(benzenesulfonamide with 1-((2,4,5-trifluorophenyl)sulfonyl)-1H-pyrazole, trans-tert-butyl 3-((4-((1H-pyrazol-1-yl)sulfonyl)-2,5-difluorophenoxy)methyl)-4-(4-fluorophenyl)piperidine-1-carboxylate was obtained as a colorless foamy solid that was used without further purification: MS (ES+) m/z 551.9 (M+1), 573.9 (M+23).

EXAMPLE 98

Synthesis of trans-3-((4-((1H-pyrazol-1-yl)sulfonyl)-2,5-difluorophenoxy)methyl)-4-(4-fluorophenyl)piperidine

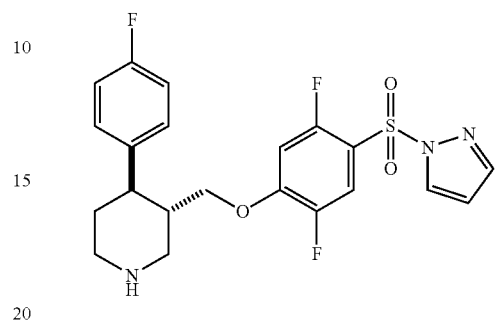

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-((4-((1H-pyrazol-1-yl)sulfonyl)-2,5-difluorophenoxy)methyl)-4-(4-fluorophenyl)piperidine-1-carboxylate, trans-3-((4-((1H-pyrazol-1-yl)sulfonyl)-2,5-difluorophenoxy)methyl)-4-(4-fluorophenyl(piperidine was obtained as the corresponding trifluoroacetic acid salt in 14% yield (0.013 g) as a colorless solid: $^1$H NMR (5% v/v D$_2$O in DMSO-d$_6$) δ 8.34-8.32 (m, 1H), 8.01 (dd, J=10.8, 6.0 Hz, 1H), 7.93 (d, J=1.6 Hz, 1H), 7.79 (dd, J=10.7, 6.0, Hz, 1H), 7.12-6.99 (m, 4H), 6.68-6.67 (m, 1H), 3.87-3.74 (m, 2H), 3.45-3.39 (m, 1H), 3.31-3.26 (m, 1H), 2.98-2.80 (m, 2H), 2.73-2.64 (m, 1H), 2.36-2.24 (m, 1H), 1.85-1.71 (m, 2H) (NH not observed); MS (ES$^+$) m/z 451.7 (M+1).

EXAMPLE 99.1

Synthesis of tert-butyl trans-4-(4-chlorophenyl)-3-(2,5-difluoro-4-(N-picolinoylsulfamoyl)phenoxy)methyl)piperidine-1-carboxylate

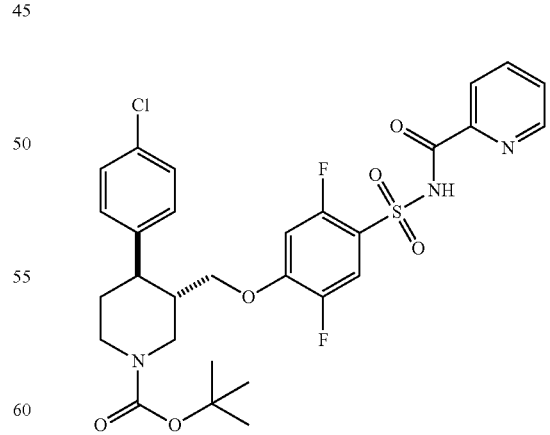

To a mixture of tert-butyl trans-4-(4-chlorophenyl)-3-((2,5-difluoro-4-sulfamoylphenoxy)methyl)piperidine-1-carboxylate (0.65 g, 1.3 mmol) and triethylamine (1.04 g, 10.0 mmol) in acetonitrile (15 mL) was added picolinoyl chloride hydrochloride (0.34 g, 1.9 mmol). The reaction mixture was stirred at ambient temperature for 72 h. The mixture was diluted with ethyl acetate (100 mL), washed with saturated aqueous ammonium chloride and brine, dried over anhydrous sodium sulfate and filtered. The filtrate was concentrated in vacuo and the residue was purified by column chromatography (0% to 15% gradient of methanol in dichloromethane) to afford tert-butyl trans-4-(4-chlorophenyl)-3-((2,5-difluoro-4-(N-picolinoylsulfamoyl)phenoxy)methyl)piperidine-1-carboxylate in 89% yield (0.70 g) as a brown solid: MS (ES+) m/z 622.9 (M+1), 624.8 (M+1).

EXAMPLE 99

Synthesis of N-((4-(((trans-4-(4-chlorophenyl)piperidin-3-yl)methoxy)-2,5-difluorophenyl)sulfonyl)picolinamide

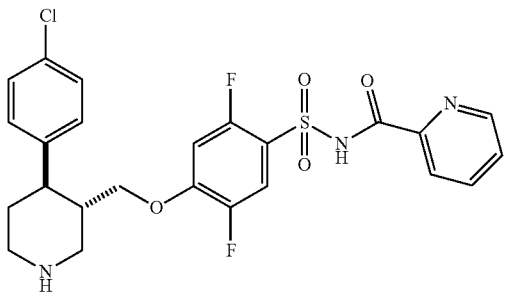

Following the procedure as described in EXAMPLE 44 and making non-critical variations to replace tert-butyl trans-4-(4-chlorophenyl)-3-((4-(N-(2,4-dimethoxybenzyl)-N-(1,2,4-thiadiazol-5-yl(sulfamoyl)-2,5-difluorophenoxy)methyl)piperidine-1-carboxylate with tert-butyl trans-4-(4-chlorophenyl)-3-((2,5-difluoro-4-(N-picolinoylsulfamoyl)phenoxy)methyl)piperidine-1-carboxylate, N-((4-(((trans-4-(4-chlorophenyl)piperidin-3-yl)methoxy)-2,5-difluorophenyl)sulfonyl)picolinamide was obtained as the corresponding trifluoroacetic acid salt in 32% yield (0.17 g): $^1$H NMR (300 MHz, DMSO-$d_6$) δ 9.04-9.01 (m, 1H), 8.88-8.78 (m, 1H), 8.73-8.71 (m, 1H), 8.21-8.15 (m, 1H), 8.07-8.04 (m, 1H), 7.83-7.71 (m, 2H), 7.38 (d, J=8.4 Hz, 2H), 7.21 (d, J=8.4 Hz, 2H), 7.16-7.10 (m, 1H), 3.89-3.85 (m, 1H), 3.79-3.73 (m, 1H), 3.57-3.54 (m, 1H), 3.43-3.39 (m, 1H), 3.03-2.82 (m, 3H), 2.54-2.44 (m, 1H), 1.95-1.89 (m, 2H); MS (ES+) m/z 521.8 (M+1), 523.7 (M+1).

EXAMPLE 100.1

Synthesis of 1-tert-butyl 3-ethyl 4-(p-tolyl)-5,6-dihydropyridine-1,3(2H)-dicarboxylate

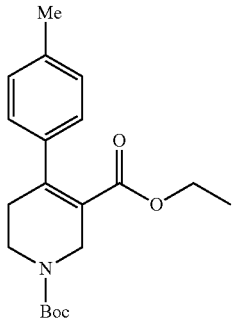 [SMILES: CCOC(=O)C1=C(c2ccc(C)cc2)CCN(C(=O)OC(C)(C)C)C1]

Following the procedure as described in EXAMPLE 94.1 and making non-critical variations to replace (4-methoxyphenyl)boronic acid with p-tolylboronic acid, 1-tert-butyl 3-ethyl 4-(p-tolyl)-5,6-dihydropyridine-1,3(2H)-dicarboxylate was obtained in quantitative yield (4.4 g) as a colorless oil: $^1$H NMR (300 MHz, CDCl$_3$) δ 7.11 (d, J=8.0 Hz, 2H), 7.01 (d, J=8.0 Hz, 2H), 4.25-4.18 (m, 2H), 3.94 (q, J=7.0 Hz, 2H), 3.58 (t, J=5.7 Hz, 2H), 2.51-2.43 (m, 2H), 2.32 (s, 3H), 1.48 (s, 9H), 0.98-0.88 (m, 3H); MS (ES+) m/z 346.0 (M+1).

EXAMPLE 100.2

Synthesis of trans-1-tert-butyl-3-methyl-4-(p-tolyl)piperidine-1,3-dicarboxylate

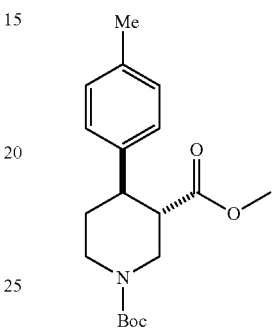

Following the procedure as described in EXAMPLE 94.2 and making non-critical variations to replace 1-tert-butyl 3-ethyl 4-(4-methoxyphenyl)-5,6-dihydropyridine-1,3(2H)-dicarboxylate with 1-tert-butyl 3-ethyl 4-(p-tolyl)-5,6-dihydropyridine-1,3(2H)-dicarboxylate, trans-1-tert-butyl-3-methyl-4-(p-tolyl)piperidine-1,3-dicarboxylate was obtained in 59% yield (0.8 g) as a colorless oil: $^1$H NMR (300 MHz, CDCl$_3$) δ 7.10-7.00 (m, 4H), 4.41-4.15 (m, 2H), 3.42 (s, 3H), 2.95-3.74 (m, 3H), 2.72-2.61 (m, 1H), 2.28 (s, 3H), 1.82-1.73 (m, 1H), 1.71-1.59 (m, 1H), 1.46 (s, 9H); MS (ES+) m/z 355.9 (M+23).

EXAMPLE 100.3

Synthesis of trans-tert-butyl 3-(hydroxymethyl)-4-(p-tolyl)piperidine-1-carboxylate

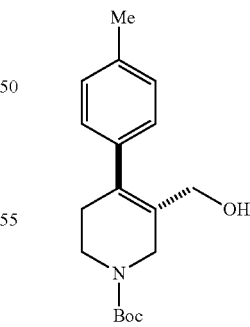

Following the procedure as described in Step B of EXAMPLE 1 and making non-critical variations to replace trans-1-tert-butyl 3-methyl 4-(4-chlorophenyl)piperidine-1,3-dicarboxylate with trans-1-tert-butyl 3-methyl 4-(p-tolyl)piperidine-1,3-dicarboxylate, trans-tert-butyl 3-(hydroxymethyl)-4-(p-tolyl)piperidine-1-carboxylate was obtained in 86% yield (0.6 g) as a colorless oil: $^1$H NMR (300 MHz, CDCl₃) δ 7.12-6.99 (m, 4H), 4.38-4.30 (m, 1H), 4.22-4.12 (m, 1H), 3.46-3.38 (m, 1H), 3.30-3.21 (m, 1H), 2.82-2.61 (m, 2H), 2.52-2.40 (m, 1H), 2.30 (s, 3H), 2.07-2.02 (m, 1H), 1.89-1.58 (m, 3H), 1.46 (s, 9H); MS (ES+) m/z 306.0 (M+1).

EXAMPLE 100.4

Synthesis of trans-tert-butyl-3-((4(4-(N-(2,4-dimethoxybenzyl)-N-(1,2,4-thiadiazol-5-yl)sulfamoyl)-2,5-difluorophenoxy)methyl)-4-(p-tolyl)piperidine-1-carboxylate

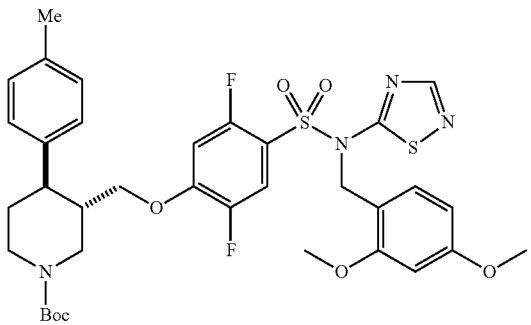

Following the procedure as described in EXAMPLE 16 and making non-critical variations to replace trans-tert-butyl 4-(4-chlorophenyl)-3-(hydroxymethyl)piperidine-1-carboxylate with trans-tert-butyl 3-(hydroxymethyl)-4-(p-tolyl)piperidine-1-carboxylate, trans-tert-butyl 3-((4-(N-(2,4-dimethoxybenzyl)-N-(1,2,4-thiadiazol-5-yl)sulfamoyl)-2,5-difluorophenoxy)methyl)-4-(p-tolyl)piperidine-1-carboxylate was obtained in 36% yield (0.52 g) as a colorless solid: ¹H NMR (300 MHz, DMSO-d₆) δ 8.13 (s, 1H), 7.51-7.43 (m, 1H), 7.16-7.00 (m, 5H), 6.34-6.20 (m, 3H), 5.26-5.21 (m, 2H), 4.48-4.38 (m, 1H), 4.30-4.17 (m, 1H), 3.71 (s, 3H), 3.67 (s, 3H), 3.65-3.53 (m, 2H), 2.87-2.70 (m, 2H), 2.65-2.52 (m, 1H), 2.29 (s, 3H), 2.17-2.05 (m, 1H), 1.86-1.64 (m, 2H), 1.48 (s, 9H); MS (ES+) m/z 730.9 (M+1).

EXAMPLE 100

2,5-difluoro-N-(1,2,4-thiadiazol-5-yl)-4-((trans-4-(p-tolyl)piperidin-3-yl)methoxy)-benzenesulfonamide

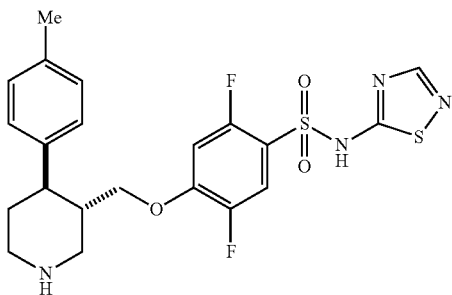

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-((4 (4-(N-(2,4-dimethoxybenzyl)-N-(1,2,4-thiadiazol-5-yl)sulfamoyl)-2,5-difluorophenoxy)methyl)-4-(p-toly)piperidine-1-carboxylate, 2,5-difluoro-N-(1,2,4-thiadiazol-5-yl)-4-((trans-4-(p-tolyl)piperidin-3-yl)methoxy)benzenesulfonamide was obtained as the corresponding trifluoroacetic acid salt in 96% yield (0.40 g) as a colorless solid: ¹H NMR (300 MHz, DMSO-d₆) δ 8.97-8.80 (m, 1H), 8.77-8.61 (m, 1H), 8.45 (s, 1H), 7.63-7.52 (m, 1H), 7.17-6.94 (m, 5H), 3.86-3.64 (m, 2H), 3.56-3.30 (m, 2H), 3.06-2.86 (m, 2H), 2.81-2.68 (m, 1H), 2.21 (s, 3H), 1.97-1.77 (m, 2H); MS (ES⁺) m/z 480.8 (M+1).

EXAMPLE 101.1

Synthesis of trans-methyl 1-(4-methoxybenzyl)-6-oxo-4-(2,4,5-trifluorophenyl)piperidine-3-carboxylate

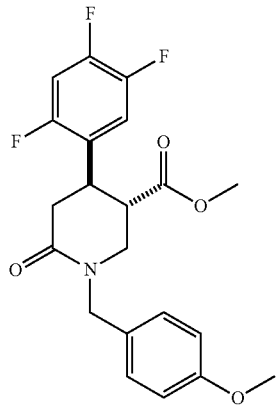

Following the procedure as described in EXAMPLE 87.1, making non-critical variations to replace methyl trans-4-(4-fluorophenyl)-6-oxopiperidine-3-carboxylate with methyl trans-6-oxo-4-(2,4,5-trifluorophenyl)piperidine-3-carboxylate (prepared according to Cox, J. M. et al.; *Bioorg. Med. Chem. Lett.* 2007, 17, 4579), methyl trans-1-(4-methoxybenzyl)-6-oxo-4-(2,4,5-trifluorophenyl)piperidine-3-carboxylate was obtained in 66% yield (3.30 g) as a colorless oil: MS (ES+) m/z 407.8 (M+1).

EXAMPLE 101.2

Synthesis of trans-5-(hydroxymethyl)-1-(4-methoxybenzyl)-4-(2,4,5-trifluorophenyl)piperidin-2-one

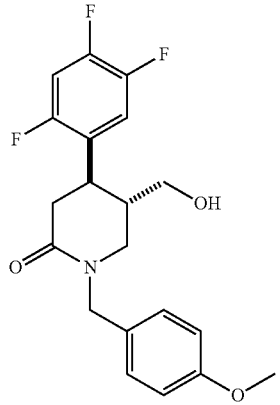

Following the procedure as described in Step B of EXAMPLE 1, making non-critical variations to replace 1-tert-butyl trans-3-methyl 4-(4-chlorophenyl)piperidine-1,3-dicarboxylate with methyl trans-1-(4-methoxybenzyl)-6-oxo-4-(2,4,5-trifluorophenyl)piperidine-3-carboxylate, trans-5-(hydroxymethyl)-1-(4-methoxybenzyl)-4-(2,4,5-trifluorophenyl)piperidin-2-one was obtained in 60% yield (1.80 g) as a colorless solid: MS (ES+) m/z 379.9 (M+1).

EXAMPLE 101.3

Synthesis of N-(2,4-dimethoxybenzyl)-2,5-difluoro-4-(((3S,4R)-1-(4-methoxybenzyl)-6-oxo-4-(2,4,5-trifluorophenyl)piperidin-3-yl)methoxy)-N-(1,2,4-thiadiazol-5-yl)benzenesulfonamide

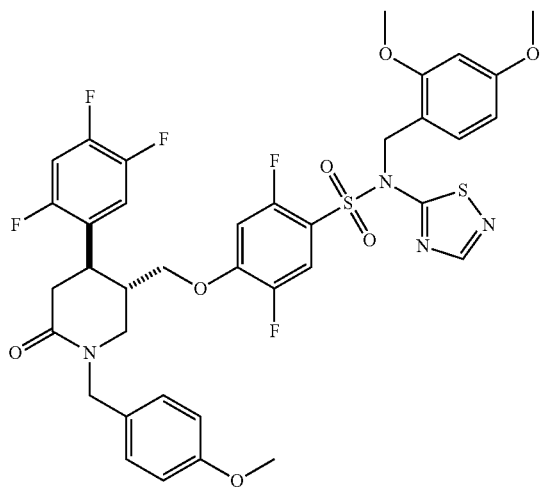

Following the procedure as described in EXAMPLE 16 and making non-critical variations to replace tert-butyl trans-4-(4-chlorophenyl)-3-(hydroxymethyl)piperidine-1-carboxylate with trans-5-(hydroxymethyl)-1-(4-methoxybenzyl)-4-(2,4,5-trifluorophenyl)piperidin-2-one, N-(2,4-dimethoxybenzyl)-2,5-difluoro-4-((trans-1-(4-methoxybenzyl)-6-oxo-4-(2,4,5-trifluorophenyl)piperidin-3-yl)methoxy)-N-(1,2,4-thiadiazol-5-yl)benzenesulfonamide was obtained in 45% yield (0.90 g) as a colorless solid: MS (ES+) m/z 805.3 (M+1).

EXAMPLE 101

Synthesis of 2,5-difluoro-4-((trans-6-oxo-4-(2,4,5-trifluorophenyl)piperidin-3-yl)methoxy)-N-(1,2,4-thiadiazol-5-yl(benzenesulfonamide

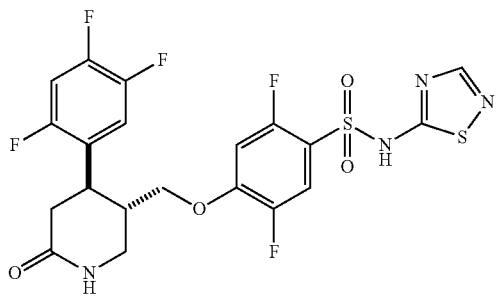

Following the procedure as described in EXAMPLE 87 and making non-critical variations to replace N-(2,4-dimethoxybenzyl)-2,5-difluoro-4-((trans-4-(4-fluorophenyl)-1-(4-methoxybenzyl)-6-oxopiperidin-3-yl)methoxy)-N-(1,2,4-thiadiazol-5-yl)benzenesulfonamide with N-(2,4-dimethoxybenzyl)-2,5-difluoro-4-((trans-1-(4-methoxybenzyl)-6-oxo-4-(2,4,5-trifluorophenyl)piperidin-3-yl)methoxy)-N-(1,2,4-thiadiazol-5-yl) benzenesulfonamide, 2,5-difluoro-4-((trans-6-oxo-4-(2,4,5-trifluorophenyl)piperidin-3-yl)methoxy)-N-(1,2,4-thiadiazol-5-yl)benzenesulfonamide was obtained in 18% yield (0.11 g) as a colorless solid: $^1$H NMR (300 MHz, DMSO-$d_6$) δ 8.53 (s, 1H), 7.72-7.55 (m, 3H), 7.50-7.40 (m, 1H), 7.24-7.18 (m, 1H), 4.90 (br s, 1H), 4.00-3.85 (m, 2H), 3.44-3.29 (m, 2H), 3.23-3.16 (m, 1H), 2.65-2.56 (m, 1H), 2.50-2.30 (m, 2H); MS (ES+) m/z 534.8 (M+1).

EXAMPLE 102.1

Synthesis of tert-butyl trans-3-((4(4-(N-acetylsulfamoyl)-2,5-difluorophenoxy)methyl)-4-(4-chlorophenyl)piperidine-1-carboxylate

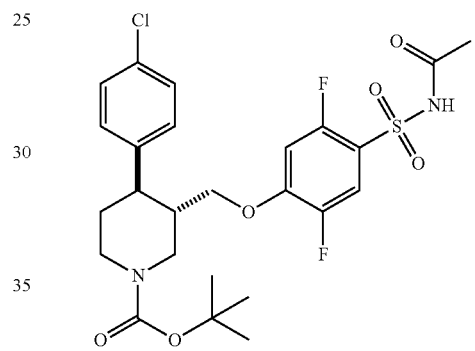

Following the procedure as described in EXAMPLE 99.1 and making non-critical variations to replace picolinoyl chloride hydrochloride with acetyl chloride, tert-butyl trans-3-((4(4-(N-acetylsulfamoyl)-2,5-difluorophenoxy)methyl)-4-(4-chlorophenyl)piperidine-1-carboxylate was obtained in 81% yield (0.35 g) a colorless solid: MS (ES$^+$) ink 580.8 (M+1), 582.8 (M+1).

EXAMPLE 102

Synthesis of N-((4-((trans-4-(4-chlorophenyl)piperidin-3-yl)methoxy)-2,5-difluorophenyl)sulfonyl)acetamide

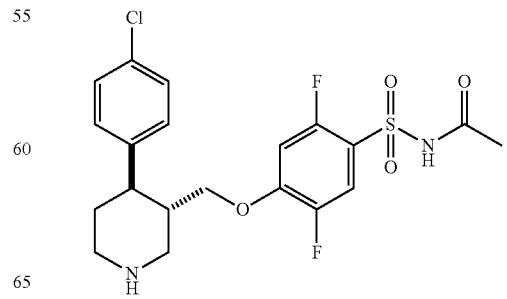

Following the procedure as described above in EXAMPLE 44 and making non-critical variations to replace tert-butyl trans-4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with tert-butyl trans-3-((4-(N-acetylsulfamoyl)-2,5-difluorophenoxy)methyl)-4-(4-chlorophenyl)piperidine-1-carboxylate, N-((4-(((trans-4-(4-chlorophenyl)piperidin-3-yl)methoxy)-2,5-difluorophenyl)sulfonyl)acetamidewas obtained as the corresponding trifluoroacetic acid salt in 66% yield (0.17 g) as a colorless solid: $^1$H NMR (300 MHz, DMSO-d$_6$) δ 12.47 (s, 1H), 8.88-8.63 (m, 2H), 7.68-7.62 (m, 1H), 7.42-7.39 (m, 2H), 7.24-7.18 (m, 3H), 3.91-3.75 (m, 2H), 3.58-3.53 (m, 1H), 3.42-3.38 (m, 1H), 3.04-2.82 (m, 3H), 2.49-2.44 (m, 1H), 1.93-1.90 (m, 5H); MS (ES+) m/z 458.9 (M+1), 460.9 (M+1).

EXAMPLE 103.1

Synthesis of tert-butyl trans-4-(4-chlorophenyl)-3-((2,5-difluoro-4-(N-nicotinoylsulfamoyl)phenoxy)methyl)piperidine-1-carboxylate

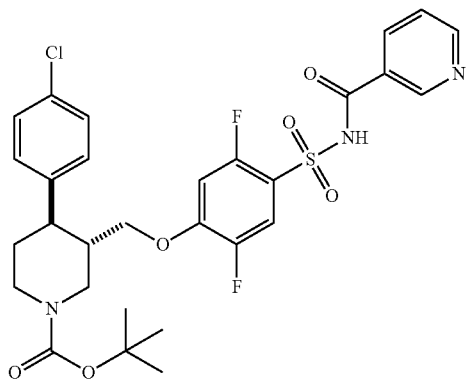

Following the procedure as described in EXAMPLE 99.1 and making non-critical variations to replace picolinoyl chloride hydrochloride with nicotinoyl chloride hydrochloride, tert-butyl trans-4-(4-chlorophenyl)-3-((2,5-difluoro-4-(N-nicotinoylsulfamoyl)phenoxy)methyl)piperidine-1-carboxylate was obtained in 77% yield (0.48 g) as a colorless solid: MS (ES+) m/z 621.9 (M+1), 623.9 (M+1).

EXAMPLE 103

Synthesis of N-((4-(((trans-4-(4-chlorophenyl)piperidin-3-yl)methoxy)-2,5-difluorophenyl)sulfonyl)nicotinamide

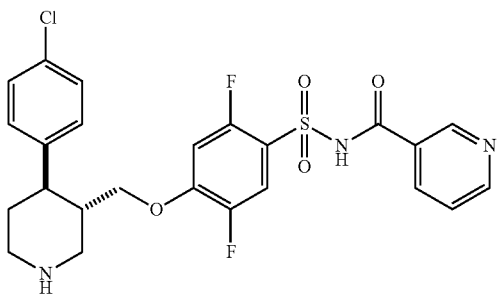

Following the procedure as described above in EXAMPLE 44 and making non-critical variations to replace tert-butyl trans-4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with tert-butyl trans-4-(4-chlorophenyl)-3-((2,5-difluoro-4-(N-nicotinoylsulfamoyl)phenoxy)methyl)piperidine-1-carboxylate, N-((4-(((trans-4-(4-chlorophenyl)piperidin-3-yl)methoxy)-2,5-difluorophenyl)sulfonyl)nicotinamide was obtained as the corresponding trifluoroacetic acid salt in 35% yield (0.14 g) as a colorless solid: $^1$H NMR (300 MHz, DMSO-d$_6$) δ 9.04 (s, 1H), 8.92-8.67 (m, 3H), 8.41-8.39 (m, 1H), 7.72-7.65 (m, 2H), 7.39 (d, J=8.4 Hz, 2H), 7.22 (d, J=8.4 Hz, 2H), 7.11-1.05 (m, 1H), 3.88-3.72 (m, 2H), 3.57-3.53 (m, 1H), 3.42-3.38 (m, 1H), 3.06-2.82 (m, 3H), 2.49-2.43 (m, 1H), 1.91-1.90 (m, 2H); MS (ES+) m/z 521.8 (M+1), 523.8 (M+1).

EXAMPLE 104.1

Synthesis of tert-butyl trans-3-((4-(N-benzoylsulfamoyl)-2,5-difluorophenoxy)methyl)-4-(4-chlorophenyl)piperidine-1-carboxylate

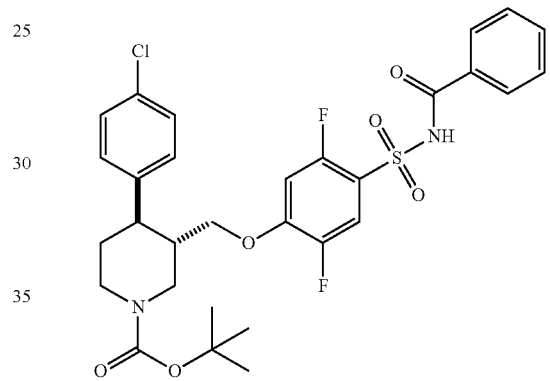

Following the procedure as described in EXAMPLE 99.1 and making non-critical variations to replace picolinoyl chloride hydrochloride with benzoyl chloride, tert-butyl trans-3-((4-(N-benzoylsulfamoyl)-2,5-difluorophenoxy)methyl)-4-(4-chlorophenyl)piperidine-1-carboxylate was obtained in 64% yield (0.40 g) as a colorless solid: MS (ES$^+$) ink 621.9 (M+1), 623.9 (M+1).

EXAMPLE 104

Synthesis of N-((4-(((trans-4-(4-chlorophenyl)piperidin-3-yl)methoxy)-2,5-difluorophenyl)sulfonyl)benzamide

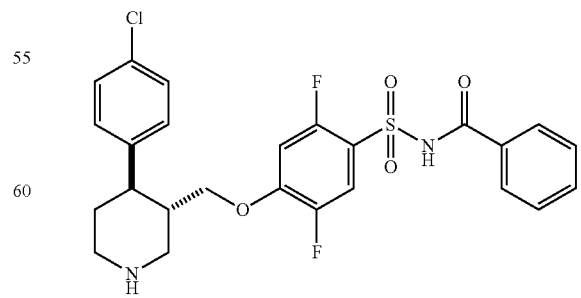

Following the procedure as described above in EXAMPLE 44 and making non-critical variations to replace tert-butyl trans-4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with tert-butyl trans-3-((4-(N-benzoylsulfamoyl)-2,5-difluorophenoxy)methyl)-4-(4-chlorophenyl)piperidine-1-carboxylate, N-((4-((trans-4-(4-chlorophenyl)piperidin-3-yl)methoxy)-2,5-difluorophenyl)sulfonyl)benzamide obtained as the corresponding trifluoroacetic acid salt in 15% yield (0.05 g) as a colorless solid: $^1$H NMR (300 MHz, DMSO-$d_6$) δ 8.98-8.95 (m, 1H), 8.78-8.75 (m, 1H), 7.85-7.82 (m, 2H), 7.72-7.67 (m, 1H), 7.59-7.54 (m, 1H), 7.46-7.41 (m, 2H), 7.36-7.33 (m, 2H), 7.19-7.09 (m, 3H), 3.87-3.71 (m, 2H), 3.54-3.50 (m, 1H), 3.39-3.35 (m, 2H), 3.00-2.78 (m, 3H), 2.47-2.41 (m, 1H), 1.92-1.85 (m, 2H); MS (ES$^+$) ink 520.8 (M+1), 522.8 (M+1).

EXAMPLE 105.1

Synthesis of tert-butyl trans-4-(4-chlorophenyl)-3-((2,5-difluoro-4-(N-(isopropylcarbamoyl)sulfamoyl)phenoxy)methyl)piperidine-1-carboxylate

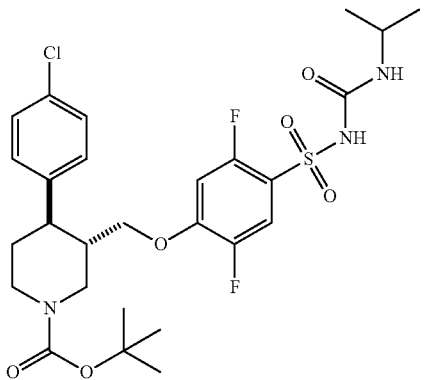

A mixture of tert-butyl trans-4-(4-chlorophenyl)-3-((2,5-difluoro-4-sulfamoylphenoxy)methyl)piperidine-1-carboxylate (0.40 g, 0.77 mmol), copper(I) chloride (0.01 g, 0.1 mmol) and 2-isocyanatopropane (0.070 g, 0.81 mmol) in anhydrous N,N-dimethylformamide (5 mL) was stirred at ambient temperature for 16 h. The mixture was diluted with ethyl acetate (100 mL), washed with 25% aqueous ammonium chloride and brine, dried over anhydrous sodium sulfate and filtered. The filtrate was concentrated in vacuo and the residue was purified by column chromatography eluting with a 10% to 100% gradient of ethyl acetate in hexanes to obtain tert-butyl trans-4-(4-chlorophenyl)-3-((2,5-difluoro-4-(N-(isopropylcarbamoyl)sulfamoyl)phenoxy)methyl)piperidine-1-carboxylate as a clear oil in 58% yield (0.35 g): MS (ES+) m/z 602.0 (M+1), 603.9 (M+1).

EXAMPLE 105

Synthesis of 4-((trans-4-(4-chlorophenyl)piperidin-3-yl)methoxy)-2,5-difluoro-N-(isopropylcarbamoyl)benzenesulfonamide

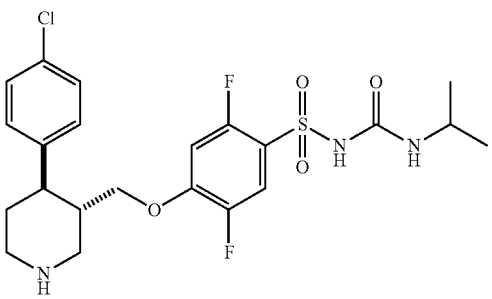

Following the procedure as described in EXAMPLE 44 and making non-critical variations to replace tert-butyl trans-4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with tert-butyl trans-4-(4-chlorophenyl)-3-((2,5-difluoro-4-(N-(isopropylcarbamoyl)sulfamoyl)phenoxy)methyl)piperidine-1-carboxylate, 4-((trans-4-(4-chlorophenyl)piperidin-3-yl)methoxy)-2,5-difluoro-N-(isopropylcarbamoyl)benzenesulfonamide obtained as the corresponding trifluoroacetic acid salt in 43% yield (0.12 g) as a colorless solid: $^1$H NMR (300 MHz, DMSO-$d_6$) δ 10.96 (s, 1H), 9.01-8.79 (m, 2H), 7.63-7.57 (m, 1H), 7.41-7.38 (m, 2H), 7.24-7.15 (m, 3H), 6.58 (d, J=7.6 Hz, 1H), 3.92-3.87 (m, 1H), 3.80-3.75 (m, 1H), 3.59-3.39 (m, 3H), 3.04-2.82 (m, 3H), 2.56-2.44 (m, 1H), 1.91-1.89 (m, 2H), 0.99 (d, J=6.6 Hz, 6H); MS (ES+) m/z 501.9 (M+1), 503.9 (M+1).

EXAMPLE 106.1

Synthesis of (trans-4-(2,4,5-trifluorophenyl)piperidin-3-yl)methanol

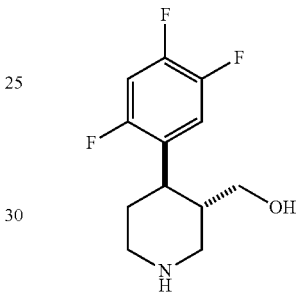

To a suspension of lithium aluminum hydride (0.90 g, 22.5 mmol) in tetrahydrofuran (80 mL) was added dropwise over 10 minutes trans-methyl 6-oxo-4-(2,4,5-trifluorophenyl)piperidine-3-carboxylate (2.28 g, 7.93 mmol) in tetrahydrofuran (20 mL). The reaction mixture was stirred for 1 h at ambient temperature and heated at reflux for 4 h. After cooling to 0° C., 5% aqueous sodium hydroxide was added and the mixture extracted with ethyl acetate (3×100 mL). The combined organic extracts were washed with brine, dried over anhydrous sodium sulfate and concentrated in vacuo to afford (trans-4-(2,4,5-trifluorophenyl)piperidin-3-yl)methanol in quantitative yield (2.00 g) as a colorless solid: MS (ES+) m/z 246.0 (M+1).

EXAMPLE 106.2

Synthesis of trans-tert-butyl 3-(hydroxymethyl)-4-(2,4,5-trifluorophenyl)piperidine-1-carboxylate

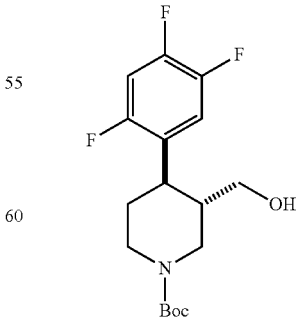

Following the procedure as described in EXAMPLE 3 and making non-critical variations to replace ((3S,4R)-4-(4- fluorophenyl)piperidin-3-yl)methanol with (trans-4-(2,4,5-trifluorophenyl)piperidin-3-yl)methanol, trans-tert-butyl 3-(hydroxymethyl)-4-(2,4,5-trifluorophenyl)piperidine-1-carboxylate was obtained in 35% yield (0.94 g) as a colorless solid: $^{1}$H NMR (300 MHz, CDCl$_3$) δ 7.05-6.83 (m, 2H), 4.41-4.05 (m, 2H), 3.48-3.24 (m, 2H), 2.94-2.65 (m, 3H), 1.84-1.63 (m, 4H), 1.45 (s, 9H).

EXAMPLE 106.3

Synthesis of trans-tert-butyl 3-((4(4-(N-(2,4-dimethoxybenzyl)-N-(1,2,4-thiadiazol-5-yl)sulfamoyl)-2,5-difluorophenoxy)methyl)-4-(2,4,5-trifluorophenyl)piperidine-1-carboxylate

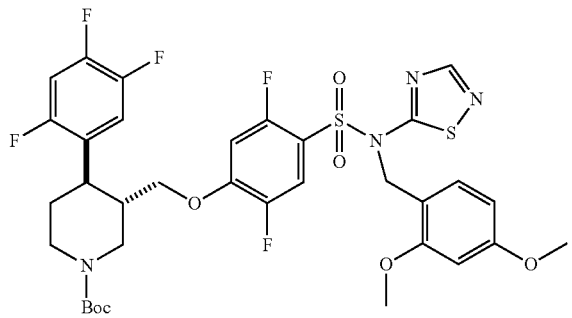

Following the procedure as described in EXAMPLE 16 and making non-critical variations to replace trans-tert-butyl 4-(4-chlorophenyl)-3-(hydroxymethyl)piperidine-1-carboxylate with trans-tert-butyl 3-(hydroxymethyl)-4-(2,4,5-trifluorophenyl)piperidine-1-carboxylate, trans-tert-butyl 3-((4-(N-(2,4-dimethoxybenzyl)-N-(1,2,4-thiadiazol-5-yl)sulfamoyl)-2,5-difluorophenoxy)methyl)-4-(2,4,5-trifluorophenyl)piperidine-1-carboxylate was obtained in 49% yield (0.38 g) as a colorless solid: $^{1}$H NMR (300 MHz, CDCl$_3$) δ 8.09 (s, 1H), 7.40-7.39 (m, 1H), 7.11-6.78 (m, 3H), 6.38-6.13 (m, 3H), 5.19 (s, 1H), 4.43-4.09 (m, 3H), 3.76-3.56 (m, 7H), 3.00-2.61 (m, 3H), 2.18-2.10 (m, 1H), 1.85-1.64 (m, 3H), 1.43 (s, 9H); MS (ES+) m/z 700.7 (M+1).

EXAMPLE 106

Synthesis of 2,5-difluoro-N-(1,2,4-thiadiazol-5-yl)-4-((trans-4-(2,4,5-trifluorophenyl)piperidin-3-yl)methoxy)benzenesulfonamide

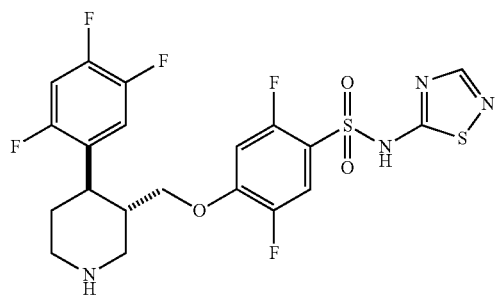

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-((4-(N-(2,4-dimethoxybenzyl)-N-(1,2,4-thiadiazol-5-yl)sulfamoyl)-2,5-difluorophenoxy)methyl)-4-(2,4,5-trifluorophenyl)piperidine-1-carboxylate, 2,5-difluoro-N-(1,2,4-thiadiazol-5-yl)-4-((trans-4-(2,4,5-trifluorophenyl)piperidin-3-yl)methoxy)benzenesulfonamide was obtained as the corresponding trifluoroacetic acid salt in 33% yield (0.10 g) as an off-white solid: $^{1}$H NMR (300 MHz, DMSO-d$_6$) δ 8.84 (br s, 1H), 8.58 (br s, 1H), 8.45 (s, 1H), 7.59-7.52 (m, 1H), 7.51-7.43 (m, 1H), 7.40-7.29 (m, 1H), 7.19-7.12 (m, 1H), 3.94-3.77 (m, 2H), 3.52-3.33 (m, 2H), 3.15-2.83 (m, 3H), 2.60-2.52 (m, 1H), 1.94-1.79 (m, 2H); (ES+) m/z 520.6 (M+1).

EXAMPLE 107.1

Synthesis of (E)-Ethyl 3-(4-fluoro-3-(trifluoromethyl)phenyl)acrylate

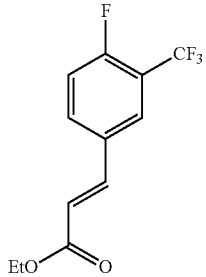 [SMILES: CCOC(=O)/C=C/c1ccc(F)c(C(F)(F)F)c1]

To a solution of 4-fluoro-3-(trifluoromethyl)benzaldehyde (25 g, 130 mmol) and triethyl phosphonoacetate (30 mL, 159 mmol) in tetrahydrofuran (200 mL) was added 1,8-diazobicyclo[5.4.0]undec-7-ene (22.4 mL, 150 mmol). The reaction mixture was stirred at ambient temperature for 18 h, concentrated in vacuo and dissolved in hexanes/ethyl acetate (10:1 v/v, 1 L). The resulting solution was washed sequentially with 10% hydrochloric acid, water, saturated aqueous sodium bicarbonate and brine (300 mL each). The organic phase was dried over anhydrous sodium sulfate, filtered, and concentrated in vacuo. Recrystallization of the residue from methanol afforded (E)-ethyl 3-(4-fluoro-3-(trifluoromethyl)phenyl)acrylate as a colorless solid in 85% yield (29.1 g): $^{1}$H NMR (300 MHz, CDCl$_3$) δ 7.79-7.58 (m, 3H), 7.32-7.16 (m, 1H), 6.43-6.37 (m, 1H), 4.25 (q, J=6.9 Hz, 2H), 1.31 (t, J=6.9 Hz, 3H).

EXAMPLE 107.2

Synthesis of dimethyl 2-cyano-3-(4-fluoro-3-(trifluoromethyl)phenyl)pentanedioate

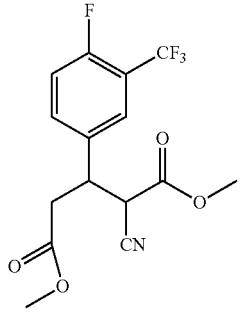 [SMILES: COC(=O)CC(c1ccc(F)c(C(F)(F)F)c1)C(C#N)C(=O)OC]

To a solution of potassium methoxide (8.93 g, 121 mmol) in methanol (300 mL) was added methyl cyanoacetate (13.0 mL, 121 mmol) and the reaction mixture was stirred at ambient temperature for 30 min. To this solution was added a solution of (E)-ethyl 3-(4-fluoro-3-(trifluoromethyl)phenyl)acrylate (29.1 g, 110 mmol) in methanol (100 mL) and the resulting reaction mixture was heated at reflux for 20 h. The reaction mixture cooled to 0° C. and 5% hydrochloric acid (200 mL) was added portionwise. The methanol was removed in vacuo and the mixture extracted with ethyl acetate (3×300 mL). The combined organic extracts were washed with water, saturated aqueous sodium bicarbonate and brine (100 mL each), dried over sodium sulfate, filtered, and concentrated in vacuo. The residue was purified by column chromatography, eluting with a 10% to 40% gradient of ethyl acetate in hexanes to afford a mixture of diastereoisomers of dimethyl 2-cyano-3-(4-fluoro-3-(trifluoromethyl)phenyl)pentanedioate in 46% yield (17.8 g) as a pale yellow oil: (ES$^+$) m/z 347.8 (M+1).

EXAMPLE 107.3

Synthesis of trans-4-(4-fluoro-3-(trifluoromethyl)phenyl)-6-oxopiperidine-3-carboxylic acid

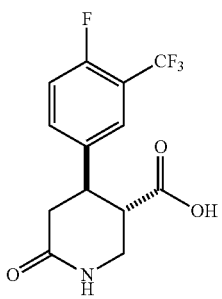

To methanol (150 mL) at 0° C. was carefully added acetyl chloride (30 mL) and the resulting solution was allowed to stir at ambient temperature for 30 minutes. This solution was added to dimethyl 2-cyano-3-(4-fluoro-3-(trifluoromethyl)phenyl)-pentanedioate (17.8 g, 51.3 mmol) and the reaction mixture was shaken with platinum (IV) oxide (0.5 g) under 50 psi of hydrogen for 20 h. The mixture was filtered through a pad of diatomaceous earth and the filter cake washed with methanol and dichloromethane. The combined filtrate and washes were concentrated in vacuo and taken up in methanol/toluene (1:1 v/v, 300 mL). Potassium carbonate (50 g, 662 mmol) was added and the mixture was heated at reflux for 36 h, cooled to 0° C. and the pH was adjusted to ~3 by the careful addition of 5% hydrochloric acid. The mixture was filtered and the solid washed with water and hexanes to afford trans-4-(4-fluoro-3-(trifluoromethyl)phenyl)-6-oxopiperidine-3-carboxylic acid in 47% yield (7.4 g) as a colorless solid: $^1$H NMR (300 MHz, DMSO-d$_6$) δ 12.42 (s, 1H), 7.72-7.64 (m, 3H), 7.47-7.39 (m, 1H), 3.40-3.23 (m, 3H), 3.09-2.98 (m, 1H), 2.45-2.29 (m, 2H); (ES+) m/z 305.9 (M+1).

EXAMPLE 107.4

Synthesis of trans-methyl 4-(4-fluoro-3-(trifluoromethyl)phenyl)-6-oxopiperidine-3-carboxylate

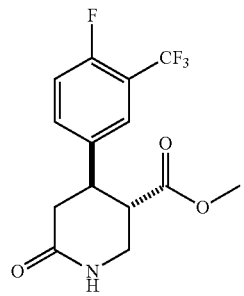

To a solution of trans-4-(4-fluoro-3-(trifluoromethyl)phenyl)-6-oxopiperidine-3-carboxylic acid (7.4 g, 24 mmol) in diethyl ether/methanol (1:1 v/v, 200 mL) at −78° C. was added trimethysilyldiazomethane (2 M solution in hexanes, 50 mL, 100 mmol) portionwise over 1 h until a yellow color persisted. After warming to 0° C., the reaction mixture was stirred for an additional 2 h and concentrated in vacuo. The residue was triturated in diethyl ether (50 mL) to afford trans-methyl 4-(4-fluoro-3-(trifluoromethyl)phenyl)-6-oxopiperidine-3-carboxylate in 73% yield (5.7 g) as a colorless solid: $^1$H NMR (300 MHz, DMSO-d$_6$) δ 7.73-7.63 (m, 3H), 7.47-7.39 (m, 1H), 3.42-3.33 (m, 6H), 3.53-2.30 (m, 3H); (ES+) m/z 319.8 (M+1).

EXAMPLE 107.5

Synthesis of trans-4-(4-fluoro-3-(trifluoromethyl)phenyl)piperidin-3-yl)methanol

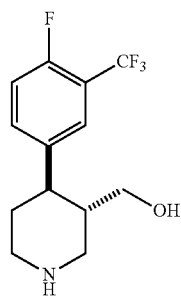

Following the procedure as described in EXAMPLE 106.1 and making non-critical variations to replace trans-methyl 6-oxo-4-(2,4,5-trifluorophenyl)piperidine-3-carboxylate with trans-methyl 4-(4-fluoro-3-(trifluoromethyl)phenyl)-6-oxopiperidine-3-carboxylate, trans-4-(4-fluoro-3-(trifluoromethyl)phenyl)piperidin-3-yl)methanol was obtained in 97% yield (1.70 g) as a colorless solid: (ES+) m/z 277.9 (M+1).

EXAMPLE 107.6

Synthesis of trans-tert-butyl 4-(4-fluoro-3-(trifluoromethyl)phenyl)-3-(hydroxymethyl)piperidine-1-carboxylate

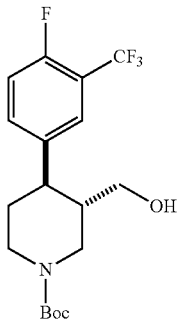

Following the procedure as described in EXAMPLE 3 and making non-critical variations to replace ((3S,4R)-4-(4-fluorophenyl)piperidin-3-yl)methanol with trans-4-(4-fluoro-3-(trifluoromethyl)phenyl)piperidin-3-yl)methanol, trans-tert-butyl 4-(4-fluoro-3-(trifluoromethyl)phenyl)-3-(hydroxymethyl)piperidine-1-carboxylate was obtained in 63% yield (1.46 g) as a colorless solid: (ES+) m/z 303.9 (M−73).

EXAMPLE 107 and 108

Synthesis of 2,5-difluoro-4-((trans-4-(4-fluoro-3-(trifluoromethyl)phenyl)piperidin-3-yl)methoxy)-N-(1,2,4-thiadiazol-5-yl)benzenesulfonamide

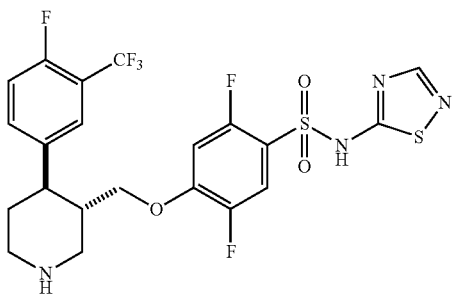

and 4-((trans-4-(3-(difluoromethyl)-4-fluorophenyl)piperidin-3-yl)methoxy)-2,5-difluoro-N-(1,2,4-thiadiazol-5-yl)benzenesulfonamide

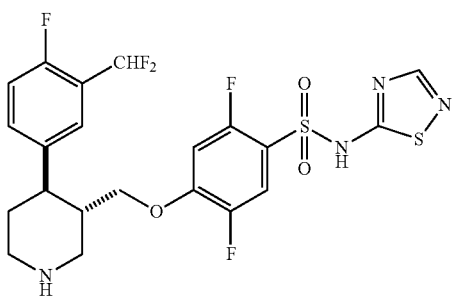

Step A: trans-tert-butyl 3-((4(4-(N-(2,4-dimethoxybenzyl)-N-(1,2,4-thiadiazol-5-yl)sulfamoyl)-2,5-difluorophenoxy)methyl)-4-(4-fluoro-3-(trifluoromethyl)phenyl)piperidine-1-carboxylate

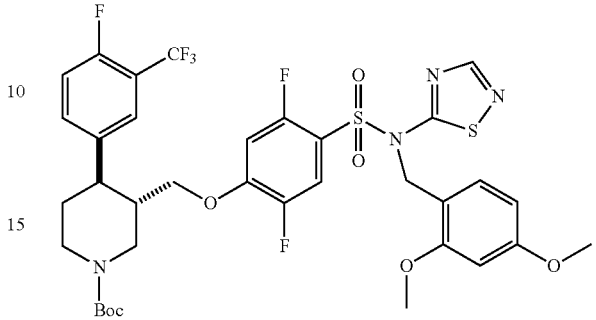

Following the procedure as described in EXAMPLE 16 and making non-critical variations to replace trans-tert-butyl 4-(4-chlorophenyl)-3-(hydroxymethyl)piperidine-1-carboxylate with trans-tert-butyl 4-(4-fluoro-3-(trifluoromethyl)phenyl)-3-(hydroxymethyl)piperidine-1-carboxylate, trans-tert-butyl 3-((4-(N-(2,4-dimethoxybenzyl)-N-(1,2,4-thiadiazol-5-yl)sulfamoyl)-2,5-difluorophenoxy)methyl)-4-(4-fluoro-3-(trifluoromethyl)phenyl)piperidine-1-carboxylate was obtained (0.69 g) as a colorless solid and was carried forward without purification.

Step B: 2,5-difluoro-4-((trans-4-(4-fluoro-3-(trifluoromethyl)phenyl)piperidin-3-yl)methoxy)-N-(1,2,4-thiadiazol-5-yl)benzenesulfonamide and 4-((trans-4-(3-(difluoromethyl)-4-fluorophenyl)piperidin-3-yl)methoxy)-2,5-difluoro-N-(1,2,4-thiadiazol-5-yl)benzenesulfonamide Following the procedure as described in EXAMPLE 44 and making non-critical variations to replace trans-tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperidine-1-carboxylate with trans-tert-butyl 3-((4(4-(N-(2,4-dimethoxybenzyl)-N-(1,2,4-thiadiazol-5-yl)sulfamoyl)-2,5-difluorophenoxy)methyl)-4-(4-fluoro-3-(trifluoromethyl)phenyl)piperidine-1-carboxylate and subsequently purifying the residue by preparative HPLC, 2,5-difluoro-4-((trans-4-(4-fluoro-3-(trifluoromethyl)phenyl)piperidin-3-yl)methoxy)-N-(1,2,4-thiadiazol-5-yl)benzenesulfonamide was obtained as the corresponding trifluoroacetic acid salt in 29% yield (0.20 g) over 2 steps as a colorless solid: $^1$H NMR (300 MHz, DMSO-$d_6$) δ 8.88 (br s, 1H), 8.62 (br s, 1H), 8.44 (s, 1H), 7.57-7.40 (m, 4H), 7.14-7.08 (m, 1H), 3.90-3.84 (m, 1H), 3.78-3.71 (m, 1H), 3.56-3.47 (m, 1H), 3.42-3.33 (m, 1H), 3.01-2.83 (m, 3H), 2.60-2.52 (m, 1H), 1.98-1.79 (m, 2H); (ES+) m/z 552.7 (M+1).

4-((trans-4-(3-(difluoromethyl)-4-fluorophenyl)piperidin-3-yl)methoxy)-2,5-difluoro-N-(1,2,4-thiadiazol-5-yl)benzenesulfonamide was also obtained from the aforementioned preparative HPLC purification as the corresponding trifluoroacetic acid salt (0.07 g) as a colorless solid: $^1$H NMR (300 MHz, DMSO-$d_6$) δ 8.92 (br s, 1H), 8.62 (br s, 1H), 8.48 (s, 1H), 7.63-7.56 (m, 1H), 7.43-7.30 (m, 3H), 7.16 (t, $J_{H\text{-}F}$=54.3 Hz, 1H), 7.18-7.11 (m, 1H), 3.91-3.86 (m, 1H), 3.79-3.73 (m, 1H), 3.59-3.51 (m, 1H), 3.45-3.37 (m, 1H), 3.12-2.84 (m, 3H), 2.60-2.52 (m, 1H), 1.98-1.77 (m, 2H); (ES+) m/z 534.7 (M+1).

EXAMPLE 109.1

Synthesis of methyl 8-(4-chlorophenyl)-1,4-dioxaspiro[4.5]dec-7-ene-7-carboxylate

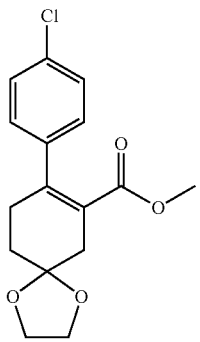 [SMILES: COC(=O)C1=C(c2ccc(Cl)cc2)CCC2(C1)OCCO2]

Following the procedure as described in EXAMPLE 5.6 and making non-critical variations to replace (4-fluorophenyl)boronic acid with (4-chlorophenyl)boronic acid, methyl 8-(4-chlorophenyl)-1,4-dioxaspiro[4.5]dec-7-ene-7-carboxylate was obtained as a yellow syrup in 98% yield (13.5 g): $^1$H NMR (300 MHz, CDCl$_3$) δ 7.25-7.22 (m, 2H), 7.05-7.02 (m, 2H), 4.00-3.95 (m, 4H), 3.41 (s, 3H), 2.61-2.52 (m, 4H), 1.83 (t, J=6.5 Hz, 2H); MS (ES+) m/z 276.8 (M−31), 278.8 (M−31).

EXAMPLE 109.2

Synthesis of trans-methyl 8-(4-chlorophenyl)-1,4-dioxaspiro[4.5]decane-7-carboxylate

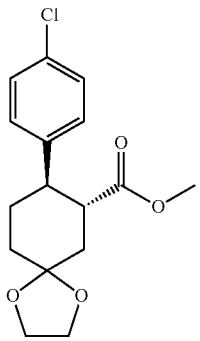 [SMILES: COC(=O)[C@@H]1CC2(CC[C@H]1c1ccc(Cl)cc1)OCCO2]

To a mixture of methyl 8-(4-chlorophenyl)-1,4-dioxaspiro[4.5]dec-7-ene-7-carboxylate (6.8 g, 22 mmol) in anhydrous methanol (200 mL) was added magnesium turnings (2.12 g, 87.2 mmol) portionwise over 3 h. The reaction was stirred at ambient temperature under a nitrogen atmosphere for 5 days. The mixture was filtered through a pad of diatomaceous earth and the pad was rinsed with ethyl acetate (200 mL). The filtrate was concentrated in vacuo to afford an off-white solid that was dissolved in dichloromethane (400 mL). The solution was washed with 1 N hydrochloric acid (400 mL) and the aqueous layer was extracted with dichloromethane (200 mL). The combined organic layers were dried over anhydrous sodium sulfate, filtered, and concentrated in vacuo. The residue was purified by column chromatography, eluting with a 0-25% gradient of ethyl acetate in hexanes to afford trans-methyl 8-(4-chlorophenyl)-1,4-dioxaspiro[4.5]decane-7-carboxylate as a colorless solid in 65% yield (4.47 g): $^1$F1 NMR (300 MHz, CDCl$_3$) δ 7.22 (s, 4H), 3.97-3.87 (m, 4H), 3.50 (s, 3H), 3.13-3.04 (m, 2H), 2.42-2.26 (m, 2H), 2.04-1.94 (m, 2H), 1.88-1.77 (m, 1H), 1.72-1.63 (m, 1H); MS (ES+) m/z 310.8 (M+1), 312.8 (M+1).

EXAMPLE 109.3

Synthesis of (trans-8-(4-chlorophenyl)-1,4-dioxaspiro[4.5]decan-7-yl)methanol

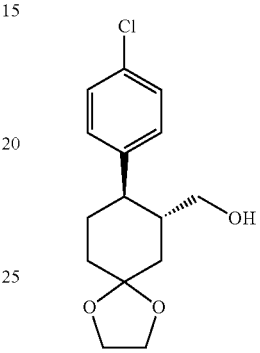

Following the procedure as described in Step B of EXAMPLE 1 and making non-critical variations to replace trans-1-tert-butyl 3-methyl 4-(4-chlorophenyl)piperidine-1,3-dicarboxylate with trans-methyl 8-(4-chlorophenyl)-1,4-dioxaspiro[4.5]decane-7-carboxylate, (trans-8-(4-chlorophenyl)-1,4-dioxaspiro[4.5]decan-7-yl)methanol was obtained as a colorless solid in 73% yield (0.794 g): $^1$H NMR (300 MHz, CDCl$_3$) δ 7.26-7.18 (m, 4H), 4.04-3.94 (m, 4H), 3.51 (dd, J=11.5, 6.7 Hz, 1H), 3.36 (dd, J=11.6, 4.3 Hz, 1H), 2.95-2.88 (m, 1H), 2.42-2.14 (m, 3H), 2.05-1.90 (m, 3H), 1.82-1.63 (m, 2H); MS (ES+) m/z 282.9 (M+1), 284.9 (M+1).

EXAMPLE 109.4

Synthesis of 4-((trans-8-(4-chlorophenyl)-1,4-dioxaspiro[4.5]decan-7-ypmethoxy)-N-(2,4-dimethoxybenzyl)-2,5-difluoro-N-(1,2,4-thiadiazol-5-yl)benzenesulfonamide

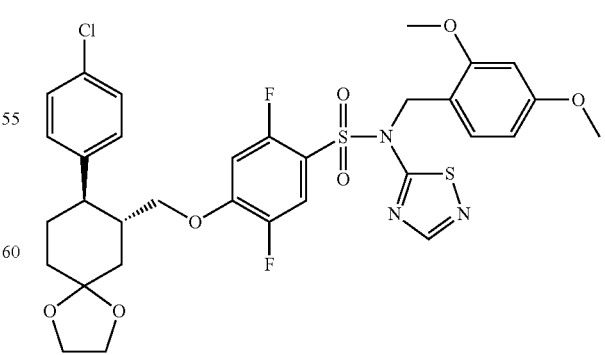

Following the procedure as described in EXAMPLE 16 and making non-critical variations to replace trans-tert-butyl 4-(4-chlorophenyl)-3-(hydroxymethyl)piperidine-1-carboxylate with (trans-8-(4-chlorophenyl)-1,4-dioxaspiro[4.5]decan-7-yl)methanol, 4-((trans-8-(4-chlorophenyl)-1,4-dioxaspiro[4.5]decan-7-yl)methoxy)-N-(2,4-dimethoxybenzyl)-2,5-difluoro-N-(1,2,4-thiadiazol-5-yl)benzenesulfonamide was obtained in 51% yield (0.984 g) as a colorless foamy solid: $^1$H NMR (300 MHz, CDCl$_3$) δ 8.14 (s, 1H), 7.42 (dd, J=10.0, 6.3 Hz, 1H), 7.25 (d, J=8.1 Hz, 2H), 7.15-7.11 (m, 3H), 6.39-6.29 (m, 2H), 6.23-6.20 (m, 1H), 5.23 (s, 2H), 4.24 (t, J=9.3 Hz, 1H), 3.93-9.85 (m, 4H), 3.69 (s, 3H), 3.68 (s, 3H), 3.50 (dd, J=8.9, 5.4 Hz, 1H), 3.08-3.02 (m, 1H), 2.63-2.57 (m, 1H), 2.17-2.02 (m, 2H), 1.97-1.73 (m, 4H); MS (ES+) m/z 713.7 (M+1), 715.7 (M+1).

EXAMPLE 109

Synthesis of 4-((trans-2-(4-chlorophenyl)-5-oxocyclohexyl)methoxy)-2,5-difluoro-N-(1,2,4-thiadiazol-5-yl)benzenesulfonamide

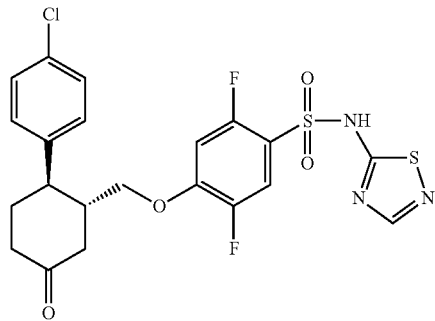 [SMILES: O=C1CC[C@@H](c2ccc(Cl)cc2)[C@H](COc2cc(F)c(S(=O)(=O)Nc3ncns3)cc2F)C1]

To a solution of 4-((trans-8-(4-chlorophenyl)-1,4-dioxaspiro[4.5]decan-7-yl)methoxy)-N-(2,4-dimethoxybenzyl)-2,5-difluoro-N-(1,2,4-thiadiazol-5-yl(benzenesulfonamide (0.984 g, 1.38 mmol) in acetone (50 mL) was added 2 N hydrochloric acid (5 mL). The solution was heated to reflux for 1.5 h, allowed to cool to ambient temperature and concentrated in vacuo. The resulting colorless solid was stirred in methanol (20 mL) for 20 minutes and filtered. The filtrate was concentrated to a tan foamy solid that was partially purified by column chromatography, eluting with a gradient of 0-10% methanol in dichloromethane to afford 4-((trans-2-(4-chlorophenyl)-5-oxocyclohexyl)methoxy)-2,5-difluoro-N-(1,2,4-thiadiazol-5-yl)benzenesulfonamide in 91% crude yield (0.641 g) as an impure colorless solid. A portion of this material was purified by reverse-phase HPLC to afford 4-((trans-2-(4-chlorophenyl)-5-oxocyclohexyl)methoxy)-2,5-difluoro-N-(1,2,4-thiadiazol-5-yl)benzenesulfonamide as a colorless solid in 2% yield (0.011 g): $^1$H NMR (300 MHz, CDCl$_3$) δ 8.06 (s, 1H), 7.60 (dd, J=9.5, 6.7 Hz, 1H), 7.30-7.27 (m, 2H), 7.17-7.15 (m, 2H), 6.46 (dd, J=10.6, 6.4 Hz, 1H), 3.77-3.76 (m, 2H), 3.49-3.45 (m, 1H), 2.80-2.38 (m, 6H), 2.22-2.17 (m, 1H) (NH not observed); MS (ES$^+$) m/z 513.6 (M+1), 515.6 (M+1).

EXAMPLE 110 and 111

Synthesis of 4-(((trans-5S)-2-(4-chlorophenyl)-5-hydroxycyclohexyl)methoxy)-2,5-difluoro-N-(1,2,4-thiadiazol-5-yl)benzenesulfonamide

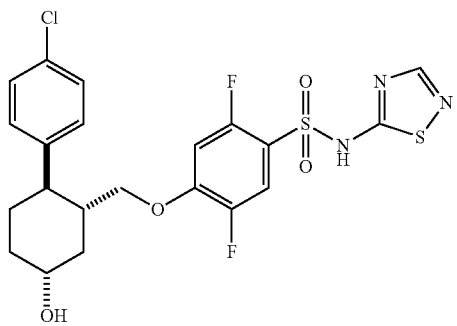

And 4-(((trans-5R)-2-(4-chlorophenyl)-5-hydroxycyclohexyl)methoxy)-2,5-difluoro-N-(1,2,4-thiadiazol-5-yl)benzenesulfonamide

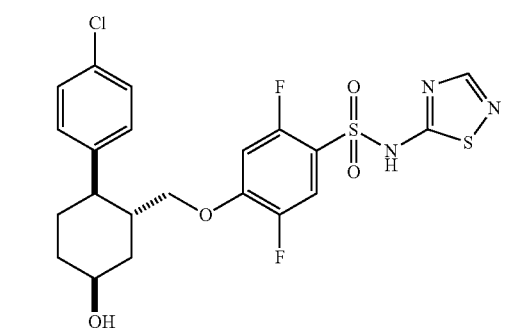

To a cold (0° C.) solution of 4-((trans-2-(4-chlorophenyl)-5-oxocyclohexyl)-methoxy)-2,5-difluoro-N-(1,2,4-thiadiazol-5-yl)benzenesulfonamide (0.112 g, 0.218 mmol) in anhydrous methanol (20 mL) and tetrahydrofuran (5 mL) was added sodium borohydride (0.010 g, 0.26 mmol). The reaction was allowed to warm to ambient temperature and stirred for 20 h. A further portion of sodium borohyride (0.008 g, 0.2 mmol) was then added. Stirring was continued for 28 h and the mixture was diluted with saturated aqueous ammonium chloride (50 mL) and water (30 mL). This mixture was extracted with ethyl acetate (2×75 mL) and the combined organic layers were dried over anhydrous sodium sulfate, filtered and concentrated in vacuo. The residue was purified by reverse-phase preparative HPLC to afford two pure isomers.

The first compound to elute, 4-(((trans-5S)-2-(4-chlorophenyl)-5-hydroxycyclohexyl)methoxy)-2,5-difluoro-N-(1,2,4-thiadiazol-5-yl)benzenesulfonamide, was obtained in 6% yield (0.007 g) as a colorless solid: $^1$H NMR (300 MHz, CDCl$_3$) δ 8.05 (s, 1H), 7.61 (dd, J=6.6, 9.9 Hz, 1H), 7.25-7.22 (m, 2H), 7.12-7.09 (m, 2H), 6.39 (dd, J=6.3, 11.0 Hz, 1H), 4.03-3.92 (m, 1H), 3.82 (t, J=8.9 Hz, 1H), 3.61 (dd, J=4.0, 9.4 Hz, 1H), 3.04-2.96 (m, 1H), 2.56-2.50 (m, 1H), 2.34-2.30 (m, 1H), 2.23-2.18 (m, 1H), 1.97-1.89 (m, 2H), 1.72-1.63 (m, 1H), 1.54-1.44 (m, 1H); MS (ES+) m/z 515.7 (M+1), 517.7 (M+1).

The second compound to elute, 4-(((trans-5R)-2-(4-chlorophenyl)-5-hydroxycyclohexyl)methoxy)-2,5-difluoro-N-(1,2,4-thiadiazol-5-yl)benzenesulfonamide was obtained in 12% yield (0.013 g) as a colorless solid: ¹H NMR (300 MHz, CDCl₃) δ 8.04 (s, 1H), 7.57 (dd, J=9.5, 6.8 Hz), 7.24-7.21 (m, 2H), 7.17-7.14 (m, 2H), 6.46 (dd, J=11.3, 6.3 Hz, 1H), 4.19-4.10 (m, 2H), 3.60 (dd, J=8.5, 6.1 Hz, 1H), 3.08-3.03 (m, 1H), 2.48-2.42 (m, 1H), 2.14-2.02 (m, 2H), 1.96-1.71 (m, 4H); MS (ES+) m/z 515.7 (M+1), 517.7 (M+1).

EXAMPLE 112.1

Synthesis of 1-tert-butyl 3-methyl 4-(4-chlorophenyl)piperazine-1,3-dicarboxylate

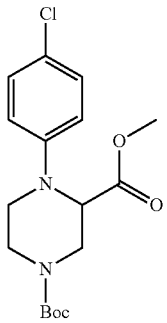

To a mixture of methyl-4-Boc-piperazine-2-carboxylate (2.2 g, 9.0 mmol), molecular sieves (4 Å, 2.2 g), pyridine (1.46 mL, 18.0 mmol) and (4-chlorophenyl)boronic acid (2.81 g, 18.0 mmol) was added copper(II) acetate (1.63 g, 9.0 mmol). The reaction mixture was stirred for 16 h under an atmosphere of dry air and concentrated in vacuo. The residue was taken up in ethyl acetate (250 mL) and filtered through a pad of diatomaceous earth. The filtrate was concentrated in vacuo and residue was purified by column chromatography (0-30% gradient of ethyl acetate in hexanes) to afford 1-tert-butyl 3-methyl 4-(4-chlorophenyl)piperazine-1,3-dicarboxylate in 36% yield (1.16 g) as a colorless solid: ¹H NMR (300 MHz, CDCl₃) δ 7.21-7.16 (m, 2H), 6.79-6.74 (m, 2H), 4.51 (d, J=13.7 Hz, 1H), 4.31 (br s, 1H), 4.20-4.02 (m, 1H), 3.63 (s, 3H), 3.54-3.42 (m, 1H), 3.37-3.25 (m, 2H), 3.15-2.98 (m, 1H), 1.44 (s, 9H); MS (ES+) m/z 298.8 (M−56), 300.8 (M−56).

EXAMPLE 112.2

Synthesis of tert-butyl 4-(4-chlorophenyl)-3-(hydroxymethyl)piperazine-1-carboxylate

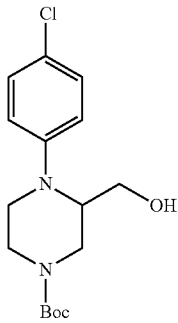 [SMILES: CC(C)(C)OC(=O)N1CCN(c2ccc(Cl)cc2)C(CO)C1]

Following the procedure as described in Step B of EXAMPLE 1 and making non-critical variations to replace trans-1-tert-butyl 3-methyl 4-(4-chlorophenyl)piperidine-1,3-dicarboxylate with 1-tert-butyl 3-methyl 4-(4-chlorophenyl)piperazine-1,3-dicarboxylate, tert-butyl 4-(4-chlorophenyl)-3-(hydroxymethyl)piperazine-1-carboxylate was obtained in 99% yield (0.54 g) as a colorless oil: ¹H NMR (300 MHz, CDCl₃) δ 7.18 (d, J=8.4 Hz, 2H), 6.80 (d, J=8.4 Hz, 2H), 4.29-4.11 (m, 1H), 3.98 (d, J=11.1 Hz, 1H), 3.81 (br s, 1H), 3.60-3.45 (m, 2H), 3.25-3.01 (m, 5H), 1.47 (s, 9H); MS (ES+) m/z 326.9 (M+1), 328.9 (M+1).

EXAMPLE 112.3

Synthesis of tert-butyl 4-(4-chlorophenyl)-3-(4-(N-(2,4-dimethoxybenzyl)-N-(1,2,4-thiadiazol-5-yl)sulfamoyl)-2,5-difluorophenoxy)methyl)piperazine-1-carboxylate

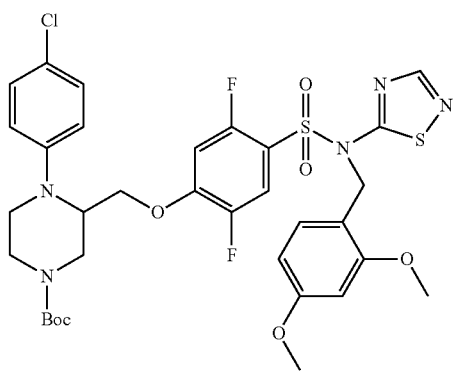 [SMILES: COc1ccc(CN(c2ncns2)S(=O)(=O)c2cc(F)c(OCC3CN(C(=O)OC(C)(C)C)CCN3c3ccc(Cl)cc3)cc2F)c(OC)c1]

Following the procedure as described in EXAMPLE 16 and making non-critical variations to replace trans-tert-butyl 4-(4-chlorophenyl)-3-(hydroxymethyl)piperidine-1-carboxylate with tert-butyl 4-(4-chlorophenyl)-3-(hydroxymethyl)piperazine-1-carboxylate, tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperazine-1-carboxylate was obtained in 89% yield (0.28 g) as a colorless oil: MS (ES+) m/z 751.8 (M+1), 753.6 (M+1).

EXAMPLE 112

Synthesis of 44(1-(4-chlorophenyl)piperazin-2-yl)methoxy)-2,5-difluoro-N-(1,2,4-thiadiazol-5-yl)benzenesulfonamide

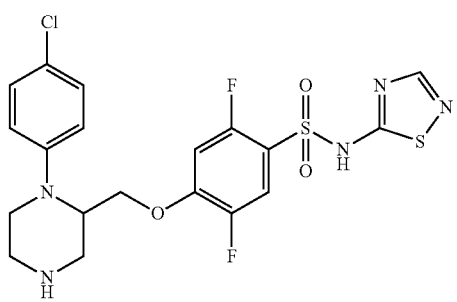 [SMILES: O=S(=O)(Nc1ncns1)c1cc(F)c(OCC2CNCCN2c2ccc(Cl)cc2)cc1F]

Following the procedure as described in EXAMPLE 44 and making non-critical variations to replace trans-tert-butyl 4-(4-chlorophenyl)-3-((4-(N-(2,4-dimethoxybenzyl)-N-(1,2,4-thiadiazol-5-yl)sulfamoyl)-2,5-difluorophenoxy)methyl)piperidine-1-carboxylate with tert-butyl 4-(4-chlorophenyl)-3-(4-(N-(2,4-dimethoxybenzyl) -N-(1,2,4-thiadiazol-5-yl(sulfamoyl)-2,5-difluorophenoxy)methyl) piperazine-1-carboxylate, 4-((1-(4-chlorophenyl)piperazin-2-yl)methoxy)-2,5-difluoro-N-(1,2,4-thiadiazol-5-yl) benzenesulfonamide was obtained as the corresponding trifluoroacetic acid salt in 53% yield (0.12 g) as an off-white solid: $^1$H NMR (300 MHz, DMSO-$d_6$) δ 9.01 (br s, 1H), 8.66 (br s, 1H), 8.24 (s, 1H), 7.53 (dd, J=10.4, 6.6 Hz, 1H), 7.29-7.21 (m, 3H), 7.02 (d, J=9.0 Hz, 2H), 4.54-4.46 (m, 1H), 4.36 (dd, J=9.5, 9.5 Hz, 1H), 4.13 (dd, 1H, J=9.7, 4.8 Hz, 1H), 3.60 (d, J=13.2 Hz, 1H), 3.47 (d, J=13.1 Hz, 1H), 3.40-3.06 (m, 4H); MS (ES+) m/z 501.7 (M+1), 503.7 (M+1).

BIOLOGICAL ASSAYS

Various techniques are known in the art for testing the activity of the compound of the invention or determining their solubility in known pharmaceutically acceptable excipients. In order that the invention described herein may be more fully understood, the following biological assays are set forth. It should be understood that these examples are for illustrative purposes only and are not to be construed as limiting this invention in any manner.

Biological Example 1

Electrophysiological Assay (In Vitro Assay)

Patch voltage clamp electrophysiology allows for the direct measurement and quantification of block of voltage-gated sodium channels ($Na_v$'s), and allows the determination of the time- and voltage-dependence of block which has been interpreted as differential binding to the resting, open, and inactivated states of the sodium channel (Hille, B., *Journal of General Physiology* (1977), 69: 497-515).

The following patch voltage clamp electrophysiology studies were performed on representative compounds of the invention using human embryonic kidney cells (HEK), permanently transfected with an expression vector containing the full-length cDNA coding for the desired human sodium channel α-subunit, grown in culture media containing 10% FBS, 1% PSG, and 0.5 mg/mL G418 at 37° C. with 5% $CO_2$. HEK cells used for the electrophysiology (EP) recordings had a passage number of less than 40 for all studies and were used within three days from the time of plating. $Na_v1.7$ and $Na_v1.5$ cDNAs (NM_002977 and AC137587; SCN5A, respectively) were stably expressed in HEK-293 cells. The β1 subunit was coexpressed only in the $Na_v1.7$ cell line.

Sodium currents were measured using the patch clamp technique in the whole-cell configuration using either a PatchXpress automated voltage clamp or manually using an Axopatch 200B (Axon Instruments) or Model 2400 (A-M systems) amplifier. The manual voltage clamp protocol was as follows: Borosilicate glass micropipettes were fire-polished to a tip diameter yielding a resistance of 2-4 Mohms in the working solutions. The pipette was filled with a solution comprised of: 5 mM NaCl, 10 mM CsCl, 120 mM CsF, 0.1 mM $CaCl_2$, 2 mM $MgCl_2$, 10 mM HEPES, 10 mM EGTA; and adjusted to pH 7.2 with CsOH. The external solution had the following composition: 140 mM NaCl, 5 mM KCl, 2 mM $CaCl_2$, 1 mM $MgCl_2$, 10 mM HEPES; and adjusted to pH 7.4 with NaOH. In some studies, the external sodium was reduced by equimolar replacement with choline. Osmolarity in the CsF internal and NaCl external solutions was adjusted to 300 mOsm/kg and 310 mOsm/kg with glucose, respectively. All recordings were performed at ambient temperature in a bath chamber with a volume of 150 μL. Control sodium currents were measured in 0.5% DMSO. Controls and representative compounds of the invention were applied to the recording chamber through a 4-pinch or 8-pinch valve bath perfusion system manufactured by ALA Scientific Instruments.

Currents were recorded at 40 kHz sampling frequency, filtered at 5 Hz, and stored using a Digidata-1322A analogue/digital interface with the pClamp software (Axon Instruments). Series resistance compensation was applied (60-80%). Cells were rejected if currents showed inadequate voltage control (as judged by the IV relationship during stepwise activation). All statistics in this study are given as mean±SD.

The membrane potential was maintained at a voltage where inactivation of the channel is complete (which was −60 mV for both $Na_v1.7$ and $Na_v1.5$). The voltage is then stepped back to a very negative (Vhold=−150 mV) voltage for 20 ms and then a test pulse is applied to quantify the compound block. The 20 ms brief repolarization was long enough for compound-free channels to completely recover from fast inactivation, but the compound-bound channels recovered more slowly such that negligible recovery could occur during this interval. The percent decrease in sodium current following wash-on of compound was taken as the percent block of sodium channels.

Representative compounds of the invention, when tested in this model, demonstrated affinities for the inactivated state of $Na_v1.7$ and $Na_v1.5$ as set forth below in Table 1 and Table 2, respectively, wherein "A" refers to an $IC_{50}$ of less than or equal to 100 nM, "B" refers to an $IC_{50}$ of greater than 100 nM and less than or equal to 1 μM, "C" refers to an $IC_{50}$ of greater than 1 μM and less than or equal to 10 μM and "D" refers to an $IC_{50}$ of greater than 10 μM. The Example numbers provided in Table 1 and Table 2 correspond to the Examples herein:

TABLE 1

Inhibition of $Na_v1.7$

| Ex. No. | Compound Name | $Na_v1.7$ | $IC_{50}$(μM) |
|---|---|---|---|
| 44 | 4-((trans-4-(4-chlorophenyl)piperidin-3-yl)methoxy)-2,5-difluoro-N-(1,2,4-thiadiazol-5-yl)benzenesulfonamide | A | 0.0033 |
| 45 | 2,5-difluoro-4-((trans-4-(4-fluorophenyl)piperidin-3-yl)methoxy)-N-(1,2,4-thiadiazol-5-yl)benzenesulfonamide | A | 0.0068 |

TABLE 1-continued

Inhibition of Na$_V$1.7

| Ex. No. | Compound Name | Na$_V$1.7 | IC$_{50}$(μM) |
|---|---|---|---|
| 46 | 2,5-difluoro-4-(((3S,4R)-4-(4-fluorophenyl)piperidin-3-yl)methoxy)-N-(1,2,4-thiadiazol-5-yl)benzenesulfonamide | B | 0.9282 |
| 47 | 2,5-difluoro-4-((3-fluoro-4-(4-fluorophenyl)piperidin-3-yl)methoxy)-N-(1,2,4-thiadiazol-5-yl)benzenesulfonamide | A | 0.0507 |
| 48 | 4-((trans-4-(3,4-difluorophenyl)piperidin-3-yl)methoxy)-2,5-difluoro-N-(1,2,4-thiadiazol-5-yl)benzenesulfonamide | A | 0.0026 |
| 49 | 4-((trans-4-(4-chlorophenyl)piperidin-3-yl)methoxy)-2,5-difluoro-N-(pyrimidin-2-yl)benzenesulfonamide | A | 0.0532 |
| 50 | 2,5-difluoro-4-((trans-4-(4-fluorophenyl)piperidin-3-yl)methoxy)-N-(pyrimidin-2-yl)benzenesulfonamide | B | 0.3229 |
| 51 | 4-((trans-4-(4-chlorophenyl)piperidin-3-yl)methoxy)-2,5-difluoro-N-(1,3,4-thiadiazol-2-yl)benzenesulfonamide | A | 0.0844 |
| 52 | 4-((trans-4-(4-chlorophenyl)piperidin-3-yl)methoxy)-2,5-difluoro-N-(3-methyl-1,2,4-thiadiazol-5-yl)benzenesulfonamide | B | 0.1943 |
| 54 | 4-((trans-4-(4-chlorophenyl)pyrrolidin-3-yl)methoxy)-2,5-difluoro-N-(1,2,4-thiadiazol-5-yl)benzenesulfonamide | A | 0.0499 |
| 56 | 4-((trans-4-(4-chlorophenyl)piperidin-3-yl)methoxy)-2,5-difluoro-N-(5-methylisoxazol-3-yl)benzenesulfonamide | C | 1.8899 |
| 57 | 4-((trans-4-(4-chlorophenyl)piperidin-3-yl)methoxy)-2,5-difluoro-N-(5-methylthiazol-2-yl)benzenesulfonamide | B | 0.1160 |
| 58 | 4-((trans-4-(4-chlorophenyl)piperidin-3-yl)methoxy)-3-cyano-N-(1,2,4-thiadiazol-5-yl)benzenesulfonamide | A | 0.0033 |
| 59 | 4-((trans-4-(4-chlorophenyl)piperidin-3-yl)methoxy)-3-fluoro-N-(1,2,4-thiadiazol-5-yl)benzenesulfonamide | A | 0.0086 |
| 60 | 4-((trans-4-(4-chlorophenyl)piperidin-3-yl)methoxy)-2,5-difluoro-N-(pyrimidin-4-yl)benzenesulfonamide | A | 0.0330 |
| 61 | N-(5-chlorothiazol-2-yl)-4-(trans-4-(3,4-difluorophenyl)piperidin-3-yl)methoxy)-2,5-difluorobenzenesulfonamide | A | 0.0216 |
| 62 | 4-((trans-4-(4-chlorophenyl)piperidin-3-yl)methoxy)-N-(5-chlorothiazol-2-yl)-2,5-difluorobenzenesulfonamide | A | 0.0230 |
| 63 | 4-((trans-4-(4-chlorophenyl)piperidin-3-yl)methoxy)-2,5-difluoro-N-(5-fluoropyridin-2-yl)benzenesulfonamide | A | 0.0705 |
| 64 | 4-((trans-4-(4-chlorophenyl)piperidin-3-yl)methoxy)-2,5-difluoro-N-(5-fluoropyrimidin-2-yl)benzenesulfonamide | A | 0.0764 |
| 65 | 4-((trans-4-(4-chlorophenyl)piperidin-3-yl)methoxy)-2,5-difluoro-N-(pyridazin-3-yl)benzenesulfonamide | B | 0.1708 |
| 66 | 4-((cis-4-(4-chlorophenyl)piperidin-3-yl)methoxy)-2,5-difluoro-N-(1,2,4-thiadiazol-5-yl)benzenesulfonamide | B | 0.2372 |
| 68 | 2,5-difluoro-4-((trans-2-(4-fluorophenyl)cyclohexyl)methoxy)-N-(1,2,4-thiadiazol-5-yl)benzenesulfonamide | B | 0.2797 |
| 69 | trans-tert-butyl 3-((4-(N-(1,2,4-thiadiazol-5-yl)sulfamoyl)-2,5-difluorophenoxy)methyl)-4-(4-chlorophenyl)piperidine-1-carboxylate | B | 0.1640 |
| 70 | 4-((trans-4-(4-chlorophenyl)-1-methylpiperidin-3-yl)methoxy)-2,5-difluoro-N-(1,2,4-thiadiazol-5-yl)benzenesulfonamide 2,2,2-trifluoroacetate | A | 0.0120 |
| 77 | 4-(((3R,4S)-4-(4-chlorophenyl)piperidin-3-yl)methoxy)-2,5-difluoro-N-(1,2,4-thiadiazol-5-yl)benzenesulfonamide | A | 0.0011 |
| 78 | 4-((trans-4-(4-chlorophenyl)piperidin-3-yl)methoxy)-2,5-difluoro-N-(4-methyl-1,2,4-thiadiazol-5(4H)-ylidene)benzenesulfonamide | 4.08 μM* | |
| 79 | 4-((trans-4-(4-chlorophenyl)piperidin-3-yl)methoxy)-2,5-difluoro-N-methyl-N-(1,2,4-thiadiazol-5-yl)benzenesulfonamide | 7.88 μM* | |

TABLE 1-continued

Inhibition of $Na_V1.7$

| Ex. No. | Compound Name | $Na_V1.7$ | $IC_{50}(\mu M)$ |
|---|---|---|---|
| 80 | 4-((trans-4-(4-chlorophenyl)-1-(2-fluoroethyl)piperidin-3-yl)methoxy)-2,5-difluoro-N-(1,2,4-thiadiazol-5-yl)benzenesulfonamide | A | 0.0937 |
| 81 | 4-((trans-4-(4-chlorophenyl)piperidin-3-yl)methoxy)-3,5-difluoro-N-(1,2,4-thiadiazol-5-yl)benzenesulfonamide | 2.32 μM* | |
| 82 | 2,5-difluoro-4-((trans-3-(4-fluorophenyl)piperidin-4-yl)methoxy)-N-(1,2,4-thiadiazol-5-yl)benzenesulfonamide | A | 0.0317 |
| 83 | 4-((trans-4-(4-chlorophenyl)-1-(2,2-difluoroethyl)piperidin-3-yl)methoxy)-2,5-difluoro-N-(1,2,4-thiadiazol-5-yl)benzenesulfonamide | A | 0.0381 |
| 84 | 4-(((3S,4R)-4-(4-chlorophenyl)piperidin-3-yl)methoxy)-2,5-difluoro-N-(1,2,4-thiadiazol-5-yl)benzenesulfonamide | A | 0.0588 |
| 85 | 4-(((3R,4S)-4-(4-chlorophenyl)-1-methylpiperidin-3-yl)methoxy)-2,5-difluoro-N-(1,2,4-thiadiazol-5-yl)benzenesulfonamide | A | 0.0048 |
| 86 | 4-(((3S,4R)-4-(4-chlorophenyl)-1-methylpiperidin-3-yl)methoxy)-2,5-difluoro-N-(1,2,4-thiadiazol-5-yl)benzenesulfonamide | B | 0.3314 |
| 87 | 2,5-difluoro-4-((trans-4-(4-fluorophenyl)-6-oxopiperidin-3-yl)methoxy)-N-(1,2,4-thiadiazol-5-yl)benzenesulfonamide | A | 0.0820 |
| 88 | 4-((trans-4-(4-chlorophenyl)-1-(2,2,2-trifluoroethyl)piperidin-3-yl)methoxy)-2,5-difluoro-N-(1,2,4-thiadiazol-5-yl)benzenesulfonamide | B | 0.1297 |
| 89 | trans-3-((4-(N-(5-chlorothiazol-2-yl)sulfamoyl)-2,5-difluorophenoxy)methyl)-4-(3,4-difluorophenyl)piperidine-1-carboxamide | B | 0.4365 |
| 90 | 4-((trans-4-(4-chlorophenyl)piperidin-3-yl)methoxy)-3-cyano-N-isopropylbenzenesulfonamide | >10 μM* | |
| 91 | 4-((trans-4-(4-chlorophenyl)piperidin-3-yl)methoxy)-3-cyano-N-(1-cyanocyclopropyl)benzenesulfonamide | >10 μM* | |
| 92 | 4-((trans-4-(3,4-dichlorophenyl)piperidin-3-yl)methoxy)-2,5-difluoro-N-(1,2,4-thiadiazol-5-yl)benzenesulfonamide | A | 0.0008 |
| 93 | 4-((trans-4-(4-chlorophenyl)piperidin-3-yl)methoxy)-3-cyano-N-(2,2,2-trifluoroethyl)benzenesulfonamide | >10 μM* | |
| 94 | 2,5-difluoro-4-((trans-4-(4-methoxyphenyl)piperidin-3-yl)methoxy)-N-(1,2,4-thiadiazol-5-yl)benzenesulfonamide | 0.132 μM* | |
| 95 | 4-((trans-4-(4-chlorophenyl)piperidin-3-yl)methoxy)-2,5-difluorobenzenesulfonamide | >10 μM* | |
| 96 | 4-((trans-4-(4-chlorophenyl)piperidin-3-yl)methoxy)-2,5-difluoro-N-isobutylbenzenesulfonamide | 4.90 μM* | |
| 97 | 4-((trans-4-(4-chloro-3-fluorophenyl)piperidin-3-yl)methoxy)-2,5-difluoro-N-(1,2,4-thiadiazol-5-yl)benzenesulfonamide | A | 0.0009 |
| 98 | trans-3-((4-((1H-pyrazol-1-yl)sulfonyl)-2,5-difluorophenoxy)methyl)-4-(4-fluorophenyl)piperidine | 7.22 μM* | |
| 99 | N-((4-((trans-4-(4-chlorophenyl)piperidin-3-yl)methoxy)-2,5-difluorophenyl)sulfonyl)picolinamide | >10 μM* | |
| 100 | 2,5-difluoro-N-(1,2,4-thiadiazol-5-yl)-4-((trans-4-(p-tolyl)piperidin-3-yl)methoxy)benzenesulfonamide | 0.393 μM* | |
| 101 | 2,5-difluoro-4-((trans-6-oxo-4-(2,4,5-trifluorophenyl)piperidin-3-yl)methoxy)-N-(1,2,4-thiadiazol-5-yl)benzenesulfonamide | 4.49 μM* | |
| 102 | N-((4-((trans-4-(4-chlorophenyl)piperidin-3-yl)methoxy)-2,5-difluorophenyl)sulfonyl)acetamide | >10 μM* | |
| 103 | N-((4-((trans-4-(4-chlorophenyl)piperidin-3-yl)methoxy)-2,5-difluorophenyl)sulfonyl)nicotinamide | >10 μM* | |
| 104 | N-((4-((trans-4-(4-chlorophenyl)piperidin-3-yl)methoxy)-2,5-difluorophenyl)sulfonyl)benzamide | >10 μM* | |

TABLE 1-continued

Inhibition of $Na_v1.7$

| Ex. No. | Compound Name | $Na_v1.7$ $IC_{50}(\mu M)$ |
|---|---|---|
| 105 | 4-((trans-4-(4-chlorophenyl)piperidin-3-yl)methoxy)-2,5-difluoro-N-(isopropylcarbamoyl)benzenesulfonamide | >10 μM* |
| 106 | 2,5-difluoro-N-(1,2,4-thiadiazol-5-yl)-4-((trans-4-(2,4,5-trifluorophenyl)piperidin-3-yl)methoxy)benzenesulfonamide | 0.181 μM* |
| 107 | 2,5-difluoro-4-((trans-4-(4-fluoro-3-(trifluoromethyl)phenyl)piperidin-3-yl)methoxy)-N-(1,2,4-thiadiazol-5-yl)benzenesulfonamide | 0.038 μM* |
| 108 | 4-((trans-4-(3-(difluoromethyl)-4-fluorophenyl)piperidin-3-yl)methoxy)-2,5-difluoro-N-(1,2,4-thiadiazol-5-yl)benzenesulfonamide | 0.071 μM* |
| 109 | 4-((2-(4-chlorophenyl)-5-oxocyclohexyl)methoxy)-2,5-difluoro-N-(1,2,4-thiadiazol-5-yl)benzenesulfonamide | 0.244 μM* |
| 110 | 4-(((trans-5S)-2-(4-chlorophenyl)-5-hydroxycyclohexyl)methoxy)-2,5-difluoro-N-(1,2,4-thiadiazol-5-yl)benzenesulfonamide | 0.426 μM* |
| 111 | 4-(((trans-5R)-2-(4-chlorophenyl)-5-hydroxycyclohexyl)methoxy)-2,5-difluoro-N-(1,2,4-thiadiazol-5-yl)benzenesulfonamide | 2.044 μM* |
| 112 | 4-((1-(4-chlorophenyl)piperazin-2-yl)methoxy)-2,5-difluoro-N-(1,2,4-thiadiazol-5-yl)benzenesulfonamide | 0.326 μM* |

*NaV flux data is included when EP data is not available

TABLE 2

Inhibition of $Na_v1.5$

| Ex. No. | Compound Name | $Na_v1.5$ $IC_{50}(\mu M)$ | $Na_v1.5$ $IC_{50}(\mu M)$ |
|---|---|---|---|
| 44 | 4-((trans-4-(4-chlorophenyl)piperidin-3-yl)methoxy)-2,5-difluoro-N-(1,2,4-thiadiazol-5-yl)benzenesulfonamide | D | >10 |
| 45 | 2,5-difluoro-4-((trans-4-(4-fluorophenyl)piperidin-3-yl)methoxy)-N-(1,2,4-thiadiazol-5-yl)benzenesulfonamide | D | >10 |
| 47 | 2,5-difluoro-4-((3-fluoro-4-(4-fluorophenyl)piperidin-3-yl)methoxy)-N-(1,2,4-thiadiazol-5-yl)benzenesulfonamide | D | >10 |
| 58 | 4-((trans-4-(4-chlorophenyl)piperidin-3-yl)methoxy)-3-cyano-N-(1,2,4-thiadiazol-5-yl)benzenesulfonamide | D | >10 |
| 59 | 4-((trans-4-(4-chlorophenyl)piperidin-3-yl)methoxy)-3-fluoro-N-(1,2,4-thiadiazol-5-yl)benzenesulfonamide | D | >10 |
| 61 | N-(5-chlorothiazol-2-yl)-4-(trans-4-(3,4-difluorophenyl)piperidin-3-yl)methoxy)-2,5-difluorobenzenesulfonamide | D | >10 |
| 70 | 4-((trans-4-(4-chlorophenyl)-1-methylpiperidin-3-yl)methoxy)-2,5-difluoro-N-(1,2,4-thiadiazol-5-yl)benzenesulfonamide 2,2,2-trifluoroacetate | D | >10 |
| 77 | 4-(((3R,4S)-4-(4-chlorophenyl)piperidin-3-yl)methoxy)-2,5-difluoro-N-(1,2,4-thiadiazol-5-yl)benzenesulfonamide | C | 5.2286 |
| 78 | 4-((trans-4-(4-chlorophenyl)piperidin-3-yl)methoxy)-2,5-difluoro-N-(4-methyl-1,2,4-thiadiazol-5(4H)-ylidene)benzenesulfonamide | NA | |
| 79 | 4-((trans-4-(4-chlorophenyl)piperidin-3-yl)methoxy)-2,5-difluoro-N-methyl-N-(1,2,4-thiadiazol-5-yl)benzenesulfonamide | >10 μM* | |
| 80 | 4-((trans-4-(4-chlorophenyl)-1-(2-fluoroethyl)piperidin-3-yl)methoxy)-2,5-difluoro-N-(1,2,4-thiadiazol-5-yl)benzenesulfonamide | NA | |
| 81 | 4-((trans-4-(4-chlorophenyl)piperidin-3-yl)methoxy)-3,5-difluoro-N-(1,2,4-thiadiazol-5-yl)benzenesulfonamide | NA | |
| 82 | 2,5-difluoro-4-((trans-3-(4-fluorophenyl)piperidin-4-yl)methoxy)-N-(1,2,4-thiadiazol-5-yl)benzenesulfonamide | NA | |

TABLE 2-continued

Inhibition of Na$_V$1.5

| Ex. No. | Compound Name | Na$_V$1.5 IC$_{50}$(μM) | Na$_V$1.5 IC$_{50}$(μM) |
|---|---|---|---|
| 83 | 4-((trans-4-(4-chlorophenyl)-1-(2,2-difluoroethyl)piperidin-3-yl)methoxy)-2,5-difluoro-N-(1,2,4-thiadiazol-5-yl)benzenesulfonamide | NA | |
| 84 | 4-(((3S,4R)-4-(4-chlorophenyl)piperidin-3-yl)methoxy)-2,5-difluoro-N-(1,2,4-thiadiazol-5-yl)benzenesulfonamide | D | >10 |
| 85 | 4-(((3R,4S)-4-(4-chlorophenyl)-1-methylpiperidin-3-yl)methoxy)-2,5-difluoro-N-(1,2,4-thiadiazol-5-yl)benzenesulfonamide | D | >10 |
| 86 | 4-(((3S,4R)-4-(4-chlorophenyl)-1-methylpiperidin-3-yl)methoxy)-2,5-difluoro-N-(1,2,4-thiadiazol-5-yl)benzenesulfonamide | D | >10 |
| 87 | 2,5-difluoro-4-((trans-4-(4-fluorophenyl)-6-oxopiperidin-3-yl)methoxy)-N-(1,2,4-thiadiazol-5-yl)benzenesulfonamide | D | >10 |
| 88 | 4-((trans-4-(4-chlorophenyl)-1-(2,2,2-trifluoroethyl)piperidin-3-yl)methoxy)-2,5-difluoro-N-(1,2,4-thiadiazol-5-yl)benzenesulfonamide | D | >10 |
| 89 | trans-3-((4-(N-(5-chlorothiazol-2-yl)sulfamoyl)-2,5-difluorophenoxy)methyl)-4-(3,4-difluorophenyl)piperidine-1-carboxamide | D | >10 |
| 90 | 4-((trans-4-(4-chlorophenyl)piperidin-3-yl)methoxy)-3-cyano-N-isopropylbenzenesulfonamide | NA | |
| 91 | 4-((trans-4-(4-chlorophenyl)piperidin-3-yl)methoxy)-3-cyano-N-(1-cyanocyclopropyl)benzenesulfonamide | NA | |
| 92 | 4-((trans-4-(3,4-dichlorophenyl)piperidin-3-yl)methoxy)-2,5-difluoro-N-(1,2,4-thiadiazol-5-yl)benzenesulfonamide | >10 μM* | |
| 93 | 4-((trans-4-(4-chlorophenyl)piperidin-3-yl)methoxy)-3-cyano-N-(2,2,2-trifluoroethyl)benzenesulfonamide | NA | |
| 94 | 2,5-difluoro-4-((trans-4-(4-methoxyphenyl)piperidin-3-yl)methoxy)-N-(1,2,4-thiadiazol-5-yl)benzenesulfonamide | >10 μM* | |
| 95 | 4-((trans-4-(4-chlorophenyl)piperidin-3-yl)methoxy)-2,5-difluorobenzenesulfonamide | NA | |
| 96 | 4-((trans-4-(4-chlorophenyl)piperidin-3-yl)methoxy)-2,5-difluoro-N-isobutylbenzenesulfonamide | 7.56 μM* | |
| 97 | 4-((trans-4-(4-chloro-3-fluorophenyl)piperidin-3-yl)methoxy)-2,5-difluoro-N-(1,2,4-thiadiazol-5-yl)benzenesulfonamide | >10 μM* | |
| 98 | trans-3-((4-((1H-pyrazol-1-yl)sulfonyl)-2,5-difluorophenoxy)methyl)-4-(4-fluorophenyl)piperidine | 7.53 μM* | |
| 99 | N-((4-((trans-4-(4-chlorophenyl)piperidin-3-yl)methoxy)-2,5-difluorophenyl)sulfonyl)picolinamide | NA | |
| 100 | 2,5-difluoro-N-(1,2,4-thiadiazol-5-yl)-4-((trans-4-(p-tolyl)piperidin-3-yl)methoxy)benzenesulfonamide | >10 μM* | |
| 101 | 2,5-difluoro-4-((trans-6-oxo-4-(2,4,5-trifluorophenyl)piperidin-3-yl)methoxy)-N-(1,2,4-thiadiazol-5-yl)benzenesulfonamide | NA | |
| 102 | N-((4-((trans-4-(4-chlorophenyl)piperidin-3-yl)methoxy)-2,5-difluorophenyl)sulfonyl)acetamide | NA | |
| 103 | N-((4-((trans-4-(4-chlorophenyl)piperidin-3-yl)methoxy)-2,5-difluorophenyl)sulfonyl)nicotinamide | NA | |
| 104 | N-((4-((trans-4-(4-chlorophenyl)piperidin-3-yl)methoxy)-2,5-difluorophenyl)sulfonyl)benzamide | NA | |
| 105 | 4-((trans-4-(4-chlorophenyl)piperidin-3-yl)methoxy)-2,5-difluoro-N-(isopropylcarbamoyl)benzenesulfonamide | NA | |
| 106 | 2,5-difluoro-N-(1,2,4-thiadiazol-5-yl)-4-((trans-4-(2,4,5-trifluorophenyl)piperidin-3-yl)methoxy)benzenesulfonamide | >10 μM* | |
| 107 | 2,5-difluoro-4-((trans-4-(4-fluoro-3-(trifluoromethyl)phenyl)piperidin-3-yl)methoxy)-N-(1,2,4-thiadiazol-5-yl)benzenesulfonamide | >10 μM* | |
| 108 | 4-((trans-4-(3-(difluoromethyl)-4-fluorophenyl)piperidin-3-yl)methoxy)-2,5-difluoro-N-(1,2,4-thiadiazol-5-yl)benzenesulfonamide | >10 μM* | |
| 109 | 4-((2-(4-chlorophenyl)-5-oxocyclohexyl)methoxy)-2,5-difluoro-N-(1,2,4-thiadiazol-5-yl)benzenesulfonamide | >10 μM* | |
| 110 | 4-(((trans-5S)-2-(4-chlorophenyl)-5-hydroxycyclohexyl)methoxy)-2,5-difluoro-N-(1,2,4-thiadiazol-5-yl)benzenesulfonamide | >10 μM | |

TABLE 2-continued

Inhibition of $Na_V1.5$

| Ex. No. | Compound Name | $Na_V1.5$ $IC_{50}(\mu M)$ | $Na_V1.5$ $IC_{50}(\mu M)$ |
|---|---|---|---|
| 111 | 4-(((trans-5R)-2-(4-chlorophenyl)-5-hydroxycyclohexyl)methoxy)-2,5-difluoro-N-(1,2,4-thiadiazol-5-yl)benzenesulfonamide | >10 µM* | |
| 112 | 4-((1-(4-chlorophenyl)piperazin-2-yl)methoxy)-2,5-difluoro-N-(1,2,4-thiadiazol-5-yl)benzenesulfonamide | >10 µM* | |

*NaV flux data is included when EP data is not available

Biological Example 2

Analgesia Induced by sodium channel Blockers

Heat Induced Tail Flick Latency Test

In this test, the analgesia effect produced by administering a compound of the invention can be observed through heat-induced tail-flick in mice. The test includes a heat source consisting of a projector lamp with a light beam focused and directed to a point on the tail of a mouse being tested. The tail-flick latencies, which are assessed prior to drug treatment, and in response to a noxious heat stimulus, i.e., the response time from applying radiant heat on the dorsal surface of the tail to the occurrence of tail flick, are measured and recorded at 40, 80, 120, and 160 minutes.

For the first part of this study, 65 animals undergo assessment of baseline tail flick latency once a day over two consecutive days. These animals are then randomly assigned to one of the 11 different treatment groups including a vehicle control, a morphine control, and 9 compounds at 30 mg/Kg are administered intramuscularly. Following dose administration, the animals are closely monitored for signs of toxicity including tremor or seizure, hyperactivity, shallow, rapid or depressed breathing and failure to groom. The optimal incubation time for each compound is determined via regression analysis. The analgesic activity of the test compounds is expressed as a percentage of the maximum possible effect (% MPE) and is calculated using the following formula:

$$\% \; MPE \; \frac{\text{Postdrug latency} - \text{Predrug latency}}{\text{Cut-off time (10 s)} - \text{Predrug latency}} \times 100\%$$

where:

Postdrug latency=the latency time for each individual animal taken before the tail is removed (flicked) from the heat source after receiving drug.

Predrug latency=the latency time for each individual animal taken before the tail is flicked from the heat source prior to receiving drug.

Cut-off time (10 s)=is the maximum exposure to the heat source.

Acute Pain (Formalin Test)

The formalin test is used as an animal model of acute pain. In the formalin test, animals are briefly habituated to the plexiglass test chamber on the day prior to experimental day for 20 minutes. On the test day, animals are randomly injected with the test articles. At 30 minutes after drug administration, 50 µL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.llii extension, and then converts it into the MPEG-4 coding. The videos are then analyzed using behaviour analysis software "The Observer 5.1", (Version 5.0, Noldus Information Technology, Wageningen, The Netherlands). The video analysis is conducted by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1,2,3) of each animal. A single value for the vehicle group is obtained by averaging all scores within the vehicle treatment group. The following calculation yields the MPIE value for each animal:

MPIE(%)=100−[(treatment sum/average vehicle value)×100%]

The pain score is calculated from a weighted scale as described above. The duration of the behaviour is multiplied by the weight (rating of the severity of the response), and divided by the total length of observation to determine a pain rating for each animal. The calculation is represented by the following formula:

Pain rating=[0($T0$)+1($T1$)+2($T2$)+3($T3$)]/($T0$+$T1$+$T2$+$T3$)

CFA Induced Chronic Inflammatory Pain

In this test, tactile allodynia is assessed with calibrated von Frey filaments. Following a full week of acclimatization to the vivarium facility, 150 µL of the "Complete Freund's Adjuvant" (CFA) emulsion (CFA suspended in an oil/saline (1:1) emulsion at a concentration of 0.5 mg/mL) is injected subcutaneously into the plantar surface of the left hind paw of rats under light isoflurane anaesthesia. Animals are allowed to recover from the anaesthesia and the baseline thermal and mechanical nociceptive thresholds of all animals are assessed one week after the administration of CFA. All animals are habituated to the experimental equipment for 20 minutes on the day prior to the start of the experiment. The test and control articles are administrated to the animals, and the nociceptive thresholds measured at defined time points after drug administration to determine the analgesic responses to each of the six available treatments. The time points used are previously determined to show the highest analgesic effect for each test compound.

Thermal nociceptive thresholds of the animals are assessed using the Hargreaves test. Animals are placed in a Plexiglas enclosure set on top of an elevated glass platform with heating units. The glass platform is thermostatically controlled at a temperature of approximately 30° C. for all test trials. Animals are allowed to accommodate for 20 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 45 respectively, and a cut off time of 20 seconds is employed to prevent tissue damage.

The response thresholds of animals to tactile stimuli are measured using the Model 2290 Electrovonfrey anesthesiometer (IITC Life Science, Woodland Hills, Calif.) following the Hargreaves test. Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isofluorane, which is delivered via a nose cone, a 1 cm longitudinal incision is made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic Pain Model; Chronic Constriction Injury

Briefly, an approximately 3 cm incision is made through the skin and the fascia at the mid thigh level of the animals' left hind leg using a no. 10 scalpel blade. The left sciatic nerve is exposed via blunt dissection through the biceps femoris with care to minimize haemorrhagia. Four loose ligatures are tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve is exposed without further manipulation. Antibacterial ointment is applied directly into the wound, and the muscle is closed using sterilized sutures. Betadine is applied onto the muscle and its surroundings, followed by skin closure with surgical clips.

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals are assessed using the Hargreaves test. Following the measurement of tactile thresholds, animals are placed in a Plexiglass enclosure set on top of an elevated glass platform with heating units. The glass platform is thermostatically controlled at a temperature of approximately 24 to 26° C. for all test trials. Animals are allowed to accommodate for 10 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 55 respectively, and a cut off time of 20 seconds is used to prevent tissue damage.

Neuropathic pain model: Spinal Nerve Ligation

The spinal nerve ligation (SNL) neuropathic pain model is used as an animal (i.e. rat) model of neuropathic pain. In the SNL test, the lumbar roots of spinal nerves L5 and L6 are tightly ligated to cause nerve injury, which results in the development of mechanical hyperalgesia, mechanical allodynia and thermal hypersensitivity. The surgery is performed two weeks before the test day in order for the pain state to fully develop in the animals. Several spinal nerve ligation variations are used to characterize the analgesic properties of a compound of the invention.

(1) Ligation of the L5 spinal nerve;
(2) Ligation of the L5 and L6 spinal nerves;
(3) Ligation and transection of the L5 spinal nerve;
(4) Ligation and transection of the L5 and L6 spinal nerves; or
(5) Mild irritation of the L4 spinal nerve in combination with any one of the above (1)-(4).

While the animals are anaesthetized under 3.5% isofluorane delivered via a nose cone, an approximately 2.5 cm longitudinal incision is made using a number 10 scalpel blade in the skin just lateral to the dorsal midline, using the level of the posterior iliac crests as the midpoint of the incision. Following the incision, the isoflourane is readjusted to maintenance levels (1.5%-2.5%). At mid-sacral region, an incision is made with the scalpel blade, sliding the blade along the side of the vertebral column (in the saggital plane) until the blade hits the sacrum. Scissors tips are introduced through the incision and the muscle and ligaments are removed from the spine to expose 2-3 cm of the vertebral column. The muscle and fascia are cleared from the spinal vertebra in order to locate the point where the nerve exits from the vertebra. A small glass hook is placed medial to the spinal nerves and the spinal nerves are gently elevated from the surrounding tissues. Once the spinal nerves have been isolated, a small length of non-degradable 6-0 sterilized silk thread is wound twice around the ball at the tip of the glass hook and passed back under the nerve.

The spinal nerves are then firmly ligated by tying a knot, ensuring that the nerve bulges on both sides of the ligature. The procedure may be repeated as needed. In some animals, the L4 spinal nerve may be lightly rubbed (up to 20 times) with the small glass hook to maximize the development of neuropathic pain. Antibacterial ointment is applied directly into the incision, and the muscle is closed using sterilized sutures. Betadine is applied onto the muscle and its surroundings, followed by skin closure with surgical staples or sterile non-absorable monofilament 5-0 nylon sutures.

The analgesic effect produced by topical administration of a compound of the invention to the animals can then be observed by measuring the paw withdrawal threshold of animals to mechanical tactile stimuli. These may be measured using either the mechanical allodynia procedure or the mechanical hyperalgesia procedure as described below. After establishment of the appropriate baseline measurements by either method, topical formulation of a compound of the invention is applied on the ipsilateral ankle and foot. The animals are then placed in plastic tunnels for 15 minutes to prevent them from licking the treated area and removing the compound. Animals are placed in the acrylic enclosure for 15 minutes before testing the ipsilateral paw by either of the methods described below, and the responses are recorded at 0.5, 1.0 and 2.0 hour post treatment.

A. Mechanical Allodynia Method

The pain threshold of animals to mechanical alloydnia for both operated and control animals can be measured approximately 14 days post-surgery using manual calibrated von Frey filaments as follows. Animals are placed in an elevated plexiglass enclosure set on a mire mesh surface. Animals are allowed to acclimate for 20-30 minutes. Pre-calibrated Von Frey hairs are applied perpendicularly to the plantar surface of the ipsilateral paw of the animals starting from the 2.0 g hair, with sufficient force to cause slight buckling of the hair against the paw to establish the baseline measurements. Stimuli are presented in a consecutive manner, either in an ascending or descending order until the first change in response is noted, after which four additional reponses are recorded for a total of six responses. The six responses measured in grams are entered into a formula as described by Chaplan, S. R. et al., *J. Neurosci. Methods*, 1994 July; 53(1):55-63, and a 50% withdrawal threshold is calculated. This constitutes the mechanical allodynia value.

B. Mechanical Hyperalgesia Method

The response thresholds of animals to tactile stimuli were measured using the Model 2290 Electrovonfrey anesthesiometer (IITC Life Science, Woodland Hills, Calif.).

Animals were placed in an elevated Plexiglas enclosure set on a wire mesh surface. After 15 minutes of accommodation in this enclosure, a von Frey hair was applied perpendicularly to the plantar surface of the ipsilateral hind paws of the animals, with sufficient force, measured in grams, to elicit a crisp response of the paw. The response indicated a withdrawal from the painful stimulus and constituted the efficacy endpoint. The data were expressed as percent change from baseline threshold measured in grams.

Biological Example 3

In Vivo Assay for Treatment of Pruritis

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/mL, 50 µL), a dose of a compound of the present invention can be applied systemically through oral, intravenous or intraperitoneal routes or topically to a circular area fixed diameter (e.g. 18 mm). Following dosing, the serotonin injections are given in the area of the topical dosing. After serotonin injection the animal behaviour is monitored by video recording for 20 min-1.5 h, and the number of scratches in this time compared to vehicle treated animals. Thus, application of a compound of the current invention could suppress serotonin-induced scratching in rats.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

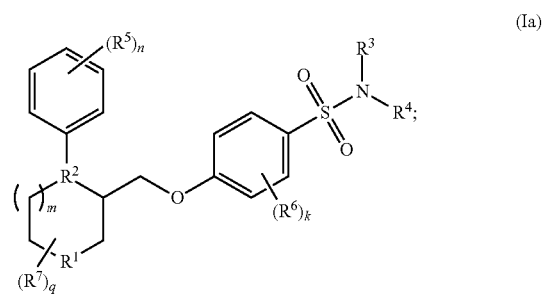

(Ia)

wherein:
k is 0, 1, 2, 3 or 4;
m is 1;
n is 0, 1, 2, 3, 4 or 5;
q is 0, 1, 2, 3, 4, 5 or 6;
$R^1$ is —N($R^{10}$)—, or —N($R^{11}$)—;
$R^2$ is C($R^9$);
$R^3$ is hydrogen, alkyl, haloalkyl, optionally substituted aryl or optionally substituted aralkyl;
or $R^3$ is a direct bond to $R^4$;

$R^4$ is H, optionally substituted alkyl, optionally substituted heterocyclyl, optionally substituted heteroaryl, optionally substituted cycloalkyl, haloalkyl, —C(O)R$^{10}$, —C(O)N(R$^{10}$)$_2$ or —C(=NCN)N(R$^{10}$)$_2$;

or $R^3$ and $R^4$, together with the nitrogen to which they are both attached, form an optionally substituted N-heterocyclyl or optionally substituted N-heteroaryl;

each $R^5$ and each $R^6$ are independently hydrogen, alkyl, halo, haloalkyl, nitro, cyano, —OR$^{10}$, —S(O)$_t$R$^{10}$ (where t is 0, 1 or 2), —C(O)OR$^{10}$, —C(O)R$^{10}$ or —C(O)N(R$^{10}$)$_2$;

each $R^7$ is independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$;

or any two $R^7$'s on the same carbon may form an oxo and the other $R^7$'s, if present, are independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$;

or any two $R^7$'s on different carbons may form an optionally substituted straight or branched alkylene chain optionally containing one or more heteroatoms, and the other $R^7$'s, if present, are independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$;

each $R^9$ is independently hydrogen, alkyl, halo, haloalkyl, —OR$^{10}$, —N(R$^{10}$)$_2$, —S(O)$_t$R$^{10}$ (where t is 0, 1 or 2), —C(O)OR$^{10}$, —C(O)R$^{10}$ or —C(O)N(R$^{10}$)$_2$;

each $R^{10}$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each $R^{11}$ is independently —C(O)R$^{10}$, —C(O)OR$^{10}$, —C(O)N(R$^{10}$)$_2$, —S(O)$_p$R$^{10}$ (where p is 1 or 2) or —S(O)$_p$N(R$^{10}$)$_2$ (where p is 1 or 2);

or an individual stereoisomer, enantiomer or tautomer thereof or a mixture thereof;

or a pharmaceutically acceptable salt thereof.

2. The compound of claim 1 wherein:
$R^3$ is hydrogen, alkyl, haloalkyl, optionally substituted aryl or optionally substituted aralkyl;
or $R^3$ is a direct bond to $R^4$;
$R^4$ is optionally substituted alkyl, optionally substituted heterocyclyl, optionally substituted heteroaryl, —C(O)N(R$^{10}$)$_2$ or —C(=NCN)N(R$^{10}$)$_2$;
or $R^3$ and $R^4$, together with the nitrogen to which they are both attached, form an optionally substituted N-heterocyclyl or optionally substituted N-heteroaryl.

3. The compound of claim 2 wherein:
$R^3$ is hydrogen, alkyl, haloalkyl, optionally substituted aryl or optionally substituted aralkyl;
or $R^3$ is a direct bond to $R^4$;
$R^4$ is optionally substituted heterocyclyl, optionally substituted heteroaryl, —C(O)N(R$^{10}$)$_2$ or —C(=NCN)N(R$^{10}$)$_2$;
or $R^3$ and $R^4$, together with the nitrogen to which they are both attached, form an optionally substituted N-heterocyclyl or optionally substituted N-heteroaryl.

4. The compound of claim 3 wherein:
n is 0, 1, or 2;
q is 0, 1 or 2; and
each $R^7$ is independently hydrogen, alkyl, halo, haloalkyl, —OR$^{10}$, —S(O)$_t$R$^{10}$ (where t is 0, 1 or 2), —C(O)OR$^{10}$, —C(O)R$^{10}$ or —C(O)N(R$^{10}$)$_2$.

5. The compound of claim 4 wherein:
k is 0, 1 or 2;
$R^3$ is hydrogen, alkyl, haloalkyl, optionally substituted aryl or optionally substituted aralkyl;
or $R^3$ is a direct bond to $R^4$;
$R^4$ is —C(O)N(R$^{10}$)$_2$, —C(=NCN)N(R$^{10}$)$_2$, optionally substituted heterocyclyl or optionally substituted heteroaryl, where the heterocyclyl is N-heterocyclyl and the heteroaryl is N-heteroaryl;
or $R^3$ and $R^4$, together with the nitrogen to which they are both attached, form an optionally substituted N-heterocyclyl or optionally substituted N-heteroaryl; and
each $R^9$ is independently hydrogen, alkyl, halo or haloalkyl.

6. The compound of claim 4 wherein:
k is 0, 1 or 2;
$R^1$ is —N(R$^{10}$)—;
$R^3$ is hydrogen, alkyl, haloalkyl, optionally substituted aryl or optionally substituted aralkyl;
or $R^3$ is a direct bond to $R^4$;
$R^4$ is —C(O)N(R$^{10}$)$_2$, —C(=NCN)N(R$^{10}$)$_2$, optionally substituted heterocyclyl or optionally substituted heteroaryl, where the heterocyclyl is N-heterocyclyl and the heteroaryl is N-heteroaryl;
or $R^3$ and $R^4$, together with the nitrogen to which they are both attached, form an optionally substituted N-heterocyclyl or optionally substituted N-heteroaryl; and
each $R^9$ is independently hydrogen, alkyl, halo, haloalkyl or —OR$^{10}$.

7. The compound of claim 6 wherein:
$R^3$ is hydrogen or optionally substituted aralkyl;
or $R^3$ is a direct bond to $R^4$;
$R^4$ is an optionally substituted N-heteroaryl or an optionally substituted N-heterocyclyl;
each $R^5$ is independently hydrogen, halo or haloalkyl;
each $R^6$ is independently hydrogen, halo, haloalkyl or cyano; and
each $R^7$ is independently hydrogen, alkyl, halo or haloalkyl.

8. The compound of claim 7 wherein:
$R^3$ is hydrogen or a direct bond to $R^4$;
$R^4$ is an optionally substituted N-heteroaryl or an optionally substituted N-heterocyclyl;
each $R^9$ is independently hydrogen; and
each $R^{10}$ is independently hydrogen or alkyl.

9. The compound of claim 8 wherein:
$R^3$ is hydrogen or a direct bond to $R^4$;
$R^4$ is optionally substituted N-heteroaryl selected from optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl;
or $R^4$ is optionally substituted 1,2,4-thiadiazol-5(4H)-ylidene.

10. The compound of claim 1 selected from:
4-((trans-4-(4-chlorophenyl)piperidin-3-yl)methoxy)-2,5-difluoro-N-(1,2,4-thiadiazol-5-yl)benzenesulfonamide;
4-((trans-4-(4-chlorophenyl)piperidin-3-yl)methoxy)-2,5-difluoro-N-(pyridin-2-yl)benzenesulfonamide;
4-((trans-4-(4-chlorophenyl)piperidin-3-yl)methoxy)-3-cyano-N-(1,2,4-thiadiazol-5-yl)benzenesulfonamide;
4-((trans-4-(4-chlorophenyl)piperidin-3-yl)methoxy)-3-fluoro-N-(1,2,4-thiadiazol-5-yl)benzenesulfonamide;

4-((trans-4-(4-chlorophenyl)-1-methylpiperidin-3-yl)methoxy)-2,5-difluoro-N-(1,2,4-thiadiazol-5-yl)benzenesulfonamide2,2,2-trifluoroacetate;

2,5-difluoro-4-((trans-4-(4-fluorophenyl)peperidin-3-yl)methoxy)-N-(1,2,4-thiadiazol-5-yl)benzenesulfonamide;

4-((trans-4-(4-chlorophenyl)piperidin-3yl)methoxy)-2,5-difluoro-N-(3-methyl-1,2,4-thiadiazol-5-yl)benzenesulfonamide;

4-((trans-4-(4-chlorophenyl)piperidin-3-yl)methoxy)-2,5-difluoro-N-(1,3,4-thiadiazol-2-yl)benzenesulfonamide;

4-((trans-4-(4-chlorophenyl)piperidin-3-yl)methoxy)-2,5-difluoro-N-(2-methyl-2H-tetrazol-5-yl)benzenesulfonamide;

4-((trans-4-(4-chlorophenyl)piperidin-3-yl)methoxy)-2,5-difluoro-N-(5-methylisoxazol-3-yl)benzenesulfonamide;

4-((trans-4-(4-chloropheny)piperidin-3-yl)methoxy)-N-(5-chlorothi azol-2-yl)-2,5-difluorobenzenesulfonamide;

4-((trans-4-(4-chlorophenyl)piperidin-3-yl)methoxy)-2,5-difluoro-N-(pyrimidin-2-yl)benzenesulfonamide;

4-((trans-4-(4-chlorophenyl)piperidin-3-yl)methoxy)-2,5-difluoro-N-(5-methylthiazol-2-yl)benzenesulfonamide;

4-((trans-4-(4-chlorophenyl)piperidin-3-yl)methoxy)-2,5-difluoro-N-(5-fluoropyridin-2-yl)benzenesulfonamide;

4-((trans-4-(4-chlorophenyl)piperidin-3-yl)methoxy)-2,5-difluoro-N-(pyrimidin-4-yl)benzenesulfonamide;

4-((trans-4-(3,4-difluorophenyl)piperidin-3-yl)methoxy)-2,5-difluoro-N-(1,2,4-thiadiazol-5-yl)benzenesulfonamide;

4-((trans-4-(4-chlorophenyl)piperidin-3-yl)methoxy)-2,5-difluoro-N-(5-fluoropyrimidin-2-yl)benzenesulfonamide;

4-((trans-4-(4-chlorophenyl)piperidin-3-yl)methoxy)-2,5-difluoro-N-(pyridazin-3-yl)benzenesulfonamide;

2,5-difluoro-4-(((3S,4R)-4-(4-fluorophenyl)piperidin-3-yl)methoxy)-N-1,2,4-thiadiazol-5-yl)benzenesulfonamide;

4-((cis-4-(4-chlorophenyl)piperidin-3-yl)methoxy)-2,5-difluoro-N-(1,2,4-thiadiazol-5-yl)benzenesulfonamide;

2,5-difluoro-4-((trans-4-(4-fluorophenyl)piperidin-3-yl)methoxy)-N-(pyrimidin-2-yl)benzenesulfonamide;

2,5-difluoro-4((3-fluorophenyl)piperidin-3-)methoxy)-N-(1,2,4-thiadiazol-5-yl)benzenesulfonamide;

N-(5-chlorothiazol-2-yl)-4-(trans-4-(3,4-difluorophenyl)piperidin-3-)methoxy)-2,5-difluorobenzenesulfonamide;

4-((trans-4-(4-chlorophenyl)piperidin-3-yl)methoxy)-2.5-difluoro-N-(pyridin-2-yl)benzenesulfonamide;

2,5-difluoro-4-((trans-4-phenylpiperidin-3 -yl)methoxy)-N-(1,2,4-thiadiazol-5-yl)benzenesulfonamide;

4-(((3R,4S)-4-(4-chlorophenyl)piperidin-3-yl)methoxy)-2,5-difluoro-N-(1,2,4-thiadiazol-5-yl)benzenesulfonamide;

4-((trans-4-(4-chlorophenyl)piperidin-3-yl)methoxy)-2,5-difluoro-N-(4-methyl-1,2,4-thiadiazol-5(4H)-ylidene)benzenesulfonamide;

4-((trans-4-(4-chlorophenyl)piperidin-3-yl)methoxy)-2,5-difluoro-N-methyl-N-(1,2,4-thiadiazol-5-yl)benzenesulfonamide;

4-((trans-4-(4-chlorophenyl)-1-(2-fluoroethyl)piperidin-3-yl)methoxy)-2,5-difluoro-N-(1,2,4-thiadiazol-5-yl)benzenesulfonamide;

4-((trans-4-(4-chlorophenyl)piperidin-3-yl)methoxy)-3,5-difluoro-N-(1,2,4-thiadiazol-5-yl)benzenesulfonamide;

4-((trans-4-(4-chlorophenyl)-1-(2,2-difluoroethyl)piperidin-3-yl)methoxy)-2,5-difluoro-N-(1,2,4-thiadiazol-5-yl)benzenesulfonamide;

4-(((3S,4R)-4-(4-chlorophenyl)piperidin-3-yl)methoxy)-2,5-difluoro-N-(1,2,4-thiadiazol-5-yl)benzenesulfonamide;

4-4(((3R,4S)-4-(4-chlorophenyl)-1-methylpiperidin-3-yl)methoxy)-2,5-difluoro-N-(1,2,4-thiadiazol-5-yl)benzenesulfonamide;

4-(((3S,4R)-4-(4-chlorophenyl)-1-methylpiperidin-3-yl)methoxy)-2,5-difluoro-N-(1,2,4-thiadiazol-5-yl)benzenesulfonamide;

2,5-difluoro-4-((trans-4-(4-fluorophenyl)-6-oxopiperidin-3 -yl)methoxy)-N-(1,2,4-thiadiazol-5-yl)benzenesulfonamide;

4-((trans-4-(4-chlorophenyl)-1-(2,2,2-trifluoroethyl)piperidin-3-yl)methoxy)-2,5-difluoro-N-(1,2,4-thiadiazol-5-yl)benzenesulfonamide;

trans-3-((4-(N-(5-chlorothiazol-2-yl)sulfamoyl)-2,5-difluorophenoxy)methyl)-4-(3,4-difluorophenyl)piperidine-1-carboxamide;

4-((trans-4-(4-chlorophenyl)piperidin-3-yl)methoxy)-3-cyano-N-isopropylbenzenesulfonamide;

4-((trans-4-(4-chlorophenyl)piperidin-3-yl)methoxy)-3-cyano-N-(1-cyanocyclopropyl)benzenesulfonamide;

4-((trans-4-(3,4-dichlorophenyl)piperidin-3-yl)methoxy)-2,5-difluoro-N-(1,2,4-thiadiazol-5-yl)benzenesulfonamide;

4-((trans-4-(4-chlorophenyl)piperidin-3-yl)methoxy)-3-cyano-N-(2,2,2-trifluoroethyl)benzenesulfonamide;

2,5-difluoro-4-((trans-4-(4-methoxyphenyl)piperidin-3-yl)methoxy)-N-(1,2,4-thiadiazol-5-yl)benzenesulfonamide;

4-((trans-4-(4-chlorophenyl)piperidin-3-yl)methoxy)-2,5-difluorobenzenesulfonamide;

4-((trans-4-(4-chlorophenyl)piperidin-3-yl)methoxy)-2,5-di fluoro-N-isobutylbenzenesulfonamide;

4-((trans-4-(4-chloro-3-fluorophenyl)piperidin-3-yl)methoxy)-2,5-difluoro-N-(1,2,4-thiadiazol-5-yl)benzenesulfonamide;

trans-3-((4-((1H-pyrazol-1-yl)sulfonyl)-2,5-di fluorophenoxy)methyl)-4-(4-fluorophenyl)piperidine;

N-((4-((trans-4-(4-chlorophenyl)piperidin-3-yl)methoxy)-2,5-difluorophenyl)sulfonyl)picolinamide;

2,5-difluoro-N-(1,2,4-thiadiazol-5-yl)-4-((trans-4-(p-tolyl)piperidin-3-yl)methoxy)benzenesulfonarnide;

2,5-difluoro-4-((trans-6-oxo-4-(2,4,5-trifluorophenyl)piperidin-3-yl)methoxy)-N-(1,2,4-thiadiazol-5-yl)benzenesulfonamide;

N-((4-((trans-4-(4-chlorophenyl)piperidin-3-yl)methoxy)-2,5-difluorophenyl)sulfonyl)acetamide;

N-((4-((trans-4-(4-chlorophenyl)piperidin-3-yl)methoxy)-2,5-difluorophenyl)sulfonyl)nicotinamide;

N-((4-((trans-4-(4-chlorophenyl)piperidin-3 -yl)methoxy)-2,5-difluorophenyl)sulfonyl)benzamide;

4-((trans-4-(4-chlorophenyl)piperidin-3-yl)methoxy)-2,5-difluoro-N-(isopropylcarbamoyl)benzenesulfonamide;

2,5-difluoro-N-(1,2,4-thiadiazol-5-yl)-4-((trans-4-(2,4,5-trifluorophenyl)piperidin-3-yl)methoxy)benzenesulfonamide;

2,5-difluoro-4-((trans-4-(4-fluoro-3-(trifluoromethyl)phenyl)piperidin-3-yl)methoxy)-N-(1,2,4-thiadiazol-5-yl)benzenesulfonamide; and 4-((trans-4-(3-(difluoromethyl)-4-fluorophenyl)piperidin-3-yl)methoxy)-2,5-difluoro-N-(1,2,4-thiadiazol-5-yl)benzenesulfonamide.

11. The compound of claim 5 wherein:
$R^1$ is —N($R^{11}$)—.

12. The compound of claim 11 wherein:
$R^3$ is hydrogen, optionally substituted aralkyl or a direct bond to $R^4$;
$R^4$ is an optionally substituted N-heteroaryl or an optionally substituted N-heterocyclyl;
each $R^5$ is independently hydrogen, halo or haloalkyl;
each $R^6$ is independently hydrogen, halo, haloalkyl or cyano; and
each $R^7$ is independently hydrogen, alkyl, halo or haloalkyl.

13. The compound of claim 12 wherein:
$R^3$ is hydrogen or a direct bond to $R^4$;
$R^4$ is an optionally substituted N-heteroaryl or an optionally substituted N-heterocyclyl;
each $R^9$ is independently hydrogen; and
each $R^{10}$ is independently hydrogen or alkyl.

14. The compound of claim 13 wherein:
$R^3$ is hydrogen or a direct bond to $R^4$;
$R^4$ is optionally substituted thiadiazolyl, optionally substituted tetrazolyl, optionally substituted isoxazolyl, optionally substituted thiazolyl, optionally substituted pyrimidinyl, optionally substituted pyridinyl, or optionally substituted pyridazinyl;
or $R^4$ is optionally substituted 1,2,4-thiadiazol-5(4H)-ylidene;
$R^{11}$ is —C(O)O$R^{10}$.

15. The compound of claim 1 having the following relative trans configuration:

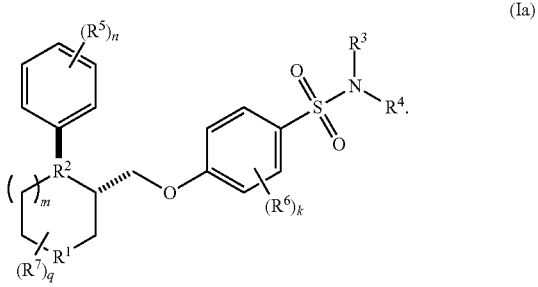

(Ia)

16. The compound trans-tert-butyl 3((4-(N-(1,2,4-thiadiazol-5-yl)sulfamoyl)-2,5-difluorophenoxy)methyl)-4-(4-chlorophenyl)piperidine-1-carboxylate.

17. A pharmaceutical composition comprising a pharmaceutically acceptable excipient and a compound of claim 1, as a stereoisomer, enantiomer or tautomer thereof or mixtures thereof; or a pharmaceutically acceptable salt thereof.

18. A method of treating a disease or condition selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury, and combinations thereof.

19. A method of treating pain in a mammal by the inhibition of ion flux through a voltage-dependent sodium channel in the mammal, wherein the method comprises administering to the mammal in need thereof a therapeutically effective amount of a compound of claim 1, as a stereoisomer, enantiomer or tautomer thereof or mixtures thereof; or a pharmaceutically acceptable salt thereof.

20. A method of decreasing ion flux through a voltage-dependent sodium channel in a cell in a mammal, wherein the method comprises contacting the cell with a compound of claim 1, as a stereoisomer, enantiomer or tautomer thereof or mixtures thereof; or a pharmaceutically acceptable salt thereof.

21. A method of treating pruritus in a mammal, wherein the method comprises administering to the mammal in need thereof a therapeutically effective amount of a compound of claim 1, as a stereoisomer, enantiomer or tautomer thereof or mixtures thereof; or a pharmaceutically acceptable salt thereof.

22. A method of treating cancer pain in a mammal, wherein the methods comprise administering to the mammal in need thereof a therapeutically effective amount of a compound of claim 1, as a stereoisomer, enantiomer or tautomer thereof or mixtures thereof; or a pharmaceutically acceptable salt thereof.

23. A method of treating or ameliorating, but not preventing, pain in a mammal, wherein the method comprises administering to the mammal in need thereof a therapeutically effective amount of a compound of claim 1, as a stereoisomer, enantiomer or tautomer thereof or mixtures thereof; or a pharmaceutically acceptable salt, thereof.

24. The method of claim 23 wherein the pain is selected from the group consisting of neuropathic pain, inflammatory pain, visceral pain, cancer pain, chemotherapy pain, trauma pain, surgical pain, post-surgical pain, childbirth pain, labor pain, dental pain, chronic pain, persistent pain, peripherally mediated pain, centrally mediated pain, chronic headache, migraine headache, sinus headache, tension headache, phantom limb pain, peripheral nerve injury, trigeminal neuralgia, post-herpetic neuralgia, eudynia, familial erythromelalgia, primary erythromelalgia, familial rectal pain or fibromyalgia, and combinations thereof.

25. The method of claim 24 wherein the pain is associated with a disease or condition selected from HIV, HIV treatment induced neuropathy, heat sensitivity, tosarcoidosis, irritable bowel syndrome, Crohns disease, multiple sclerosis, amyotrophic lateral sclerosis, diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, neurogenic bladder, ulcerative colitis, cancer, epilepsy, partial and general tonic seizures, restless leg syndrome, arrhythmias, ischaemic conditions caused by stroke or neural trauma, tachy-arrhythmias, atrial fibrillation and ventricular fibrillation.

26. A method of selectively modulating a first voltage-gated sodium channel over a second voltage-gated sodium channel in a mammal, wherein the method comprises administering to the mammal a modulating amount of a compound of claim 1, as a stereoisomer, enantiomer or tautomer thereof or mixtures thereof; or a pharmaceutically acceptable salt thereof.

27. The method of claim 26 wherein the method is selectively inhibiting a first voltage-gated sodium channel over a second voltage-gated sodium channel in a mammal, wherein the method comprises administering to the mammal an inhibitory amount of a compound of claim 1, as a stereoisomer, enantiomer or tautomer thereof or mixtures thereof; or a pharmaceutically acceptable salt thereof.

28. The method of claim 27 wherein the first voltage-gated sodium channel is $Na_v1.7$.

29. The method of claim 28 wherein the second voltage-gated sodium channel is $Na_v1.5$.

* * * * *

UNITED STATES PATENT AND TRADEMARK OFFICE
CERTIFICATE OF CORRECTION

PATENT NO. : 9,630,929 B2  
APPLICATION NO. : 14/355552  
DATED : April 25, 2017  
INVENTOR(S) : Shaoyi Sun et al.

Page 1 of 1

It is certified that error appears in the above-identified patent and that said Letters Patent is hereby corrected as shown below:

In the Claims

Column 191, Line 27, Claim 1, please delete ", -N($R^{10}$)$_2$, -S((O))$_t$$R^{10}$" and insert -- , -N($R^{10}$)$_2$, -N($R^{11}$)$_2$, -S((O))$_t$$R^{10}$ --;

Column 193, Line 20, Claim 13, please delete "5-chlorothi azol-2-yl)" and insert -- 5-chlorothiazol-2-yl) --;

Column 193, Line 54, Claim 13, please delete "piperidin-3 -yl)" and insert -- piperidin-3-yl) --;

Column 194, Line 10, Claim 13, please delete "4-4(((3R,4S)-" and insert -- 4(((3R,4S)- --;

Column 194, Line 17, Claim 13, please delete "din-3 -yl)" and insert -- din-3-yl) --;

Column 194, Line 44, Claim 13, please delete "-di fluoro" and insert -- -difluoro --;

Column 194, Line 57, Claim 13, please delete "piperidin-3 -yl)" and insert -- piperidin-3-yl) --;

Column 195, Line 64, Claim 18, please delete "and combinations thereof." and insert -- and combinations thereof, wherein the method comprises administering to the mammal in need thereof a therapeutically effective amount of compound of claim 1, as a stereoisomer, enantiomer or tautomer thereof or mixtures thereof; or a pharmaceutically acceptable salt thereof. -- therefor.

Signed and Sealed this  
Twelfth Day of December, 2017

Joseph Matal  
*Performing the Functions and Duties of the*  
*Under Secretary of Commerce for Intellectual Property and*  
*Director of the United States Patent and Trademark Office*